United States Patent
Lin et al.

(10) Patent No.: US 11,786,553 B2
(45) Date of Patent: Oct. 17, 2023

(54) CHIMERIC CYTOKINE RECEPTORS BEARING A PD-1 ECTODOMAIN

(71) Applicant: Allogene Therapeutics, Inc., South San Francisco, CA (US)

(72) Inventors: Regina Junhui Lin, San Mateo, CA (US); Thomas John Van Blarcom, Oakland, CA (US); Siler Panowski, Berkeley, CA (US); Barbra Johnson Sasu, San Francisco, CA (US)

(73) Assignee: ALLOGENE THERAPEUCTICS, INC., South San Francisco, CA (US)

(*) Notice: Subject to any disclaimer, the term of this patent is extended or adjusted under 35 U.S.C. 154(b) by 568 days.

(21) Appl. No.: 16/804,545

(22) Filed: Feb. 28, 2020

(65) Prior Publication Data

US 2020/0276238 A1 Sep. 3, 2020

Related U.S. Application Data

(60) Provisional application No. 62/980,737, filed on Feb. 24, 2020, provisional application No. 62/894,659, filed on Aug. 30, 2019, provisional application No. 62/812,799, filed on Mar. 1, 2019.

(51) Int. Cl.
| | |
|---|---|
| C07K 14/715 | (2006.01) |
| C07K 16/28 | (2006.01) |
| C07K 16/30 | (2006.01) |
| A61K 35/17 | (2015.01) |
| C12N 15/67 | (2006.01) |
| A61K 38/00 | (2006.01) |

(52) U.S. Cl.
CPC .......... A61K 35/17 (2013.01); C07K 14/7155 (2013.01); C07K 16/2818 (2013.01); C07K 16/30 (2013.01); C12N 15/67 (2013.01); *A61K 38/00* (2013.01); *C07K 2319/03* (2013.01); *C07K 2319/33* (2013.01); *C07K 2319/74* (2013.01)

(58) Field of Classification Search
CPC .. A61K 35/17; C12N 5/0636; C07K 2319/03; C07K 2319/33; C07K 2319/74; C07K 14/7155; C07K 14/715
See application file for complete search history.

(56) References Cited

U.S. PATENT DOCUMENTS

| | | |
|---|---|---|
| 8,389,282 B2 | 3/2013 | Sadelain et al. |
| 9,434,935 B2 | 9/2016 | Spencer et al. |
| 9,913,882 B2 | 3/2018 | Slawin et al. |
| 9,944,690 B2 | 4/2018 | Spencer et al. |
| 10,287,354 B2 | 3/2019 | Brogdon et al. |
| 10,294,304 B2 | 5/2019 | Kuo et al. |
| 10,336,810 B2 | 7/2019 | Tanaka |
| 10,548,921 B2 | 2/2020 | Leen et al. |
| 2014/0050709 A1 | 2/2014 | Leen et al. |
| 2014/0087468 A1 | 3/2014 | Spencer et al. |
| 2015/0111294 A1 | 4/2015 | Spencer et al. |
| 2016/0175359 A1 | 6/2016 | Spencer et al. |
| 2016/0297884 A1 | 10/2016 | Kuo et al. |
| 2016/0297885 A1 | 10/2016 | Kuo et al. |
| 2018/0037630 A1 | 2/2018 | Tanaka et al. |
| 2019/0000881 A1 | 1/2019 | Sadelain et al. |

FOREIGN PATENT DOCUMENTS

| | | | | |
|---|---|---|---|---|
| CA | 2842368 A1 | * | 2/2013 | ............. A61K 35/17 |
| WO | 1996004389 A1 | | 2/1996 | |
| WO | 199802558 A1 | | 1/1998 | |
| WO | WO9802558 A2 | | 1/1998 | |
| WO | WO2007075899 A2 | | 7/2007 | |
| WO | WO2011069004 A1 | | 6/2011 | |
| WO | WO2012138858 A1 | | 10/2012 | |
| WO | WO2014151960 A2 | | 9/2014 | |
| WO | WO2016055551 A1 | | 4/2016 | |
| WO | 2016127257 A1 | | 8/2016 | |
| WO | WO2017029512 A1 | | 2/2017 | |
| WO | 2017068360 A1 | | 4/2017 | |
| WO | WO2017103596 A1 | | 6/2017 | |
| WO | WO2018038945 A1 | | 3/2018 | |
| WO | WO2018094244 A1 | | 5/2018 | |
| WO | WO2018104473 A1 | | 6/2018 | |
| WO | 2018150187 A1 | | 8/2018 | |
| WO | 2018161064 A1 | | 9/2018 | |
| WO | 2019055946 A1 | | 3/2019 | |
| WO | 2019102207 A1 | | 5/2019 | |
| WO | WO2019118508 A1 | | 6/2019 | |
| WO | 2019169290 A1 | | 9/2019 | |
| WO | 2019232425 A1 | | 12/2019 | |
| WO | 2019246563 A1 | | 12/2019 | |
| WO | 2020044055 A1 | | 3/2020 | |
| WO | WO2020180694 A1 | | 9/2020 | |
| WO | WO2016168612 A1 | | 10/2020 | |

OTHER PUBLICATIONS

Xie et al., Oncology Letter, 2018, 16:157-166.*
Ajina, Adam , et al., "Strategies to Address Chimeric Antigen Receptor Tonic Signaling", Mol Cancer Ther; . Sep. 2018;17(9):1795-1815. doi: 10.1158/1535-7163.MCT-17-1097.
Gacerez, Albert T., et al., "How Chimeric Antigen Receptor Design Affects Adoptive T Cell Therapy", J Cell Physiol; Dec. 2016;231(12):2590-8. doi: 10.1002/jcp.25419. Epub Jun. 2, 2016.
Grotzinger, Joachim , "Molecular mechanisms of cytokine receptor activation", Biochim Biophys Acta; Nov. 11, 2002;1592(3):215-23.
Hu, Yuan , et al., "Chimeric antigen receptor (CAR)-transduced natural killer cells in tumor immunotherapy", Acta Pharmacol Sin; Feb. 2018;39(2):167-176. doi: 10.1038/aps.2017.125. Epub Sep. 7, 2017.

(Continued)

*Primary Examiner* — Hong Sang
(74) *Attorney, Agent, or Firm* — Allogene Therapeutics, Inc.

(57) ABSTRACT

Provided herein are PD-1 chimeric cytokine receptors. When present on chimeric antigen receptor (CAR)-bearing immune cells, such receptors allow for increased immune cell activation, proliferation, persistence, and/or potency, when engaged with PD-1 ligands or activation with an anti-PD-1 antibody. Also provided are methods of making and using the chimeric cytokine receptors described herein.

33 Claims, 31 Drawing Sheets

Specification includes a Sequence Listing.

(56) References Cited

OTHER PUBLICATIONS

Kim, Jin Hee, et al., "High cleavage efficiency of a 2A peptide derived from porcine teschovirus-1 in human cell lines, zebrafish and mice", PLoS One; 2011;6(4):e18556. doi: 10.1371/journal.pone. 0018556. Epub Apr. 29, 2011.
Shao, Huang, "Structural requirements for signal transducer and activator of transcription 3 binding to phosphotyrosine ligands containing the YXXQ motif", J Biol Chem; Apr. 30, 2004;279(18):18967-73. doi: 10.1074/jbc.M314037200. Epub Feb. 13, 2004.
Shochat, "Gain-of-function mutations in interleukin-7 receptor-α (IL7R) in childhood acute lymphoblastic leukemias", Journal of Experimental Medicine; 2(2011) 208 (5): 901-908; https://doi.org/10.1084/jem.20110580.
Zenatti, "Oncogenic IL7R gain-of-function mutations in childhood T-cell acute lymphoblastic leukemia", Nature Genetics; Sep. 4, 2011;43(10):932-9. doi: 10.1038/ng.924.
Zhang, Cheng, et al., "Engineering CAR-T cells", Biomarker Research vol. 5, Article No. 22 (2017).
EPO, "International Search Report & Written Opinion", mailed for PCT/US2020/048402 dated Nov. 27, 2020, 23 pages.
Saur, Sebastian J., et al., "Ubiquitination and degradation of the thrombopoietin receptor c-Mpl", Blood, Feb. 11, 2010 vol. 115, No. 6, pp. 1254-1263.
Bajgain, Pradip, "CAR T Cell Therapy for Breast Cancer: Harnessing the Tumor Milieu to Drive T Cell Activation", Research Article, J Immunother Cancer. May 10, 2018;6(1):34. doi: 10.1186/s40425-018-0347-5.
Behrmann, Iris, et al., "A single STAT recruitment module in a chimeric cytokine receptor complex is sufficient for STAT activation.", J Biol Chem.;272(8):5269-74., 1997.
Boger, Dale L., et al., "Cytokine receptor dimerization and activation: prospects for small molecule agonists.", Bioorg Med Chem.; 9(3):557-62., 2001.
Boyerinas, B., et al., "Abstract 602: A novel TGF-B/IL-12R signal conversion platform that protects CAR T cells from TGF-B-mediated immune suppression and concurrently amplifies effector function", Proceedings of the American Association for Cancer Research Annual Meeting 2017; Apr. 1-5, 2017; Washington, DC. Philadelphia (PA): AACR; Cancer Res 2017;77(13 Suppl):Abstract 602, 4 total pages.
Cherkassky, L., et al., "Human CAR T cells with cell-intrinsic PD-1 checkpoint blockade resist tumor-mediated inhibition", J. Clin. Invest. 126:3130-3144, 2016.
Defour, J P, et al., "Oncogenic activation of MPL/thrombopoietin receptor by 17 mutations at W515: implications for myeloproliferative neoplasms", Leukemia 30, 1214-1216; doi:10.1038/leu.2015. 271, 2016.
Defour, J P, et al., "Tryptophan at the transmembrane-cytosolic junction modulates thrombopoietin receptor dimerization and activation", PNAS 110:2540-2545, 2013.
EPO, "International Search Report & Written Opinion", dated May 29, 2020 for PCT Application No. PCT/US2020/020415; 17 pages.
EPO, "International Search Report and Written Opinion", dated Jun. 4, 2020 for PCT Application No. PCT/US2020/020340; 15 pages.
EPO, "International Search Report and Written Opinion", dated May 31, 2019 for PCT Application No. PCT/US2019/020340; 18 pages.
Friedmann, Michael C., et al., "Different interleukin 2 receptor beta-chain tyrosines couple to at least two signaling pathways and synergistically mediate interleukin 2-induced proliferation", Immunology; Proc. Natl. Acad. Sci. USA, vol. 93, pp. 2077-2082, Mar. 1996.
Hoyos, V., et al., "Engineering CD19-specific T lymphocytes with interleukin-15 and a suicide gene to enhance their anti-lymphoma/leukemia effects and safety", Leukemia 24:1160-1170, 2010.
Hurton, L. V., et al., "Tethered IL-15 augments antitumor activity and promotes a stem-cell memory subset in tumor-specific T cells", PNAS E7788-E7797, 2016.
Johnson, L.A., et al., "Rational development and characterization of humanized anti-EGFR variant III chimeric antigen receptor T cells for glioblastoma", Science Translational Medicine, vol. 7, No. 275, Feb. 18, 2015, pp. 1-16, XP055362795, US ISSN: 1946-6234, DOI: 10.1126/scitranslmed.aaa4963.
Kagoya, Yuki, et al., "A Novel Chimeric Antigen Receptor Containing a JAK-STAT Signaling Domain Mediates Superior Antitumor Effects", Nat Med. Feb. 2018; 24(3): 352-359; doi: 10.1038/nm.4478, Feb. 5, 2018.
Kloss, C., "TGFBeta signaling blockade within PSMA targeted CAR human T cells for the eradication of metastatic prostate cancer", Abstract 638, Molucular Therapy vol. 24, Supplement 1, 2 total pages, 2016.
Leen, Ann M, et al., "Reversal of Tumor Immune Inhibition Using a Chimeric Cytokine Receptor", Molecular Therapy vol. 22 No. 6, 1211-1220 Jun. 2014, Mar. 2014.
Leroy, Emilie, et al., "His 499 Regulates Dimerization and Prevents Oncogenic Activation by Asparagine Mutations of the Human Thrombopoietin Receptor", Journal of Biological Chemistry, vol. 291, No. 6, pp. 2974-2987, XP055696813, US ISSN: 0021-9258, DOI: 10.1074/jbc.M115.696534, 2015.
Liu, X., et al., "A chimeric switch-receptor targeting PD1 augments the efficacy of second-generation CAR T cells in advanced solid tumors", Cancer Res. 76:1578-1590, 2016.
Lu, Xiaohui, et al., "Dimerization by a Cytokine Receptor Is Necessary for Constitutive Activation of JAK2V617F", J Biol Chem; . Feb. 29, 2008;283(9):5258-66. doi: 10.1074/jbc. M707125200; Epub Dec. 23, 2007.
Malek, Thomas R., et al., "Interleukin-2 Receptor Signaling: At the Interface between Tolerance and Immunity", Immunity. Aug. 27, 2010; 33(2): 153-165. doi:10.1016/j.immuni.2010.08.004, 2010.
Matthews, E E, et al., "Thrombopoietin receptor activation: Transmembrane helix dimerization, rotation, and allosteric modulation", FASEB J. 25:2234-2244, 2011.
Maute, R L, "Engineering high-affinity PD-1 variants for optimized immunotherapy and immuno-PET imaging", PNAS 112:E6506-E6514, 2015.
Murray, P J, "The JAK-STAT signaling pathway: input and output integration.", J Immunol. Mar. 1, 2007;178 (5):2623-9., Feb. 2007.
Nakamura, T, et al., "A selective switch-on system for self-renewal of embryonic stem cells using chimeric cytokine receptors.", Biochem Biophys Res Commun. Jul. 9, 1998;248(1):22-7., Jul. 1998.
Shum, T, et al., "Constitutive signaling from an engineered IL7 receptor promotes durable tumor elimination by tumor-redirected T cells", Cancer Discovery 7:1-10, 2017.
Sukumaran, S., "Enhancing the potency and specificity of engineered T cells for cancer treatment", Cancer Discovery 8:972-987, 2018.
Tokarew, Nicholas, et al., "Teaching an old dog new tricks: next-generation CAR T cells", British Journal Cancer, Nature Publishing Group; 120, 26-37. https://doi.org/10.1038/s41416-018-0325-1, Nov. 6, 2018.
Varghese, Lelia N., et al., "The Thrombopoietin Receptor: Structural Basis of Traffic and Activation by Ligand, Mutations, Agonists, and Mutated Calreticulin", Frontiers in Endocrinology, Mar. 2017, vol. 8, Article 59; doi: 10.3389/fendo.2017.00059.
Vong, Q, et al., "Inhibiting TGFbeta signaling in CAR T-cells may significantly enhance efficacy of tumor immunotherapy", Blood 130:1791, 5 total pages, 2017.
Wu, C-Y, et al., "Remote control of therapeutic T cells through a small molecule-gated chimeric receptor", Science 350:aab4077, 21 total pages, 2015.
EPO, "International Search Report & Written Opinion", dated Jun. 21, 2021 for International Application No. PCT/US2021/019362.
Morris, Rhiannon, et al., "The molecular details of cytokine signaling via the JAK/STAT pathway", Protein Science 2018 ; vol. 27; pp. 1984-2009;, Dec. 1, 2018.
Behncken, Stuart N., et al., "Growth Hormone (GH)-independent Dimerization of GH Receptor by a Leucine Zipper Results in

(56) References Cited

OTHER PUBLICATIONS

Constitutive Activation", Journal of Biological Chemistry; vol. 275 Issue 22 pp. 17000-17007 (Jun. 2000) DOI: 10.1074/jbc.275.22.17000.

Ding, Jiamin, et al., "Asn 505 Mutation of the C-MPL Gene, A Cause of Familial Essential Thrombocythemia, Induces the Autonomous Homodimerizaton of the C-Mpl Independent of Ligand Stimulation", Blood; vol. 104, Issue 11, Nov. 16, 2004, p. 738.

Metcalfe, Riley D., et al., "Structural Understanding of Interleukin 6 Family Cytokine Signaling and Targeted Therapies: Focus on Interleukin 11", Front. Immunol., Jul. 16, 2020; Sec. Cytokines and Soluble Mediators in Immunity https://doi.org/10.3389/fimmu_2020.01424.

Suthaus, Jan, et al., "Forced Homo- and Heterodimerization of All gp130-Type Receptor Complexes Leads to Constitutive Ligand-independent Signaling and Cytokine-independent Growth", Molecular Biology of the Cellvol. 21, No. 15; 2797-2807; Aug. 1, 2010; https://doi.org/10.1091/mbc.e10-03-0240.

Babon, Jeffrey J., et al., "The molecular regulation of Janus kinase (JAK) activation", Biochem J. Aug. 15, 2014;462(1):1-13. doi: 10.1042/BJ20140712.

Clackson, Tim, et al., "Redesigning an FKBP-ligand interface to generate chemical dimerizers with novel specificity", Proc. Natl. Acad. Sci. USA, vol. 95, Sep. 1998, pp. 10437-10442.

Floss, Dorreen, et al., "Naturally occurring and synthetic constitutive active cytokine receptors in disease and therapy", Cytokine & Growth Factor Reviews; vol. 47, Jun. 2019, pp. 1-20.

Genbank, Accession No. AAB08425; thrombopoietin receptor [*Homo sapiens*]; 2016.

Genbank, Accession No. MN366105.1Synthetic construct 11D5-3-CD8BBZ gene, complete cds; 2019.

Silvennoinen, Olli, et al., "Cytokine receptor signal transduction through Jak tyrosine kinases and Stat transcription factor", APMIS, vol. 105, Issue7-12, Jul. 1997, pp. 497-509.

Wilmes, Stephan, et al., "Mechanism of homodimeric cytokine receptor activation and dysregulation by oncogenic mutations", Science; Feb. 7, 2020;367(6478):643-652. doi: 10.1126/science.aaw3242.

* cited by examiner

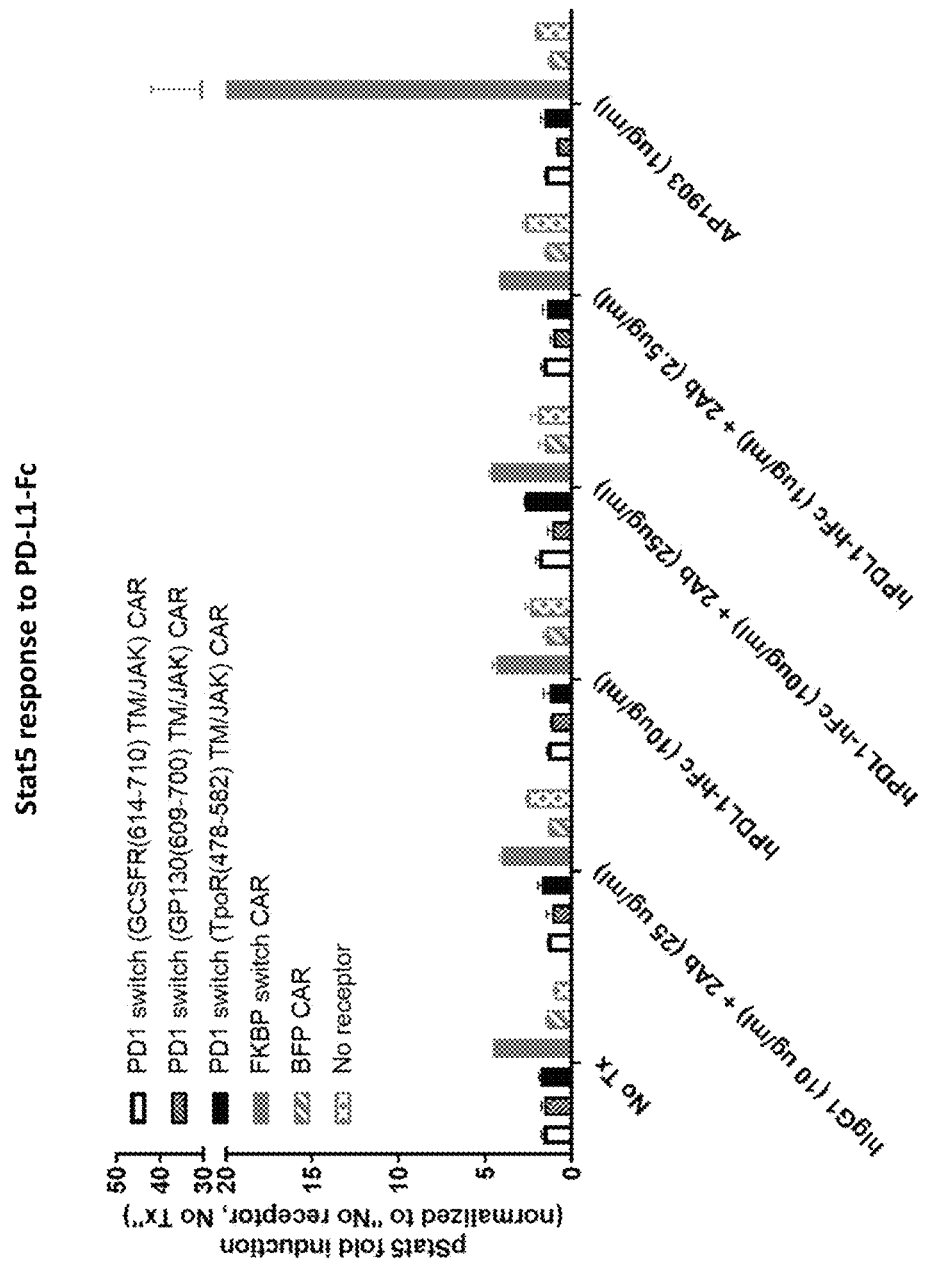

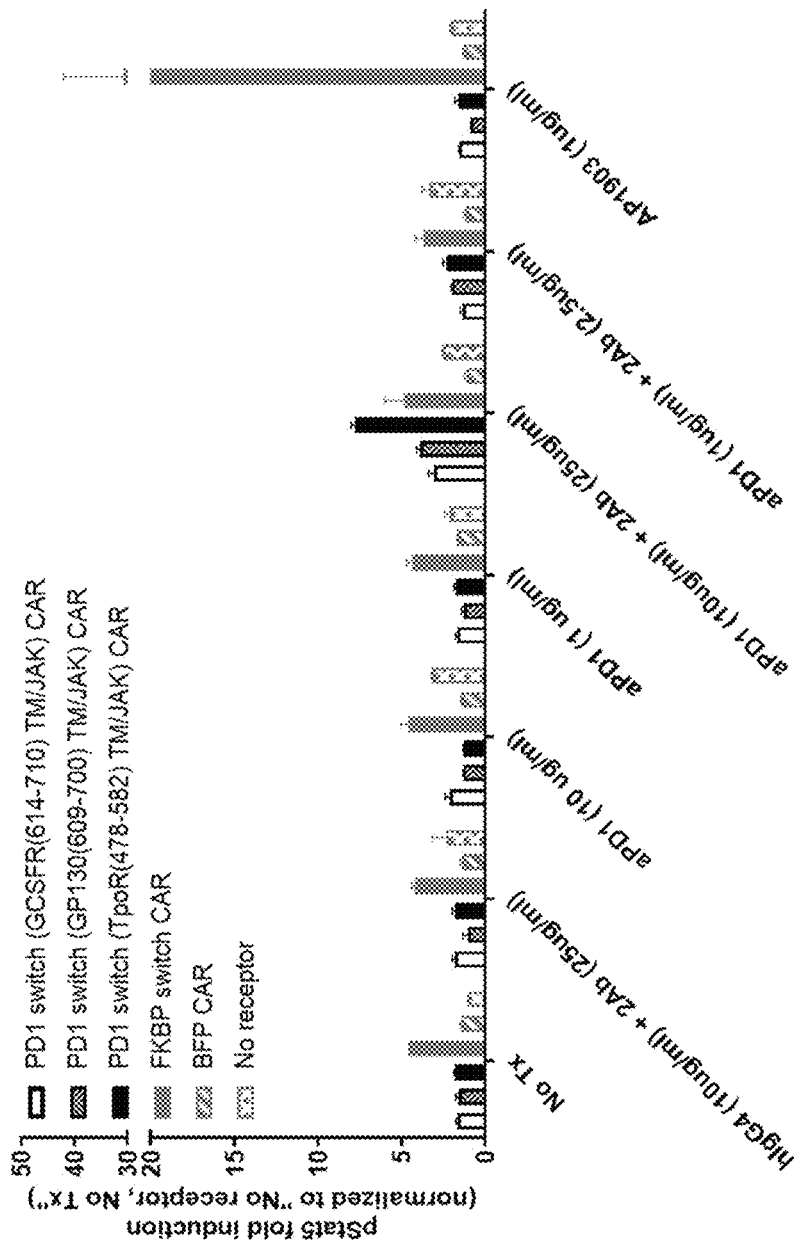

FIG. 10A

Underlined: wildtype TpoR TM region
Bold: means insertion

```
                                                                      (4138 - 4302 bp)
Template:  SDPTRVETATETAWISLVTALHLVLGLSAVLGLILLRWQFPAHYRLRHALWPSL
N-1:       SDPTRVETATET-WISLVTALHLVLGLSAVLGLILLRWQFPAHYRLRHALWPSL   SEQ. ID NO: 146
N-2:       SDPTRVETATET---ISLVTALHLVLGLSAVLGLILLRWQFPAHYRLRHALWPSL  SEQ. ID NO: 147
N-2+1:     SDPTRVETATET-LISLVTALHLVLGLSAVLGLILLRWQFPAHYRLRHALWPSL   SEQ. ID NO: 148
N-3:       SDPTRVETATET----SLVTALHLVLGLSAVLGLILLRWQFPAHYRLRHALWPSL  SEQ. ID NO: 149
N-4:       SDPTRVETATET-----LVTALHLVLGLSAVLGLILLRWQFPAHYRLRHALWPSL  SEQ. ID NO: 150
N-4+1:     SDPTRVETATET-ILVTALHLVLGLSAVLGLILLRWQFPAHYRLRHALWPSL     SEQ. ID NO: 151
N-5:       SDPTRVETATET------VTALHLVLGLSAVLGLILLRWQFPAHYRLRHALWPSL  SEQ. ID NO: 152
N-6:       SDPTRVETATET-------TALHLVLGLSAVLGLILLRWQFPAHYRLRHALWPSL  SEQ. ID NO: 153
N-7:       SDPTRVETATET--------ALHLVLGLSAVLGLILLRWQFPAHYRLRHALWPSL  SEQ. ID NO: 154
N-8:       SDPTRVETATET---------LHLVLGLSAVLGLILLRWQFPAHYRLRHALWPSL  SEQ. ID NO: 155
N-9:       SDPTRVETATET----------HLVLGLSAVLGLILLRWQFPAHYRLRHALWPSL  SEQ. ID NO: 156
```

FIG. 10B

```
                                                                      (4138 - 4302 bp)
Template:  SDPTRVETATETAW--------ISLVTALHLVLGLSAVLGLILLRWQFPAHYRLRHALWPSL
N+1:       SDPTRVETATETAW-L------ISLVTALHLVLGLSAVLGLILLRWQFPAHYRLRHALWPSL  SEQ. ID NO: 158
N+2:       SDPTRVETATETAW-VL-----ISLVTALHLVLGLSAVLGLILLRWQFPAHYRLRHALWPSL  SEQ. ID NO: 159
N+3:       SDPTRVETATETAW-LVL----ISLVTALHLVLGLSAVLGLILLRWQFPAHYRLRHALWPSL  SEQ. ID NO: 160
N+4:       SDPTRVETATETAW-ILVL---ISLVTALHLVLGLSAVLGLILLRWQFPAHYRLRHALWPSL  SEQ. ID NO: 161
N+5:       SDPTRVETATETAW-LILVL--ISLVTALHLVLGLSAVLGLILLRWQFPAHYRLRHALWPSL  SEQ. ID NO: 162
N+6:       SDPTRVETATETAW-LLILVL-ISLVTALHLVLGLSAVLGLILLRWQFPAHYRLRHALWPSL  SEQ. ID NO: 163
N+7:       SDPTRVETATETAW-VLLILVL-ISLVTALHLVLGLSAVLGLILLRWQFPAHYRLRHALWPSL SEQ. ID NO: 164
N+8:       SDPTRVETATETAW-LVLLILVL-ISLVTALHLVLGLSAVLGLILLRWQFPAHYRLRHALWPSL SEQ. ID NO: 165
```

CHIMERIC CYTOKINE RECEPTORS BEARING A PD-1 ECTODOMAIN

CROSS REFERENCE TO RELATED APPLICATIONS

The present application claims the benefit of priority to U.S. Provisional Application No. 62/812,799, filed on Mar. 1, 2019; U.S. Provisional Application No. 62/894,659, filed on Aug. 30, 2019; and U.S. Provisional Application No. 62/980,737, filed on Feb. 24, 2020, the contents of all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 24, 2020, is named AT-024_04US_SL.txt and is 554,240 bytes in size.

BACKGROUND

Adoptive transfer of immune cells (e.g. T-cells) genetically modified to recognize malignancy-associated antigens is showing promise as a new approach to treating cancer. For example, T-cells can be genetically modified to express chimeric antigen receptors (CARs), which are fusion proteins comprised of an antigen recognition moiety and T-cell activation domains.

T-cell proliferation, cytotoxic potency and persistence is driven by signal transduction pathways. Conventional CAR designs provide two signals—CD3zeta activation (Signal 1) and co-stimulation (Signal 2, e.g. via 4-1BB, OX40, and/or CD28 expression). In some contexts, a third signal (Signal 3), cytokine-induced cytokine receptor signaling (e.g. cytokine support for immune potentiation), may be desirable. Approaches to provide Signal 3 have however been met with significant limitations.

One approach to provide cytokine support includes combining CAR-T-cell therapy with systemic infusions of recombinant cytokines/cytokine mimetics, and engineering CAR-T-cells to secrete/express cytokines extracellularly. As cytokines have pleiotropic effects and can also impact the function of other cell types, the systemic administration or production of immune-potentiating cytokines by CAR-T-cells have at least two major drawbacks: (i) these approaches can cause systemic toxicity in humans, and (ii) in the context of allogeneic CAR-T-cell therapy, these approaches may cause bystander host immune-activation that could accelerate the rejection of allogeneic CAR-T-cells, thereby compromising therapeutic efficacy. Another approach to provide cytokine support was based on introducing a constitutively activated dimerized cytokine receptor, an IL-7Ra—this limits the nature (IL-7 signaling only) and magnitude of signaling output. Yet another approach to provide cytokine support involved incorporating Signal 3 directly into the CAR molecule (Nat Med. 2018 March; 24(3):352-359.). A limitation of this approach is that the strength of Signal 3 dependent on the strength of CAR activation. In the absence of target (and CAR activation), Signal 3 would not be transduced.

Needed are solutions to circumvent these drawbacks by targeting cytokine signals specifically to CAR-T-cells in a context-dependent manner, thus allowing for an improved safety profile and therapeutic efficacy. Provided herein and compositions and methods that address this need.

SUMMARY

Provided herein are inducible PD-1 chimeric cytokine receptors, active, for example, when engaged with PD-1 ligands or activated with an anti-PD-1 antibody. When present on chimeric antigen receptor (CAR)-bearing immune cells, and engaged with PD-1 ligands and/or activated with an anti-PD-1 antibody, such receptors allow for increased cytokine receptor signaling (Signal 3), leading to increased immune cell activation, proliferation, persistence, and/or potency of the CAR-bearing immune cells. Accordingly, the PD-1 chimeric cytokine receptors of the disclosure allow for cytokine signals to be transmitted into the immune cell with endogenous PD-1 ligands (PD-L1, PD-L2), whereby blocking their immune-suppressive signals, and converting them into immune-potentiating signals that can work in concert with, or synergize, CAR-driven activity. Moreover, as clinically approved anti-PD-1 antibodies can cluster and activate the PD-1 chimeric cytokine receptors of the disclosures, patients treated with anti-PD-1 may benefit not only from the blockage of the endogenous PD-1 signaling, but from also the activation of cytokine signaling in cells bearing the PD-1 chimeric cytokine receptors.

In some embodiments, provided herein are constitutively active PD-1 chimeric cytokine receptors. When present on chimeric antigen receptor (CAR)-bearing immune cells, these constitutively active receptors allow for increased basal cytokine receptor signaling (Signal 3). In some embodiments, the activity of the constitutively active PD-1 chimeric cytokine receptors can be increased when engaged with PD-1 ligands or activated with an anti-PD-1 antibody.

Accordingly, in one aspect, provided herein is a PD-1 chimeric cytokine receptor comprising: (a) a PD-1 ectodomain; (b) a transmembrane domain; (c) a Janus Kinase (JAK)-binding domain; and (d) a recruiting domain. The PD-1 ectodomain may comprise a portion of the extracellular region of a PD-1 protein, or may comprise a PD-1 ligand antigen binding domain.

In a related aspect provided herein is a polynucleotide encoding any one of the chimeric cytokine receptors of the disclosure, and an expression vector comprising such polynucleotide. In some embodiments, the polynucleotide further encodes for a chimeric antigen receptor (CAR), wherein the CAR binds to a target of interest. The target of interest can be any molecule of interest, including, for example, without limitation any one or more of those presented in Table 11.

In another aspect, provided herein is an engineered immune cells comprising at least one chimeric antigen receptor (CAR) and at least one chimeric cytokine receptor of the disclosure. In some embodiments the immune cell is a T-cell. In some embodiments the immune cell is an allogeneic immune cell. In other embodiments, the immune cell is an autologous immune cell. The immune cell may be selected from the group consisting of: T-cell, dendritic cell, killer dendritic cell, mast cell, NK-cell, macrophage, monocyte, B-cell and an immune cell derived from a stem cell. In a related aspect, provided herein is a pharmaceutical composition comprising any of the engineered immune cells of the disclosure, and a kit comprising such a pharmaceutical composition.

In another aspect, provided herein is a method of treating a cancer in a subject, comprising administering to the subject a therapeutically effective amount of any of the engineered immune cells described herein.

BRIEF DESCRIPTION OF THE DRAWINGS

FIG. 1B also shows a schematic of the PD-1 chimeric cytokine receptor—CAR vector

FIGS. 2A-2D show Stat reporter activity of the PD-1 chimeric cytokine receptor in response to PD-L1-Fc (FIGS. 2A-B) and anti-PD-1 (FIGS. 2C-D).

FIG. 5A shows the prototypic WT PD-1 chimeric cytokine receptor bearing the TpoR(478-582) TM/JAK2-activating domain;

FIG. 5B shows the 2xPD-1 chimeric cytokine receptor bearing two WT PD-1 ectodomains in tandem; FIG. 5C shows the 3xPD-1 chimeric cytokine receptor bearing three WT PD-1 ectodomains in tandem; FIG. 5D shows the high affinity (HA) PD-1 chimeric cytokine receptor with ectodomain mutations.

FIGS. 10A-10B show the amino acid sequences for the wild type TpoR and the various TM deletion (FIG. 10a) or insertion (FIG. 10b) variants.

DETAILED DESCRIPTION

Figure 1A:
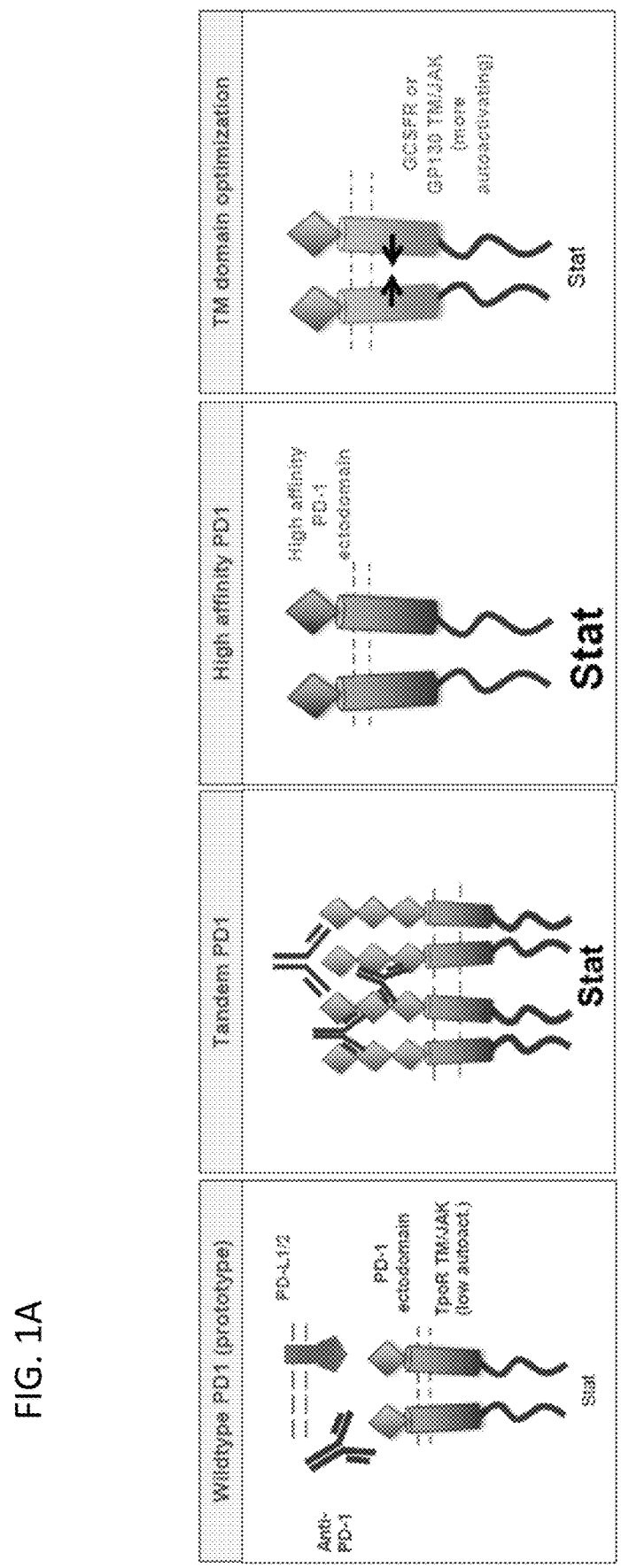
FIG. 1A shows a schematic of the certain embodiments of the PD-1 chimeric cytokine receptors of the disclosure.

Provided herein are inducible PD-1 chimeric cytokine receptors, active when engaged with PD-1 ligands or activated with an anti-PD-1 antibody. Also provided herein are constitutively active PD-1 chimeric cytokine receptors. Provided herein are chimeric antigen receptor (CAR)-bearing immune cells (CAR-I cells, e.g. CAR-T-cells), expressing the PD-1 chimeric cytokine receptors of the disclosure. Also provided herein are methods of making and using the PD-1 chimeric cytokine receptors.

I. PD-1 Chimeric Cytokine Receptors

The inducible PD-1 chimeric cytokine receptors of the disclosure activate signaling upon, for example, binding a PD-1 ligand (e.g. PD-L1, PD-L2), or a PD-1 antibody. These receptors activate signaling when monomers of the receptor cluster and/or dimerize. In some embodiments, a monomer of the PD-1 chimeric cytokine receptor of the disclosure comprises: (a) a PD-1 ectodomain; (b) a transmembrane domain; (c) a Janus Kinase (JAK)-binding domain; and; (d) a STAT-recruiting domain (e.g. from the cytoplasmic domain of a receptor; e.g. from a cytokine receptor). In some embodiments, a monomer of the PD-1 chimeric cytokine receptor of the disclosure comprises: (a) a PD-1 ectodomain; (b) a transmembrane domain; (c) a Janus Kinase (JAK)-binding domain; and; (d) a recruiting domain (e.g. from the cytoplasmic domain of a receptor; e.g. from a cytokine receptor). The recruiting domain can be a STAT-recruiting domain, an AP1-recruiting domain, a Myc/Max-recruiting domain; or a NFkB-recruiting domain. The PD-1 chimeric cytokine receptors can bind to PD-1 ligands, and/or are clustered and activated with an anti-PD-1 antibody. The PD-1 chimeric cytokine receptors activate signaling upon for example binding a PD-L1 ligand, PD-L2 ligand, and/or a PD-1 antibody.

The constitutively active PD-1 chimeric cytokine receptors of the disclosure are active regardless of PD-1 ligand availability, but may increase activity in the presence of a PD-ligand. In some embodiments, a monomer of the constitutively active PD-1 chimeric cytokine receptor of the disclosure comprises: (a) a PD-1 ectodomain; (b) a transmembrane domain; (c) a Janus Kinase (JAK)-binding domain; and; (d) a STAT-recruiting domain (e.g. from the cytoplasmic domain of a receptor; e.g. from a cytokine receptor). In some embodiments, a monomer of the constitutively active PD-1 chimeric cytokine receptor of the disclosure comprises: (a) a PD-1 ectodomain; (b) a transmembrane domain; (c) a Janus Kinase (JAK)-binding domain; and; (d) a recruiting domain (e.g. from the cytoplasmic domain of a receptor; e.g. from a cytokine receptor). The recruiting domain can be a STAT-recruiting domain, an AP1-recruiting domain, a Myc/Max-recruiting domain; or a NFkB-recruiting domain. In some embodiments, constitutively active PD-1 chimeric cytokine receptors can bind to PD-1 ligands or an anti-PD-1 antibody, and/or are clustered and the activity of the receptors can be further increased by engagement with PD-1 ligands or an anti-PD-1 antibody.

A. PD-1 Ectodomains

The PD-1 chimeric cytokine receptors of the disclosure comprise a PD-1 ectodomain. The PD-1 ectodomain is the domain of the chimeric cytokine receptor that extends into the extracellular space. PD-1 ectodomains of the disclosure are capable of binding PD-1 ligands (e.g. PD-L1, PD-L2) and anti-PD-1 antibodies, leading to binding-induced signal transduction. As contemplated herein, the term "PD-1 ectodomain" comprises at least a portion of the extracellular domain of a PD-1 protein or comprises a PD-1 ligand antigen binding domain (e.g. a PD-L1 antigen binding domain, or a PD-L2 antigen binding domain).

In some embodiments, the PD-1 ectodomain comprises a portion of a wild type PD-1. In some embodiments, the PD-1 ectodomain comprises mutations to the wild-type PD-1. In some embodiments, the PD-1 ectodomain comprises repeats of wild-type and/or mutated PD-1 amino acid sequences.

In some embodiments, the PD-1 ectodomain comprises a PD-1 ligand antigen binding domain, for example, the antigen binding domain of an anti-PD-L1 antibody or an anti-PD-L2 antibody. In some embodiments, the antigen binding domain is an scFv. In some embodiments, the antigen binding domain is a single chain antibody. In some embodiments, the antigen binding domain comprises a Fab portion of a PD-1 ligand antibody.

Table 1 shows exemplary PD1 amino acid ectodomain sequences of the disclosure. It is noted that the expression and extracellular location of the exemplary PD1 amino acid sequences can be achieved with the use of a signal sequence. In an exemplary embodiment, a CD8 signal sequence (CD8SS) MALPVTALLLPLALLLHAARP (SEQ ID NO: 1) is utilized.

TABLE 1

Exemplary Ectodomain Sequences

| Ectodomain | Amino acid sequence | SEQ ID NO: |
|---|---|---|
| Wild type (WT) PD1 ectodomain (PD-1(21-207)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLV VGVVGGLLGSLVLLVWVLAVICSRAARGTIGAR RTGQ | 2 |
| 2x WTPD1 ectodomain (PD-1(21-207)-PD-1(21-207)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVVGVVGGLLGSLVLLVWVLA VICSRAARGTIGARRTGQPGWFLDSPDRPWNPPT FSPALLVVTEGDNATFTCSFSNTSESFVLNWYRM SPSNQTDKLAAFPEDRSQPGQDCRFRVTQLPNGR DFHMSVVRARRNDSGTYLCGAISLAPKAQIKESL RAELRVTERRAEVPTAHPSPSPRPAGQFQTLVVG VVGGLLGSLVLLVWVLAVICSRAARGTIGARRT GQ | 3 |
| 3x WTPD1 ectodomain (PD-1(21-207)-PD-1(21-207)-PD-1(21-207)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVVGVVGGLLGSLVLLVWVLA VICSRAARGTIGARRTGQPGWFLDSPDRPWNPPT FSPALLVVTEGDNATFTCSFSNTSESFVLNWYRM SPSNQTDKLAAFPEDRSQPGQDCRFRVTQLPNGR DFHMSVVRARRNDSGTYLCGAISLAPKAQIKESL RAELRVTERRAEVPTAHPSPSPRPAGQFQTLVVG VVGGLLGSLVLLVWVLAVICSRAARGTIGARRT GQPGWFLDSPDRPWNPPTFSPALLVVTEGDNATF TCSFSNTSESFVLNWYRMSPSNQTDKLAAFPEDR SQPGQDCRFRVTQLPNGRDFHMSVVRARRNDSG TYLCGAISLAPKAQIKESLRAELRVTERRAEVPTA HPSPSPRPAGQFQTLVVGVVGGLLGSLVLLVWV LAVICSRAARGTIGARRTGQ | 4 |
| High-affinity (HA) PD1 ectodomain | PGWFLDSPDRPWNPPTFSPALLVVTEGDNATFTC SFSNTSESFHVIWHRESPSGQTDTLAAFPEDRSQP GQDCRFRVTQLPNGRDFHMSVVRARRNDSGTY VCGVISLAPKIQIKESLRAELRVTERRAEVPTAHP SPSPRPAGQFQTLVVGVVGGLLGSLVLLVWVLA VICSRAARGTIGARRTGQ | 5 |
| FKBP(F36V) | MGVQVETISPGDGRTFPKRGQTCVVHYTGMLED GKKVDSSRDRNKPFKFMLGKQEVIRGWEEGVA QMSVGQRAKLTISPDYAYGATGHPGIIPPHATLV FDVELLKLE | 6 |

TABLE 1-continued

Exemplary Ectodomain Sequences

| Ectodomain | Amino acid sequence | SEQ ID NO: |
|---|---|---|
| Wildtype (WT) PD1 ectodomain (PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLV | 132 |
| High-affinity (HA) PD1 ectodomain (21-170) | PGWFLDSPDRPWNPPTFSPALLVVTEGDNATFTC SFSNTSESFHVIWHRESPSGQTDTLAAFPEDRSQP GQDCRFRVTQLPNGRDFHMSVVRARRNDSGTY VCGVISLAPKIQIKESLRAELRVTERRAEVPTAHP SPSPRPAGQFQTLV | 133 |
| 2x WTPD1 ectodomain (PD-1(21-170)-G-PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVGPGWFLDSPDRPWNPPTFSP ALLVVTEGDNATFTCSFSNTSESFVLNWYRMSPS NQTDKLAAFPEDRSQPGQDCRFRVTQLPNGRDF HMSVVRARRNDSGTYLCGAISLAPKAQIKESLRA ELRVTERRAEVPTAHPSPSPRPAGQFQTLV | 168 |
| 3x WTPD1 ectodomain (PD-1(21-170)-G-PD-1(21-170)-G-PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVGPGWFLDSPDRPWNPPTFSP ALLVVTEGDNATFTCSFSNTSESFVLNWYRMSPS NQTDKLAAFPEDRSQPGQDCRFRVTQLPNGRDF HMSVVRARRNDSGTYLCGAISLAPKAQIKESLRA ELRVTERRAEVPTAHPSPSPRPAGQFQTLVGPGW FLDSPDRPWNPPTFSPALLVVTEGDNATFTCSFSN TSESFVLNWYRMSPSNQTDKLAAFPEDRSQPGQ DCRFRVTQLPNGRDFHMSVVRARRNDSGTYLCG AISLAPKAQIKESLRAELRVTERRAEVPTAHPSPS PRPAGQFQTLV | 169 |

In some embodiments, the PD-1 ectodomain comprises a wild type PD-1 ectodomain.

In some embodiments, the PD-1 ectodomain comprises a wild type PD-1 and comprises the amino acid sequence of SEQ ID NO: 2. In some embodiments, the PD-1 ectodomain comprises a wild type PD-1 and comprises the amino acid sequence of SEQ ID NO: 132.

In some embodiments, the PD-1 ectodomain comprises mutations to the wild type PD-1 ectodomain sequence. In some embodiments, the PD-1 ectodomain sequence is a high affinity PD-1 ectodomain. In some embodiments, the PD-1 ectodomain sequence is a high affinity PD-1 ectodomain and comprises the amino acid sequence of SEQ ID NO: 5. In some embodiments, the PD-1 ectodomain sequence is a high affinity PD-1 ectodomain and comprises the amino acid sequence of SEQ ID NO: 133.

In some embodiments, the PD-1 ectodomain comprises a tandem arrangement of greater than one wild type PD-1 ectodomain sequence, for example at least two, at least three, at least four, or at least five wild type PD-1 ectodomain sequences. In some embodiments, the PD-1 ectodomain comprises a tandem arrangement of two wild type PD-1 ectodomain sequences and comprises the amino acid sequence of SEQ ID NO: 3. In some embodiments, the PD-1 ectodomain comprises a tandem arrangement of two wild type PD-1 ectodomain sequences and comprises the amino acid sequence of SEQ ID NO: 168. In some embodiments, the PD-1 ectodomain comprises a tandem arrangement of three wild type PD-1 ectodomain sequences and comprises the amino acid sequence of SEQ ID NO: 4. In some embodiments, the PD-1 ectodomain comprises a tandem arrangement of three wild type PD-1 ectodomain sequences and comprises the amino acid sequence of SEQ ID NO: 169.

In some embodiments, the PD-1 ectodomain comprises a tandem arrangement of greater than one high affinity PD-1 ectodomain sequence, for example at least two, at least three, at least four, or at least five high affinity PD-1 ectodomain sequences.

In some embodiments, the PD-1 ectodomain comprises a high affinity PD-1 and comprises the amino acid sequence of SEQ ID NO: 5. In some embodiments, the high affinity PD-1 ectodomain comprises the amino acid sequence of SEQ ID NO: 133. In some embodiments, the PD-1 ectodomain comprises a tandem arrangement of two high affinity PD-1 ectodomain sequences. In some embodiments, the PD-1 ectodomain comprises a tandem arrangement of three high affinity PD-1 ectodomain sequences.

In some embodiments, the PD-1 ectodomain comprises a tandem arrangement of a combination of wild type and high affinity PD-1 ectodomain sequences, for example a combination of at least two, at least three, at least four, or at least five wild type and high affinity PD-1 ectodomain sequences.

In some embodiments, the greater than one wide type PD-1 ectodomain, or greater than one high affinity PD-1 ectodomain, or a combination thereof, can be connected either directly, or via a linker. In some embodiments, the linker can comprise one or more amino acid residues. In some embodiments, the linker is a Gly.

In some embodiments, the PD-1 ectodomain is a dominant negative. Table 2 shows exemplary PD-1 dominant negative (DN) sequences of the disclosure. The DN sequences of Table 2 may be expressed with the aid of a signal sequence, e.g. a CD8SS signal sequence of SEQ ID NO: 1

TABLE 2

PD1 dominant negative (DN) sequences:

| PD1 DN | Amino acid sequence | SEQ ID NO: |
|---|---|---|
| Dominant negative wild type PD1 (21-207) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ | 7 |
| Dominant negative high affinity PD1 | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 8 |

B. Transmembrane Domains

The PD-1 chimeric cytokine receptors of the disclosure comprise transmembrane domains. Such transmembrane domains are coupled to the extracellular PD-1 ectodomain on the N-terminus, and to additional intracellular/cytoplasmic domains on the C-terminus. In some embodiments, the coupling is achieved optionally through a linker. In some embodiments, the linker can comprise one or more amino acid residues.

As used herein, the transmembrane domains are capable of insertion into the membrane of a cell in which it is expressed. In some embodiments, the transmembrane domains of the disclosure span a cellular membrane, and comprise an extracellular portion, and/or an intracellular portion.

In some embodiments, the transmembrane domains of the disclosure are engineered and do not resemble any naturally occurring transmembrane domain, e.g. they are non-naturally occurring.

In other embodiments, the transmembrane domains of the disclosure are derived from naturally occurring receptors.

In some embodiments, the transmembrane and/or JAK domains of the disclosure are derived from, for example, one or more of the following receptors: erythropoietin receptor (EpoR), Interleukin 6 signal transducer (GP130 or IL6ST), prolactin receptor (PrlR), growth hormone receptor (GHR), granulocyte colony-stimulating factor receptor (GCSFR), and thrombopoietin receptor/myeloproliferative leukemia protein receptor (TPOR/MPLR). When derived from naturally occurring receptors, the entire receptor, or the entire transmembrane sequence of the receptor may not be necessary to effectuate constitutive activation and constitutive JAK binding/activation on the intracellular portion. Accordingly fragments of naturally occurring receptors may be utilized. Furthermore, certain mutations may be introduced into the transmembrane domains derived from naturally occurring receptors, to further tune the downstream JAK-dependent signaling.

In some embodiments, the transmembrane and/or JAK domains of the disclosure is derived from the naturally occurring EpoR receptor.

In some embodiments, the transmembrane and/or JAK domains of the disclosure is derived from the naturally occurring GP130 receptor.

In some embodiments, the transmembrane and/or JAK domains of the disclosure is derived from the naturally occurring PrlR receptor.

In some embodiments, the transmembrane and/or JAK domains of the disclosure is derived from the naturally occurring GHR receptor.

In some embodiments, the transmembrane and/or JAK domains of the disclosure is derived from the naturally occurring GCSF receptor.

In some embodiments, the transmembrane and/or JAK domains of the disclosure is derived from the naturally occurring TPOR receptor.

Table 3 provides exemplary full length sequences of naturally occurring receptors provided in the disclosure, from which the transmembrane and/or JAK domains are derived.

TABLE 3

Exemplary Naturally Occurring Receptors

| Naturally Occurring Receptor Name | SEQ ID NO: |
|---|---|
| >AAI12154.1 Erythropoietin receptor sapiens<br>MDHLGASLWPQVGSLCLLLAGAAWAPPPNLPDPKFESKAALLAARGPEELLCFTERLEDLVCFWEEAASA<br>GVGPGNYSFSYQLEDEPWKLCRLHQAPTARGAVRFWCSLPTADTSSFVPLELRVTAASGAPRYHRVIHIN<br>EVVLLDAPVGLVARLADESGHVVLRWLPPPETPMTSHIRYEVDVSAGNGAGSVQRVEILEGRTECVLSNL<br>RGRTRYTFAVRARMAEPSFGGFWSAWSEPVSLLTPSDLDPLILTLSLILVVILVLLTVLALLSHRRALKQ<br>KIWPGIPSPESEFEGLFTTHKGNFQLWLYQNDGCLWWSPCTPFTEDPPASLEVLSERCWGTMQAVEPGTD<br>DEGPLLEPVGSEHAQDTYLVLDKWLLPRNPPSEDLPGPGGSVDIVAMDEGSEASSCSSALASKPSPEGAS<br>AASFEYTILDPSSQLLRPWTLCPELPPTPPHLKYLYLVVSDSGISTDYSSGDSQGAQGGLSDGPYSNPYE<br>NSLIPAAEPLPPSYVACS | 9 |
| >AA117403.1 Interleukin 6 signal transducer (GP130, oncostatin M receptor) [Homo sapiens]<br>MLTLQTWLVQALFIFLTTESTGELLDPCGYISPESPVVQLHSNFTAVCVLKEKCMDYFHVNANYIVWKTN<br>HFTIPKEQYTIINRTASSVTFTDIASLNIQLTCNILTFGQLEQNVYGITIISGLPPEKPKNLSCIVNEGK<br>KMRCEWDRGRETHLETNFTLKSEWATHKFADCKAKRDTPTSCTVDYSTVYFVNIEVWVEAENALGKVTSD | 10 |

TABLE 3-continued

Exemplary Naturally Occurring Receptors

| Naturally Occurring Receptor Name | SEQ ID NO: |
|---|---|
| HINFDPVYKVKPNPPHNLSVINSEELSSILKLTWTNPSIKSVIILKYNIQYRTKDASTWSQIPPEDTAST<br>RSSFTVQDLKPFTEYVFRIRCMKEDGKGYWSDWSEEASGITYEDRPSKAPSFWYKIDPSHTQGYRTVQLV<br>WKTLPPPFEANGKILDYEVTLTRWKSHLQNYTVNATKLTVNLTNDRVVATLTVRNLVGKSDAAVLTIPACD<br>FQATHPVMDLKAFPKDNMLWVEWTTPRESVKKYILEWCVLSDKAPCITDWQQEDGTVHRTYLRGNLAESK<br>CYLITVTPVYADGPGSPESIKAYLKQAPPSKGPTVRTKKVGKNEAVLEWDQLPVDVQNGFIRNYTIFYRT<br>IIGNETAVNVDSSHTEYTLSSLTSDTLYMVRMAAYTDEGGKDGPEFTFTTPKFAQGEIEAIVVPVCLAFL<br>LTTLLGVLFCFNKRDLIKKHIWPNVPDPSKSHIAQWSPHTPPRHNFNSKDQMYSDGNFTDVSVVEIEAND<br>KKPFPEDLKSLDLFKKEKINTEGHSSGIGGSSCMSSSRPSISSSDENESSQNTSSTVQYSTVVHSGYRHQ<br>VPSVQVFSRSESTQPLLDSEERPEDLQLVDHVDGGDGILPRQQYFKQNCSQHESSPDISHFERSKQVSSV<br>NEEDFVRLKQQISDHISQSCGSGQMKMFQEVSAADAFGPGTEGQVERFETVGMEAATDEGMPKSYLPQT<br>V<br>RQGGYMPQ | |
| >XP_011512371.1 prolactin receptor isoform X2 [Homo sapiens]<br>MKENVASATVFTLLLFLNTCLLNGQLPPGKPEIFKCRSPNKETFTCWWRPGTDGGLPTNYSLTYHREGET<br>LMHECPDYITGGPNSCHFGKQYTSMWRTYIMMVNATNQMGSSFSDELYVDVTYIVQPDPPLELAVEVKQP<br>EDRKPYLWIKWSPPTLIDLKTGWFTLLYEIRLKPEKAAEWEIHFAGQQTEFKILSLHPGQKYLVQVRCKP<br>DHGYWSAWSPATFIQIPSDFTMNDTTVWISVAVLSAVICLIIVWAVALKGYSMVTCIFPPVPGPKIKGFD<br>AHLLEKGKSEELLSALGCQDFPPTSDYEDLLVEYLEVDDSEDQHLMSVHSKEHPSQGMKPTYLDPDTDSG<br>RGSCDSPSLLSEKCEEPQANPSTFYDPEVIEKPENPETTHTWDPQCISMEGKIPYFHAGGSKCSTWPLPQ<br>PSQHNPRSSYHNITDVCELAVGPAGAPATLLLNEAGKDALKSSQTIKSREEGKATQQREVESFHSETDQDT<br>PWLLPQEKTPFGSAKPLDYVEIHKVNKDGALSLLPKQRENSGKPKKPGTPENNKEYAKVSGVMDNNILVL<br>VPDPHAKNVACFEESAKEAPPSLEQNQAEKALANFTATSSKCRLQLGGLDYLDPACFTHSFH | 11 |
| >NP_000154.1 growth hormone receptor isoform 1 precursor [Homo sapiens]<br>MDLWQLLLTLALAGSSDAFSGSEATAAILSRAPWSLQSVNPGLKTNSSKEPKFTKCRSPERETFSCHWTD<br>EVHHGTKNLGPIQLFYTRRNTQEWTQEWKECPDYVSAGENSCYFNSSFTSIWIPYCIKLTSNGGTVDEKC<br>FSVDEIVQPDPPIALNWTLLNVSLTGIHADIQVRWEAPRNADIQKGWMVLEYELQYKEVNETKWKMMDPI<br>LTTSVPVYSLKVDKEYEVRVRSKQRNSGNYGEFSEVLYVTLPQMSQFTCEEDFYFPWLLIIIFGIFGLTV<br>MLFVFLFSKQQRIKMLILPPVPVPKIKGIDPDLLKEGKLEEVNTILAIHDSYKPEFHSDDSWVEFIELDI<br>DEPDEKTEESDTDRLLSSDHEKSHSNLGVKDGDSGRTSCCEPDILETDFNANDIHEGTSEVAQPQRLKGE<br>ADLLCLDQKNQNNSPYHDACPATQQPSVIQAEKNKPQPLPTEGAESTHQAAHIQLSNPSSLSNIDFYAQV<br>SDITPAGSVVLSPGQKNKAGMSQCDMHPEMVSLCQENFLMDNAYFCEADAKKCIPVAPHIKVESHIQPSL<br>NQEDIYITTESLTTAAGRPGTGEHVPGSEMPVPDYTSIHIVQSPQGLILNATALPLPDKEFLSSCGYVST<br>DQLNKIMP | 12 |
| >XP_016855859.1 granulocyte colony-stimulating factor receptor isoform X1 [Homo sapiens]<br>MARLGNCSLTWAALIILLLPGSLEECGHISVSAPIVHLGDPITASCIIKQNCSHLDPEPQILWRLGAELQ<br>PGGRQQRLSDGTQESIITLPHLNHTQAFLSCCLNWGNSLQILDQVELRAGYPPAIPHNLSCLMNLTTSSL<br>ICQWEPGPETHLPTSFTLKSFKSRGNCQTQGDSILDCVPKDGQSHCCIPRKHLLLYQNMGIWVQAENALG<br>TSMSPQLCLDPMDVVKLEPPMLRTMDPSPEAAPPQAGCLQLCWEPWQPGLHINQKCELRHKPQRGEASWA<br>LVGPLPLEALQYELCGLLPATAYTLQIRCIRWPLPGHWSDWSPSLELRTTERAPTVRLDTWWRQRQLDPR<br>TVQLFWKPVPLEEDSGRIQGYVVSWRPSGQAGAILPLCNTTELSCTFHLPSEAQEVALVAYNSAGTSRPT<br>PVVFSESRGPALTRLHAMARDPHSLWVGWEPPNPWPQGYVIEWGLGPPSASNSNKTWRMEQNGRATGFLL<br>KENIRPFQLYEIIVTPLYQDTMGPSQHVYAYSQEMAPSHAPELHLKHIGKTWAQLEWVPEPPELGKSPLT<br>HYTIFWTNAQNQSFSAILNASSRGFVLHGLEPASLYHIHLMAASQAGATNSTVLTLMTLTPEGSELHIIL<br>GLFGLLLLLTCLCGTAWLCCSPNRKNPLWPSVPDPAHSSLGSWVPTIMEELPGPRQGQWLGQTSEMSRAL<br>TPHPCVQDAFQLPGLGTPPITKLTVLEEDEKKPVPWESHNSSETCGLPTLVQTYVLQGDPRAVSTQPQSQ<br>SGTSDQVLYGQLLGSPTSPGPGHYLRCDSTQPLLAGLTPSPKSYENLWFQASPLGTLVTPAPSQEDDCVF<br>GPLLNFPLLQGIRVHGMEALGSF | 13 |
| >NP_005364.1 thrombopoietin receptor precursor [Homo sapiens]<br>MPSWALFMVTSCLLLAPQNLAQVSSQDVSLLASDSEPLKCFSRTFEDLTCFWDEEEAAPSGTYQLLYAYP<br>REKPRACPLSSQSMPHFGTRYVCQFPDQEEVRLFFPLHLWVKNVFLNQTRTQRVLFVDSVGLPAPPSIIK<br>AMGGSQPGELQISWEEPAPEISDFLRYELRYGPRDPKNSTGPTVIQLIATETCCPALQRPHSASALDQSP<br>CAQPTMPWQDGPKQTSPSREASALTAEGGSCLISGLQPGNSYWLQLRSEPDGISLGGSWGSWSLPVTVDL<br>PGDAVALGLQCFTLDLKNVTCQWQQQDHASSQGFFYHSRARCCPRDRYPIWENCEEEEKTNPGLQTPQFS<br>RCHFKSRNDSIIHILVEVTTAPGTVHSYLGSPFWIHQAVRLPTPNLHWREISSGHLELEWQHPSSWAAQE<br>TCYQLRYTGEGHQDWKVLEPPLGARGGTLELRPRSRYRLQLRARLNGPTYQGPWSSWSDPTRVETATETA<br>WISLVTALHLVLGLSAVLGLLLLRWQFPAHYRRLRHALWPSLPDLHRVLGQYLRDTAALSPPKATVSDTC<br>EEVEPSLLEILPKSSERTPLPLCSSQAQMDYRRLQPSCLGTMPLSVCPPMAESGSCCTTHIANHSYLPLS<br>YWQQP | 131 |

In some embodiments, the transmembrane domain of the disclosure is derived from a truncated, or otherwise modified version of the naturally occurring TPOR/MPLR receptor shown in Table 3.

FIGS. 10A-B show the amino acid sequences for the wild type TpoR and the various transmembrane deletion (FIG. 10A) or insertion (FIG. 10B) variants.

Table 4 shows exemplary transmembrane amino acid sequences, coupled to intracellular JAK2 binding domain sequences.

In some embodiments, the transmembrane domain of the PD-1 chimeric cytokine receptor comprises the amino acid sequence of SEQ ID NO: 14. In some embodiments, the transmembrane domain of the PD-1 chimeric cytokine receptor comprises the amino acid sequence of SEQ ID NO:

15. In some embodiments, the transmembrane domain of the PD-1 chimeric cytokine receptor comprises the amino acid sequence of SEQ ID NO: 16. In some embodiments, the transmembrane domain of the PD-1 chimeric cytokine receptor comprises the amino acid sequence of SEQ ID NO: 17. In some embodiments, the transmembrane domain of the PD-1 chimeric cytokine receptor comprises the amino acid sequence of SEQ ID NO: 18. In some embodiments, the transmembrane domain of the PD-1 chimeric cytokine receptor comprises the amino acid sequence of SEQ ID NO: 19. In some embodiments, the transmembrane domain of the PD-1 chimeric cytokine receptor comprises the amino acid sequence of SEQ ID NO: 20. In some embodiments, the transmembrane domain of the PD-1 chimeric cytokine receptor comprises the amino acid sequence of SEQ ID NO: 21. In some embodiments, the transmembrane domain of the PD-1 chimeric cytokine receptor comprises the amino acid sequence of SEQ ID NO: 22. In some embodiments, the transmembrane domain of the PD-1 chimeric cytokine receptor comprises the amino acid sequence of SEQ ID NO: 23. In some embodiments, the transmembrane domain of the PD-1 chimeric cytokine receptor comprises the amino acid sequence of SEQ ID NO: 24. In some embodiments, the transmembrane domain of the PD-1 chimeric cytokine receptor comprises the amino acid sequence of SEQ ID NO: 25. In some embodiments, the transmembrane domain of the PD-1 chimeric cytokine receptor comprises the amino acid sequence of SEQ ID NO: 26. In some embodiments, the transmembrane domain of the PD-1 chimeric cytokine receptor comprises the amino acid sequence of SEQ ID NO: 27. In some embodiments, the transmembrane domain of the PD-1 chimeric cytokine receptor comprises the amino acid sequence of SEQ ID NO: 28. In some embodiments, the transmembrane domain of the PD-1 chimeric cytokine receptor comprises the amino acid sequence of SEQ ID NO: 29. In some embodiments, the transmembrane domain of the PD-1 chimeric cytokine receptor comprises the amino acid sequence of SEQ ID NO: 30. In some embodiments, the transmembrane domain of the PD-1 chimeric cytokine receptor comprises the amino acid sequence of SEQ ID NO: 31. In some embodiments, the transmembrane domain of the PD-1 chimeric cytokine receptor comprises the amino acid sequence of SEQ ID NO: 32. In some embodiments, the transmembrane domain of the PD-1 chimeric cytokine receptor comprises the amino acid sequence of SEQ ID NO: 33. In some embodiments, the transmembrane domain of the PD-1 chimeric cytokine receptor comprises the amino acid sequence of SEQ ID NO: 34. In some embodiments, the transmembrane domain of the PD-1 chimeric cytokine receptor comprises the amino acid sequence of SEQ ID NO: 35. In some embodiments, the transmembrane domain of the PD-1 chimeric cytokine receptor comprises the amino acid sequence of SEQ ID NO: 36. In some embodiments, the transmembrane domain of the PD-1 chimeric cytokine receptor comprises the amino acid sequence of SEQ ID NO: 37. In some embodiments, the transmembrane domain of the PD-1 chimeric cytokine receptor comprises the amino acid sequence of SEQ ID NO: 38. In some embodiments, the transmembrane domain of the PD-1 chimeric cytokine receptor comprises the amino acid sequence of SEQ ID NO: 39. In some embodiments, the transmembrane domain of the PD-1 chimeric cytokine receptor comprises the amino acid sequence of SEQ ID NO: 40. In some embodiments, the transmembrane domain of the PD-1 chimeric cytokine receptor comprises the amino acid sequence of SEQ ID NO: 41. In some embodiments, the transmembrane domain of the PD-1 chimeric cytokine receptor comprises the amino acid sequence of SEQ ID NO: 42. In some embodiments, the transmembrane domain of the PD-1 chimeric cytokine receptor comprises the amino acid sequence of SEQ ID NO: 43. In some embodiments, the transmembrane domain of the PD-1 chimeric cytokine receptor comprises the amino acid sequence of SEQ ID NO: 44. In some embodiments, the transmembrane domain of the PD-1 chimeric cytokine receptor comprises the amino acid sequence of SEQ ID NO: 134. In some embodiments, the transmembrane domain of the PD-1 chimeric cytokine receptor comprises the amino acid sequence of SEQ ID NO: 135. In some embodiments, the PD-1 chimeric cytokine receptor of the disclosure comprises an amino acid sequence of the transmembrane+JAK2 binding domain that is at least 80%, 85%, 90%, 95%, 98%, 99%, or 100% identical to the amino acid sequence of any one of the sequences shown in Table 4.

TABLE 4

Exemplary Transmembrane + JAK2 Binding Domain Sequences

| Transmembrane and JAK2 binding domain | Amino acid sequence | SEQ ID NO: |
|---|---|---|
| GCSFR(614-710) | LTLMTLTPEGSELHIILGLFGLLLLLTCLCGTAWL CCSPNRKNPLWPSVPDPAHSSLGSWVPTIMEEDA FQLPGLGTPPITKLTVLEEDEKKPVPWE | 14 |
| GP130(609-700) | TTPKFAQGEIEAIVVPVCLAFLLTTLLGVLFCFNK RDLIKKHIWPNVPDPSKSHIAQWSPHTPPRHNFN SKDQMYSDGNFTDVSVVEIEAND | 15 |
| TPOR/MPLR(478-582) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL | 16 |
| TPOR/MPLR(N-1) | SDPTRVETATETWISLVTALHLVLGLSAVLGLLL LRWQFPAHYRRLRHALWPSLPDLHRVLGQYLRD TAALSPPKATVSDTCEEVEPSLLEILPKSSERTPLP L | 17 |
| TPOR/MPLR(N-2) | SDPTRVETATETISLVTALHLVLGLSAVLGLLLLR WQFPAHYRRLRHALWPSLPDLHRVLGQYLRDT AALSPPKATVSDTCEEVEPSLLEILPKSSERTPLPL | 18 |

TABLE 4-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N-2+1) | SDPTRVETATETLISLVTALHLVLGLSAVLGLLLL RWQFPAHYRRLRHALWPSLPDLHRVLGQYLRDT AALSPPKATVSDTCEEVEPSLLEILPKSSERTPLPL | 19 |
| TPOR/MPLR(N-3) | SDPTRVETATETSLVTALHLVLGLSAVLGLLLLR WQFPAHYRRLRHALWPSLPDLHRVLGQYLRDT AALSPPKATVSDTCEEVEPSLLEILPKSSERTPLPL | 20 |
| TPOR/MPLR(N-4) | SDPTRVETATETLVTALHLVLGLSAVLGLLLLRW QFPAHYRRLRHALWPSLPDLHRVLGQYLRDTAA LSPPKATVSDTCEEVEPSLLEILPKSSERTPLPL | 21 |
| TPOR/MPLR(N-4+1) | SDPTRVETATETILVTALHLVLGLSAVLGLLLLR WQFPAHYRRLRHALWPSLPDLHRVLGQYLRDT AALSPPKATVSDTCEEVEPSLLEILPKSSERTPLPL | 22 |
| TPOR/MPLR(N-5) | SDPTRVETATETVTALHLVLGLSAVLGLLLLRW QFPAHYRRLRHALWPSLPDLHRVLGQYLRDTAA LSPPKATVSDTCEEVEPSLLEILPKSSERTPLPL | 23 |
| TPOR/MPLR(N-6) | SDPTRVETATETTALHLVLGLSAVLGLLLLRWQF PAHYRRLRHALWPSLPDLHRVLGQYLRDTAALS PPKATVSDTCEEVEPSLLEILPKSSERTPLPL | 24 |
| TPOR/MPLR(N-7) | SDPTRVETATETALHLVLGLSAVLGLLLLRWQFP AHYRRLRHALWPSLPDLHRVLGQYLRDTAALSP PKATVSDTCEEVEPSLLEILPKSSERTPLPL | 25 |
| TPOR/MPLR(N-8) | SDPTRVETATETLHLVLGLSAVLGLLLLRWQFPA HYRRLRHALWPSLPDLHRVLGQYLRDTAALSPP KATVSDTCEEVEPSLLEILPKSSERTPLPL | 26 |
| TPOR/MPLR(N-9) | SDPTRVETATETHLVLGLSAVLGLLLLRWQFPAH YRRLRHALWPSLPDLHRVLGQYLRDTAALSPPK ATVSDTCEEVEPSLLEILPKSSERTPLPL | 27 |
| TPOR/MPLR(N-10) | SDPTRVETATETLVLGLSAVLGLLLLRWQFPAHY RRLRHALWPSLPDLHRVLGQYLRDTAALSPPKA TVSDTCEEVEPSLLEILPKSSERTPLPL | 28 |
| TPOR/MPLR(N-11) | SDPTRVETATETVLGLSAVLGLLLLRWQFPAHYR RLRHALWPSLPDLHRVLGQYLRDTAALSPPKAT VSDTCEEVEPSLLEILPKSSERTPLPL | 29 |
| TPOR/MPLR(N-12) | SDPTRVETATETLGLSAVLGLLLLRWQFPAHYRR LRHALWPSLPDLHRVLGQYLRDTAALSPPKATV SDTCEEVEPSLLEILPKSSERTPLPL | 30 |
| TPOR/MPLR(N-13) | SDPTRVETATETGLSAVLGLLLLRWQFPAHYRRL RHALWPSLPDLHRVLGQYLRDTAALSPPKATVS DTCEEVEPSLLEILPKSSERTPLPL | 31 |
| TPOR/MPLR(N-14) | SDPTRVETATETLSAVLGLLLLRWQFPAHYRRLR HALWPSLPDLHRVLGQYLRDTAALSPPKATVSD TCEEVEPSLLEILPKSSERTPLPL | 32 |
| TPOR/MPLR(N-15) | SDPTRVETATETSAVLGLLLLRWQFPAHYRRLRH ALWPSLPDLHRVLGQYLRDTAALSPPKATVSDT CEEVEPSLLEILPKSSERTPLPL | 33 |
| TPOR/MPLR(N-16) | SDPTRVETATETAVLGLLLLRWQFPAHYRRLRH ALWPSLPDLHRVLGQYLRDTAALSPPKATVSDT CEEVEPSLLEILPKSSERTPLPL | 34 |
| TPOR/MPLR(N-17) | SDPTRVETATETVLGLLLLRWQFPAHYRRLRHA LWPSLPDLHRVLGQYLRDTAALSPPKATVSDTCE EVEPSLLEILPKSSERTPLPL | 35 |
| TPOR/MPLR(N-18) | SDPTRVETATETLGLLLLRWQFPAHYRRLRHAL WPSLPDLHRVLGQYLRDTAALSPPKATVSDTCEE VEPSLLEILPKSSERTPLPL | 36 |

TABLE 4-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N+1) | SDPTRVETATETAWLISLVTALHLVLGLSAVLGL LLLRWQFPAHYRRLRHALWPSLPDLHRVLGQYL RDTAALSPPKATVSDTCEEVEPSLLEILPKSSERTP LPL | 37 |
| TPOR/MPLR(N+2) | SDPTRVETATETAWVLISLVTALHLVLGLSAVG LLLLRWQFPAHYRRLRHALWPSLPDLHRVLGQY LRDTAALSPPKATVSDTCEEVEPSLLEILPKSSER TPLPL | 38 |
| TPOR/MPLR(N+3) | SDPTRVETATETAWLVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 39 |
| TPOR/MPLR(N+4) | SDPTRVETATETAWILVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 40 |
| TPOR/MPLR(N+5) | SDPTRVETATETAWLILVLISLVTALHLVLGLSAV LGLLLLRWQFPAHYRRLRHALWPSLPDLHRVLG QYLRDTAALSPPKATVSDTCEEVEPSLLEILPKSS ERTPLPL | 41 |
| TPOR/MPLR(N+6) | SDPTRVETATETAWLLILVLISLVTALHLVLGLSA VLGLLLLRWQFPAHYRRLRHALWPSLPDLHRVL GQYLRDTAALSPPKATVSDTCEEVEPSLLEILPKS SERTPLPL | 42 |
| TPOR/MPLR(N+7) | SDPTRVETATETAWVLLILVLISLVTALHLVLGLS AVLGLLLLRWQFPAHYRRLRHALWPSLPDLHRV LGQYLRDTAALSPPKATVSDTCEEVEPSLLEILPK SSERTPLPL | 43 |
| TPOR/MPLR(N+8) | SDPTRVETATETAWLVLLILVLISLVTALHLVLGL SAVLGLLLLRWQFPAHYRRLRHALWPSLPDLHR VLGQYLRDTAALSPPKATVSDTCEEVEPSLLEILP KSSERTPLPL | 44 |
| TPOR/MPLR(478-582, H499L, S505N, W515K) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL | 134 |
| TPOR/MPLR(478-582, S505N, W515K) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL | 135 |

C. Janus Kinase (JAK)-Binding Domains

The PD-1 chimeric cytokine receptors of the disclosure comprise intracellular JAK-binding domains. The JAK-binding domain is coupled to the C-terminus of the transmembrane domain, either directly, or via a linker. In some embodiments, the linker can comprise one or more amino acid residues. The JAK-binding domain is coupled to the transmembrane domain on the intracellular side of the chimeric cytokine receptor.

In some embodiments, the JAK-binding domain is a JAK-1-binding domain, a JAK-2 binding domain, a JAK-3 binding domain, or a TYK2 binding domain.

In some embodiments, the JAK-binding domains of the PD-1 chimeric cytokine receptors of the disclosure are naturally occurring, and derived from a naturally occurring receptor.

In some embodiments, the JAK-binding domains of the PD-1 chimeric cytokine receptors of the disclosure are synthetic.

Table 4 provides exemplary amino acid sequences for Transmembrane and JAK2 Binding domains of the disclosure.

D. Recruiting Domains

The PD-1 chimeric cytokine receptors of the disclosure comprise cytoplasmic domains comprising recruiting domains. The recruiting domain can be a STAT-recruiting domain, an AP1-recruiting domain, a Myc/Max-recruiting domain; or an NFkB-recruiting domain. In some embodiments, the recruiting domain is a Signal Transducer and Activator of Transcription (STAT)-recruiting (Stat-activating) domains from receptor tails (cytotails) or from cytokine receptor tails. These intracellular recruiting domains of the PD-1 chimeric cytokine receptors of the disclosure allow for the propagation of Signal 3 in an immune cell comprising a CAR and a chimeric cytokine receptor (e.g. a CAR-T-cell with a chimeric cytokine receptor of the disclosure). Cytokine signaling propagated through the Stat-recruiting domain allows for the cytokine-based immune potentiation of the cell. In some embodiments, the immune-potentiation is homeostatic, e.g. signaling gives rise to increase in immune cells bearing the CAR. In some embodiments, the immune-potentiation is inflammatory, e.g. signaling gives rise to increase in the potency of the immune cells bearing the CAR. In some embodiments, the immune-potentiation prevents exhaustion, e.g. signaling maintains the long-term functionality of immune cells bearing the CAR.

In some embodiments, the recruiting domains of the disclosure are synthetic, and do not resemble any naturally occurring receptor fragment.

In some embodiments, the Stat-recruiting domains of the disclosure are synthetic, and do not resemble any naturally occurring receptor fragment.

In some embodiments the recruiting domain is connected to the C-terminus of the JAK binding domain, either directly, or via a linker. In some embodiments, the linker can comprise one or more amino acid residues.

In other embodiments, the Stat-recruiting domains of the disclosure are derived from cytoplasmic tails of naturally occurring receptors, e.g. derived from naturally occurring cytokine receptors. These cytoplasmic tails of naturally occurring receptors may be the regions downstream of the JAK-activating domains of the transmembrane domain of the receptor. The Stat-recruiting domains of the chimeric cytokine receptors comprise at least one STAT-recruiting domain from at least one receptor. In some embodiments, the Stat-recruiting domain comprises at least one STAT1-recruiting domain. In some embodiments, the Stat-recruiting domain comprises at least one STAT2-recruiting domain. In some embodiments, the Stat-recruiting domain comprises at least one STAT3-recruiting domain. In some embodiments, the Stat-recruiting domain comprises at least one STAT4-recruiting domain. In some embodiments, the Stat-recruiting domain comprises at least one STAT5-recruiting domain. In some embodiments, the Stat-recruiting domain comprises at least one STAT6-recruiting domain. In some embodiments, the Stat-recruiting domain comprises at least one STAT7-recruiting domain.

In some embodiments, the naturally occurring receptor from which the Stat-recruiting domain is derived, is a not a cytokine receptor.

In some embodiments, the naturally occurring receptor from which the Stat-recruiting domain is derived, is a cytokine receptor. Exemplary cytokine receptors through which T-cell-immune potentiating cytokines signal include, but are not limited to IL-2 receptor, IL-7 receptor, IL-15 receptor and IL-21 receptor. In alternative embodiments, the receptor from which the Stat-recruiting domain is derived, is not a cytokine receptor. By choosing the Stat-recruiting domain of the chimeric cytokine receptor, the receptor can be redirected to signaling of choice.

Table 5 provides exemplary receptors from which Stat-recruiting domains of the chimeric cytokine receptors of the disclosure are derived. Table 6a provides exemplary amino acid sequences of recruiting domains of the disclosure.

In some embodiments, the PD-1 chimeric cytokine receptor of the disclosure comprises the amino acid sequence of the STAT-recruiting domain of SEQ ID NO: 45. In some embodiments, the PD-1 chimeric cytokine receptor of the disclosure comprises the amino acid sequence of the STAT-recruiting domain of SEQ ID NO: 46. In some embodiments, the PD-1 chimeric cytokine receptor of the disclosure comprises the amino acid sequence of the STAT-recruiting domain of SEQ ID NO: 47. In some embodiments, the PD-1 chimeric cytokine receptor of the disclosure comprises the amino acid sequence of the STAT-recruiting domain of SEQ ID NO: 48. In some embodiments, the PD-1 chimeric cytokine receptor of the disclosure comprises the amino acid sequence of the STAT-recruiting domain of SEQ ID NO: 49. In some embodiments, the PD-1 chimeric cytokine receptor of the disclosure comprises the amino acid sequence of the STAT-recruiting domain of SEQ ID NO: 50. In some embodiments, the PD-1 chimeric cytokine receptor of the disclosure comprises the amino acid sequence of the STAT-recruiting domain of SEQ ID NO: 51. In some embodiments, the PD-1 chimeric cytokine receptor of the disclosure comprises the amino acid sequence of the STAT-recruiting domain of SEQ ID NO: 52. In some embodiments, the PD-1 chimeric cytokine receptor of the disclosure comprises the amino acid sequence of the STAT-recruiting domain of SEQ ID NO: 53. In some embodiments, the PD-1 chimeric cytokine receptor of the disclosure comprises the amino acid sequence of the STAT-recruiting domain of SEQ ID NO: 54. In some embodiments, the PD-1 chimeric cytokine receptor of the disclosure comprises the amino acid sequence of the STAT-recruiting domain of SEQ ID NO: 55. In some embodiments, the PD-1 chimeric cytokine receptor of the disclosure comprises the amino acid sequence of the STAT-recruiting domain of SEQ ID NO: 56. In some embodiments, the PD-1 chimeric cytokine receptor of the disclosure comprises the amino acid sequence of the STAT-recruiting domain of SEQ ID NO: 57. In some embodiments, the PD-1 chimeric cytokine receptor of the disclosure comprises the amino acid sequence of the STAT-recruiting domain of SEQ ID NO: 58. In some embodiments, the PD-1 chimeric cytokine receptor of the disclosure comprises the amino acid sequence of the STAT-recruiting domain of SEQ ID NO: 59. In some embodiments, the PD-1 chimeric cytokine receptor of the disclosure comprises the amino acid sequence of the STAT-recruiting domain of SEQ ID NO: 60. In some embodiments, the PD-1 chimeric cytokine receptor of the disclosure comprises the amino acid sequence of the STAT-recruiting domain of SEQ ID NO: 61. In some embodiments, the PD-1 chimeric cytokine receptor of the disclosure comprises the amino acid sequence of the STAT-recruiting domain of SEQ ID NO: 62. In some embodiments, the PD-1 chimeric cytokine receptor of the disclosure comprises the amino acid sequence of the STAT-recruiting domain of SEQ ID NO: 63. In some embodiments, the PD-1 chimeric cytokine receptor of the disclosure comprises the amino acid sequence of the STAT-recruiting domain of SEQ ID NO: 64. In some embodiments, the PD-1 chimeric cytokine receptor of the disclosure comprises the amino acid sequence of the STAT-recruiting domain of SEQ ID NO: 65. In some embodiments, the PD-1 chimeric cytokine receptor of the disclosure comprises the amino acid sequence of the STAT-recruiting domain of SEQ ID NO: 66. In some embodiments, the PD-1 chimeric cytokine receptor of the disclosure comprises the amino acid sequence of the STAT-recruiting domain of SEQ ID NO: 67. In some embodiments, the PD-1 chimeric cytokine receptor of the disclosure comprises the amino acid sequence of the STAT-recruiting domain of SEQ ID NO: 68. In some embodiments, the PD-1 chimeric cytokine receptor of the disclosure comprises the amino acid sequence of the STAT-recruiting domain of SEQ ID NO: 69. In some embodiments, the PD-1 chimeric cytokine receptor of the disclosure comprises the amino acid sequence of the STAT-recruiting domain of SEQ ID NO: 70. In some embodiments, the PD-1 chimeric cytokine receptor of the disclosure comprises the amino acid sequence of the STAT-recruiting domain of SEQ ID NO: 71. In some embodiments, the PD-1 chimeric cytokine receptor of the disclosure comprises the amino acid sequence of the STAT-recruiting domain of SEQ ID NO: 72. In some embodiments, the PD-1 chimeric cytokine receptor of the disclosure comprises the amino acid sequence of the STAT-recruiting domain of SEQ ID NO: 73. In some embodiments, the PD-1 chimeric cytokine receptor of the disclosure comprises the amino acid sequence of the STAT-recruiting domain of SEQ ID NO: 74. In some embodiments, the PD-1 chimeric cytokine receptor of the disclosure comprises the amino acid sequence of the STAT-recruiting domain of SEQ ID NO: 75. In some embodiments, the PD-1 chimeric cytokine receptor of the disclosure comprises the amino acid sequence of the STAT-recruiting domain of SEQ ID NO: 76. In some embodiments, the PD-1 chimeric cytokine receptor of the disclosure comprises the amino acid sequence of the STAT-recruiting domain of SEQ ID NO: 77. In some embodiments, the PD-1 chimeric cytokine receptor of the disclosure comprises the amino acid sequence of the STAT-recruiting domain of SEQ ID NO: 78. In some embodiments, the PD-1 chimeric cytokine receptor of the disclosure comprises the amino acid sequence of the STAT-recruiting domain of SEQ ID NO: 79. In some embodiments, the PD-1 chimeric cytokine receptor of the disclosure comprises the amino acid sequence of the STAT-recruiting domain of SEQ ID NO: 80. In some embodiments, the PD-1 chimeric cytokine receptor of the disclosure comprises the amino acid sequence of the STAT-recruiting domain of SEQ ID NO: 81. In some embodiments, the PD-1 chimeric cytokine receptor of the disclosure comprises the amino acid sequence of the STAT-recruiting domain of SEQ ID NO: 82. In some embodiments, the PD-1 chimeric cytokine receptor of the disclosure comprises the amino acid sequence of the STAT-recruiting domain of SEQ ID NO: 83. In some embodiments, the PD-1 chimeric cytokine receptor of the disclosure comprises the amino acid sequence of the STAT-recruiting domain of SEQ ID NO: 84. In some embodiments, the PD-1 chimeric cytokine receptor of the disclosure comprises the amino acid sequence of the STAT-recruiting domain of SEQ ID NO: 85. In some embodiments, the PD-1 chimeric cytokine receptor of the disclosure comprises the amino acid sequence of the STAT-recruiting domain of SEQ ID NO: 86. In some embodiments, the PD-1 chimeric cytokine receptor of the disclosure comprises the amino acid sequence of the STAT-recruiting domain of SEQ ID NO: 87. In some embodiments, the PD-1 chimeric cytokine receptor of the disclosure comprises the amino acid sequence of the STAT-recruiting domain of SEQ ID NO: 170. In some embodiments, the PD-1 chimeric cytokine receptor of the disclosure comprises the amino acid sequence of the STAT-recruiting domain of SEQ ID NO: 171. In some embodiments, the PD-1 chimeric cytokine receptor of the disclosure comprises an amino acid sequence of the STAT-recruiting domain that is at least 80%, 85%, 90%, 95%, 98%, 99%, or 100% identical to the amino acid sequence of any one of the sequences shown in Table 6a.

TABLE 5

| Source for recruiting domains |
|---|
| BLNK |
| IL2RG |
| EGFR |
| EpoR |
| GHR |
| IFNAR1 |
| IFNAR2 |
| IFNAR1/2 |
| IFNLR1 |
| IL10R1 |
| IL12Rb1 |
| IL12Rb2 |
| IL21R |
| IL2Rb |
| IL2small |
| IL7R |
| IL7Ra |
| IL9R |
| IL15R |
| IL21R |

TABLE 6a

Recruiting domain Sequences (Cytotail Sequences)

| Recruiting domain | Amino acid sequence | SEQ ID NO: |
|---|---|---|
| IL7R(316-459) | ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 45 |
| IL2Rb(333-551) | VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPTPGVPDLVDFQPPPELVLREAGEEVPDA GPREGVSFPWSRPPGQGEFRALNARLPLNTDAYL SLQELQGQDPTHLV | 46 |
| IFNAR1(508-557) | ISTIATVEETNQTDEDHKKYSSQTSQDSGNYSNE DESESKTSEELQQDFV | 47 |
| IFNAR2(310-515) | KKKVWDYNYDDESDSDTEAAPRTSGGGYTMHG LTVRPLGQASATSTESQLIDPESEEEPDLPEVDVE LPTMPKDSPQQLELLSGPCERRKSPLQDPFPEEDY SSTEGSGGRITFNVDLNSVFLRVLDDEDSDDLEA PLMLSSHLEEMVDPEDPDNVQSNHLLASGEGTQ PTFPSPSSEGLWSEDAPSDQSDTSESDVDLGDGYI MR | 48 |

TABLE 6a-continued

Recruiting domain Sequences (Cytotail Sequences)

| Recruiting domain | Amino acid sequence | SEQ ID NO: |
|---|---|---|
| IFNAR1/2 (IFNAR1 residues 508-557-IFNAR2 residues 310-515) | ISTIATVEETNQTDEDHKKYSSQTSQDSGNYSNE DESESKTSEELQQDFVKKKVWDYNYDDESDSDT EAAPRTSGGGYTMHGLTVRPLGQASATSTESQLI DPESEEEPDLPEVDVELPTMPKDSPQQLELLSGPC ERRKSPLQDPFPEEDYSSTEGSSGGRITFNVDLNSV FLRVLDDEDSDDLEAPLMLSSHLEEMVDPEDPD NVQSNHLLASGEGTQPTFPSPSSEGLWSEDAPSD QSDTSESDVDLGDGYIMR | 49 |
| IFNLR1 (300-520) | RGVRPTPRVRAPATQQTRWKKDLAEDEEEEDEE DTEDGVSFQPYIEPPSFLGQEHQAPGHSEAGGVD SGRPRAPLVPSEGSSAWDSSDRSWASTVDSSWD RAGSSGYLAEKGPGQGPGGDGHQESLPPPEFSKD SGFLEELPEDNLSSWATWGTLPPEPNLVPGGPPV SLQTLTFCWESSPEEEEEARESEIEDSDAGSWGAE STQRTEDRGRTLGHYMAR | 50 |
| Common Gamma Chain (335-369) | IPPKGGALGEGPGASPCNQHSPYWAPPCYTLKPE T | 51 |
| IL9R (356-521) | TALLTCGPARPWKSVALEEEQEGPGTRLPGNLSS EDVLPAGCTEWRVQTLAYLPQEDWAPTSLTRPA PPDSEGSRSSSSSSSSNNNNYCALGCYGGWHLSA LPGNTQSSGPIPALACGLSCDHQGLETQQGVAW VLAGHCQRPGLHEDLQGMLLPSVLSKARSWTF | 52 |
| IL21R (322-538) | PRSPAKRLQLTELQEPAELVESDGVPKPSFWPTA QNSGGSAYSEERDRPYGLVSIDTVTVLDAEGPCT WPCSCEDDGYPALDLDAGLEPSPGLEDPLLDAG TTVLSCGCVSAGSPGLGGPLGSLLDRLKPPLADG EDWAGGLPWGGRSPGGVSESEAGSPLAGLDMD TFDSGFVGSDCSSPVECDFTSPGDEGPPRSYLRQ WVVIPPPLSSPGPQAS | 53 |
| GHR (353-638) | PDEKTEESDTDRLLSSDHEKSHSNLGVKDGDSGR TSCCEPDILETDFNANDIHEGTSEVAQPQRLKGE ADLLCLDQKNQNNSPYHDACPATQQPSVIQAEK NKPQPLPTEGAESTHQAAHIQLSNPSSLSNIDFYA QVSDITPAGSVVLSPGQKNKAGMSQCDMHPEM VSLCQENFLMDNAYFCEADAKKCIPVAPHIKVES HIQPSLNQEDIYITTESLTTAAGRPGTGEHVPGSE MPVPDYTSIHIVQSPQGLILNATALPLPDKEFLSS CGYVSTDQLNKIMP | 54 |
| EpoR (339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 55 |
| murine IL2Rb (337-539) | AVQLLLLQKDSAPLPSPSGHSQASCFTNQGYFFF HLPNALEIESCQVYFTYDPCVEEEVEEDGSRLPE GSPHPPLLPLAGEQDDYCAFPPRDDLLLFSPSLST PNTAYGGSRAPEERSPLSLHEGLPSLASRDLMGL QRPLERMPEGDGEGLSANSSGEQASVPEGNLHG QDQDRGQGPILTLNTDAYLSLQELQAQDSVHLI | 56 |
| murine IL7Ra (316-459) | RDEVESFLPNDLPAQPEELETQGHRAAVHSAN RSPETSVSPPETVRRESPLRCLARNLSTCNAPPLL SSRSPDYRDGDRNRPPVYQDLLPNSGNTNVPVPV PQPLPFQSGILIPVSQRQPISTSSVLNQEEAYVTMS SFYQNK | 57 |
| EGFR (955-1186) | VIQGDERMHLPSPTDSNFYRALMDEEDMDDVVD ADEYLIPQQGFFSSPSTSRTPLLSSLSATSNNSTVA CIDRNGLQSCPIKEDSFLQRYSSDPTGALTEDSID DTFLPVPEYINQSVPKRPAGSVQNPVYHNQPLNP APSRDPHYQDPHSTAVGNPEYLNTVQPTCVNSTF DSPAHWAQKGSHQISLDNPDYQQDFFPKEAKPN GIFKGSTAENAEYLRVAPQSSEFIGA | 58 |
| EGFR (955-1186; Y974F, d1045-1057) | VIQGDERMHLPSPTDSNFFRALMDEEDMDDVVD ADEYLIPQQGFFSSPSTSRTPLLSSLSATSNNSTVA CIDRNGLQSCPIKEDSFLQRIDDTFLPVPEYINQSV PKRPAGSVQNPVYHNQPLNPAPSRDPHYQDPHS | 59 |

TABLE 6a-continued

Recruiting domain Sequences (Cytotail Sequences)

| Recruiting domain | Amino acid sequence | SEQ ID NO: |
|---|---|---|
| | TAVGNPEYLNTVQPTCVNSTFDSPAHWAQKGSH QISLDNPDYQQDFFPKEAKPNGIFKGSTAENAEY LRVAPQSSEFIGA | |
| EGFR(955-1009; Y974F) | VIQGDERMHLPSPTDSNFFRALMDEEDMDDVVD ADEYLIPQQGFFSSPSTSRTP | 60 |
| EGFR(1019-1085) | NNSTVACIDRNGLQSCPIKEDSFLQRIDDTFLPVP EYINQSVPKRPAGSVQNPV | 61 |
| EGFR(1037-1103, Y1068/1101F, d1045-1057) | KEDSFLQRIDDTFLPVPEFINQSVPKRPAGSVQNP VYHNQPLNPAPSRDPHFQD | 62 |
| EGFR(1066-1118, Y1068/1086F) | VPEFINQSVPKRPAGSVQNPVFHNQPLNPAPSRD PHYQDPHSTAVGNPEYLNTV | 63 |
| EGFR(1122-1165) | PEYLNTVQPTCVNSTFDSPAHWAQKGSHQISLDN PDYQQDFFPKEAKPNGIFKG | 64 |
| EGFR(1133-1186, Y1148F) | WAQKGSHQISLDNPDFQQDFFPKEAKPNGIFKGS TAENAEYLRVAPQSSEFIGA | 65 |
| IL12Rb2(775-825) | SDPKPENPACPWTVLPAGDLPTHDGYLPSNIDDL PSHEAPLADSLEELEPQ | 66 |
| IL7R(376-416) | ACDAPILSSSRSLDCRESGKNGPHVYQDLLLSLG TTNSTLP | 67 |
| IL7R(424-459) | GILTLNPVAQGQPILTSLGSNQEEAYVTMSSFYQ NQ | 68 |
| IL7R(376-416, 424-459) | ACDAPILSSSRSLDCRESGKNGPHVYQDLLLSLG TTNSTLPQGQPILTSLGSNQEEAYVTMSSFYQNQ | 69 |
| IL7R(424-459, Y456F) | GILTLNPVAQGQPILTSLGSNQEEAYVTMSSFFQN Q | 70 |
| IL7R(376-416, 424-459, Y456F) | ACDAPILSSSRSLDCRESGKNGPHVYQDLLLSLG TTNSTLPQGQPILTSLGSNQEEAYVTMSSFFQNQ | 71 |
| IL2Rbsmall(393-433) | DEGVAGAPTGSSPQPLQPLSGEDDAYCTFPSRDD LLLFSPSGQGEFRALNARLPLNTDAYLSLQELQG QDPTHLV | 72 |
| IL2Rbsmall(518-551) | GQGEFRALNARLPLNTDAYLSLQELQGQDPTHL V | 73 |
| IL2Rbsmall(339-379, 393-433) | QQDKVPEPASLSSNHSLTSCFTNQGYFFFHLPDA LEIEACQDEGVAGAPTGSSPQPLQPLSGEDDAYC TFPSRDDLLLFSPS | 74 |
| IL2Rbsmall(339-379, 518-551) | QQDKVPEPASLSSNHSLTSCFTNQGYFFFHLPDA LEIEACQ GQGEFRALNARLPLNTDAYLSLQELQGQDPTHL V | 75 |
| IL2Rbsmall(393-433, 518-551) | DEGVAGAPTGSSPQPLQPLSGEDDAYCTFPSRDD LLLFSPSGQGEFRALNARLPLNTDAYLSLQELQG QDPTHLV | 76 |
| IL2Rbsmall(339-379, 393-433, 518-551) | QQDKVPEPASLSSNHSLTSCFTNQGYFFFHLPDA LEIEACQDEGVAGAPTGSSPQPLQPLSGEDDAYC TFPSRDDLLLFSPSGQGEFRALNARLPLNTDAYLS LQELQGQDPTHLV | 77 |
| IFNAR2small(310-352) | KKKVWDYNYDDESDSDTEAAPRTSGGGYTMHG LTVRPLGQASA | 78 |
| IFNAR2small(486-515) | EGLWSEDAPSDQSDTSESDVDLGDGYIMR | 79 |
| IFNAR2small(310-352, 486-515) | KKKVWDYNYDDESDSDTEAAPRTSGGGYTMHG LTVRPLGQASA EGLWSEDAPSDQSDTSESDVDLGDGYIMR | 80 |

TABLE 6a-continued

Recruiting domain Sequences (Cytotail Sequences)

| Recruiting domain | Amino acid sequence | SEQ ID NO: |
|---|---|---|
| BLNK(53-208) | ASESPADEEEQWSDDFDSDYENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 81 |
| BLNK(53-208, Y72F) | ASESPADEEEQWSDDFDSDFENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 82 |
| BLNK(53-208, Y72F, Y96F) | ASESPADEEEQWSDDFDSDFENPDEHSDSEMYV MPAEENADDSFEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 83 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 84 |
| IL12Rb2(714-862) | VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 85 |
| IL12Rb1(622-662) | WDKGERTEPLEKTELPEGAPELALDTELSLEDGD RCKAKM | 86 |
| IL10R1(304-578) | VSPELKNLDLHGSTDSGFGSTKPSLQTEEPQFLLP DPHPQADRTLGNREPPVLGDSCSSGSSNSTDSGIC LQEPSLSPSTGPTWEQQVGSNSRGQDDSGIDLVQ NSEGRAGDTQGGSALGHHSPPEPEVPGEEDPAA VAFQGYLRQTRCAEEKATKTGCLEEESPLTDGL GPKFGRCLVDEAGLHPPALAKGYLKQDPLEMTL ASSGAPTGQWNQPTEEWSLLALSSCSDLGISDWS FAHDLAPLGCVAAPGGLLGSFNSDLVTLPLISSLQ SSE | 87 |
| IL2Rb(333-551, Y381S, Y384S, Y387S) | VTQLLLQQDKVPEPASLSSNHSLTSCFTNQGYFF FHLPDALEIEACQVSFTSDPSSEEDPDEGVAGAPT GSSPQPLQPLSGEDDAYCTFPSRDDLLLFSPSLLG GPSPPSTAPGGSGAGEERMPPSLQERVPRDWDPQ PLGPPTPGVPDLVDFQPPPELVLREAGEEVPDAG PREGVSFPWSRPPGQGEFRALNARLPLNTDAYLS LQELQGQDPTHLV | 170 |
| IL2Rb(333-551, Y364S, Y381S, Y384S, Y387S) | VTQLLLQQDKVPEPASLSSNHSLTSCFTNQGSFFF HLPDALEIEACQVSFTSDPSSEEDPDEGVAGAPTG SSPQPLQPLSGEDDAYCTFPSRDDLLLFSPSLLGG PSPPSTAPGGSGAGEERMPPSLQERVPRDWDPQP LGPPTPGVPDLVDFQPPPELVLREAGEEVPDAGP REGVSFPWSRPPGQGEFRALNARLPLNTDAYLSL QELQGQDPTHLV | 171 |

In some embodiments, the Stat-recruiting domain of a chimeric cytokine receptor of the disclosure comprises a STAT-recruiting domain from one receptor.

In order to generate multiple outputs, one or more STAT-recruiting domains may be joined in tandem to mimic signaling from one or more cytokines.

In some embodiments, the STAT-recruiting domain comprises portions of more than one receptor, e.g. comprising more than one STAT-recruiting domain. In such embodiments, a tandem cytokine signaling domain is provided, allowing for enhanced signaling. Accordingly, in some embodiments, the STAT-recruiting domain of a monomer of the chimeric cytokine receptor of the disclosure comprises the STAT-recruiting domains from more than one receptor, e.g. comprises the STAT-recruiting domains from two, three, four, five, or even six receptors. For example, in some embodiments, STAT-recruiting domains can be linked in tandem to stimulate multiple pathways (e.g., the IL7R(316-459)-IL12Rb2(775-825) fragment fusion for pro-persistence STAT5 and pro-inflammatory STAT4; IL7R(316-459)-IL2Rbsmall(393-433, 518-551) for pro-persistence; IL7R (316-459)-EGFR(1122-1165) for pro-persistence and anti-exhaustion; IL2Rbsmall(393-433, 518-551)-EGFR(1122-1165) for pro-persistence and anti-exhaustion).

In some embodiments, the more than one STAT-recruiting domains can be connected either directly, or via a linker. In some embodiments, the linker can comprise one or more amino acid residues.

When generating multiple outputs, the proximity of individual STAT-recruiting domains to the cell membrane can influence the strength of their respective signaling outputs. Table 6b shows examples of PD-1 chimeric cytokine receptors with the dual outputs, where each output can be placed either proximal or distal to the cell membrane.

TABLE 6b

Examples of PD-1 chimeric cytokine receptors with dual outputs

| Dual output STAT-recruiting domain | Membrane proximal | Membrane distal |
|---|---|---|
| IL2Rbsmall(393-433, 518-551)/ IL21R(322-538) | IL2Rbsmall(393-433, 518-551) | IL21R(322-538) |
| IL21R(322-538)/ IL2Rbsmall(393-433, 518-551) | IL21R(322-538) | IL2Rbsmall(393-433, 518-551) |
| IL2Rbsmall(339-379, 393-433, 518-551)/IL21R(322-538) | IL2Rbsmall(339-379, 393-433, 518-551) | IL21R(322-538) |
| IL21R(322-538)/ IL2Rbsmall(339-379, 393-433, 518-551) | IL21R(322-538) | IL2Rbsmall(339-379, 393-433, 518-551) |
| IL7R (316-459)/IL21R(322-538) | IL7R (316-459) | IL21R(322-538) |
| IL21R(322-538)/IL7R (316-459) | IL21R(322-538) | IL7R (316-459) |

Without being bound to theory or mechanism, in some embodiments, a JAK-protein (JAK1, JAK2, JAK3, or TYK2) is bound to a PD-1 chimeric cytokine receptor of the disclosure (comprising a PD-1 ectodomain, a transmembrane domain, a JAK-binding domain, and a recruiting domain). In some embodiments, in the presence of (e.g. binding to) PD-L1, PD-L2, or an anti-PD-1 antibody, the PD-1 chimeric cytokine receptor clusters and allows for the two bound JAK-proteins to become activated, which in turn phosphorylate tyrosine residues on the recruiting domain of the chimeric receptor. The phosphorylated recruiting domains are then capable of binding the recruited proteins (e.g. a phosphorylated STAT-recruiting domain binds a STAT-protein), which in turn effectuate transcription events in the nucleus.

E. Exemplary PD-1 Chimeric Cytokine Receptors

Table 7 shows exemplary context-dependent cytokine receptor sequences of the disclosure. The receptors may be expressed with a signal sequence, e.g. a CD8SS of SEQ ID NO: 1.

In some embodiments, the PD-1 chimeric cytokine receptor of the disclosure comprises the amino acid sequence of SEQ ID NO: 88. In some embodiments, the PD-1 chimeric cytokine receptor of the disclosure comprises the amino acid sequence of SEQ ID NO: 89. In some embodiments, the PD-1 chimeric cytokine receptor of the disclosure comprises the amino acid sequence of SEQ ID NO: 90. In some embodiments, the PD-1 chimeric cytokine receptor of the disclosure comprises the amino acid sequence of SEQ ID NO: 91. In some embodiments, the PD-1 chimeric cytokine receptor of the disclosure comprises the amino acid sequence of SEQ ID NO: 92. In some embodiments, the PD-1 chimeric cytokine receptor of the disclosure comprises the amino acid sequence of SEQ ID NO: 93. In some embodiments, the PD-1 chimeric cytokine receptor of the disclosure comprises the amino acid sequence of SEQ ID NO: 94. In some embodiments, the PD-1 chimeric cytokine receptor of the disclosure comprises the amino acid sequence of SEQ ID NO: 95. In some embodiments, the PD-1 chimeric cytokine receptor of the disclosure comprises the amino acid sequence of SEQ ID NO: 96. In some embodiments, the PD-1 chimeric cytokine receptor of the disclosure comprises the amino acid sequence of SEQ ID NO: 97. In some embodiments, the PD-1 chimeric cytokine receptor of the disclosure comprises the amino acid sequence of SEQ ID NO: 98. In some embodiments, the PD-1 chimeric cytokine receptor of the disclosure comprises the amino acid sequence of SEQ ID NO: 99. In some embodiments, the PD-1 chimeric cytokine receptor of the disclosure comprises the amino acid sequence of SEQ ID NO: 100. In some embodiments, the PD-1 chimeric cytokine receptor of the disclosure comprises the amino acid sequence of SEQ ID NO: 101. In some embodiments, the PD-1 chimeric cytokine receptor of the disclosure comprises the amino acid sequence of SEQ ID NO: 102. In some embodiments, the PD-1 chimeric cytokine receptor of the disclosure comprises the amino acid sequence of SEQ ID NO: 103. In some embodiments, the PD-1 chimeric cytokine receptor of the disclosure comprises the amino acid sequence of SEQ ID NO: 104. In some embodiments, the PD-1 chimeric cytokine receptor of the disclosure comprises the amino acid sequence of SEQ ID NO: 105. In some embodiments, the PD-1 chimeric cytokine receptor of the disclosure comprises the amino acid sequence of SEQ ID NO: 106. In some embodiments, the PD-1 chimeric cytokine receptor of the disclosure comprises the amino acid sequence of SEQ ID NO: 107. In some embodiments, the PD-1 chimeric cytokine receptor of the disclosure comprises the amino acid sequence of SEQ ID NO: 108. In some embodiments, the PD-1 chimeric cytokine receptor of the disclosure comprises the amino acid sequence of SEQ ID NO: 109. In some embodiments, the PD-1 chimeric cytokine receptor of the disclosure comprises the amino acid sequence of SEQ ID NO: 110. In some embodiments, the PD-1 chimeric cytokine receptor of the disclosure comprises the amino acid sequence of SEQ ID NO: 111. In some embodiments, the PD-1 chimeric cytokine receptor of the disclosure comprises the amino acid sequence of SEQ ID NO: 112. In some embodiments, the PD-1 chimeric cytokine receptor of the disclosure comprises the amino acid sequence of SEQ ID NO: 113. In some embodiments, the PD-1 chimeric cytokine receptor of the disclosure comprises the amino acid sequence of SEQ ID NO: 114. In some embodiments, the PD-1 chimeric cytokine receptor of the disclosure comprises the amino acid sequence of SEQ ID NO: 115. In some embodiments, the PD-1 chimeric cytokine receptor of the disclosure comprises the amino acid sequence of SEQ ID NO: 116. In some embodiments, the PD-1 chimeric cytokine receptor of the disclosure comprises the amino acid sequence of SEQ ID NO: 117. In some embodiments, the PD-1 chimeric cytokine receptor of the disclosure comprises the amino acid sequence of SEQ ID NO: 118. In some embodiments, the PD-1 chimeric cytokine receptor of the disclosure comprises the amino acid sequence of SEQ ID NO: 119. In some embodiments, the PD-1 chimeric cytokine receptor of the disclosure comprises the amino acid sequence of SEQ ID NO: 120. In some embodiments, the PD-1 chimeric cytokine receptor of the disclosure comprises the amino acid sequence of SEQ ID NO: 121. In some embodiments, the PD-1 chimeric cytokine receptor of the disclosure comprises the amino acid sequence of any one of SEQ ID NOs: 88-121, SEQ ID NOs: 136-145, and SEQ ID NOs: 172-213. In some embodiments, the PD-1 chimeric cytokine receptor of the disclosure comprises an amino acid sequence that is at least 80%, 85%, 90%, 95%, 98%, 99%, or 100% identical to the amino acid sequence of any one of SEQ ID NOs: 88-121, SEQ ID NOs: 172-213.

TABLE 7

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| WTPD1(21-207).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 88 |
| WTPD1(21-207).GCSFR(614-710).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ LTLMTLTPEGSELHIILGLFGLLLLLTCLCGTAWLCCSPNRKN PLWPSVPDPAHSSLGSWVPTIMEEDAFQLPGLGTPPITKLTVL EEDEKKPVPWE ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 89 |
| WTPD1(21-207).GP130(609-700).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ TTPKFAQGEIEAIVVPVCLAFLLTTLLGVLFCFNKRDLIKKHI WPNVPDPSKSHIAQWSPHTPPRHNFNSKDQMYSDGNFTDVS VVEIEAND ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 90 |
| 2xWTPD1(21-207).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQPGWFLDSPDRPWNPPTFSPALL VVTEGDNATFTCSFSNTSESFVLNWYRMSPSNQTDKLAAFPE DRSQPGQDCRFRVTQLPNGRDFHMSVVRARRNDSGTYLCG AISLAPKAQIKESLRAELRVTERRAEVPTAHPSPSPRPAGQFQ TLVVGVVGGLLGSLVLLVWVLAVICSRAARGTIGARRTGQ SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 91 |
| 3xWTPD1(21-207).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQPGWFLDSPDRPWNPPTFSPALL VVTEGDNATFTCSFSNTSESFVLNWYRMSPSNQTDKLAAFPE DRSQPGQDCRFRVTQLPNGRDFHMSVVRARRNDSGTYLCG AISLAPKAQIKESLRAELRVTERRAEVPTAHPSPSPRPAGQFQ TLVVGVVGGLLGSLVLLVWVLAVICSRAARGTIGARRTGQP GWFLDSPDRPWNPPTFSPALLVVTEGDNATFTCSFSNTSESF | 92 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | |
| HAPD1.TpoR (478-582).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 93 |
| HAPD1.TpoR (N-1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETWISLVTALHLVLGLSAVLGLLLLRWQFPAH YRRLRHALWPSLPDLHRVLGQYLRDTAALSPPKATVSDTCE EVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 94 |
| HAPD1.TpoR (N-2).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETISLVTALHLVLGLSAVLGLLLLRWQFPAHY RRLRHALWPSLPDLHRVLGQYLRDTAALSPPKATVSDTCEE VEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 95 |
| HAPD1.TpoR (N-2+1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLISLVTALHLVLGLSAVLGLLLLRWQFPAH YRRLRHALWPSLPDLHRVLGQYLRDTAALSPPKATVSDTCE EVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 96 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | SDPKPENPACPWTVLPAGDLPTHDGYLPSNIDDLPSHEAPLADSLEELEPQ | |
| HAPD1.TpoR (N-3).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETSLVTALHLVLGLSAVLGLLLLRWQFPAHYR RLRHALWPSLPDLHRVLGQYLRDTAALSPPKATVSDTCEEV EPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLADSLEELEPQ | 97 |
| HAPD1.TpoR (N-4).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLVTALHLVLGLSAVLGLLLLRWQFPAHYR RLRHALWPSLPDLHRVLGQYLRDTAALSPPKATVSDTCEEV EPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLADSLEELEPQ | 98 |
| HAPD1.TpoR (N-4+1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETILVTALHLVLGLSAVLGLLLLRWQFPAHYR RLRHALWPSLPDLHRVLGQYLRDTAALSPPKATVSDTCEEV EPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLADSLEELEPQ | 99 |
| HAPD1.TpoR (N-5).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETVTALHLVLGLSAVLGLLLLRWQFPAHYRR LRHALWPSLPDLHRVLGQYLRDTAALSPPKATVSDTCEEVEP SLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLADSLEELEPQ | 100 |
| HAPD1.TpoR (N-6).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETTALHLVLGLSAVLGLLLLRWQFPAHYRRLR HALWPSLPDLHRVLGQYLRDTAALSPPKATVSDTCEEVEPSL LEILPKSSERTPLPL | 101 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTLSGSN QEEAYVTMSSFYQNQ SDPKPENPACPWTVLPAGDLPTHDGYLPSNIDDLPSHEAPLA DSLEELEPQ | |
| HAPD1.TpoR (N-7) .IL7Ra (316- 459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETALHLVLGLSAVLGLLLLRWQFPAHYRRLR HALWPSLPDLHRVLGQYLRDTAALSPPKATVSDTCEEVEPSL LEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTLSGSN QEEAYVTMSSFYQNQ SDPKPENPACPWTVLPAGDLPTHDGYLPSNIDDLPSHEAPLA DSLEELEPQ | 102 |
| HAPD1.TpoR (N-8) .IL7Ra (316- 459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLHLVLGLSAVLGLLLLRWQFPAHYRRLRH ALWPSLPDLHRVLGQYLRDTAALSPPKATVSDTCEEVEPSLL EILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTLSGSN QEEAYVTMSSFYQNQ SDPKPENPACPWTVLPAGDLPTHDGYLPSNIDDLPSHEAPLA DSLEELEPQ | 103 |
| HAPD1.TpoR (N-9) .IL7Ra (316- 459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETHLVLGLSAVLGLLLLRWQFPAHYRRLRHA LWPSLPDLHRVLGQYLRDTAALSPPKATVSDTCEEVEPSLLEI LPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTLSGSN QEEAYVTMSSFYQNQ SDPKPENPACPWTVLPAGDLPTHDGYLPSNIDDLPSHEAPLA DSLEELEPQ | 104 |
| HAPD1.TpoR (N-10) .IL7Ra (316- 459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLVLGLSAVLGLLLLRWQFPAHYRRLRHAL WPSLPDLHRVLGQYLRDTAALSPPKATVSDTCEEVEPSLLEIL PKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTLSGSN QEEAYVTMSSFYQNQ SDPKPENPACPWTVLPAGDLPTHDGYLPSNIDDLPSHEAPLA DSLEELEPQ | 105 |
| HAPD1.TpoR (N-11) .IL7Ra (316- 459).IL12Rb2 | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 106 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| (775-825) | SDPTRVETATETVLGLSAVLGLLLLRWQFPAHYRRLRHALW PSLPDLHRVLGQYLRDTAALSPPKATVSDTCEEVEPSLLEILP KSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | |
| HAPD1.TpoR (N-12) .IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLGLSAVLGLLLLRWQFPAHYRRLRHALWP SLPDLHRVLGQYLRDTAALSPPKATVSDTCEEVEPSLLEILPK SSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 107 |
| HAPD1.TpoR (N-13) .IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETGLSAVLGLLLLRWQFPAHYRRLRHALWPS LPDLHRVLGQYLRDTAALSPPKATVSDTCEEVEPSLLEILPKS SERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 108 |
| HAPD1.TpoR (N-14) .IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLSAVLGLLLLRWQFPAHYRRLRHALWPSLP DLHRVLGQYLRDTAALSPPKATVSDTCEEVEPSLLEILPKSSE RTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 109 |
| HAPD1.TpoR (N-15) .IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETSAVLGLLLLRWQFPAHYRRLRHALWPSLP DLHRVLGQYLRDTAALSPPKATVSDTCEEVEPSLLEILPKSSE RTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 110 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1.TpoR (N-16).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAVLGLLLLRWQFPAHYRRLRHALWPSLPD LHRVLGQYLRDTAALSPPKATVSDTCEEVEPSLLEILPKSSER TPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 111 |
| HAPD1.TpoR (N-17).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETVLGLLLLRWQFPAHYRRLRHALWPSLPDL HRVLGQYLRDTAALSPPKATVSDTCEEVEPSLLEILPKSSERT PLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 112 |
| HAPD1.TpoR (N-18).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLGLLLLRWQFPAHYRRLRHALWPSLPDH RVLGQYLRDTAALSPPKATVSDTCEEVEPSLLEILPKSSERTP LPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 113 |
| HAPD1.TpoR (N+1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLISLVTALHLVLGLSAVGLLLLRWQFP AHYRRLRHALWPSLPDLHRVLGQYLRDTAALSPPKATVSDT CEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 114 |
| HAPD1.TpoR (N+2).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLISLVTALHLVLGLSAVGLLLLRWQF PAHYRRLRHALWPSLPDLHRVLGQYLRDTAALSPPKATVSD TCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 115 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | SDPKPENPACPWTVLPAGDLPTHDGYLPSNIDDLPSHEAPLA DSLEELEPQ | |
| HAPD1.TpoR (N+3).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLVLISLVTALHLVLGLSAVLGLLLLRWQ FPAHYRRLRHALWPSLPDLHRVLGQYLRDTAALSPPKATVS DTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 116 |
| HAPD1.TpoR (N+4).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWILVLISLVTALHLVLGLSAVLGLLLLRW QFPAHYRRLRHALWPSLPDLHRVLGQYLRDTAALSPPKATV SDTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 117 |
| HAPD1.TpoR (N+5).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLILVLISLVTALHLVLGLSAVLGLLLLR WQFPAHYRRLRHALWPSLPDLHRVLGQYLRDTAALSPPKAT VSDTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 118 |
| HAPD1.TpoR (N+6).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLLILVLISLVTALHLVLGLSAVLGLLLLR WQFPAHYRRLRHALWPSLPDLHRVLGQYLRDTAALSPPKAT VSDTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 119 |
| HAPD1.TpoR (N+7).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWVLLILVLISLVTALHLVLGLSAVLGLLLL RWQFPAHYRRLRHALWPSLPDLHRVLGQYLRDTAALSPPKA TVSDTCEEVEPSLLEILPKSSERTPLPL ARDEVEGFLQDTFPQQLEESEKQRLGGDVQSPNCPSEDVVIT | 120 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | |
| HAPD1.TpoR (N+8).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLVLLILVLISLVTALHLVLGLSAVLGLLL LRWQFPAHYRRLRHALWPSLPDLHRVLGQYLRDTAALSPPK ATVSDTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 121 |
| HAPD1(21-170).TPOR/ MPLR(478-582, H499L, S505N, W515K) IL7Ra (316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTALLLVLGLNAVLGLLLLRKQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 136 |
| HAPD1(21-170).TpoR (478-582, S505N, W515K), IL2small(393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTAHLVLGLNAVLGLLLLRKQFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSQELQGQDPTHLV | 137 |
| HAPD1DN (HAPD1 Dominant Negative) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 138 |
| HAPD1(21-170).TpoR (478-582).IL7Ra (316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTAHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 139 |
| HAPD1(21-170).TpoR (478-582).IL2small (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTAHLVLGLSAVLGLLLLRWQFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSQELQGQDPTHLV | 140 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| WTPD1(21-170).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVSDPTRVETATETAWISLVT ALHLVLGLSAVLGLLLLRWQFPAHYRRLRHALWPSLPDLHR VLGQYLRDTAALSPPKATVSDTCEEVEPSLLEILPKSSERTPL PLLEARDEVEGFLQDTFPQQLEESEKQRLGGDVQSPNCPSED VVITPESFGRDSSLTCLAGNVSACDAPILSSSRSLDCRESGKN GPHVYQDLLLSLGTTNSTLPPPFSLQSGILTLNPVAQGQPILTS LGSNQEEAYVTMSSFYQNQGSGSRSDPKPENPACPWTVLPA GDLPTHDGYLPSNIDDLPSHEAPLADSLEELEPQ | 172 |
| WTPD1(21-170).GCSFR(614-710).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVLTLMTLTPEGSELHIILGLF GLLLLLTCLCGTAWLCCSPNRKNPLWPSVPDPAHSSLGSWV PTIMEEDAFQLPGLGTPPITKLTVLEEDEKKPVPWELEARDEV EGFLQDTFPQQLEESEKQRLGGDVQSPNCPSEDVVITPESFGR DSSLTCLAGNVSACDAPILSSSRSLDCRESGKNGPHVYQDLL LSLGTTNSTLPPPFSLQSGILTLNPVAQGQPILTSLGSNQEEAY VTMSSFYQNQGSGSRSDPKPENPACPWTVLPAGDLPTHDGY LPSNIDDLPSHEAPLADSLEELEPQ | 173 |
| WTPD1(21-170).GP130(609-700).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVTTPKFAQGEIEAIVVPVCL AFLLTTLLGVLFCFNKRDLIKKHIWPNVDPSKSHIAQWSPHT PPRHNFNSKDQMYSDGNFTDVSVVEIEANDLEARDEVEGFL QDTFPQQLEESEKQRLGGDVQSPNCPSEDVVITPESFGRDSSL TCLAGNVSACDAPILSSSRSLDCRESGKNGPHVYQDLLLSLG TTNSTLPPPFSLQSGILTLNPVAQGQPILTSLGSNQEEAYVTM SSFYQNQGSGSRSDPKPENPACPWTVLPAGDLPTHDGYLPSN IDDLPSHEAPLADSLEELEPQ | 174 |
| 2xWTPD1(21-170).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVGPGWFLDSPDRPWNPPTF SPALLVVTEGDNATFTCSFSNTSESFVLNWYRMSPSNQTDKL AAFPEDRSQPGQDCRFRVTQLPNGRDFHMSVVRARRNDSGT YLCGAISLAPKAQIKESLRAELRVTERRAEVPTAHPSPSPRPA GQFQTLVSDPTRVETATETAWISLVTALHLVLGLSAVLGLLL LRWQFPAHYRRLRHALWPSLPDLHRVLGQYLRDTAALSPPK ATVSDTCEEVEPSLLEILPKSSERTPLPLLEARDEVEGFLQDTF PQQLEESEKQRLGGDVQSPNCPSEDVVITPESFGRDSSLTCLA GNVSACDAPILSSSRSLDCRESGKNGPHVYQDLLLSLGTTNS TLPPPFSLQSGILTLNPVAQGQPILTSLGSNQEEAYVTMSSFY QNQGSGSRSDPKPENPACPWTVLPAGDLPTHDGYLPSNIDDL PSHEAPLADSLEELEPQ | 175 |
| 3xWTPD1(21-170).TpoR(478-582).IL7Ra(316-459).IL12Rb2(775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVGPGWFLDSPDRPWNPPTF SPALLVVTEGDNATFTCSFSNTSESFVLNWYRMSPSNQTDKL AAFPEDRSQPGQDCRFRVTQLPNGRDFHMSVVRARRNDSGT YLCGAISLAPKAQIKESLRAELRVTERRAEVPTAHPSPSPRPA GQFQTLVGPGWFLDSPDRPWNPPTFSPALLVVTEGDNATFTC SFSNTSESFVLNWYRMSPSNQTDKLAAFPEDRSQPGQDCRFR VTQLPNGRDFHMSVVRARRNDSGTYLCGAISLAPKAQIKESL RAELRVTERRAEVPTAHPSPSPRPAGQFQTLVSDPTRVETAT ETAWISLVTALHLVLGLSAVLGLLLLRWQFPAHYRRLRHAL WPSLPDLHRVLGQYLRDTAALSPPKATVSDTCEEVEPSLLEIL PKSSERTPLPLLEARDEVEGFLQDTFPQQLEESEKQRLGGDV QSPNCPSEDVVITPESFGRDSSLTCLAGNVSACDAPILSSSRSL DCRESGKNGPHVYQDLLLSLGTTNSTLPPPFSLQSGILTLNPV AQGQPILTSLGSNQEEAYVTMSSFYQNQGSGSRSDPKPENPA CPWTVLPAGDLPTHDGYLPSNIDDLPSHEAPLADSLEELEPQ | 176 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-170).TpoR (478-582).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLSAVLGLLLLRWQFPAHYRRLRHALWPSLPDLHRV LGQYLRDTAALSPPKATVSDTCEEVEPSLLEILPKSSERTPLPL LEARDEVEGFLQDTFPQQLEESEKQRLGGDVQSPNCPSEDVV ITPESFGRDSSLTCLAGNVSACDAPILSSSRSLDCRESGKNGP HVYQDLLLSLGTTNSTLPPPFSLQSGILTLNPVAQGQPILTSLG SNQEEAYVTMSSFYQNQGSGSRSDPKPENPACPWTVLPAGD LPTHDGYLPSNIDDLPSHEAPLADSLEELEPQ | 177 |
| HAPD1(21-170).TpoR (N-1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETWISLVTAL HLVLGLSAVLGLLLLRWQFPAHYRRLRHALWPSLPDLHRVL GQYLRDTAALSPPKATVSDTCEEVEPSLLEILPKSSERTPLPLL EARDEVEGFLQDTFPQQLEESEKQRLGGDVQSPNCPSEDVVI TPESFGRDSSLTCLAGNVSACDAPILSSSRSLDCRESGKNGPH VYQDLLLSLGTTNSTLPPPFSLQSGILTLNPVAQGQPILTSLGS NQEEAYVTMSSFYQNQGSGSRSDPKPENPACPWTVLPAGDL PTHDGYLPSNIDDLPSHEAPLADSLEELEPQ | 178 |
| HAPD1(21-170).TpoR (N-2).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETISLVTALH LVLGLSAVLGLLLLRWQFPAHYRRLRHALWPSLPDLHRVLG QYLRDTAALSPPKATVSDTCEEVEPSLLEILPKSSERTPLPLLE ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQGSGSRSDPKPENPACPWTVLPAGDLP THDGYLPSNIDDLPSHEAPLADSLEELEPQ | 179 |
| HAPD1(21-170).TpoR (N-2+1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLISLVTAL HLVLGLSAVLGLLLLRWQFPAHYRRLRHALWPSLPDLHRVL GQYLRDTAALSPPKATVSDTCEEVEPSLLEILPKSSERTPLPLL EARDEVEGFLQDTFPQQLEESEKQRLGGDVQSPNCPSEDVVI TPESFGRDSSLTCLAGNVSACDAPILSSSRSLDCRESGKNGPH VYQDLLLSLGTTNSTLPPPFSLQSGILTLNPVAQGQPILTSLGS NQEEAYVTMSSFYQNQGSGSRSDPKPENPACPWTVLPAGDL PTHDGYLPSNIDDLPSHEAPLADSLEELEPQ | 180 |
| HAPD1(21-170).TpoR (N-3).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETSLVTALHL VLGLSAVLGLLLLRWQFPAHYRRLRHALWPSLPDLHRVLGQ YLRDTAALSPPKATVSDTCEEVEPSLLEILPKSSERTPLPLLEA RDEVEGFLQDTFPQQLEESEKQRLGGDVQSPNCPSEDVVITP ESFGRDSSLTCLAGNVSACDAPILSSSRSLDCRESGKNGPHVY QDLLLSLGTTNSTLPPPFSLQSGILTLNPVAQGQPILTSLGSNQ EEAYVTMSSFYQNQGSGSRSDPKPENPACPWTVLPAGDLPT HDGYLPSNIDDLPSHEAPLADSLEELEPQ | 181 |
| HAPD1(21-170).TpoR (N-4).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLVTALHL VLGLSAVLGLLLLRWQFPAHYRRLRHALWPSLPDLHRVLGQ YLRDTAALSPPKATVSDTCEEVEPSLLEILPKSSERTPLPLLEA RDEVEGFLQDTFPQQLEESEKQRLGGDVQSPNCPSEDVVITP ESFGRDSSLTCLAGNVSACDAPILSSSRSLDCRESGKNGPHVY QDLLLSLGTTNSTLPPPFSLQSGILTLNPVAQGQPILTSLGSNQ EEAYVTMSSFYQNQGSGSRSDPKPENPACPWTVLPAGDLPT HDGYLPSNIDDLPSHEAPLADSLEELEPQ | 182 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-170).TpoR(N-4+1).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETILVTALHL VLGLSAVLGLLLLRWQFPAHYRRLRHALWPSLPDLHRVLGQ YLRDTAALSPPKATVSDTCEEVEPSLLEILPKSSERTPLPLLEA RDEVEGFLQDTFPQQLEESEKQRLGGDVQSPNCPSEDVVITP ESFGRDSSLTCLAGNVSACDAPILSSSRSLDCRESGKNGPHVY QDLLLSLGTTNSTLPPPFSLQSGILTLNPVAQGQPILTSLGSNQ EEAYVTMSSFYQNQGSGSRSDPKPENPACPWTVLPAGDLPT HDGYLPSNIDDLPSHEAPLADSLEELEPQ | 183 |
| HAPD1(21-170).TpoR(N-5).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETVTALHLV LGLSAVLGLLLLRWQFPAHYRRLRHALWPSLPDLHRVLGQY LRDTAALSPPKATVSDTCEEVEPSLLEILPKSSERTPLPLLEAR DEVEGFLQDTFPQQLEESEKQRLGGDVQSPNCPSEDVVITPES FGRDSSLTCLAGNVSACDAPILSSSRSLDCRESGKNGPHVYQ DLLLSLGTTNSTLPPPFSLQSGILTLNPVAQGQPILTSLGSNQE EAYVTMSSFYQNQGSGSRSDPKPENPACPWTVLPAGDLPTH DGYLPSNIDDLPSHEAPLADSLEELEPQ | 184 |
| HAPD1(21-170).TpoR(N-6).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETTALHLVL GLSAVLGLLLLRWQFPAHYRRLRHALWPSLPDLHRVLGQYL RDTAALSPPKATVSDTCEEVEPSLLEILPKSSERTPLPLLEARD EVEGFLQDTFPQQLEESEKQRLGGDVQSPNCPSEDVVITPESF GRDSSLTCLAGNVSACDAPILSSSRSLDCRESGKNGPHVYQD LLLSLGTTNSTLPPPFSLQSGILTLNPVAQGQPILTSLGSNQEE AYVTMSSFYQNQGSGSRSDPKPENPACPWTVLPAGDLPTHD GYLPSNIDDLPSHEAPLADSLEELEPQ | 185 |
| HAPD1(21-170).TpoR(N-7).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETALHLVLG LSAVLGLLLLRWQFPAHYRRLRHALWPSLPDLHRVLGQYLR DTAALSPPKATVSDTCEEVEPSLLEILPKSSERTPLPLLEARDE VEGFLQDTFPQQLEESEKQRLGGDVQSPNCPSEDVVITPESFG RDSSLTCLAGNVSACDAPILSSSRSLDCRESGKNGPHVYQDL LLSLGTTNSTLPPPFSLQSGILTLNPVAQGQPILTSLGSNQEEA YVTMSSFYQNQGSGSRSDPKPENPACPWTVLPAGDLPTHDG YLPSNIDDLPSHEAPLADSLEELEPQ | 186 |
| HAPD1(21-170).TpoR(N-8).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLHLVLGLS AVLGLLLLRWQFPAHYRRLRHALWPSLPDLHRVLGQYLRDT AALSPPKATVSDTCEEVEPSLLEILPKSSERTPLPLLEARDEVE GFLQDTFPQQLEESEKQRLGGDVQSPNCPSEDVVITPESFGRD SSLTCLAGNVSACDAPILSSSRSLDCRESGKNGPHVYQDLLLS LGTTNSTLPPPFSLQSGILTLNPVAQGQPILTSLGSNQEEAYVT MSSFYQNQGSGSRSDPKPENPACPWTVLPAGDLPTHDGYLP SNIDDLPSHEAPLADSLEELEPQ | 187 |
| HAPD1(21-170).TpoR(N-9).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEARDEVE GFLQDTFPQQLEESEKQRLGGDVQSPNCPSEDVVITPESFGRD SSLTCLAGNVSACDAPILSSSRSLDCRESGKNGPHVYQDLLLS LGTTNSTLPPPFSLQSGILTLNPVAQGQPILTSLGSNQEEAYVT MSSFYQNQGSGSRSDPKPENPACPWTVLPAGDLPTHDGYLP SNIDDLPSHEAPLADSLEELEPQ | 188 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-170).TpoR(N-10).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLVLGLSA VLGLLLLRWQFPAHYRRLRHALWPSLPDLHRVLGQYLRDTA ALSPPKATVSDTCEEVEPSLLEILPKSSERTPLPLLEARDEVEG FLQDTFPQQLEESEKQRLGGDVQSPNCPSEDVVITPESFGRDS SLTCLAGNVSACDAPILSSSRSLDCRESGKNGPHVYQDLLLS LGTTNSTLPPPFSLQSGILTLNPVAQGQPILTSLGSNQEEAYVT MSSFYQNQGSGSRSDPKPENPACPWTVLPAGDLPTHDGYLP SNIDDLPSHEAPLADSLEELEPQ | 189 |
| HAPD1(21-170).TpoR(N-11).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLVLGLSAV LGLLLLRWQFPAHYRRLRHALWPSLPDLHRVLGQYLRDTAA LSPPKATVSDTCEEVEPSLLEILPKSSERTPLPLLEARDEVEGF LQDTFPQQLEESEKQRLGGDVQSPNCPSEDVVITPESFGRDSS LTCLAGNVSACDAPILSSSRSLDCRESGKNGPHVYQDLLLSL GTTNSTLPPPFSLQSGILTLNPVAQGQPILTSLGSNQEEAYVT MSSFYQNQGSGSRSDPKPENPACPWTVLPAGDLPTHDGYLP SNIDDLPSHEAPLADSLEELEPQ | 190 |
| HAPD1(21-170).TpoR(N-12).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLGLSAVL GLLLLRWQFPAHYRRLRHALWPSLPDLHRVLGQYLRDTAAL SPPKATVSDTCEEVEPSLLEILPKSSERTPLPLLEARDEVEGFL QDTFPQQLEESEKQRLGGDVQSPNCPSEDVVITPESFGRDSSL TCLAGNVSACDAPILSSSRSLDCRESGKNGPHVYQDLLLSLG TTNSTLPPPFSLQSGILTLNPVAQGQPILTSLGSNQEEAYVTM SSFYQNQGSGSRSDPKPENPACPWTVLPAGDLPTHDGYLPSN IDDLPSHEAPLADSLEELEPQ | 191 |
| HAPD1(21-170).TpoR(N-13).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLGLSAVLG LLLLRWQFPAHYRRLRHALWPSLPDLHRVLGQYLRDTAALS PPKATVSDTCEEVEPSLLEILPKSSERTPLPLLEARDEVEGFLQ DTFPQQLEESEKQRLGGDVQSPNCPSEDVVITPESFGRDSSLT CLAGNVSACDAPILSSSRSLDCRESGKNGPHVYQDLLLSLGT TNSTLPPPFSLQSGILTLNPVAQGQPILTSLGSNQEEAYVTMSS FYQNQGSGSRSDPKPENPACPWTVLPAGDLPTHDGYLPSNID DLPSHEAPLADSLEELEPQ | 192 |
| HAPD1(21-170).TpoR(N-14).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLSAVLGLL LLRWQFPAHYRRLRHALWPSLPDLHRVLGQYLRDTAALSPP KATVSDTCEEVEPSLLEILPKSSERTPLPLLEARDEVEGFLQD TFPQQLEESEKQRLGGDVQSPNCPSEDVVITPESFGRDSSLTC LAGNVSACDAPILSSSRSLDCRESGKNGPHVYQDLLLSLGTT NSTLPPPFSLQSGILTLNPVAQGQPILTSLGSNQEEAYVTMSSF YQNQGSGSRSDPKPENPACPWTVLPAGDLPTHDGYLPSNIDD LPSHEAPLADSLEELEPQ | 193 |
| HAPD1(21-170).TpoR(N-15).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETSAVLGLLL LRWQFPAHYRRLRHALWPSLPDLHRVLGQYLRDTAALSPPK ATVSDTCEEVEPSLLEILPKSSERTPLPLLEARDEVEGFLQDTF PQQLEESEKQRLGGDVQSPNCPSEDVVITPESFGRDSSLTCLA GNVSACDAPILSSSRSLDCRESGKNGPHVYQDLLLSLGTTNS TLPPPFSLQSGILTLNPVAQGQPILTSLGSNQEEAYVTMSSFY QNQGSGSRSDPKPENPACPWTVLPAGDLPTHDGYLPSNIDDL PSHEAPLADSLEELEPQ | 194 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-170).TpoR (N-16).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAVLGLLLL RWQFPAHYRRLRHALWPSLPDLHRVLGQYLRDTAALSPPKA TVSDTCEEVEPSLLEILPKSSERTPLPLLEARDEVEGFLQDTFP QQLEESEKQRLGGDVQSPNCPSEDVVITPESFGRDSSLTCLAG NVSACDAPILSSSRSLDCRESGKNGPHVYQDLLLSLGTTNSTL PPPFSLQSGILTLNPVAQGQPILTSLGSNQEEAYVTMSSFYQN QGSGSRSDPKPENPACPWTVLPAGDLPTHDGYLPSNIDDLPS HEAPLADSLEELEPQ | 195 |
| HAPD1(21-170).TpoR (N-17).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETVLGLLLLR WQFPAHYRRLRHALWPSLPDLHRVLGQYLRDTAALSPPKAT VSDTCEEVEPSLLEILPKSSERTPLPLLEARDEVEGFLQDTFPQ QLEESEKQRLGGDVQSPNCPSEDVVITPESFGRDSSLTCLAGN VSACDAPILSSSRSLDCRESGKNGPHVYQDLLLSLGTTNSTLP PPFSLQSGILTLNPVAQGQPILTSLGSNQEEAYVTMSSFYQNQ GSGSRSDPKPENPACPWTVLPAGDLPTHDGYLPSNIDDLPSH EAPLADSLEELEPQ | 196 |
| HAPD1(21-170).TpoR (N-18).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLGLLLLR WQFPAHYRRLRHALWPSLPDLHRVLGQYLRDTAALSPPKAT VSDTCEEVEPSLLEILPKSSERTPLPLLEARDEVEGFLQDTFPQ QLEESEKQRLGGDVQSPNCPSEDVVITPESFGRDSSLTCLAGN VSACDAPILSSSRSLDCRESGKNGPHVYQDLLLSLGTTNSTLP PPFSLQSGILTLNPVAQGQPILTSLGSNQEEAYVTMSSFYQNQ GSGSRSDPKPENPACPWTVLPAGDLPTHDGYLPSNIDDLPSH EAPLADSLEELEPQ | 197 |
| HAPD1(21-170).TpoR (N+1).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLISLVT ALHLVLGLSAVLGLLLLRWQFPAHYRRLRHALWPSLPDLHR VLGQYLRDTAALSPPKATVSDTCEEVEPSLLEILPKSSERTPL PLLEARDEVEGFLQDTFPQQLEESEKQRLGGDVQSPNCPSED VVITPESFGRDSSLTCLAGNVSACDAPILSSSRSLDCRESGKN GPHVYQDLLLSLGTTNSTLPPPFSLQSGILTLNPVAQGQPILTS LGSNQEEAYVTMSSFYQNGSGSRSDPKPENPACPWTVLPA GDLPTHDGYLPSNIDDLPSHEAPLADSLEELEPQ | 198 |
| HAPD1(21-170).TpoR (N+2).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWVLISLV TALHLVLGLSAVLGLLLLRWQFPAHYRRLRHALWPSLPDLH RVLGQYLRDTAALSPPKATVSDTCEEVEPSLLEILPKSSERTP LPLLEARDEVEGFLQDTFPQQLEESEKQRLGGDVQSPNCPSE DVVITPESFGRDSSLTCLAGNVSACDAPILSSSRSLDCRESGK NGPHVYQDLLLSLGTTNSTLPPPFSLQSGILTLNPVAQGQPIL TSLGSNQEEAYVTMSSFYQNGSGSRSDPKPENPACPWTVLP AGDLPTHDGYLPSNIDDLPSHEAPLADSLEELEPQ | 199 |
| HAPD1(21-170).TpoR (N+3).IL7Ra (316-459).IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLVLISL VTALHLVLGLSAVLGLLLLRWQFPAHYRRLRHALWPSLPDL HRVLGQYLRDTAALSPPKATVSDTCEEVEPSLLEILPKSSERT PLPLLEARDEVEGFLQDTFPQQLEESEKQRLGGDVQSPNCPS EDVVITPESFGRDSSLTCLAGNVSACDAPILSSSRSLDCRESG KNGPHVYQDLLLSLGTTNSTLPPPFSLQSGILTLNPVAQGQPI LTSLGSNQEEAYVTMSSFYQNQGSGSRSDPKPENPACPWTV LPAGDLPTHDGYLPSNIDDLPSHEAPLADSLEELEPQ | 200 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-170).TpoR(N+4).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWILVLIS LVTALHLVLGLSAVLGLLLLRWQFPAHYRRLRHALWPSLPD LHRVLGQYLRDTAALSPPKATVSDTCEEVEPSLLEILPKSSER TPLPLLEARDEVEGFLQDTFPQQLEESEKQRLGGDVQSPNCP SEDVVITPESFGRDSSLTCAGNVSACDAPILSSSRSLDCRESG KNGPHVYQDLLLSLGTTNSTLPPPFSLQSGILTLNPVAQGPI LTSLGSNQEEAYVTMSSFYQNQGSGSRSDPKPENPACPWTV LPAGDLPTHDGYLPSNIDDLPSHEAPLADSLEELEPQ | 201 |
| HAPD1(21-170).TpoR(N+5).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLILVLI SLVTALHLVLGLSAVLGLLLLRWQFPAHYRRLRHALWPSLP DLHRVLGQYLRDTAALSPPKATVSDTCEEVEPSLLEILPKSSE RTPLPLLEARDEVEGFLQDTFPQQLEESEKQRLGGDVQSPNC PSEDVVITPESFGRDSSLTCAGNVSACDAPILSSSRSLDCRES GKNGPHVYQDLLLSLGTTNSTLPPPFSLQSGILTLNPVAQGQP ILTSLGSNQEEAYVTMSSFYQNQGSGSRSDPKPENPACPWTV LPAGDLPTHDGYLPSNIDDLPSHEAPLADSLEELEPQ | 202 |
| HAPD1(21-170).TpoR(N+6).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLLILVL ISLVTALHLVLGLSAVLGLLLLRWQFPAHYRRLRHALWPSLP DLHRVLGQYLRDTAALSPPKATVSDTCEEVEPSLLEILPKSSE RTPLPLLEARDEVEGFLQDTFPQQLEESEKQRLGGDVQSPNC PSEDVVITPESFGRDSSLTCAGNVSACDAPILSSSRSLDCRES GKNGPHVYQDLLLSLGTTNSTLPPPFSLQSGILTLNPVAQGQP ILTSLGSNQEEAYVTMSSFYQNQGSGSRSDPKPENPACPWTV LPAGDLPTHDGYLPSNIDDLPSHEAPLADSLEELEPQ | 203 |
| HAPD1(21-170).TpoR(N+7).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLLIL VLISLVTALHLVLGLSAVLGLLLLRWQFPAHYRRLRHALWP SLPDLHRVLGQYLRDTAALSPPKATVSDTCEEVEPSLLEILPK SSERTPLPLLEARDEVEGFLQDTFPQQLEESEKQRLGGDVQSP NCPSEDVVITPESFGRDSSLTCAGNVSACDAPILSSSRSLDCR ESGKNGPHVYQDLLLSLGTTNSTLPPPFSLQSGILTLNPVAQG QPILTSLGSNQEEAYVTMSSFYQNQGSGSRSDPKPENPACPW TVLPAGDLPTHDGYLPSNIDDLPSHEAPLADSLEELEPQ | 204 |
| HAPD1(21-170).TpoR(N+8).IL7Ra(316-459).IL12Rb2(775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWLVLLIL VLISLVTALHLVLGLSAVLGLLLLRWQFPAHYRRLRHALWP SLPDLHRVLGQYLRDTAALSPPKATVSDTCEEVEPSLLEILPK SSERTPLPLLEARDEVEGFLQDTFPQQLEESEKQRLGGDVQSP NCPSEDVVITPESFGRDSSLTCAGNVSACDAPILSSSRSLDCR ESGKNGPHVYQDLLLSLGTTNSTLPPPFSLQSGILTLNPVAQG QPILTSLGSNQEEAYVTMSSFYQNQGSGSRSDPKPENPACPW TVLPAGDLPTHDGYLPSNIDDLPSHEAPLADSLEELEPQ | 205 |
| HAPD1(21-107).TPOR/MPLR(478-582, H499L, S505N, W515K).IL7Ra(316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LLLVLGLNAVLGLLLLRKQFPAHYRRLRHALWPSLPDLHRV LGQYLRDTAALSPPKATVSDTCEEVEPSLLEILPKSSERTPLPL LEARDEVEGFLQDTFPQQLEESEKQRLGGDVQSPNCPSEDVV ITPESFGRDSSLTCAGNVSACDAPILSSSRSLDCRESGKNGP HVYQDLLLSLGTTNSTLPPPFSLQSGILTLNPVAQGQPILTSLG SNQEEAYVTMSSFYQNQ | 206 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1.TpoR (478-582, S505N, W515K) .IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLNAVLGLLLLRKQFPAHYRRLRHALWPSLPDLHRV LGQYLRDTAALSPPKATVSDTCEEVEPSLLEILPKSSERTPLPL LEDEGVAGAPTGSSPQPLQPLSGEDDAYCTFPSRDDLLLFSPS GQGEFRALNARLPLNTDAYLSLQELQGQDPTHLV | 207 |
| HAPD1(21-107).TpoR (478-582).IL7Ra (316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLSAVLGLLLLRWQFPAHYRRLRHALWPSLPDLHRV LGQYLRDTAALSPPKATVSDTCEEVEPSLLEILPKSSERTPLPL LEARDEVEGFLQDTFPQQLEESEKQRLGGDVQSPNCPSEDVV ITPESFGRDSSLTCLAGNVSACDAPILSSSRSLDCRESGKNGP HVYQDLLLSLGTTNSTLPPPFSLQSGILTLNPVAQGQPILTSLG SNQEEAYVTMSSFYQNQ | 208 |
| HAPD1.TpoR (478-582).IL2Rbsmall(393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLSAVLGLLLLRWQFPAHYRRLRHALWPSLPDLHRV LGQYLRDTAALSPPKATVSDTCEEVEPSLLEILPKSSERTPLPL LEDEGVAGAPTGSSPQPLQPLSGEDDAYCTFPSRDDLLLFSPS GQGEFRALNARLPLNTDAYLSLQELQGQDPTHLV | 209 |
| HAPD1(21-107)TpoR (478-582, S505N, W515K).IL2Rbsmall(339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLNAVLGLLLLRKQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 214 |
| HAPD1(21-107).TpoR (478-582, H499L, S505N, W515K).IL2Rbsmall (339-379,393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LLLVLGLNAVLGLLLLRKQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 215 |
| HAPD1(21-170).TpoR (478-582) IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLSAVLGLLLLRWQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 216 |
| HAPD1(21-107).TpoR (N-7) .IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETALHLVLG LSAVLGLLLLRWQFPAHYRRLRHALWPSLPDLHRVLGQYLR DTAALSPPKATVSDTCEEVEPSLLEILPKSSERTPLPLLEDEGV AGAPTGSSPQPLQPLSGEDDAYCTFPSRDDLLLFSPSGQGEFR ALNARLPLNTDAYLSLQELQGQDPTHLV | 217 |
| HAPD1(21-107).TpoR (N-8) .IL2Rbsmall | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLHLVLGLS | 218 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| (393-433, 518-551) | AVLGLLLLRWQFPAHYRRLRHALWPSLPDLHRVLGQYLRDT AALSPPKATVSDTCEEVEPSLLEILPKSSERTPLPLLEDEGVAG APTGSSPQPLQPLSGEDDAYCTFPSRDDLLLFSPSGQGEFRAL NARLPLNTDAYLSLQELQGQDPTHLV | |
| HAPD1(21-107).TpoR (N-9).IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEDEGVAG APTGSSPQPLQPLSGEDDAYCTFPSRDDLLLFSPSGQGEFRAL NARLPLNTDAYLSLQELQGQDPTHLV | 219 |
| HAPD1(21-107).TpoR (N-7).IL2Rbsmall (339-379, 393-433,518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETALHLVLG LSAVLGLLLLRWQFPAHYRRLRHALWPSLPDLHRVLGQYLR DTAALSPPKATVSDTCEEVEPSLLEILPKSSERTPLPLLEQQDK VPEPASLSSNHSLTSCFTNQGYFFFHLPDALEIEACQDEGVAG APTGSSPQPLQPLSGEDDAYCTFPSRDDLLLFSPSGQGEFRAL NARLPLNTDAYLSLQELQGQDPTHLV | 220 |
| HAPD1(21-107).TpoR (N-8).IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEQQDKVP EPASLSSNHSLTSCFTNQGYFFFHLPDALEIEACQDEGVAGAP TGSSPQPLQPLSGEDDAYCTFPSRDDLLLFSPSGQGEFRALNA RLPLNTDAYLSLQELQGQDPTHLV | 221 |
| HAPD1(21-107).TpoR (N-9).IL2Rbsmall (339-379,393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEQQDKVP EPASLSSNHSLTSCFTNQGYFFFHLPDALEIEACQDEGVAGAP TGSSPQPLQPLSGEDDAYCTFPSRDDLLLFSPSGQGEFRALNA RLPLNTDAYLSLQELQGQDPTHLV | 222 |
| HAPD1(21-170).TpoR (478-582, H499L, S505N, W515K).IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LLLVLGLNAVLGLLLLRKQFPAHYRRLRHALWPSLPDLHRV LGQYLRDTAALSPPKATVSDTCEEVEPSLLEILPKSSERTPLPL LEDEGVAGAPTGSSPQPLQPLSGEDDAYCTFPSRDDLLLFSPS GQGEFRALNARLPLNTDAYLSLQELQGQDPTHLV | 223 |
| HAPD1(21-170).TpoR (478-582, S505N, W515K).IL7Ra (316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLNAVLGLLLLRKQFPAHYRRLRHALWPSLPDLHRV LGQYLRDTAALSPPKATVSDTCEEVEPSLLEILPKSSERTPLPL LEARDEVEGFLQDTFPQQLEESEKQRLGGDVQSPNCPSEDVV ITPESFGRDSSLTCAGNVSACDAPILSSSRSLDCRESGKNGP HVYQDLLLSLGTTNSTLPPPFSLQSGILTLNPVAQGQPILTSLG SNQEEAYVTMSSFYQNQ | 224 |

F. Expression of PD-1 Chimeric Cytokine Receptors

Provided herein are polynucleotides encoding any one of the chimeric cytokine receptors provided herein. Likewise, provided herein are expression vectors comprising such polynucleotides. In some embodiments, the vector is a viral vector. In some embodiments, the vector is not a viral vector.

In some embodiments, the vector comprises a polynucleotide encoding a PD-1 chimeric cytokine receptor, and a polynucleotide expressing a chimeric antigen receptor (CAR).

In some embodiments, expression of the chimeric cytokine receptor and the CAR are expressed as a single polypeptide chain, separated by a linker. FIGS. 1B and 1D show schematics of a vector that can be used to co-express the chimeric cytokine receptor and CAR of the disclosure. One or more STAT-recruiting domains may be joined in tandem to mimic signaling from one or more cytokines.

II. CAR-Bearing Immune Cells

Provided herein are engineered immune cells comprising a polynucleotide encoding a chimeric antigen receptor and a PD-1 chimeric cytokine receptor of the disclosure; and provided herein are engineered immune cells expressing a chimeric antigen receptor (CAR-I cell) and a PD-1 chimeric cytokine receptor of the disclosure. Examples of immune cells include T-cells, e.g., alpha/beta T-cells and gamma/delta T-cells, B cells, natural killer (NK) cells, natural killer T (NKT) cells, invariant NKT cells, mast cells, myeloic-derived phagocytes, dendritic cells, killer dendritic cells, macrophages, and monocytes. Immune cells also refer to cells derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

Accordingly in some embodiments, provided herein are CAR-T-cells comprising a PD-1 chimeric cytokine receptor of the disclosure.

In some embodiments, a CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain of a CAR specifically binds to a target of interest. The target of interest can be any molecule of interest, including, for example, without limitation any one or more of those presented in Table 11.

TABLE 11

List of targets of interest

BCMA
EGFRvIII
Flt-3
WT-1
CD20
CD23
CD30
CD38
CD70
CD33
CD133
MHC-WT1
TSPAN10
MHC-PRAME
Liv1
ADAM10
CHRNA2
LeY
NKG2D
CS1

TABLE 11-continued

List of targets of interest

CD44v6
ROR1
CD19
Claudin-18.2 (Claudin-18A2 or Claudin18 isoform 2)
DLL3 (Delta-like protein 3, *Drosophila* Delta homolog 3, Delta3)
Muc17 (Mucin17, Muc3, Muc3)
FAP alpha (Fibroblast Activation Protein alpha)
Ly6G6D (Lymphocyte antigen 6 complex locus protein G6d
c6orf23
G6D
MEGT1
NG25)
RNF43 (E3 ubiquitin-protein ligase RNF43, RING finger protein 43)
ErbB2 (HER2/neu)
carcinoembryonic antigen (CEA)
epithelial cell adhesion molecule (EpCAM)
epidermal growth factor receptor (EGFR)
CD40
disialoganglioside GD2
GD3
C-type lectin-like molecule-1 (CLL-1)
ductal-epithelial mucine
gp36
TAG-72
glycosphingolipids
glioma-associated antigen
β-human chorionic gonadotropin
alphafetoprotein (AFP)
lectin-reactive AFP
thyroglobulin
RAGE-1
MN-CA IX
human telomerase reverse transcriptase
RU1
RU2 (AS)
intestinal carboxyl esterase
mut hsp70-2
M-CSF
prostase
prostase specific antigen (PSA)
PAP
NY-ESO-1
LAGA-1a
p53
prostein
PSMA
survivin and telomerase
prostate-carcinoma tumor antigen-1 (PCTA-1)
MAGE
ELF2M
neutrophil elastase
ephrin B2
CD22
insulin growth factor (IGFl)-1
IGF-II
IGFI receptor
mesothelin
a major histocompatibility complex (MHC) molecule presenting a tumor-specific peptide epitope
5T4
O 1
Nkp30
tumor stromal antigens
the extra domain A (EDA) and extra domain B (EDB) of fibronectin and the AI domain of tenascin-C (TnC AI) and fibroblast associated protein (fap)
LRP6
melamona-associated Chondroitin Sulfate Proteoglycan (MCSP)
MARTI
MUC1
LMP2
Idiotype
NY-ESO-1
Ras mutant
gp100
proteinase 3
bcr-abl
tyrosinase TABLE 11-continued List of targets of interest hTERT
EphA2
ML-IAP
ERG
NA17
PAX3
ALK
Androgen receptor
a lineage-specific or tissue specific antigen such as CD3
CD4
CD8
CD24
CD25
CD34
CD79
CD116
CD117
CD135
CD123
CD138
CTLA-4
B7-1 (CD80)
B7-2 (CD86)
endoglin
a major histocompatibility complex (MHC) molecule
MUC16
PSCA
Trop2
CD171 (L1CAM)
CA9
STEAP1
VEGFR2

In some embodiments, the extracellular ligand-binding domain of a CAR comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988) (e.g. glycine-serine containing linkers). In general, linkers can be short, flexible polypeptides and are generally comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The intracellular signaling domain of a CAR according to the invention is responsible for intracellular signaling following the binding of extracellular ligand-binding domain to the target resulting in the activation of the immune cell and immune response (Signals 1 and/or 2). The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3 signaling domain. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP 006130.1).

CARs are expressed on the surface membrane of the cell. Thus, the CAR comprises a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The transmembrane domain can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, said transmembrane and hinge domains comprise a part of human CD8α chain. In some embodiments, CARs disclosed herein can comprise an extracellular ligand-binding domain that specifically binds BCMA, CD8α human hinge and transmembrane domains, the CD3ζ signaling domain, and 4-1BB signaling domain.

In some embodiments, a CAR can be introduced into an immune cell as a transgene via a plasmid vector. In some embodiments, the plasmid vector can also contain, for example, a selection marker which provides for identification and/or selection of cells which received the vector.

Table 8 provides exemplary sequences of CAR components that can be used in the CARs disclosed herein.

TABLE 8

Exemplary Sequences

| Domain | Amino acid sequence | SEQ ID NO: |
|---|---|---|
| V5 epitope tag | IPNPLLGLDST | 122 |
| 2173 scFv | ETQLVQSGAEVKKPGESLRISCKGSGFNIEDYYIH WVRQMPGKGLEWMGRIDPENDETKYGPIFQGH VTISADTSINTVYLQWSSLKASDTAMYYCAFRG GVYWGQGTTVTVSSGGGGSGGGGSGGGGSGGG GSDVVMTQSPDSLAVSLGERATINCKSSQSLLDS DGKTYLNWLQQKPGQPPKRLISLVSKLDSGVPD RFSGSGSGTDFTLTISSLQAEDVAVYYCWQGTHF PGTFGGGTKVEIK | 123 |
| CD8 hinge and transmembrane | TTTPAPRPPTPAPTIASQPLSLRPEACRPAAGGAV HTRGLDFACDIYIWAPLAGTCGVLLLSLVITLYC | 124 |
| 4-1BB intracellular signaling | KRGRKKLLYIFKQPFMRPVQTTQEEDGCSCRFPE EEEGGCEL | 125 |
| CD3z intracellular signaling | RVKFSRSADAPAYQQGQNQLYNELNLGRREEYD VLDKRRGRDPEMGGKPRRKNPQEGLYNELQKD KMAEAYSEIGMKGERRRGKGHDGLYQGLSTAT KDTYDALHMQALPPR | 126 |
| BFP (blue fluorescent protein) | MSELIKENMHMKLYMEGTVDNHHFKCTSEGEG KPYEGTQTMRIKVVEGGPLPFAFDILATSFLYGS KTFINHTQGIPDFFKQSFPEGFTWERVTTYEDGG VLTATQDTSLQDGCLIYNVKIRGVNFTSNGPVM QKKTLGWEAFTETLYPADGGLEGRNDMALKLV GGSHLIANIKTTYRSKKPAKNLKMPGVYYVDYR LERIKEANNETYVEQHEVAVARYCDLPSKLGHK LN | 127 |
| P2A | GSGATNFSLLKQAGDVEENPGP | 128 |

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of any one of CARs disclosed herein may comprise one or more epitopes specific for (specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to a target of interest and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, allowing for depletion provides a safety switch in case of deleterious effects, e.g., upon administration to a subject.

Methods of preparing immune cells for use in immunotherapy are also provided herein. In some embodiments, the methods comprise introducing a PD-1 chimeric cytokine receptor and a CAR into immune cells, and expanding the cells. In some embodiments, the invention relates to a method of engineering an immune cell comprising: providing a cell and expressing a PD-1 chimeric cytokine receptor, and expressing at the surface of the cell at least one CAR. In some embodiments, the method comprises: transfecting the cell with at least one polynucleotide encoding a PD-1 chimeric cytokine receptor, and at least one polynucleotide encoding a CAR, and expressing the polynucleotides in the cell. In some embodiments, the method comprises: transfecting the cell with at least one polynucleotide encoding a PD-1 chimeric cytokine receptor, at least one polynucleotide encoding a CAR, and expressing the polynucleotides in the cell.

In some embodiments, the polynucleotides encoding the PD-1 chimeric cytokine receptor and CAR are present in one or more expression vectors for stable expression in the cells. In some embodiments, the polynucleotides are present in viral vectors for stable expression in the cells. In some embodiments, the viral vectors may be for example, lentiviral vectors or adenoviral vectors.

In some embodiments, polynucleotides encoding polypeptides according to the present disclosure can be mRNA which is introduced directly into the cells, for example by electroporation. In some embodiments, CytoPulse electroporation technology, such as PulseAgile, can be used to transiently permeabilize living cells for delivery of material into the cells (e.g. U.S. Pat. No. 6,078,490; PCT/US2011/000827; and PCT/US2004/005237). Parameters can be modified in order to determine conditions for high transfection efficiency with minimal mortality.

Also provided herein are methods of transfecting an immune cell, e.g a T-cell. In some embodiments, the method comprises: contacting a T-cell with RNA and applying to the T-cell an agile pulse sequence. In some embodiments, a method of transfecting an immune cell (e.g. T-cell) comprising contacting the immune cell with RNA and applying to the cell an agile pulse sequence.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, deoxycytidine kinase (DCK), PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or CRISPR-based endonuclease (e.g Cas-9 or Cas12a).

In another aspect, a step of genetically modifying cells can comprise: modifying immune cells (e.g. T-cells) by inactivating at least one gene expressing a target for an immunosuppressive agent, and; expanding the cells, optionally in presence of the immunosuppressive agent.

In some embodiments, the engineered immune cells (e.g. T-cells) provided herein exhibit improved cytotoxicity, increased expansion, and/or increased levels of memory phenotype markers upon contact with a PD-L1 or PD-L2 ligand or PD-1 antibody that binds to the ectodomain of the PD-1 chimeric cytokine receptor relative to engineered immune cells that do not express the PD-1 chimeric cytokine receptor.

In some embodiments, the engineered immune cells (e.g. T-cells) provided herein exhibit (i) increased in vivo persistence, (ii) increased STAT activation, (iii) increased cytotoxicity, (iv) increased levels of memory phenotype markers, (v) increased expansion (proliferation), or combinations of these functional features, upon contact with a PD-L1 or PD-L2 ligand or PD-1 antibody that binds to the ectodomain of the PD-1 chimeric cytokine receptor relative to engineered immune cells that do not express the PD-1 chimeric cytokine receptor. In some embodiments, the improvement in the one or more functional features described herein is dose-dependent, i.e., the functional activity of the immune cell comprising the PD-1 chimeric cytokine receptors increases upon contact with increasing doses of the PD-L1/PD-L2/PD-1 antibody. In some embodiments, STAT5 activated by the engineered immune cell comprising one or more PD-1 chimeric cytokine receptors disclosed are STAT1, STAT2, STAT3, STAT4, STAT5, STAT6, or combinations thereof. In one embodiment, memory phenotype markers increased or maintained by the immune cell comprising the inducible chimeric cytokine receptor include stem cell memory (Tscm) marker and central memory (Tcm) marker.

In some embodiments, the improvement in one or more functional features exhibited by an engineered immune cell comprising an inducible chimeric cytokine receptor provided herein is at least about 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, 100 fold, 125 fold, 150 fold, 200 fold, 250 fold, 300 fold, 350 fold, 400 fold, 450 fold, or even about 10500 fold, including values and ranges therebetween, compared to an immune cell that does not express the PD-1 chimeric cytokine receptor.

In some embodiments, the improvement in one or more functional features exhibited by an engineered immune cell comprising a PD-1 chimeric cytokine receptor provided herein is at least about 10%, 20%, 25%, 30%, 35%, 40%, 45%, 50%, 55%, 60%, 70%, 75%, 80%, 90%, 100%, 125%, 150%, 200%, 250%, 300%, 350%, 400%, or even about 80%500%, including values and ranges therebetween, compared to an engineered immune cell that does not express the PD-1 chimeric cytokine receptor.

III. Therapeutic Methods

Provided herein are pharmaceutical compositions comprising cells bearing the chimeric cytokine receptors and CARs of the disclosure.

Engineered PD-1 chimeric cytokine receptor-bearing and CAR-bearing immune cells (e.g. T-cells) obtained by the methods described above, or cell lines derived from such engineered immune cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer is a solid cancer. In some embodiments the cancer is a liquid cancer. The cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, engineered immune cells, or cell line derived from the engineered immune cells, can be used in the manufacture of a medicament for treatment of a disorder in a subject in need thereof. In some embodiments, the disorder can be, for example, a cancer, an autoimmune disorder, or an infection.

Also provided herein are methods for treating subjects in need of such treatment.

As used herein, the term "subject" refers to any vertebrate including, without limitation, humans and other primates (e.g., chimpanzees, cynomologous monkeys, and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In exemplary embodiments, the subject is a human.

In some embodiments the method comprises providing immune cells of the disclosure, bearing the PD-1 chimeric cytokine receptors and CARs described herein to a subject in need thereof.

In some embodiments, PD-1 chimeric cytokine receptor and CAR-bearing T-cells of the invention can undergo robust in vivo T-cell expansion and can persist for an extended amount of time.

Methods of treatment of the invention can be ameliorating, curative or prophylactic. The method of the invention may be either part of an autologous immunotherapy or part of an allogenic immunotherapy treatment.

In another aspect, the invention provides a method of inhibiting tumor growth or progression in a subject who has a tumor, comprising administering to the subject an effective amount of PD-1 chimeric cytokine receptor-expressing and CAR-expressing immune cells as described herein. In another aspect, the invention provides a method of inhibiting or preventing metastasis of cancer cells in a subject, comprising administering to the subject in need thereof an effective amount of engineered immune cells as described herein. In another aspect, the invention provides a method of inducing tumor regression in a subject who has a tumor, comprising administering to the subject an effective amount of engineered immune cells as described herein.

In some embodiments, the engineered T-cells herein can be administered parenterally in a subject.

Also provided is the use of any of the engineered T-cells provided herein in the manufacture of a medicament for the treatment of cancer or for inhibiting tumor growth or progression in a subject in need thereof.

In some embodiments, treatment can be administrated into subjects undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. Cells bearing the CARs of the disclosure or the pharmaceutical compositions thereof may be administered via one or more of the following routes of administration: intravenous, intraocular, intravitreal, intramuscular, subcutaneous, topical, oral, transdermal, intraperitoneal, intraorbital, by implantation, by inhalation, intrathecal, intraventricular, via the ear, or intranasal.

In some embodiments the administration of the cells or population of cells (bearing the chimeric cytokine receptors and CARs of the disclosure) can comprise administration of, for example, about $10^4$ to about $10^9$ cells per kg body weight including all integer values of cell numbers within those ranges. In some embodiments the administration of the cells or population of cells can comprise administration of about $10^4$ to $10^5$ cells per kg body weight, $10^5$ to $10^6$ cells per kg body weight, $10^6$ to $10^7$ cells per kg body weight, $10^7$ to $10^8$ cells per kg body weight, or $10^8$ to $10^9$ cells per kg body weight. The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

The methods can further comprise administering one or more agents to a subject prior to administering the engineered immune cells bearing a CAR and a PD-1 chimeric cytokine receptor provided herein. In certain embodiments, the agent is a lymphodepleting (preconditioning) regimen. For example, methods of lymphodepleting a subject in need of such therapy comprise administering to the subject specified beneficial doses of cyclophosphamide (between 200 mg/m²/day and 2000 mg/m²/day, about 100 mg/m²/day and about 2000 mg/m²/day; e.g., about 100 mg/m²/day, about 200 mg/m²/day, about 300 mg/m²/day, about 400 mg/m²/day, about 500 mg/m²/day, about 600 mg/m²/day, about 700 mg/m²/day, about 800 mg/m²/day, about 900 mg/m²/day, about 1000 mg/m²/day, about 1500 mg/m²/day or about 2000 mg/m²/day) and specified doses of fludarabine (between 20 mg/m²/day and 900 mg/m²/day, between about 10 mg/m²/day and about 900 mg/m²/day; e.g., about 10 mg/m²/day, about 20 mg/m²/day, about 30 mg/m²/day, about 40 mg/m²/day, about 40 mg/m²/day, about 50 mg/m²/day, about 60 mg/m²/day, about 70 mg/m²/day, about 80 mg/m²/day, about 90 mg/m²/day, about 100 mg/m²/day, about 500 mg/m²/day or about 900 mg/m²/day). An exemplary dosing regimen involves treating a subject comprising administering daily to the patient about 300 mg/m²/day of cyclophosphamide in combination or before or after administering about 30 mg/m²/day of fludarabine for three days prior to administration of a therapeutically effective amount of engineered immune cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3 or more days. The antibody can be administered in combination with, before, or after administration of other elements of a lymphodepletion regime (e.g., cyclophosphamide and/or fludarabine).

In certain embodiments, compositions comprising CAR-expressing immune effector cells disclosed herein may be administered in conjunction with any number of chemotherapeutic agents.

IV. Kits and Articles of Manufacture

The present disclosure provides kits comprising any one or more of the PD-1 chimeric cytokine receptors and PD-1 chimeric cytokine receptors-bearing cells described herein, and pharmaceutical compositions thereof. The present disclosure also provides articles of manufacture comprising any one or more of the PD-1 chimeric cytokine receptors and PD-1 chimeric cytokine receptors-bearing CAR-I cells described herein, pharmaceutical compositions thereof, and kits described herein.

The following examples are included for illustrative purposes and are not intend to limit the scope of the disclosure.

All patent and non-patent documents referenced throughout this disclosure are incorporated by reference herein in their entirety for all purposes.

EXAMPLES

In referring to the chimeric cytokine receptors of the disclosure it is noted that certain figures refer to a "switch." As used herein, a "switch" is used interchangeably with a "chimeric cytokine receptor".

The following notations are used throughout the drawings and examples.

FKBP switch=a FKBP chimeric cytokine receptor
WT PD1 switch=a chimeric cytokine receptor with a wild type PD-1 ectodomain
2×PD1 switch=a chimeric cytokine receptor with 2 PD-1 ectodomains in tandem
3×PD1 switch=a chimeric cytokine receptor with 3 PD-1 ectodomains in tandem
HA PD1 switch=a chimeric cytokine receptor with a high affinity PD-1 ecotodomain
HA PD1 DN=a chimeric cytokine receptor with a dominant negative high affinity PD-1 domain

Example 1: Coupling of PD-1 Engagement with Cytokine Signaling

To couple simultaneous PD-1 engagement with cytokine signaling, a PD-1 chimeric cytokine receptor was constructed, composed of the following modules: (i) the wild type (WT) PD-1 ectodomain (21-207), (ii) a transmembrane domain with an intracellular portion having a JAK2-activating domain and (iii) STAT-recruiting domains comprising Stat-recruiting (Stat-activating) domains from cytokine receptor tails (cytotails). With this design, it was determined whether clustering or dimerization of the PD-1 chimeric cytokine receptor, in response to PD-1 ligands or anti-PD-1 antibodies, respectively, could activate the JAK-Stat pathway and mimic cytokine signaling. In order to minimize the transgene payload in the lentiviral vector, JAK2-activating domains derived from natural cytokine receptors known to signal as homodimers, such as TpoR (TPOR/MPLR(478-582)), GCSFR (GCSFR(614-710)) and GP130 (GP130(609-700)), were selected for initial evaluation.

Two Stat-activating cytoplasmic domains derived from IL7R(316-459) and IL12Rb(775-825) were linked in tandem mimic signaling in response to IL7 and IL12, respectively. To demonstrate the utility of the PD-1 chimeric cytokine receptor in the context of CAR-T-cells, the PD-1 chimeric cytokine receptor was cloned into a lentiviral vector encoding a second generation EGFRvIII-specific CAR (2173scFv; described in Sci Transl Med. 2015 Feb. 18; 7(275): 275ra22.); furthermore, to permit stoichiometric co-expression of the PD-1 chimeric cytokine receptor and the CAR, both genes were linked via a P2A peptide linker. To facilitate the detection of transduced cells, a v5 epitope tag (KPIPNPLLGLDST (SEQ ID NO: 167)) was inserted between the scFv and CD8 hinge domain of the CAR.

A HEK293T-cell reporter assay was used to test the inducibility and magnitude of cytokine signaling. Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was used, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor and that were left untreated.

Figure 1B:
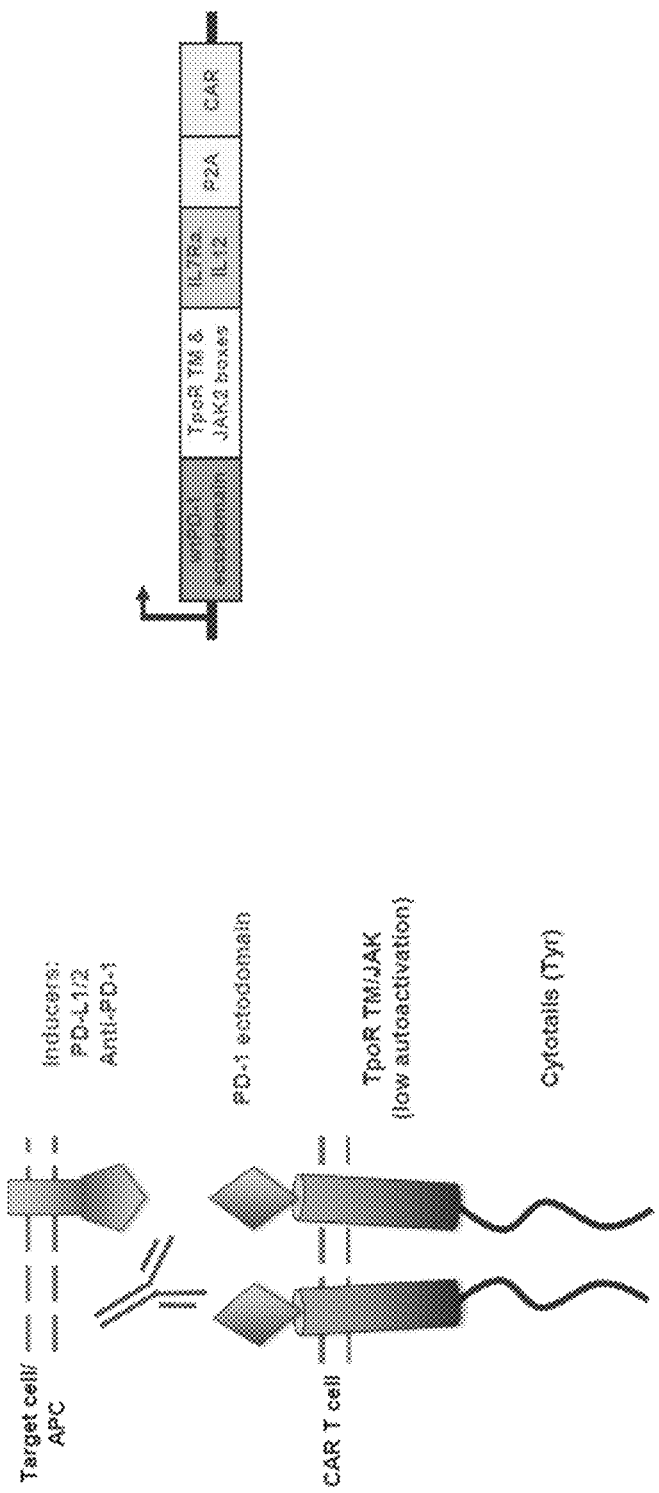
FIG. 1B shows a schematic of the PD-1 chimeric cytokine receptor of the disclosure with a wild type PD-1 ectodomain.
Figure 1C:
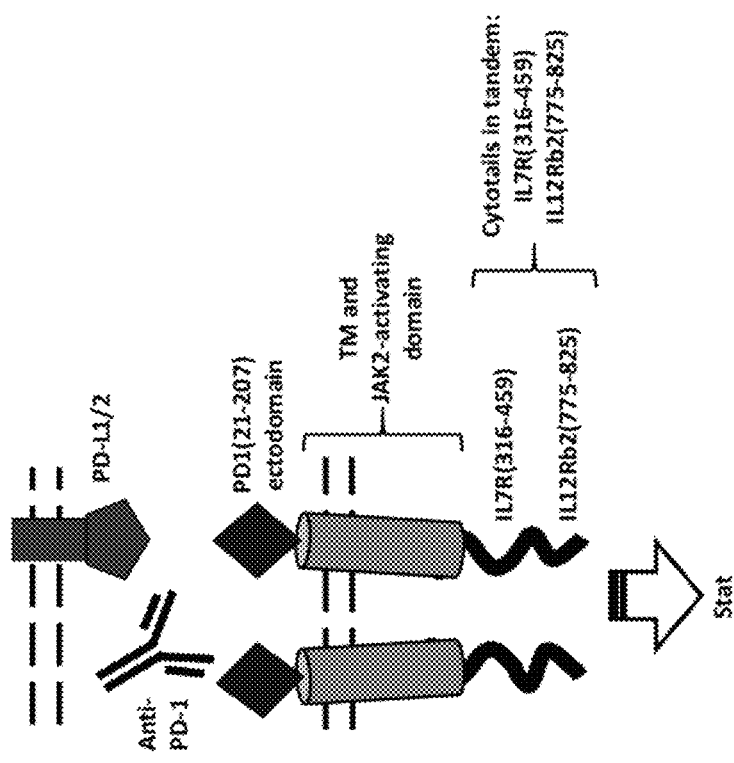
FIG. 1C shows a schematic of an exemplary PD-1 chimeric cytokine receptor of the disclosure.
Figure 1D:
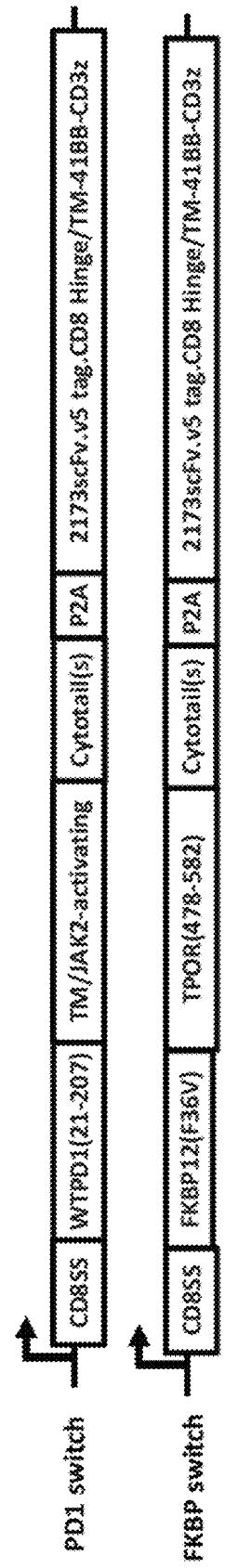
FIG. 1D shows a schematic of the PD-1 chimeric cytokine receptor—CAR vector, and the control FKBP chimeric cytokine receptor CAR vector.

FIGS. 1A-C show schematics of the various embodiments of the PD-1 chimeric cytokine receptor.

FIG. 1B shows a schematic of the PD-1 chimeric cytokine receptor CAR vector. FIG. 1D shows a schematic of the PD-1 chimeric cytokine receptor CAR vector, and the positive control FKBP chimeric cytokine receptor CAR vector.

Figure 2B:
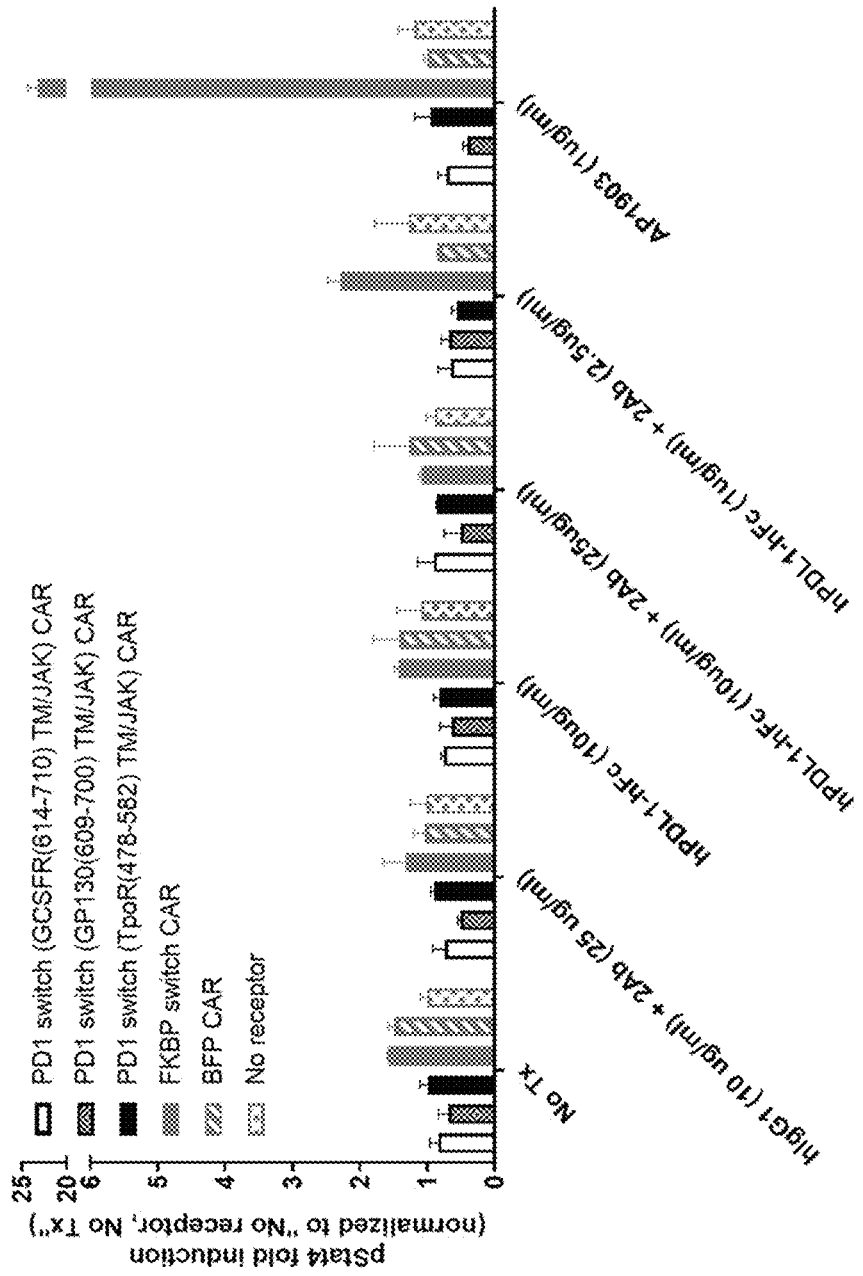
Figure 2D:
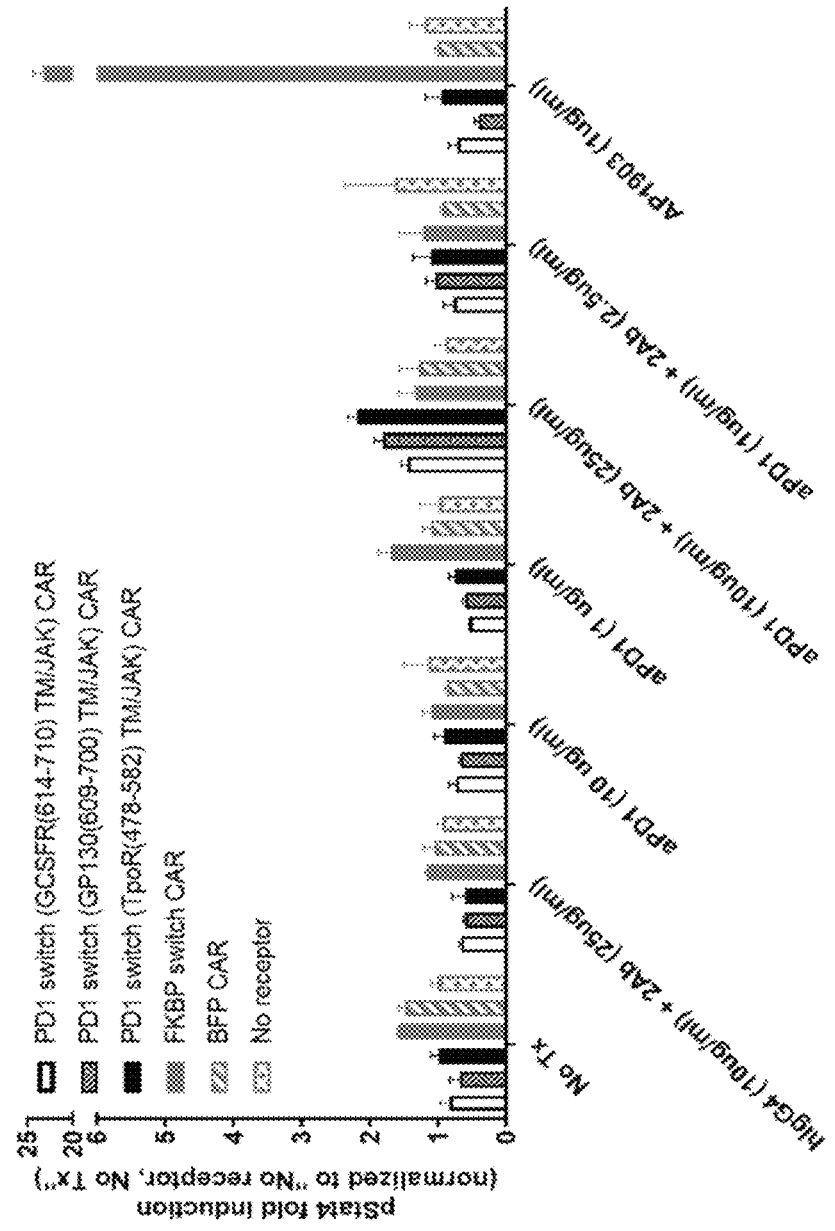

FIGS. 2A-D show Stat reporter activity in response to PD-L1-Fc (FIGS. 2A-B) and anti-PD-1 (FIGS. 2C-D). FIGS. 2A-B show that as compared to their untreated counterparts, PD-1 chimeric cytokine receptors induced weak Stat reporter activity in response to high concentrations of crosslinked PD-L1 (i.e. hPD-L1-Fc (10 ug/ml)+2Ab (25 ug/ml)). FIGS. 2C-D show that as compared to their untreated counterparts, PD-1 chimeric cytokine receptors induced weak Stat reporter activity in response to high concentrations of crosslinked anti-PD-1 (i.e. aPD-1 (10 ug/ml)+2Ab (25 ug/ml)), with the TpoR(478-582) TM/JAK variant showing the best response. Although the FKBP chimeric cytokine receptor positive control showed basal activity in the absence of AP1903, it induced high Stat reporter activity in response to AP1903.

Similar experiments were then carried out in the context of primary human CAR-T-cells. To make lentivirus encoding PD-1 chimeric cytokine receptor CARs, HEK293T-cells were plated at 0.45 million cells per mL in 2 mL of DMEM (Gibco) supplemented with 10% FBS (Hyclone) per well of a 6-well plate on Day −1. On Day 0, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. On Day 0, purified T-cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 1, the media from each well of HEK293T-cells in the 6-well plate was replaced with 2 mL per well of T-cell transduction media, i.e., X-Vivo-15 supplemented with 10% FBS. On Day 2, T-cells were resuspended at 0.5 million cells per mL in 1 mL of T-cell transduction media per well of a Grex-24 plate. The lentiviral supernatants from HEK293T-cells were harvested and passed through a 0.45 micron filter (EMD Millipore) to remove cell debris, and then added to the T-cells along with 100 IU/mL human IL-2. On Day 5, 4.5 mL of T-cell expansion media, i.e., X-Vivo-15 supplemented with 5% human AB serum (Gemini Bio) and 100 IU/mL human IL-2 was added to each well of a Grex-24 plate. Cells were expanded into larger G-Rex vessels (Wilson Wolf) as needed using T-cell expansion media. On Day 13 or 14, transduction efficiency and PD-1 chimeric cytokine receptor expression was determined by detecting the percentage of T-cells that bound a FITC-conjugated v5 tag monoclonal antibody (Thermo Fisher) and a PE/Cy7-conjugated anti-human PD-1 (Biolegend) using flow cytometry. On Day 14 or 15, the CAR-T-cell products were cryopreserved and thawed as needed for further assays.

Figure 3:
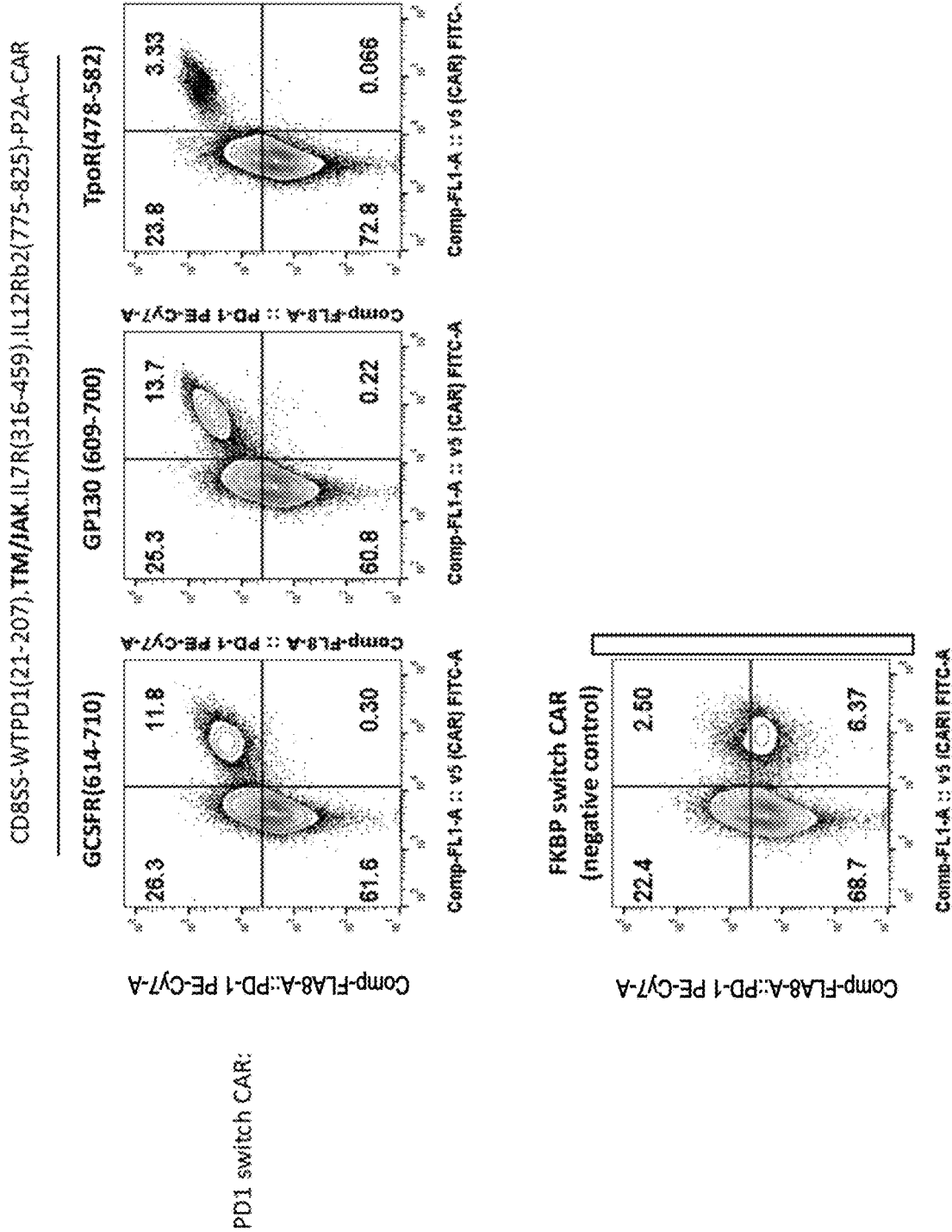
FIG. 3 shows CAR and PD-1 chimeric cytokine receptor co-expression on the Day 14 following transduction of the CAR and the PD-1 chimeric cytokine receptor.

FIG. 3 shows CAR and PD-1 chimeric cytokine receptor expression on the Day 14 CAR-T-cell product. As compared to FKBP chimeric cytokine receptor CAR-T-cells on which little to no PD-1 was detected, high levels of PD-1 was detected on PD-1 chimeric cytokine receptor CAR-T-cells, indicating that the CAR and PD-1 chimeric cytokine receptor were coexpressed.

To determine the inducibility and magnitude of cytokine signaling in PD-1 chimeric cytokine receptor CAR-T-cells, the thawed CAR-T-cell product was serum starved in 100 uL serum-free RPMI (Corning) for 4 hours in humidified incubator at 37° C. with 5% $CO_2$, then treated with anti-PD-1 (10 ug/mL Nivolumab; Selleck Chemical), recombinant human PD-L1-Fc (10 ug/mL; Biolegend), anti-Human IgG Fc gamma secondary antibody (25 ug/mL; Thermo Fisher) for 1 hour. 40 minutes into the treatment, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. After 1 hour of treatment, cells were fixed by the addition of 35 uL of 16% paraformaldehyde was added to each 100 uL sample and allowed to incubate for 15 minutes at 37° C. Cells were then washed three times with PBS, and permeabilized in 100% cold methanol for 1 or 2 nights at −20° C. On the day of FACS analysis, cells were washed three times with PBS, Fc-blocked, and stained with AlexaFluor647-conjugated anti-mouse/human Stat5 (pY694) (BD Biosciences) diluted in PBS+1% BSA. After a 1 hour incubation at room temperature in the dark, cells were washed three times before FACS analysis.

Figure 4A:
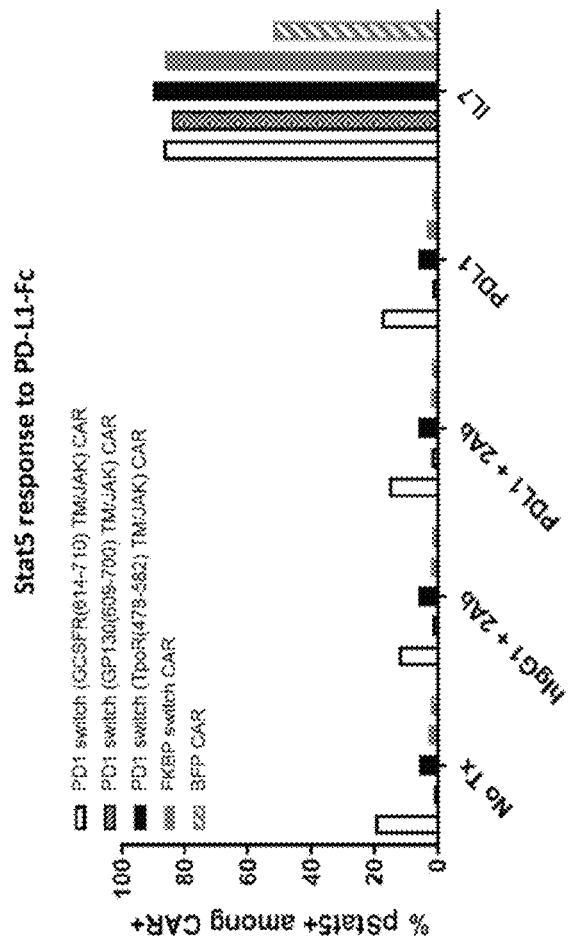
FIGS. 4A-4B show phospho-Stat5 staining in human CAR-T-cells following the treatment with PD-L1-Fc (FIG. 4A) or anti-PD-1 (FIG. 4B).
Figure 4B:
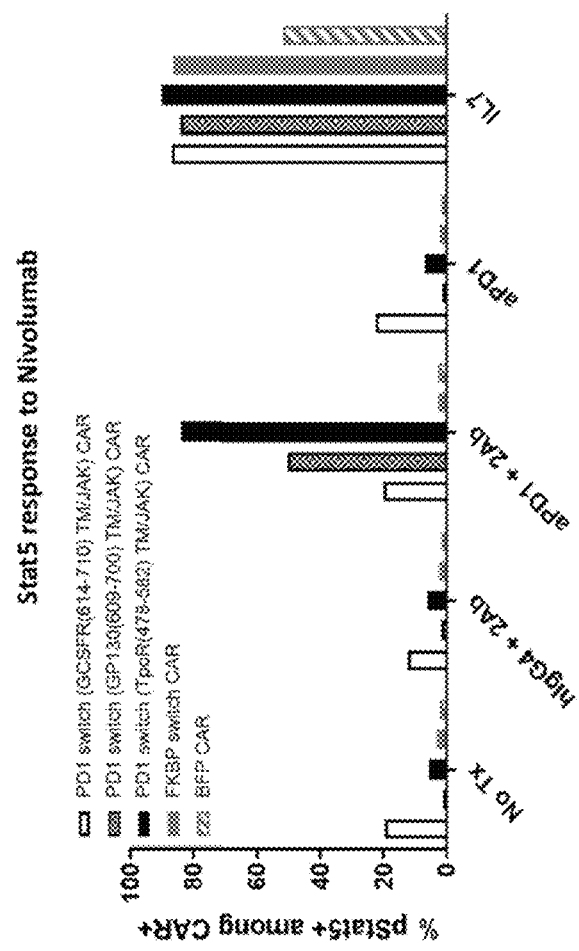

FIGS. 4A-B show phospho-Stat5 staining in human CAR-T-cells following the treatment with PD-L1-Fc (FIG. 4A) or anti-PD-1 (FIG. 4B). PD-1 chimeric cytokine receptor CAR-T-cells bearing the GCSFR(614-710) TM/JAK2-activating domain showed high basal activity in the absence of treatment, and no induction of pStat5 in the presence of treatment. PD-1 chimeric cytokine receptor CAR-T-cells bearing the GP130(609-700) TM/JAK2-activating domain showed the lowest basal activity in the absence of treatment, no pStat5 induction in response to PD-L1 or anti-PD-1, and moderate pStat5 induction in response to crosslinked anti-PD-1. PD-1 chimeric cytokine receptor CAR-T-cells bearing the TpoR(478-582) TM/JAK2-activating domain showed the moderate basal activity in the absence of treatment, no pStat5 induction in response to PD-L1 or anti-PD-1, and strong pStat5 induction in response to crosslinked anti-PD-1.

Example 2: Optimization of the PD-1 Chimeric Cytokine Receptor

Compared to the high affinity interaction between Nivolumab and PD-1 (<10 pM), PD-1 binds to PD-L1 and PD-L2 through a low-affinity (1-10 uM), monomeric interaction. The observation that crosslinked anti-PD-1 (Nivolumab) was able to activate the PD-1 chimeric cytokine receptor bearing the TpoR(478-582) TM/JAK2-activating domain indicating that PD-1 chimeric cytokine receptor activation could be made more efficient by enhancing its affinity or avidity of interaction with its inducer (PD-1 ligands or anti-PD-1). To increase the avidity of the PD-1 chimeric cytokine receptor, multiple WT PD-1 ectodomains were engineered in tandem. To increase the affinity of the PD-1 chimeric cytokine receptor, mutations to the PD-1 ectodomains were introduced, aimed at increasing binding affinity to its ligands (henceforth referred to as "high affinity (HA) PD-1").

To demonstrate the utility of these PD-1 chimeric cytokine receptors in the context of CAR-T-cells, each PD-1 chimeric cytokine receptor was cloned into a lentiviral vector encoding a second generation EGFRvIII-specific CAR (2173scFv; described in Sci Transl Med. 2015 Feb. 18; 7(275): 275ra22.); furthermore, to permit stoichiometric co-expression of the PD-1 chimeric cytokine receptor and the CAR, both genes were linked via a P2A peptide linker. To facilitate the detection of transduced cells, a v5 epitope tag (KPIPNPLLGLDST (SEQ ID NO: 167)) was inserted between the scFv and CD8 hinge domain.

Figure 5A:
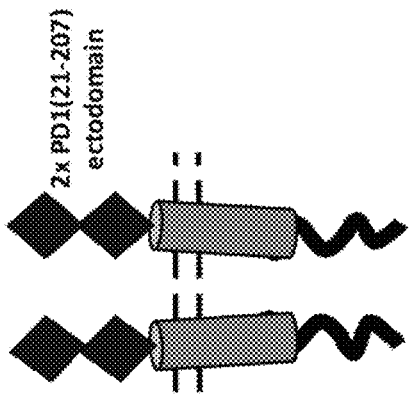
FIGS. 5A-5D show a schematic of PD-1 chimeric cytokine receptors with various ectodomains engineered for enhanced avidity or affinity.
Figure 5B:
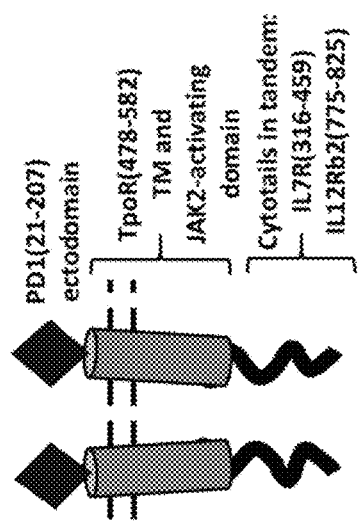
Figure 5D:
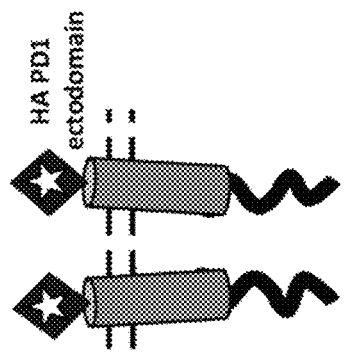
Figure 5C:
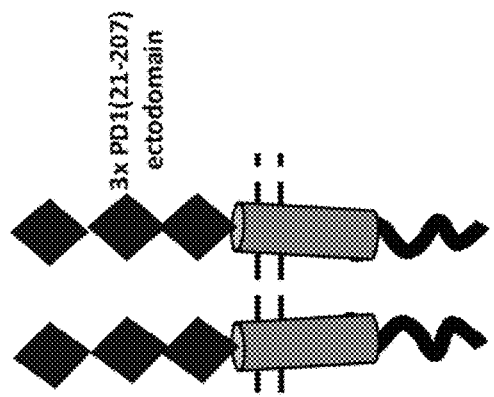

FIGS. 5A-D show a schematic of PD-1 chimeric cytokine receptors with various ectodomains engineered for enhanced avidity or affinity. FIG. 5A shows the prototypic WT PD-1 chimeric cytokine receptor bearing the TpoR(478-582) TM/JAK2-activating domain; FIG. 5B shows the 2×PD-1 chimeric cytokine receptor bearing two WT PD-1 ectodomains in tandem; FIG. 5C shows the 3×PD-1 chimeric cytokine receptor bearing three WT PD-1 ectodomains in tandem; FIG. 5D shows the high affinity (HA) PD-1 chimeric cytokine receptor with ectodomain mutations.

A HEK293T-cell reporter assay was used to test the inducibility and magnitude of cytokine signaling. Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was used, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor receptor and that were left untreated.

Figure 6A:
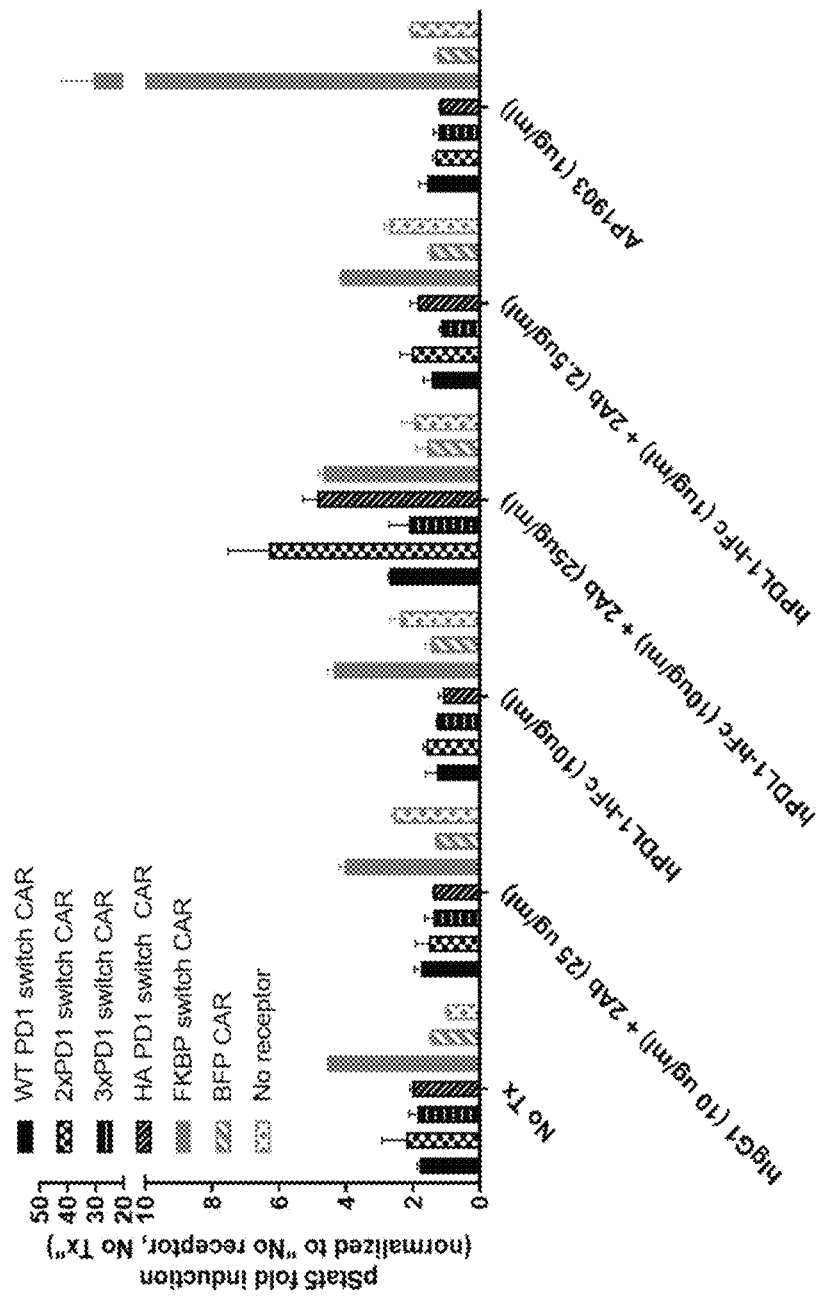
FIGS. 6A-6D show the response of PD-1 chimeric cytokine receptors bearing ectodomain modifications following treatment with PD-L1-Fc (FIGS. 6A-6B) and anti-PD-1 (FIGS. 6C-D).
Figure 6B:
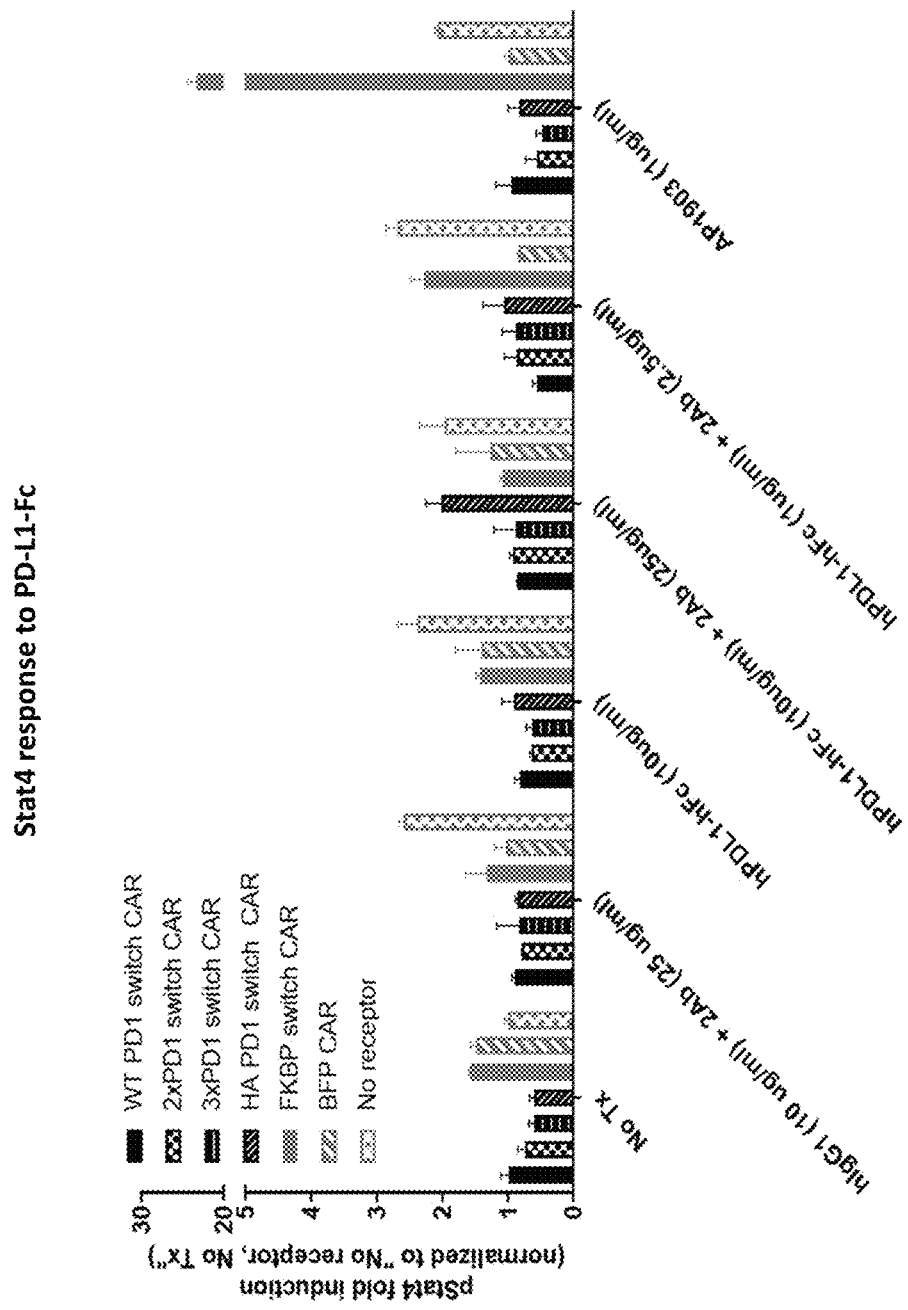
Figure 6C:
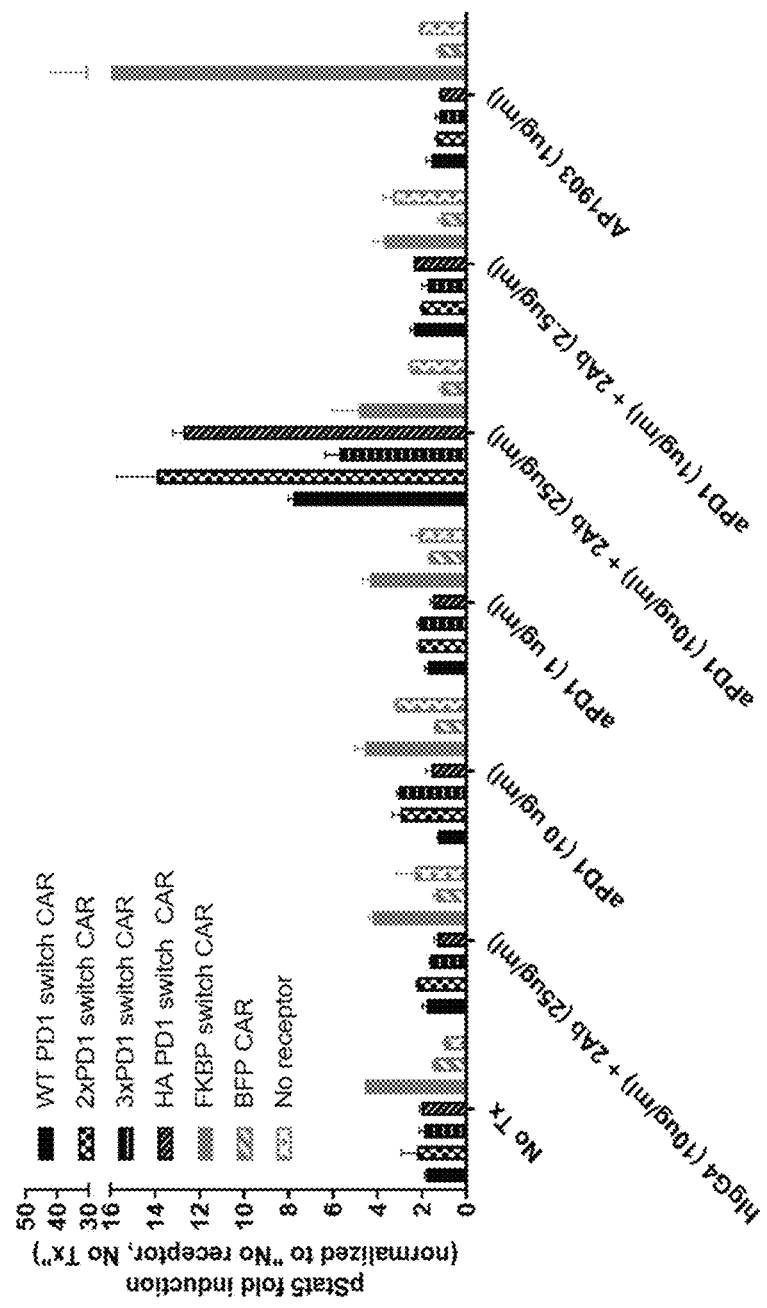
Figure 6D:
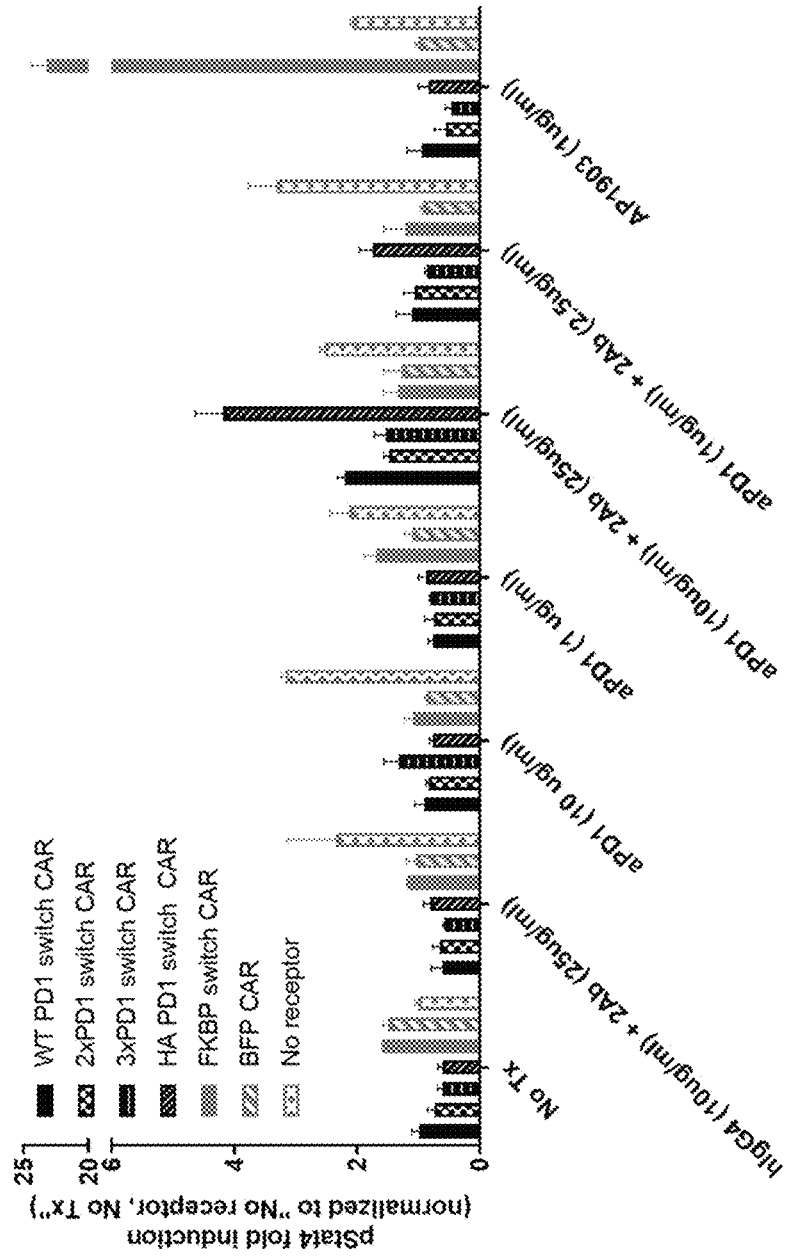

FIGS. 6A-D show the response of PD-1 chimeric cytokine receptors bearing ectodomain modifications following treatment with PD-L1-Fc (FIGS. 6A-B) and anti-PD-1 (FIGS. 6C-D). FIGS. 6A-B show that compared to its untreated counterpart and to the WT PD-1 chimeric cytokine receptor, the HA PD-1 chimeric cytokine receptor permitted enhanced Stat5 (FIG. 6A) and Stat4 (FIG. 6B) reporter activity in response to high concentrations of crosslinked PD-L1-Fc; whereas the 2×PD-1 chimeric cytokine receptor permitted enhanced Stat5, but not Stat4, reporter activity. FIGS. 6C-d show that compared to its untreated counterpart and to the WT PD-1 chimeric cytokine receptor, the HA PD-1 chimeric cytokine receptor permitted enhanced Stat5 (FIG. 6C) and Stat4 (FIG. 6D) reporter activity in response to high concentrations of crosslinked anti-PD-1; whereas the 2×PD-1 chimeric cytokine receptor permitted enhanced Stat5, but not Stat4, reporter activity. These indicated that enhancing the avidity of the ectodomain via tandem PD-1, or enhancing the affinity of the ectodomain via mutations, increase the responsiveness of the PD-1 chimeric cytokine receptor. Furthermore, the fact that the HA PD-1 chimeric cytokine receptor may be activated by anti-PD-1 indicates that the mutant HA ectodomain retains the ability to bind anti-PD-1 (i.e. Nivolumab).

Similar experiments were then carried out in the context of primary human CAR-T-cells. To make lentivirus encoding PD-1 chimeric cytokine receptor CARs, HEK293T-cells were plated at 0.45 million cells per mL in 2 mL of DMEM (Gibco) supplemented with 10% FBS (Hyclone) per well of a 6-well plate on Day −1. On Day 0, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. On Day 0, purified T-cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 1, the media from each well of HEK293T-cells in the 6-well plate was replaced with 2 mL per well of T-cell transduction media, i.e., X-Vivo-15 supplemented with 10% FBS. On Day 2, T-cells were resuspended at 0.5 million cells per mL in 1 mL of T-cell transduction media per well of a Grex-24 plate. The lentiviral supernatants from HEK293T-cells were harvested and passed through a 0.45 micron filter (EMD Millipore) to remove cell debris, and then added to the T-cells along with 100 IU/mL human IL-2. On Day 5, 4.5 mL of T-cell expansion media, i.e., X-Vivo-15 supplemented with 5% human AB serum (Gemini Bio) and 100 IU/mL human IL-2 was added to each well of a Grex-24 plate. Cells were expanded into larger G-Rex vessels (Wilson Wolf) as needed using T-cell expansion media. On Day 13 or 14, transduction efficiency and PD-1 chimeric cytokine receptor expression was determined by detecting the percentage of T-cells that bound a FITC-conjugated v5 tag monoclonal antibody (Thermo Fisher) using flow cytometry. On Day 14 or 15, the CAR-T-cell products were cryopreserved and thawed as needed for further assays.

To determine if the HA PD-1 ectodomain indeed enhances binding affinity to PD-L1, while retaining interactions with clinically-approved anti-PD-1 antibodies, the ability of HA PD-1 chimeric cytokine receptor CAR-T-cells to bind Nivolumab and Pembrolizumab was tested in a cell-binding assay. Briefly, WT PD-1 chimeric cytokine receptor CAR-T-cells or HA PD-1 chimeric cytokine receptor CAR-T-cells were Fc-blocked, and then incubated with the indicated concentrations of anti-PD-1 (i.e. Nivolumab or Pembrolizumab) diluted in PBS+1% BSA. After a 20 minute incubation at 4° C., cells were washed in PBS, and incubated with a PE-conjugated anti-human IgG Fc secondary antibody (Biolegend) diluted in PBS+1% BSA. After a 20 minute incubation at 4° C., cells were washed in PBS and analyzed by flow cytometry.

Figure 7A:
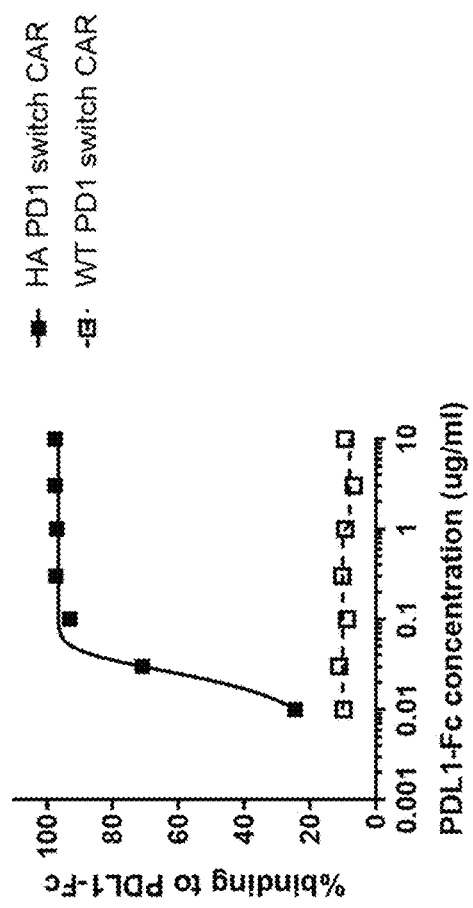
FIGS. 7A-7B show results from the cell binding assay between PD-1 chimeric cytokine receptor CAR-T-cells and PD-L1-Fc (FIG. 7A) or clinically-approved anti-PD-1 antibodies (FIG. 7B).
Figure 7B:
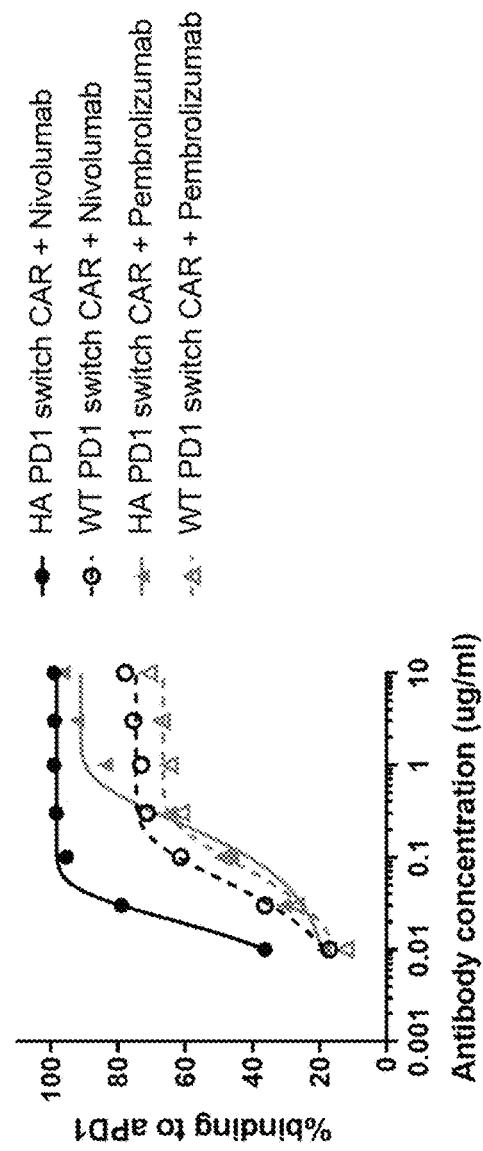

FIGS. 7A-B show results from the cell binding assay between PD-1 chimeric cytokine receptor CAR-T-cells and PD-L1-Fc (FIG. 7A) or clinically-approved anti-PD-1 antibodies (FIG. 7B). FIG. 7A shows that while the WT PD-1 chimeric cytokine receptor did not bind to PD-L1-Fc at the concentrations tested, the HA PD-1 chimeric cytokine receptor dramatically improved binding to PD-L1-Fc. FIG. 7B shows that modification to the HA PD-1 ectodomain improved maximal binding ($C_{max}$) to Pembrolizumab, and improved both maximal binding ($C_{max}$) and sensitivity ($EC_{50}$) to Nivolumab. The HA PD-1 ectodomain variant improves responsiveness to both PD-L1 and clinically-approved anti-PD-1 antibodies.

To analyze the inducibility and magnitude of cytokine signaling in CAR-T-cells bearing these PD-1 chimeric cytokine receptor ectodomain variants, the thawed CAR-T-cell product was serum starved in 100 uL serum-free RPMI (Corning) for 4 hours in humidified incubator at 37° C. with 5% $CO_2$, then treated with anti-PD-1 (10 ug/mL Nivolumab; Selleck Chemical), recombinant human PD-L1-Fc (10 ug/mL; Biolegend), anti-Human IgG Fc gamma secondary antibody (25 ug/mL; Thermo Fisher) for 1 hour. 40 minutes into the treatment, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. After 1 hour of treatment, cells were fixed by the addition of 35 uL of 16% paraformaldehyde was added to each 100 uL sample and allowed to incubate for 15 minutes at 37° C. Cells were then washed three times with PBS, and permeabilized in 100% cold methanol for 1 or 2 nights at −20° C. On the day of FACS analysis, cells were washed three times with PBS, Fc-blocked, and stained with AlexaFluor647-conjugated anti-mouse/human Stat5 (pY694) (BD Biosciences) diluted in PBS+1% BSA. After a 1 hour incubation at room temperature in the dark, cells were washed three times before FACS analysis.

Figure 8A:
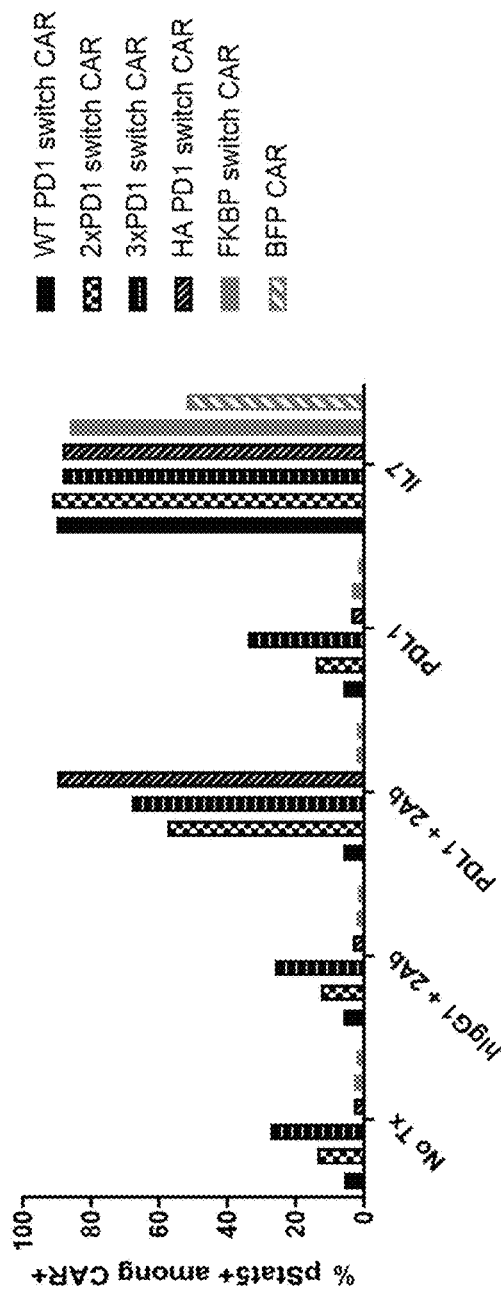
FIGS. 8A-8B show the response of CAR-T-cells bearing PD-1 chimeric cytokine receptor ectodomain variants following treatment with PD-L1-Fc (FIG. 8A) or anti-PD-1 (FIG. 8B).
Figure 8B:
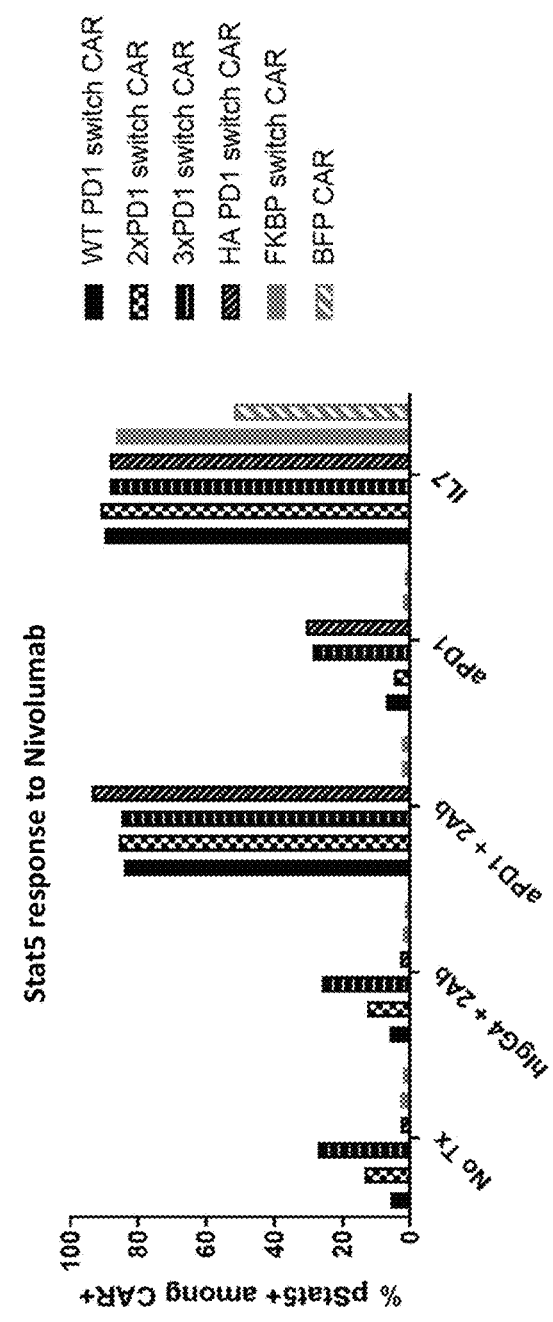

FIGS. 8A-B show the response of CAR-T-cells bearing PD-1 chimeric cytokine receptor ectodomain variants following treatment with PD-L1-Fc (FIG. 8A) or anti-PD-1 (FIG. 8B). 2×PD-1 and 3×PD-1 chimeric cytokine receptor CAR-T-cells showed high levels of basal signaling, even in the absence of PD-L1 or anti-PD-1. Compared to WT PD-1 chimeric cytokine receptor CAR-T-cells, CAR-T-cells bearing the 2×PD-1 chimeric cytokine receptor, 3×PD-1 chimeric cytokine receptor and HA PD-1 chimeric cytokine receptor showed enhanced response to crosslinked PD-L1-Fc, with the HA PD-1 chimeric cytokine receptor providing the greatest response (FIG. 8A). In response to anti-PD-1 alone, the HA PD-1 chimeric cytokine receptor was the only ectodomain variant that induced increased pStat5; neither the 2×PD-1 chimeric cytokine receptor nor the 3×PD-1 chimeric cytokine receptor induced pStat5 beyond their levels of basal activity (FIG. 8B). Based on this analysis, the HA PD-1 chimeric cytokine receptor was the ectodomain variant that provided the lowest basal activity and greatest inducibility.

To evaluate the cytotoxic activity of PD-1 chimeric cytokine receptor CAR-T-cells, the U87KO-EGFRvIII-nucGFP target cell line that endogenously expresses PD-L1 and PD-L2. U87KO-EGFRvIII (gift from Cellectis SA (Paris, France)). U87KO-EGFRvIII was derived from the parental cell line, U87MG (ATCC), by first knocking out endogenous wild type EGFR using Transcription Activator-Like Effector Nucleases (TALEN), and then stably overexpressing full-length human EGFRvIII via lentiviral transduction. To facilitate target cell imaging via the IncuCyte Live Cell Analysis Imaging System, U87KO-EGFRvIII-nucGFP target cells were derived from U87KO-EGFRvIII by a second lentiviral transduction with IncuCyte NucLight Green Lentivirus Reagent (Sartorius). PD-L1 and PD-L2 expression on U87KO-EGFRvIII-nucGFP was determined by staining with an APC-conjugated anti-human PD-L1 (Biolegend) and a PE-conjugated anti-human PD-L2 (Biolegend), followed by flow cytometry analysis. For the in vitro cytotoxicity assay, 5,000 U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T-cells bearing the respective PD-1 chimeric cytokine receptor ectodomain variants were thawed and added to plated target cells at an Effector:Target (E:T) ratio of 1:4. FKBP chimeric cytokine receptor CAR-T-cells that do not activate cytokine signaling in response to PD-1 ligands were used as a control. Duplicate wells were set up for each condition. The number of live target cells at each timepoint was determined by enumerating the number of live nucGFP+ target cells using the IncuCyte Live Cell Analysis Imaging System.

Figure 9A:
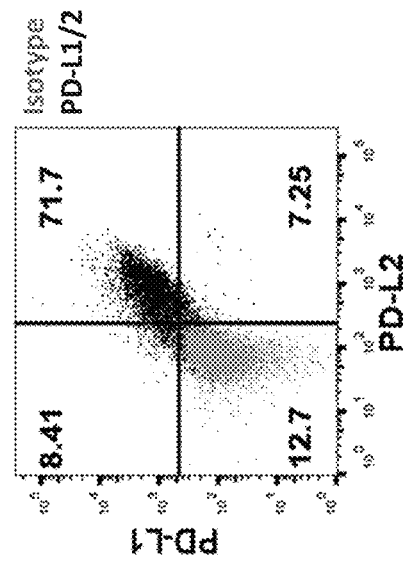
FIGS. 9A-9B show the cytotoxic response of the PD-1 chimeric cytokine receptor CAR-T-cells against target cells expressing PD-1 ligands.
Figure 9B:
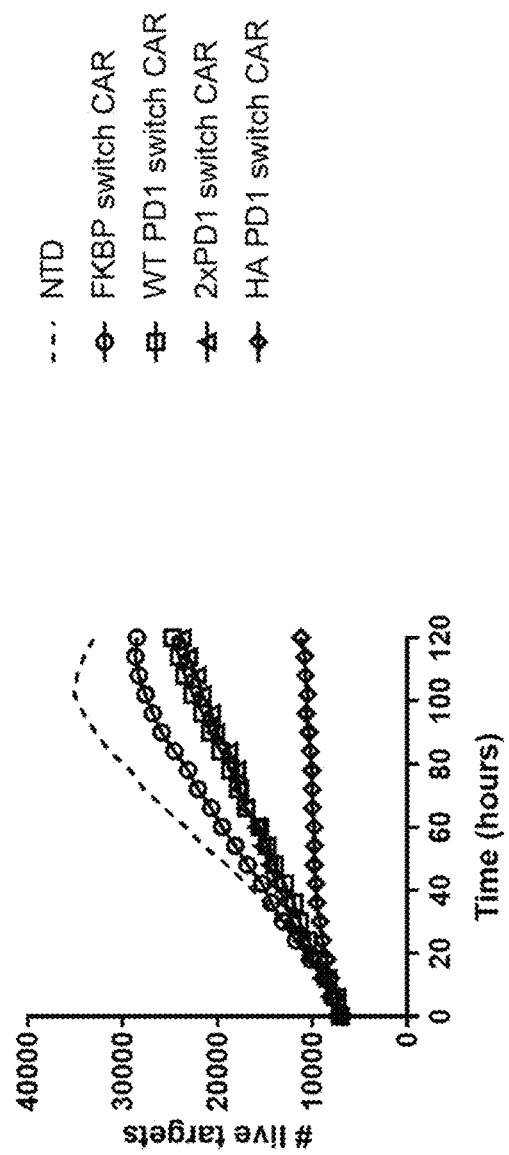

FIGS. 9A-B show the cytotoxic response of the PD-1 chimeric cytokine receptor CAR-T-cells against target cells expressing PD-1 ligands. FIG. 9A shows that U87KO-EGFRvIII-nucGFP cells express high levels of endogenous PD-L1 and PD-L2. FIG. 9B shows the results of the in vitro cytotoxic assay against U87KO-EGFRvIII-nucGFP target cells. Compared to FKBP chimeric cytokine receptor CAR-T-cells, WT PD-1 chimeric cytokine receptor CAR-T-cells showed marginally improved cytotoxic responses. While the 2×PD-1 chimeric cytokine receptor did not enhance cytotoxicity beyond that of the WT PD-1 chimeric cytokine receptor, the HA PD-1 chimeric cytokine receptor significantly enhanced CAR-T-cell cytotoxicity.

Example 3: Optimization of the HA PD-1 Chimeric Cytokine Receptor

The HA PD-1 ectodomain variant afforded a significant enhancement over the WT PD-1 chimeric cytokine receptor. The helical transmembrane (TM) region of TpoR is critical for ligand-induced receptor signaling by controlling JAK2 activation. It was analyzed whether in a chimeric cytokine receptor where a different ectodomain (e.g. PD-1) is fused with the TpoR TM/JAK2-activating domain, the optimal structural conformation for receptor activation is perturbed. The responsiveness of the HA PD-1 chimeric cytokine receptor was attempted to be increased by modifying the TpoR TM region. To this end, HA PD-1 chimeric cytokine receptor variants with either deletions or insertions in the TpoR TM region were generated and tested in the HEK293T-cell reporter assay.

Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was usedwe, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor receptor and that were left untreated.

FIGS. 10A-B show the amino acid sequences for the wild type TpoR and the various TM deletion (FIG. 10A) or insertion (FIG. 10B) variants.

Figure 11A:
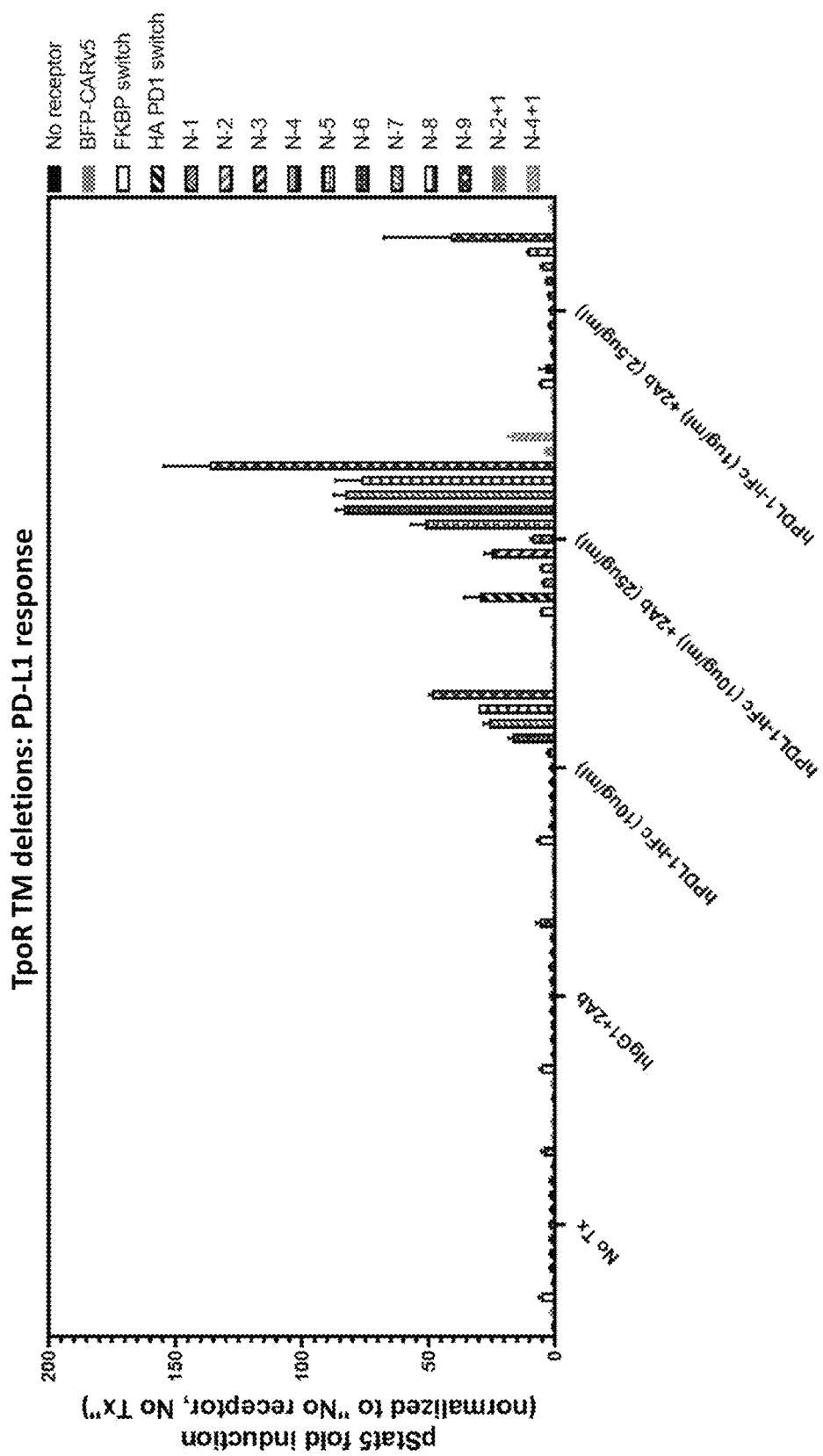
FIGS. 11A-11B show the response of a HA PD-1 chimeric cytokine receptor bearing TpoR TM deletions (FIG. 11A) and extensions (FIG. 11B) following treatment with PD-L1-Fc.
Figure 11B:
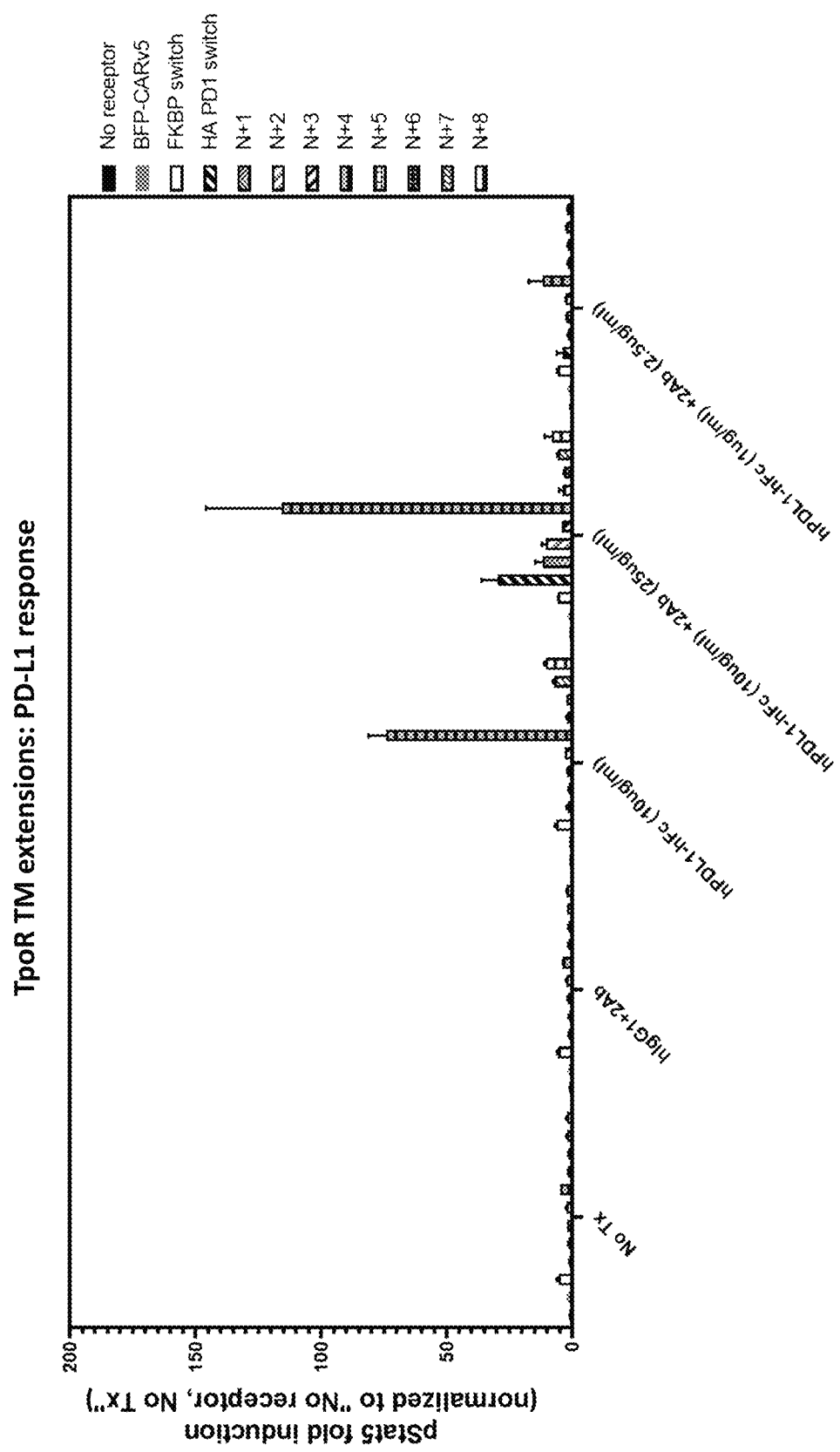

FIGS. 11A-B show the response of a HA PD-1 chimeric cytokine receptor bearing TpoR TM deletions (FIG. 11A) and extensions (FIG. 11B) following treatment with PD-L1-Fc. Unlike the HA PD-1 chimeric cytokine receptor that did not respond to PD-L1-Fc alone, the N-6, N-7, N-8, N-9 and N+4 TpoR TM variants were able to induce Stat5 activity in response to PD-L1 alone. Furthermore, compared to the HA PD-1 chimeric cytokine receptor, the N-5, N-6, N-7, N-8, N-9 and N+4 TpoR TM variants improved Stat5 activity in response to high concentrations of crosslinked PD-L1. The N-9 and N+4 TpoR TM variants retained the ability to respond to low concentrations of crosslinked PD-L1. These demonstrate that modulating the TpoR TM region enhanced the responsiveness and sensitivity of the HA PD-1 chimeric cytokine receptor to PD-1 ligands.

Figure 12A:
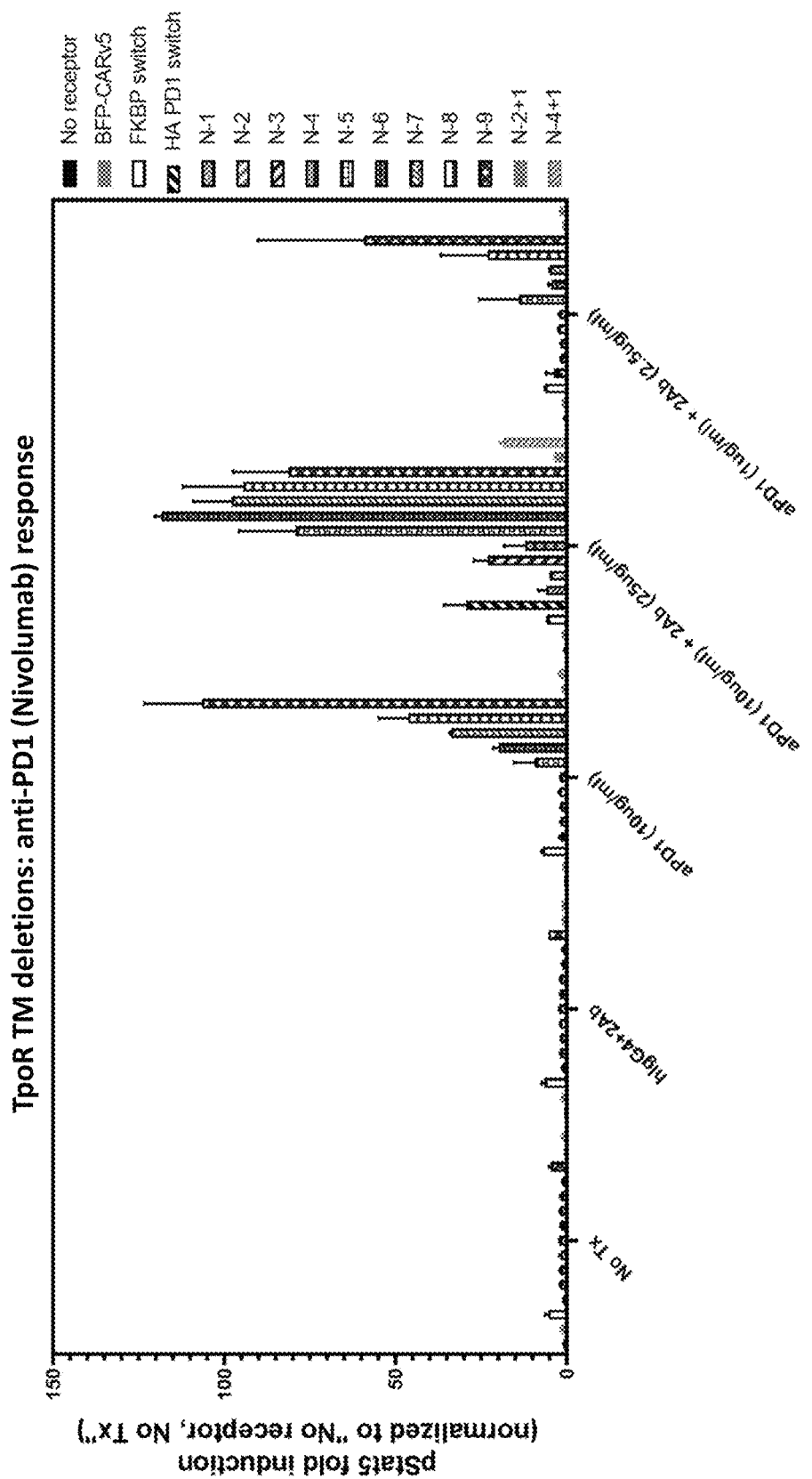
FIGS. 12A-12B shows the response of HA PD-1 chimeric cytokine receptor bearing TpoR TM deletions (FIG. 12A) and extensions (FIG. 12B) following treatment with anti-PD-1 (Nivolumab).
Figure 12B:
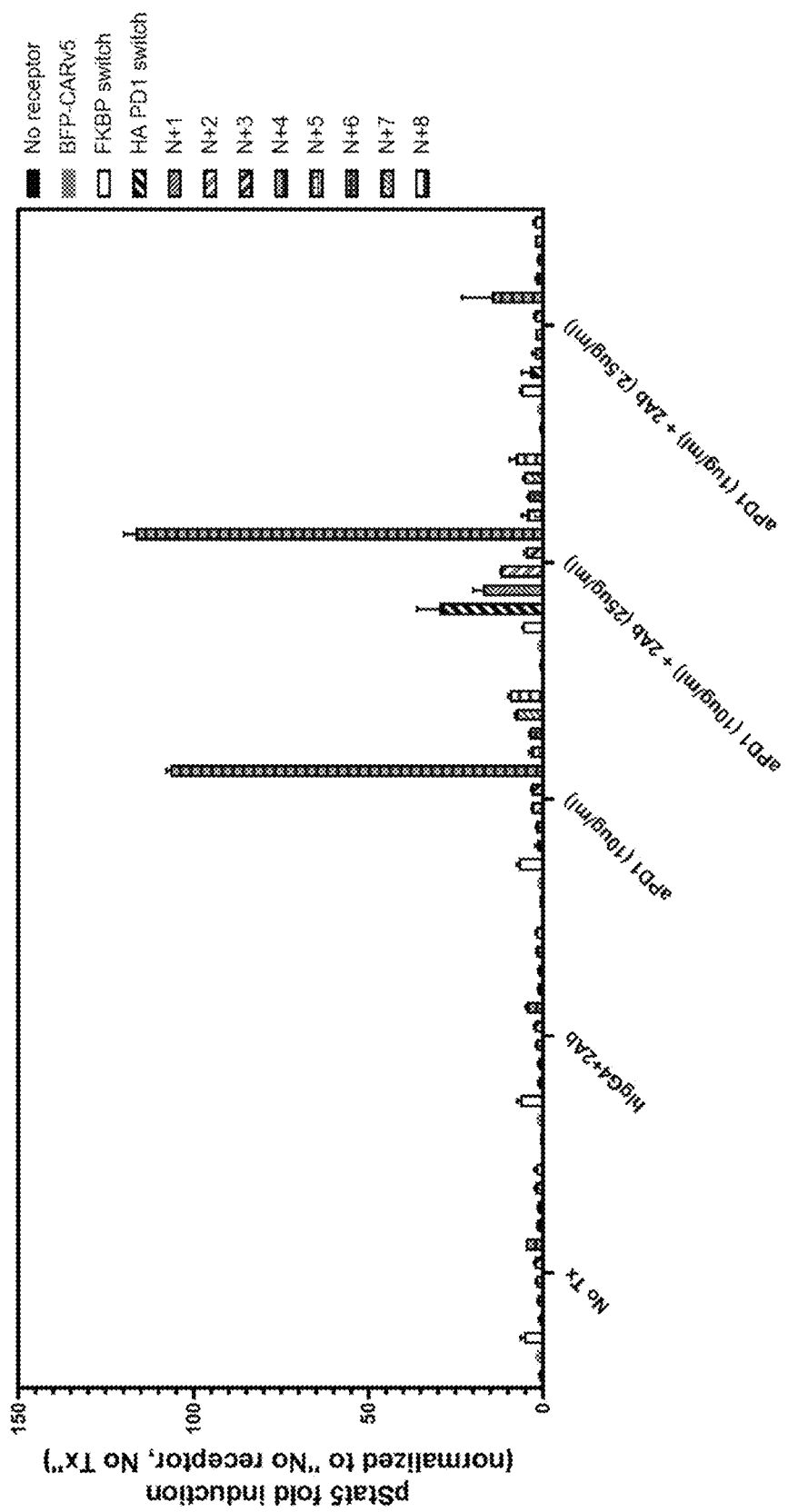

FIGS. 12A-B shows the response of HA PD-1 chimeric cytokine receptor bearing TpoR TM deletions (FIG. 12A) and extensions (FIG. 12B) following treatment with anti-PD-1 (Nivolumab). Unlike the HA PD-1 chimeric cytokine receptor that did not respond to anti-PD-1 alone, the N-5, N-6, N-7, N-8, N-9 and N+4 TpoR TM variants were able to induce Stat5 activity in response to anti-PD-1 alone, without the need for further crosslinking. These demonstrate that modulating the TpoR TM region enhanced the responsiveness and sensitivity of the HA PD-1 chimeric cytokine receptor to anti-PD-1.

Example 4: Effect of the HA PD-1 Chimeric Cytokine Receptor on CAR-T-Cell Cytotoxic Activity PD-1 blockade strategies, such as combination with anti-PD-1 or forced overexpression of a dominant-negative (DN) PD-1 decoy receptor, can ameliorate CAR-T-cell exhaustion. While PD-1 blockade prevents a negative signal from being transmitted into CAR-T-cells, it does not actively transmit any positive signals. It was therefore tested whether the HA PD-1 chimeric cytokine receptor, which couples PD-1 inhibition with simultaneous immune-potentiating cytokine signals, is more effective than PD-1 blockade alone. The cytotoxic activity of HA PD-1 chimeric cytokine receptor CAR-T-cells was compared against CAR-T-cells combined with Nivolumab, and against CAR-T-cells expressing a dominant-negative (DN) PD-1. (amino acid sequences in Table 9).

TABLE 9

PD1 dominant negative (DN) sequences:

| PD1 DN | Amino acid sequence | SEQ ID NO: |
|---|---|---|
| CD8SS-PD1(21-207) (Dominant negative wild type PD1) | MALPVTALLLPLALLLHAARP PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTI GARRTGQ | 129 |
| CD8SS-HAPD1 (Dominant negative high affinity PD1) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTI GARRTGQ | 130 |

To assess in vitro cytotoxicity, 5,000 PD-L1+/PD-L2+ U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T-cells bearing the respective PD-1 chimeric cytokine receptors or DN PD-1 were thawed and added to plated target cells at an Effector:Target (E:T) ratio of 1:4. FKBP chimeric cytokine receptor CAR-T-cells that do not activate cytokine signaling in response to PD-1 ligands were used as a control. Where indicated, anti-PD-1 (Nivolumab) or hIgG4 isotype control antibodies were added at a concentration of 10 ug/mL. Duplicate wells were set up for each condition. The number of live target cells at each timepoint was determined by enumerating the number of live nucGFP+ target cells using the IncuCyte Live Cell Analysis Imaging System.

Figure 13B:
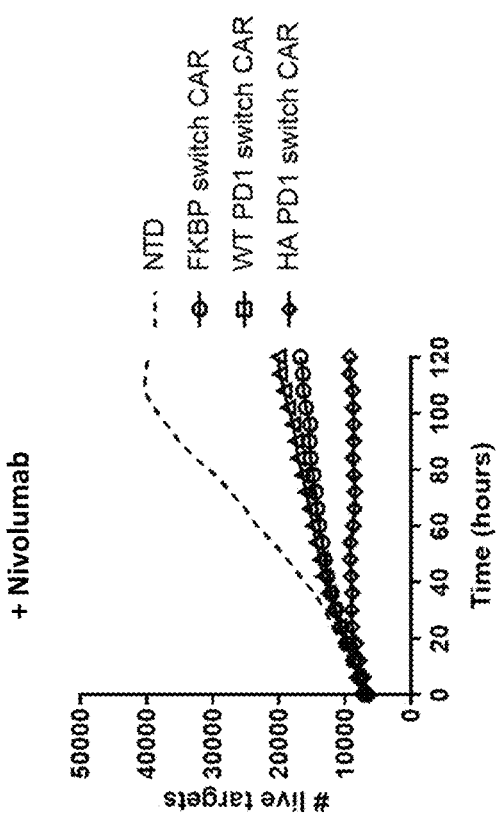
FIGS. 13A-13B show the cytotoxic response of PD-1 chimeric cytokine receptor CAR-T-cells in the absence (FIG. 13A) or presence (FIG. 13B) of anti-PD-1.
Figure 13A:
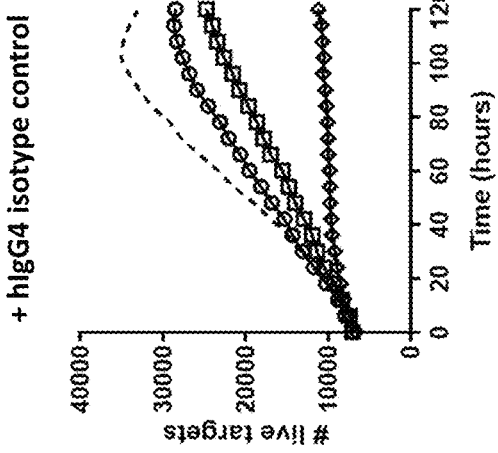

FIGS. 13A-B show the cytotoxic response of PD-1 chimeric cytokine receptor CAR-T-cells in the absence (FIG. 13A) or presence (FIG. 13B) of anti-PD-1. Although combination with anti-PD-1 did improve the activity of FKBP chimeric cytokine receptor CAR-T-cells and WT PD-1 CAR-T-cells, HA PD-1 chimeric cytokine receptor CAR-T-cells were more effective at target cell lysis. Combination with anti-PD-1 did not further improve the activity of HA PD-1 chimeric cytokine receptor CAR-T-cells, indicating that PD-1 ligands expressed on the target cells could bind to and activate the PD-1 chimeric cytokine receptor.

Figure 14:
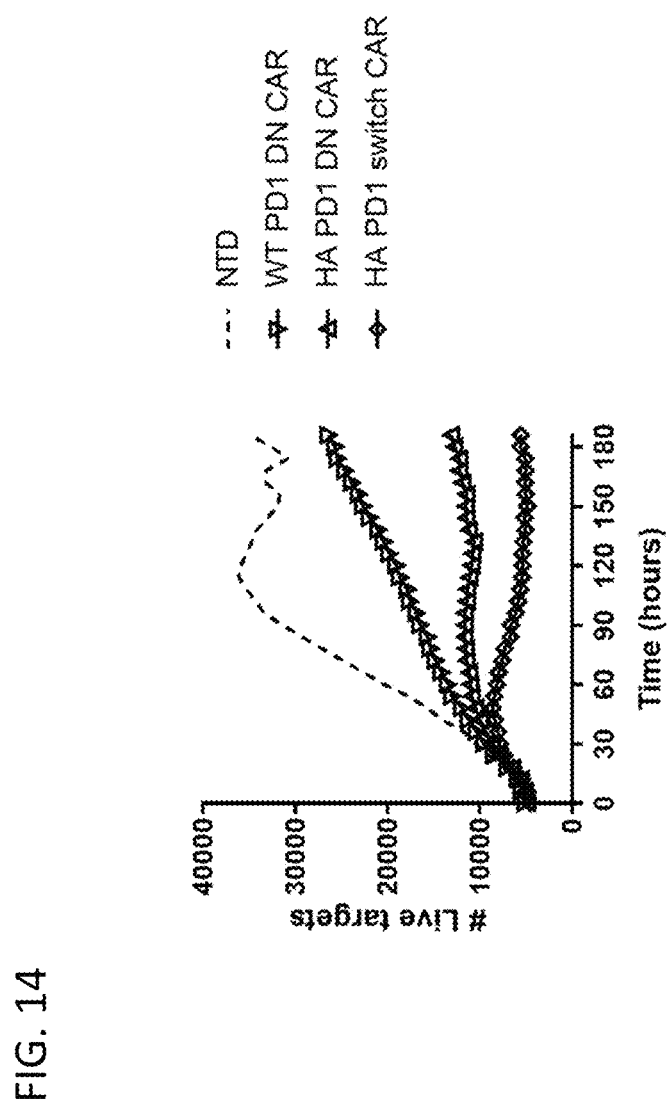
FIG. 14 shows the cytotoxic response of CAR-T-cells coexpressing either a DN WT PD-1, a DN HA PD-1 or the HA PD-1 chimeric cytokine receptor.

FIG. 14 shows the cytotoxic response of CAR-T-cells coexpressing either a DN WT PD-1, a DN HA PD-1 or the HA PD-1 chimeric cytokine receptor. HA PD-1 DN CAR-T-cells were more effective than WT PD-1 CAR-T-cells. Without being bound by any theory, this could be due to more effective sequestration and blockade of PD-1 ligands. However, HA PD-1 chimeric cytokine receptor CAR-T-cells were more cytotoxic than HA PD-1 DN CAR-T-cells. Without being bound by any theory, this could be due to the coupling of PD-1 blockade with simultaneous cytokine signaling.

Example 5: PD-1 Chimeric Cytokine Receptor that Delivers Constitutive Cytokine Signals in a Ligand-Independent Fashion The TM/JAK2-activating domain of PD1 chimeric cytokine receptors in some of the examples above is derived from TpoR, whose signaling activity can be modulated by key residues within the TpoR transmembrane (TM) domain. For instance, single point mutations within the TpoR TM domain, such as at S505 or W515, have been reported to cause constitutive TpoR signaling; on the other hand, mutating H499 in the TpoR TM domain dampens signaling from these activating mutations (Proc Natl Acad Sci USA. 2013 Feb. 12; 110(7):2540-5; FASEB J. 2011 July; 25(7):2234-44; J Biol Chem. 2016 Feb. 5; 291(6):2974-87.). It was analyzed whether a PD-1 chimeric cytokine receptor can be constitutively active by introducing the above-described single point mutations into the TpoR TM region of the receptor. To this end, HA PD-1 chimeric cytokine receptor variants with constitutively active single point mutations (S505 and/or W515) of the TpoR TM region and a single point mutation that reduces the activity of the TpoR TM region were generated. To mimic signaling from either IL-7 or IL-2/IL15, recruiting domains derived from the IL-7Ra and IL-2/IL15Rb receptors, respectively, were fused downstream of the TpoR TM/JAK2-activating domain. Exemplary amino acid sequences of the constructs are in Table 10.

TABLE 10

PD1 chimeric cytokine receptor sequences:

| Receptor | Amino acid sequence | SEQ ID NO: |
|---|---|---|
| CD8SS-HAPD1.TPOR/MPLR(478-582; H499L, S505N, W515K).IL7Ra (316-459) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSRPAGQFQTLV SDPTRVETATETAWISLVTALLLVLGLNAVLGLLLLLRKQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 141 |
| CD8SS-HAPD1.TpoR (478-582; S505N, W515K).IL2Rbsmall (393-433, 518-551) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSRPAGQFQTLV SDPTRVETATETAWISLVTALHLVLGLNAVLGLLLLRKQFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSLQELQGQDPTHLV | 142 |
| CD8SS-HAPD1DN | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSRPAGQFQTLVVGVVGGLLGSLVLLVWVL AVICSRAARGTI GARRTGQ | 143 |
| CD8SS-HAPD1.TpoR (478-582).IL7Ra (316-459) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSRPAGQFQTLV SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 144 |
| CD8SS-HAPD1.TpoR (478-582).IL2Rbsmall (393-433, 518-551) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSRPAGQFQTLV SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSLQELQGQDPTHLV | 145 |
| CD8SS-HAPD1.TPOR/MPLR(478-582; H499L, S505N, W515K).IL7Ra (316-459) | MALPVTALLLPLALLLHAARPPGWFLDSPDRPWNPPTFSPAL LVVTEGDNATFTCSFSNTSESFHVIWHRESPSGQTDTLAAFPE DRSQPGQDCRFRVTQLPNGRDFHMSVVRARRNDSGTYVCG VISLAPKIQIKESLRAELRVTERRAEVPTAHPSPSRPAGQFQT LVSDPTRVETATETAWISLVTALLLVLGLNAVLGLLLLRKQF PAHYRRLRHALWPSLPDLHRVLGQYLRDTAALSPPKATVSD TCEEVEPSLLEILPKSSERTPLPLLEARDEVEGFLQDTFPQQLE ESEKQRLGGDVQSPNCPSEDVVITPESFGRDSSLTCLAGNVS ACDAPILSSSRSLDCRESGKNGPHVYQDLLLSLGTTNSTLPPP FSLQSGILTLNPVAQGQPILTSLGSNQEEAYVTMSSFYQNQ | 210 |
| CD8SS-HAPD1.TpoR (478-582; S505N, W515K).IL2Rbsmall (393-433, 518-551) | MALPVTALLLPLALLLHAARPPGWFLDSPDRPWNPPTFSPAL LVVTEGDNATFTCSFSNTSESFHVIWHRESPSGQTDTLAAFPE DRSQPGQDCRFRVTQLPNGRDFHMSVVRARRNDSGTYVCG VISLAPKIQIKESLRAELRVTERRAEVPTAHPSPSRPAGQFQT LVSDPTRVETATETAWISLVTALHLVLGLNAVLGLLLLRKQF PAHYRRLRHALWPSLPDLHRVLGQYLRDTAALSPPKATVSD TCEEVEPSLLEILPKSSERTPLPLLEDEGVAGAPTGSSPQPLQP LSGEDDAYCTFPSRDDLLLFSPSGQGEFRALNARLPLNTDAY LSLQELQGQDPTHLV | 211 |

TABLE 10-continued

PD1 chimeric cytokine receptor sequences:

| Receptor | Amino acid sequence | SEQ ID NO: |
|---|---|---|
| CD8SS-HAPD1.TpoR (478-582).IL7Ra 316-459) | MALPVTALLLPLALLLHAARPPGWFLDSPDRPWNPPTFSPAL LVVTEGDNATFTCSFSNTSESFHVIWHRESPSGQTDTLAAFPE DRSQPGQDCRFRVTQLPNGRDFHMSVVRARRNDSGTYVCG VISLAPKIQIKESLRAELRVTERRAEVPTAHPSPSPRPAGQFQT LVSDPTRVETATETAWISLVTALHLVLGLSAVLGLLLLRWQF PAHYRRLRHALWPSLPDLHRVLGQYLRDTAALSPPKATVSD TCEEVEPSLLEILPKSSERTPLPLLEARDEVEGFLQDTFPQQLE ESEKQRLGGDVQSPNCPSEDVVITPESFGRDSSLTCLAGNVS ACDAPILSSSRSLDCRESGKNGPHVYQDLLLSLGTTNSTLPPP FSLQSGILTLNPVAQGQPILTSLGSNQEEAYVTMSSFYQNQ | 212 |
| CD8SS-HAPD1.TpoR (478-582). IL2Rbsmall (393-433, 518-551) | MALPVTALLLPLALLLHAARPPGWFLDSPDRPWNPPTFSPAL LVVTEGDNATFTCSFSNTSESFHVIWHRESPSGQTDTLAAFPE DRSQPGQDCRFRVTQLPNGRDFHMSVVRARRNDSGTYVCG VISLAPKIQIKESLRAELRVTERRAEVPTAHPSPSPRPAGQFQT LVSDPTRVETATETAWISLVTALHLVLGLSAVLGLLLLRWQF PAHYRRLRHALWPSLPDLHRVLGQYLRDTAALSPPKATVSD TCEEVEPSLLEILPKSSERTPLPLLEDEGVAGAPTGSSPQPLQP LSGEDDAYCTFPSRDDLLLFSPSGQGEFRALNARLPLNTDAY LSLQELQGQDPTHLV | 213 |

A HEK293T cell reporter assay was used to test for constitutive cytokine signaling by PD1 chimeric cytokine receptors. Briefly, 20,000 HEK293T cells were plated into each well of a poly-L-lysine-coated 96-well flat-bottom plate and allowed to adhere overnight. A PD1 chimeric cytokine receptor-CAR construct (2.5 ng), a Stat5 response element that drives Firefly Luciferase (100 ng; Promega) and Renilla Luciferase control reporter vector (1 ng; Promega) were mixed in a final volume of 5 µL in Opti-MEM (Gibco) ("DNA mix"). As negative controls, cells were transfected with either a BFP CAR construct that expresses BFP instead of a PD1 chimeric cytokine receptor, or a dominant negative HA PD1 ectodomain CAR construct. As a comparison, cells were transfected with a vector encoding an inducible PD1 chimeric cytokine receptor (SEQ ID NOs: 213-214). As a positive control, cells were transfected with a vector encoding full-length human EpoR (in place of the cytokine receptor-CAR construct) so that Stat5 signaling could be induced by the addition of exogenous recombinant human Epo. 0.3 µL Lipofectamine 2000 (Invitrogen) in 5 µL Opti-MEM was incubated at room temperature for 5 minutes and then added to the DNA mix. The mixture was incubated at room temperature for 20 minutes and the total volume of 10 µL was added to each well containing HEK-293T. 24 hours after transfection, human PD-L1 Fc, a secondary crosslinking antibody, or an isotype control antibody were added at the indicated final concentrations. 48 hours after transfection, Stat5 reporter activity was evaluated using the Dual-Glo Luciferase Assay System (Promega). Fold induction of Stat5 reporter activity was normalized to that of HEK293T cells transfected with all vectors except for the cytokine receptor and that were left untreated.

Figure 15:
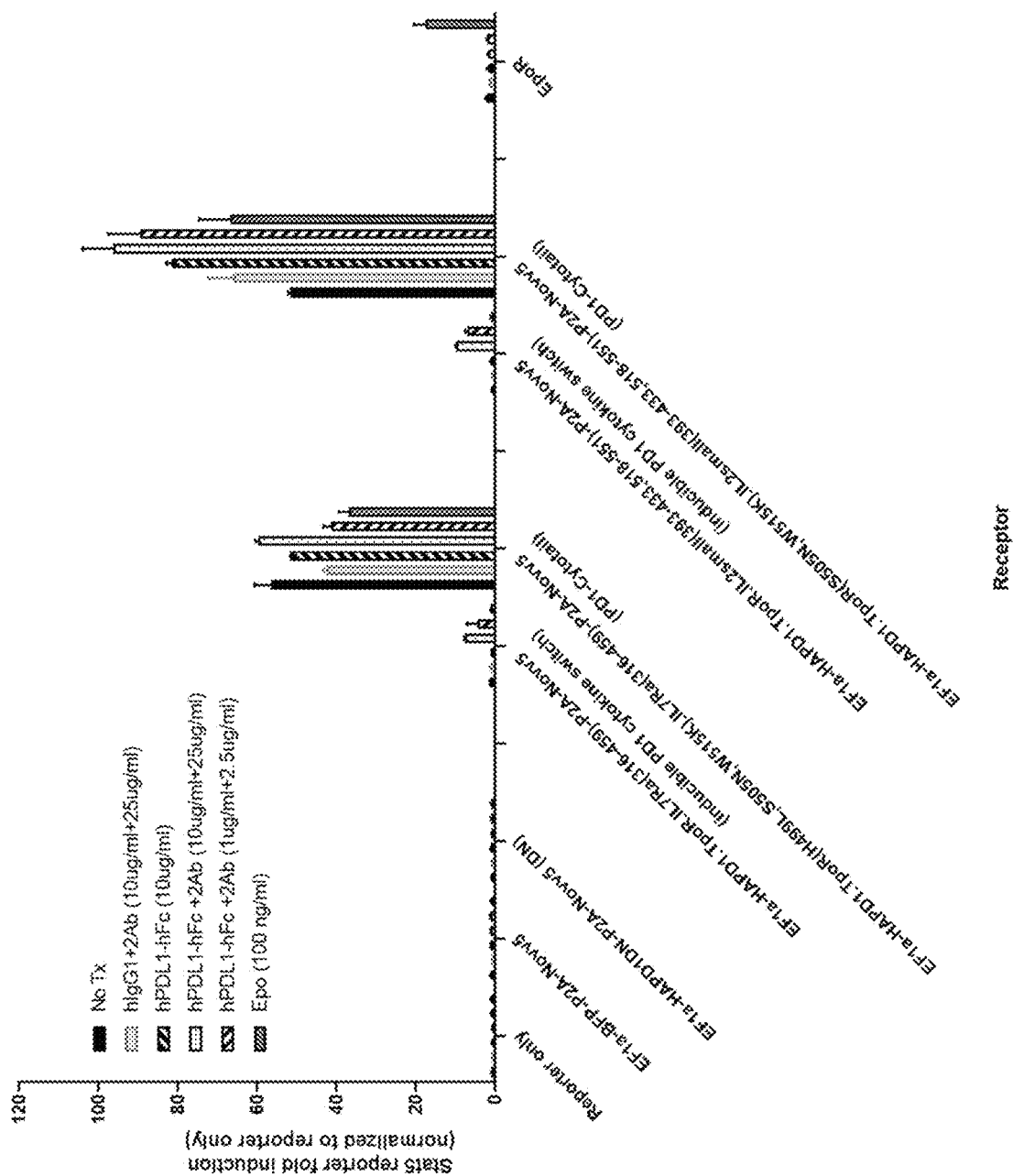
FIG. 15 shows a Stat reporter activity of the constitutively active, dominant negative, and inducible PD-1 chimeric cytokine receptors in response to PD-L1-Fc and crosslinked PD-L1-Fc.

FIG. 15 shows Stat5 reporter activity in the absence and presence of PD-L1. As expected, negative controls (i.e. BFP CAR and dominant negative HA PD1 ectodomain CAR constructs) did not induce Stat5 reporter activity. The inducible PD1 chimeric cytokine receptors bearing a TM/JAK2-activating domain derived from wild type TpoR ((SEQ ID NOs: 213-214) was active in the presence of crosslinked PD-L1, but was inactive in the absence of ligand. In contrast, strong, constitutive signaling was generated from PD1 chimeric cytokine receptors comprising a TM/JAK2-activating domain derived from a TpoR transmembrane domain with constitutively active point mutations (SEQ ID NOs.: 210-211) in a ligand-independent fashion. This ligand-independence is in contrast to an inducible PD1 chimeric cytokine receptor—bearing the wild type TpoR transmembrane domain—where the presence of PD1 ligands is required for cytokine signaling to occur. The constitutive activity of the PD1 chimeric cytokine receptor comprising the TM/JAK2-activating domain derived from a TpoR transmembrane domain with constitutively active point mutations (SEQ ID NO.: 2211) was increased in the presence of PD-L1 and crosslinked PD-L1. The activity of the PD1 chimeric cytokine receptor that comprises the constitutively active TpoR TM mutations and the inhibitor mutation (H499) (SEQ ID NO.: 210) showed a slight dampening of the constitutive activity in the presence of PD-L1 and crosslinked PD-L1.

Example 6 Increasing the Sensitivity and Responsiveness of the HA PD1 Switch Further Improves CAR T Cell Cytotoxicity As demonstrated above, the HA PD1 switch could be engineered for increased sensitivity and responsiveness towards PD-1 ligands and anti-PD-1 by modifying the TpoR TM helix. Specifically, in the HEK293T cell reporter assay, the N-5, N-6, N-7, N-8, N-9 and N+4 TpoR TM variants enhanced STAT5 activation in response to crosslinked PD-L1 (FIG. 11) and anti-PD-1 (FIG. 12). To evaluate if this translated into improved CAR T cell cytotoxicity in the presence of PD-1 ligands and anti-PD-1, we compared the killing activity of HA PD1 switch CART cells bearing either the wildtype (WT) or variant TpoR TM domains.

Briefly, 5,000 PD-L1+/PD-L2+U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T cells coexpressing a HA PD1 switch with the indicated TpoR TM domain were thawed and added to plated target cells at an Effector:Target (E:T) ratio of 1:4 or 1:8. As a control, CAR T cells coexpressing BFP in place of a HA PD1 switch, and that do not activate cytokine signaling in response to PD-1 ligands, were used. Where indicated, anti-PD-1 (nivolumab) or hIgG4 isotype control antibodies were added at a concentration of 10 ug/mL. Duplicate wells were set up for each condition. The number of live target cells at each timepoint was determined by enumerating the number of live nucGFP+ target cells using the IncuCyte Live Cell Analysis Imaging System.

Figure 16:
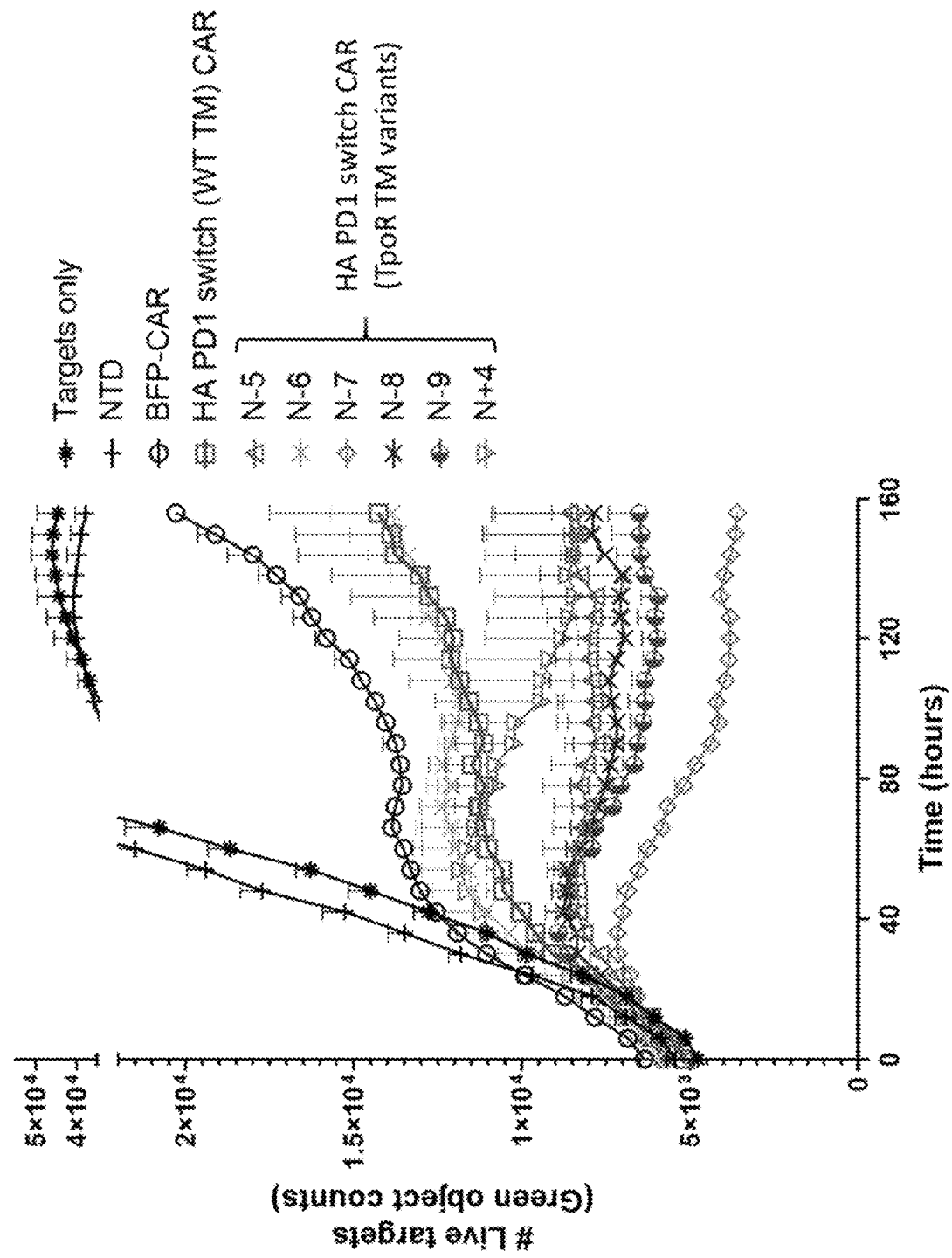
FIG. 16 shows the cytotoxic activity of HA PD1 switch CART cells with the indicated TpoR TM domains at an E:T ratio of 1:4 and in the absence of anti-PD-1.

FIG. 16 shows the cytotoxic activity of HA PD1 switch CART cells with the indicated TpoR TM domains at an E:T ratio of 1:4 and in the absence of anti-PD-1. As expected, compared to the control BFP-CAR T cells, HA PD1 switch CAR T cells with the WT TpoR TM domain showed improved target cell lysis in vitro. However, cytotoxic activity was further enhanced in HA PD1 switch CAR T cell variants bearing the N-5, N-7, N-8, N-9 or N+4 TpoR TM domains. Concordant with FIGS. 11 and 12, these data indicate that TpoR TM domain variants allow more effective cytotail activation in response to PD-1 ligands, thereby further enhancing the cytotoxic potency of HA PD1 switch CAR T cells.

Figure 17A:
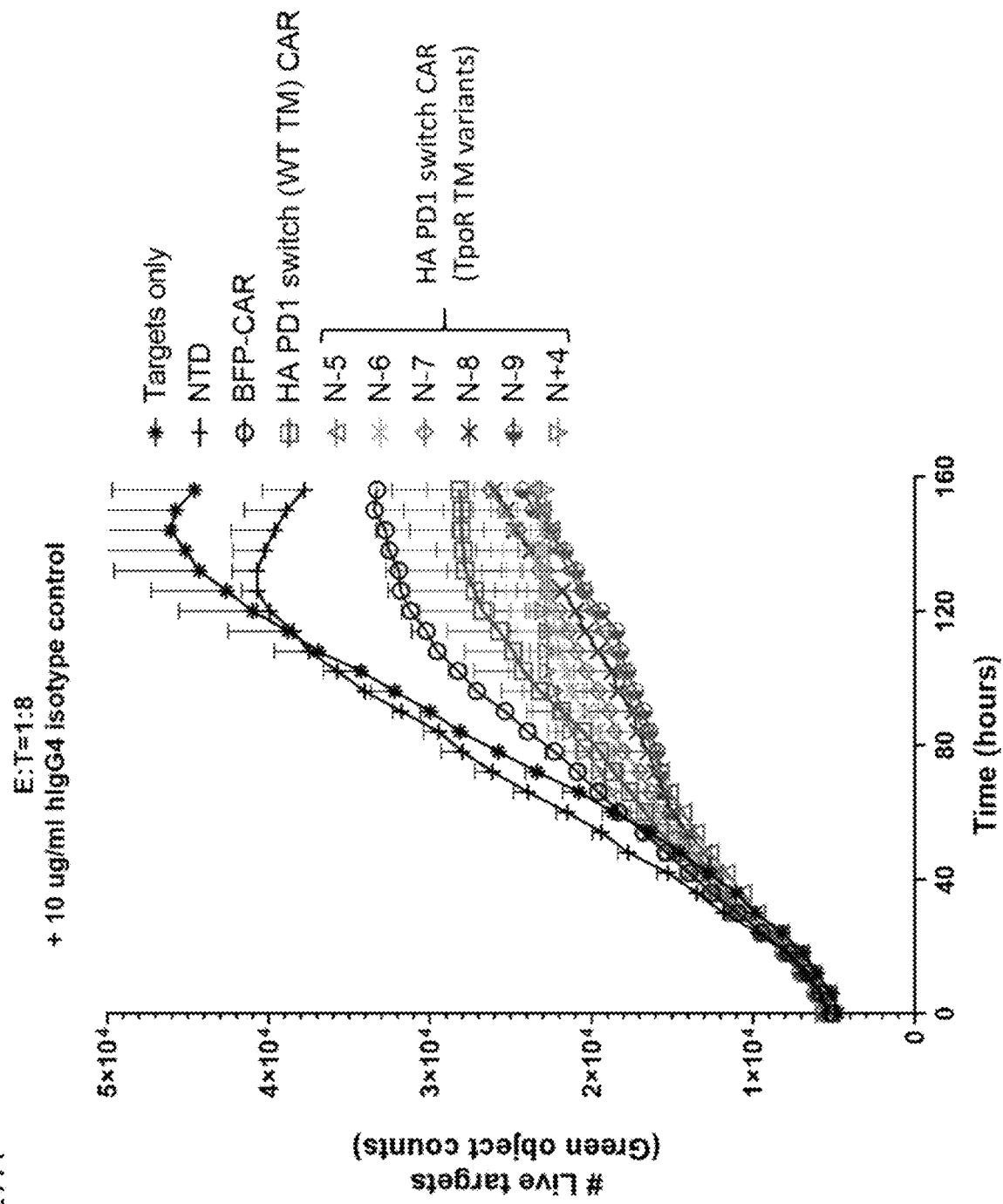
FIGS. 17A-17E show the cytotoxic activity of HA PD1 switch CART cells with the indicated TpoR TM domains at an E:T ratio of 1:8, and in the absence or presence of anti-PD-1.
Figure 17B:
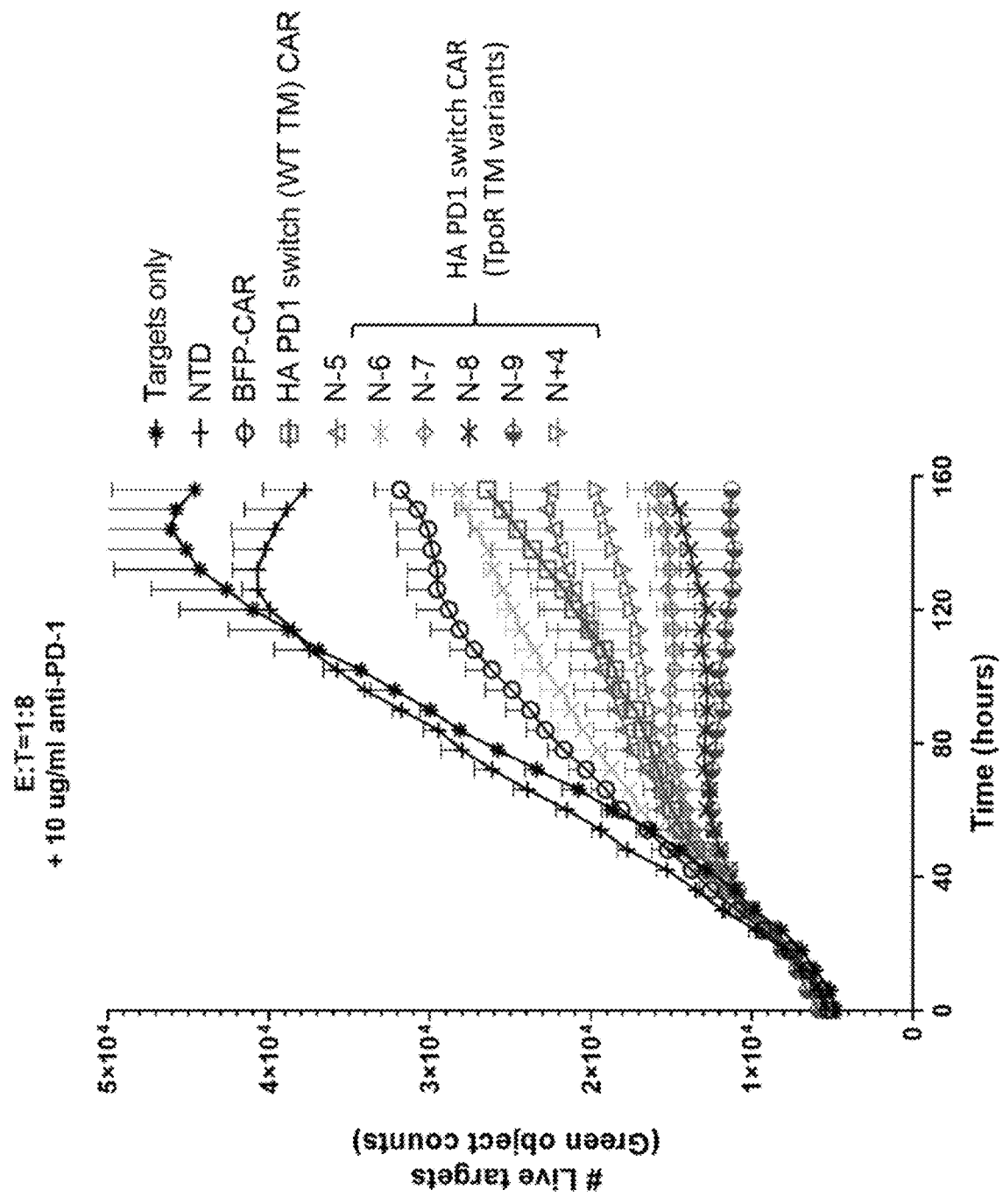
Figure 17C:
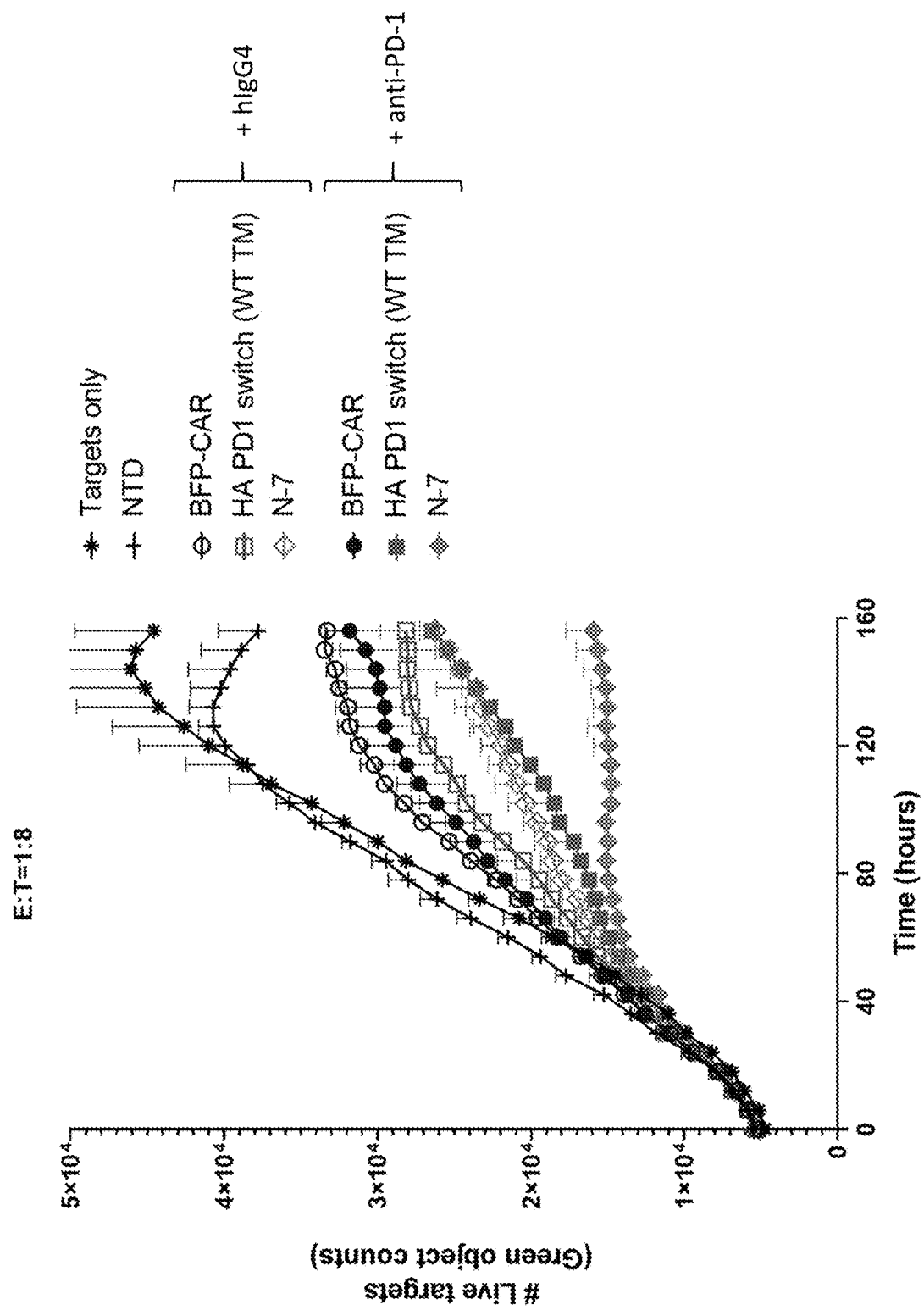
Figure 17D:
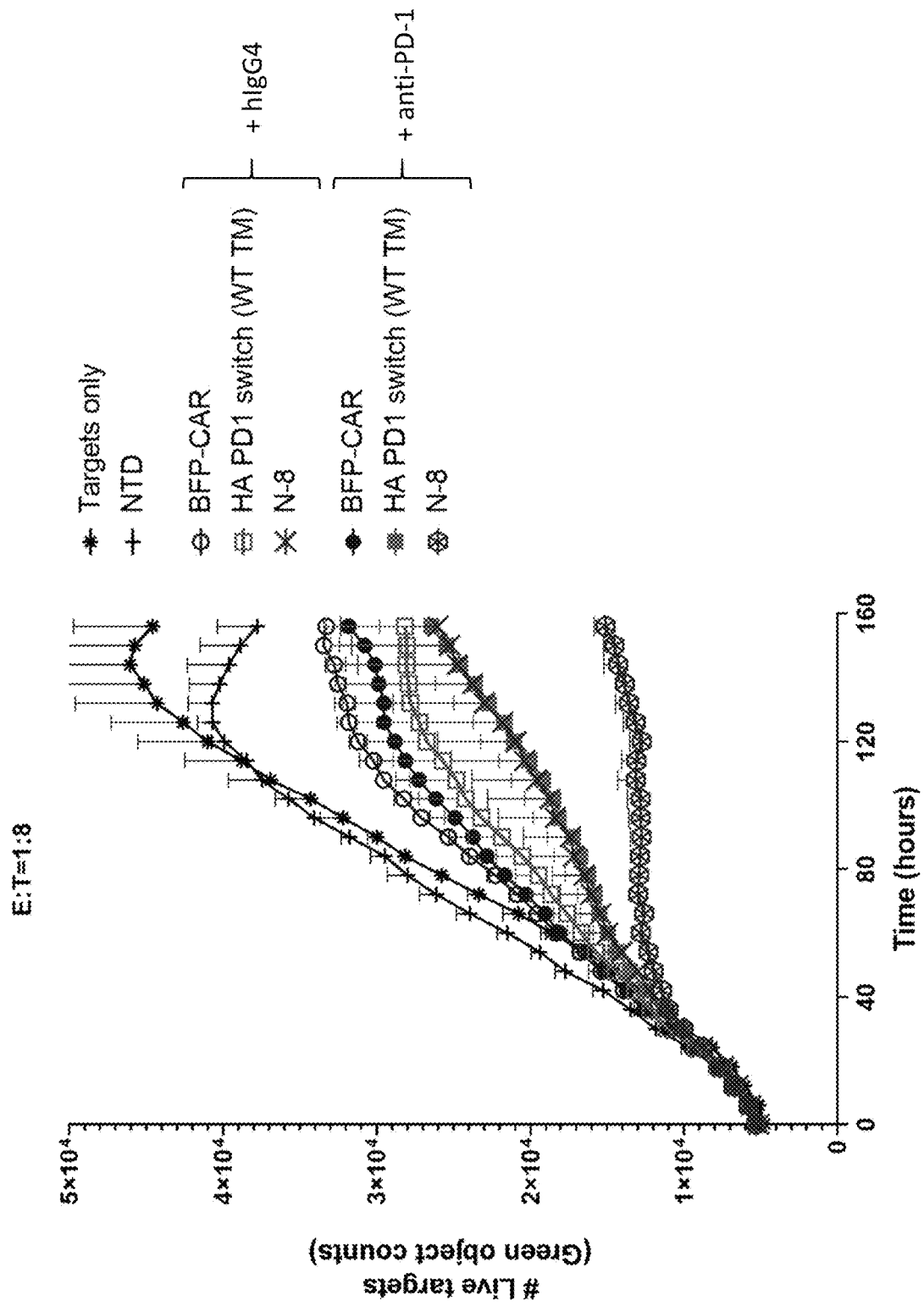
Figure 17E:
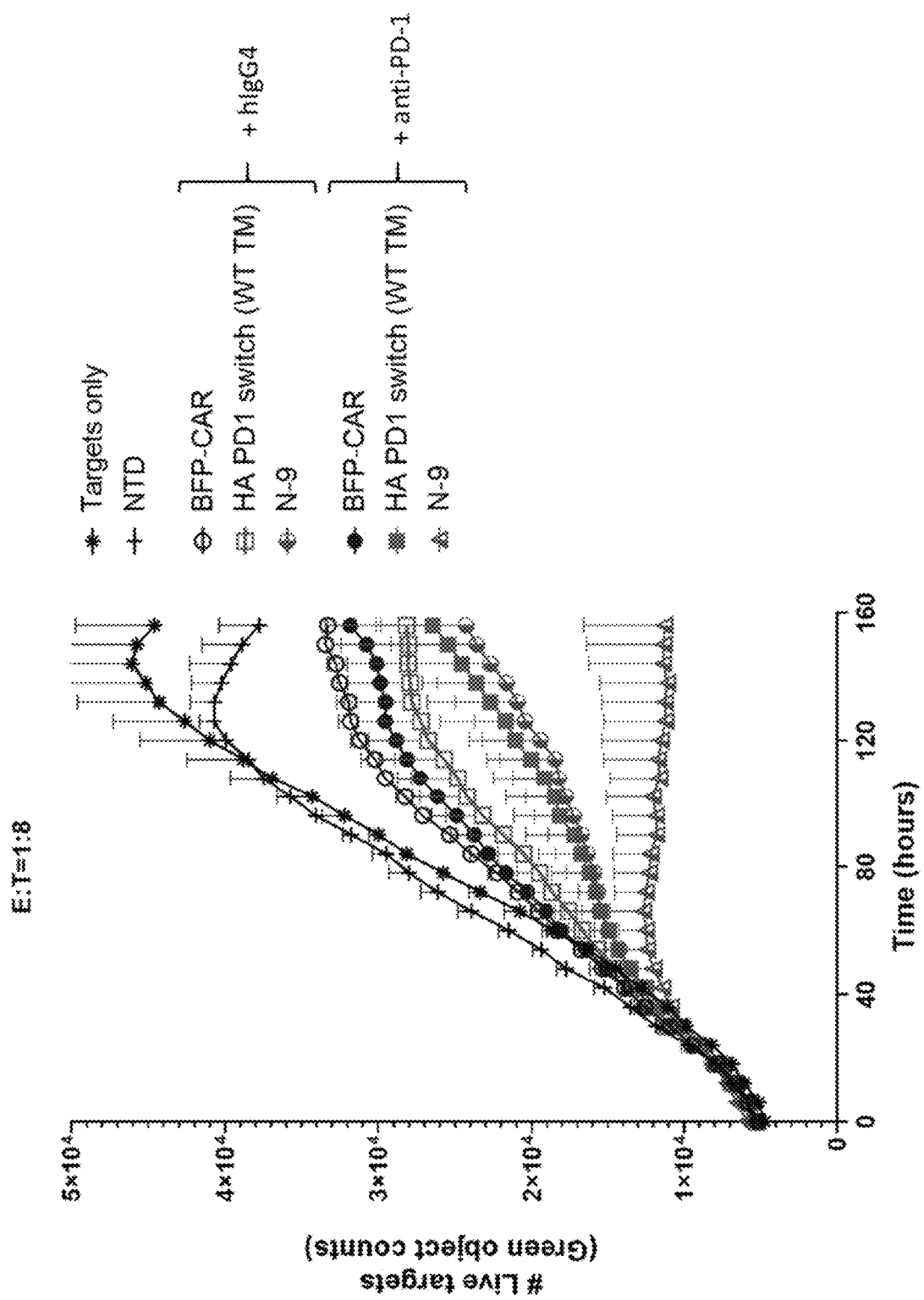

FIGS. 17A-B show the cytotoxic activity of HA PD1 switch CAR T cells with the indicated TpoR TM domains at an E:T ratio of 1:8, and in the absence or presence of anti-PD-1. FIG. 17A shows HA PD1 switch CART cell cytotoxicity in the absence of anti-PD-1. As expected, target cell lysis was less efficient at this lower E:T ratio as compared to the 1:4 ratio. Compared to the control BFP-CAR T cells, co-expression of a HA PD1 switch improved CAR T cell cytotoxicity, with the TpoR TM variants showing better activity than their WT TpoR TM counterpart. FIG. 17B shows HA PD1 switch CART cell cytotoxicity in the presence of anti-PD-1. Cytotoxic activity of control BFP-CAR T cells was not markedly improved even when combined with anti-PD-1. Additional dimerization and activation by anti-PD-1 improved the activity of HA PD1 switch with WT TpoR TM domain, and this was further enhanced in the N-7, N-8 and N-9 TpoR TM variants. FIGS. 17C-E show a comparison of the N-7 (FIG. 17C), N-8 (FIG. 17D) and N-9 (FIG. 17E) TpoR TM variants in the absence or presence of anti-PD-1. Without being limited to any specific mechanisms, the engagement of the PD-1 ectodomain with monomeric PD-L1/2 expressed on tumor cells or with a dimeric anti-PD-1 antibody may affect the conformation of the TpoR TM helix and different strength of signal transduction. Taken together, increasing the sensitivity and responsiveness of the HA PD1 switch via TpoR TM modifications can markedly improve the efficiency of cytotail signaling and enhance CAR T cell cytotoxic potency.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

What is claimed is:

1. A PD-1 chimeric cytokine receptor comprising:
   a. a PD-1 ectodomain or an antigen binding domain of an anti-PD-L1 or an anti-PD-L2 antibody;
   b. a transmembrane domain;
   c. a Janus Kinase (JAK)-binding domain; and
   d. a recruiting domain comprising a STAT-recruiting domain from IL2Rb,
   wherein the transmembrane domain and JAK-binding domain comprise SEQ ID NO: 40, SEQ ID NO: 23, SEQ ID NO: 24, SEQ ID NO: 25, SEQ ID NO: 26, or SEQ ID NO: 27.

2. The chimeric cytokine receptor of claim 1, wherein the PD-1 chimeric cytokine receptor is dimerized, and each monomer comprises:
   a. the PD-1 ectodomain;
   b. the transmembrane domain;
   c. the Janus Kinase (JAK)-binding domain; and
   d. the recruiting domain.

3. The chimeric cytokine receptor of claim 1, wherein the PD-1 ectodomain comprises a wild type PD-1 ectodomain sequence.

4. The chimeric cytokine receptor of claim 1, wherein the PD-1 ectodomain comprises one or more mutations to the wild type PD-1 ectodomain sequence.

5. The chimeric cytokine receptor of claim 4, wherein the PD-1 ectodomain comprising one or more mutations has a higher binding affinity for its ligand than a wild type PD-1 ectodomain.

6. The chimeric cytokine receptor of claim 1, wherein the PD-1 ectodomain comprises an amino acid sequence selected from SEQ ID NOs: 2-5, 132-133, and 168-169.

7. The chimeric cytokine receptor of claim 1, wherein the antigen binding domain is a scFv.

8. The chimeric cytokine receptor of claim 1, wherein the chimeric cytokine receptor is activated when the PD-1 ectodomain is bound to PD-L1 or PD-L2.

9. The chimeric cytokine receptor of claim 1, wherein the chimeric cytokine receptor is activated when the PD-1 ectodomain is bound to an anti-PD-1 antibody.

10. The chimeric cytokine receptor of claim 9, wherein the anti-PD-1 antibody is nivolumab or pembrolizumab.

11. The chimeric cytokine receptor of claim 1, wherein the JAK-binding domain is a JAK2-binding domain.

12. The chimeric cytokine receptor of claim 1, wherein the STAT-recruiting domain from IL2Rb comprises SEQ ID NO: 77.

13. The chimeric cytokine receptor of claim 1, wherein the receptor is constitutively active and can be further induced.

14. The chimeric cytokine receptor of claim 1, wherein the STAT-recruiting domain from IL2Rb comprises SEQ ID NO: 76.

15. The chimeric cytokine receptor of claim 2, wherein the PD-1 ectodomain comprises a wild type PD-1 ectodomain sequence.

16. The chimeric cytokine receptor of claim 1, wherein the transmembrane domain and JAK-binding domain comprise SEQ ID NO: 40.

17. The chimeric cytokine receptor of claim 16, wherein the STAT-recruiting domain from IL2Rb comprises SEQ ID NO: 77.

18. The chimeric cytokine receptor of claim 16, wherein the STAT-recruiting domain from IL2Rb comprises SEQ ID NO: 76.

19. The chimeric cytokine receptor of claim 1, wherein the transmembrane domain and JAK-binding domain comprise SEQ ID NO: 23.

20. The chimeric cytokine receptor of claim 19, wherein the STAT-recruiting domain from IL2Rb comprises SEQ ID NO: 77.

21. The chimeric cytokine receptor of claim 19, wherein the STAT-recruiting domain from IL2Rb comprises SEQ ID NO: 76.

22. The chimeric cytokine receptor of claim 1, wherein the transmembrane domain and JAK-binding domain comprise SEQ ID NO: 24.

23. The chimeric cytokine receptor of claim 22, wherein the STAT-recruiting domain from IL2Rb comprises SEQ ID NO: 77.

24. The chimeric cytokine receptor of claim 22, wherein the STAT-recruiting domain from IL2Rb comprises SEQ ID NO: 76.

25. The PD-1 chimeric cytokine receptor of claim 1, wherein the transmembrane domain and JAK-binding domain comprise SEQ ID NO: 25.

26. The chimeric cytokine receptor of claim 25, wherein the STAT-recruiting domain from IL2Rb comprises SEQ ID NO: 77.

27. The chimeric cytokine receptor of claim 25, wherein the STAT-recruiting domain from IL2Rb comprises SEQ ID NO: 76.

28. The chimeric cytokine receptor of claim 1, wherein the transmembrane domain and JAK-binding domain comprise SEQ ID NO: 26.

29. The chimeric cytokine receptor of claim 28, wherein the STAT-recruiting domain from IL2Rb comprises SEQ ID NO: 77.

30. The chimeric cytokine receptor of claim 28, wherein the STAT-recruiting domain from IL2Rb comprises SEQ ID NO: 76.

31. The PD-1 chimeric cytokine receptor of claim 1, wherein the transmembrane domain and JAK-binding domain comprise SEQ ID NO: 27.

32. The chimeric cytokine receptor of claim 31, wherein the STAT-recruiting domain from IL2Rb comprises SEQ ID NO: 77.

33. The chimeric cytokine receptor of claim 31, wherein the STAT-recruiting domain from IL2Rb comprises SEQ ID NO: 76.

* * * * *

SEQUENCE LISTING

```
<160> NUMBER OF SEQ ID NOS: 224

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 187
<212> TYPE: PRT
<213> ORGANISM: Unknown
<220> FEATURE:
<223> OTHER INFORMATION: Description of Unknown:
      PD1 ectodomain sequence

<400> SEQUENCE: 2

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45
```

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
            165                 170                 175

Arg Gly Thr Ile Gly Ala Arg Arg Thr Gly Gln
            180                 185

<210> SEQ ID NO 3
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
            165                 170                 175

Arg Gly Thr Ile Gly Ala Arg Arg Thr Gly Gln Pro Gly Trp Phe Leu
            180                 185                 190

Asp Ser Pro Asp Arg Pro Trp Asn Pro Pro Thr Phe Ser Pro Ala Leu
            195                 200                 205

Leu Val Val Thr Glu Gly Asp Asn Ala Thr Phe Thr Cys Ser Phe Ser

```
            210                 215                 220
Asn Thr Ser Glu Ser Phe Val Leu Asn Trp Tyr Arg Met Ser Pro Ser
225                 230                 235                 240

Asn Gln Thr Asp Lys Leu Ala Ala Phe Pro Glu Asp Arg Ser Gln Pro
                245                 250                 255

Gly Gln Asp Cys Arg Phe Arg Val Thr Gln Leu Pro Asn Gly Arg Asp
                260                 265                 270

Phe His Met Ser Val Val Arg Ala Arg Arg Asn Asp Ser Gly Thr Tyr
            275                 280                 285

Leu Cys Gly Ala Ile Ser Leu Ala Pro Lys Ala Gln Ile Lys Glu Ser
        290                 295                 300

Leu Arg Ala Glu Leu Arg Val Thr Glu Arg Arg Ala Glu Val Pro Thr
305                 310                 315                 320

Ala His Pro Ser Pro Ser Pro Arg Pro Ala Gly Gln Phe Gln Thr Leu
                325                 330                 335

Val Val Gly Val Val Gly Gly Leu Leu Gly Ser Leu Val Leu Leu Val
                340                 345                 350

Trp Val Leu Ala Val Ile Cys Ser Arg Ala Ala Arg Gly Thr Ile Gly
            355                 360                 365

Ala Arg Arg Thr Gly Gln
        370
```

```
<210> SEQ ID NO 4
<211> LENGTH: 561
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Gly Trp Phe Leu
            180                 185                 190
```

```
Asp Ser Pro Asp Arg Pro Trp Asn Pro Pro Thr Phe Ser Pro Ala Leu
            195                 200                 205

Leu Val Val Thr Glu Gly Asp Asn Ala Thr Phe Thr Cys Ser Phe Ser
210                 215                 220

Asn Thr Ser Glu Ser Phe Val Leu Asn Trp Tyr Arg Met Ser Pro Ser
225                 230                 235                 240

Asn Gln Thr Asp Lys Leu Ala Ala Phe Pro Glu Asp Arg Ser Gln Pro
            245                 250                 255

Gly Gln Asp Cys Arg Phe Arg Val Thr Gln Leu Pro Asn Gly Arg Asp
            260                 265                 270

Phe His Met Ser Val Val Arg Ala Arg Arg Asn Asp Ser Gly Thr Tyr
            275                 280                 285

Leu Cys Gly Ala Ile Ser Leu Ala Pro Lys Ala Gln Ile Lys Glu Ser
290                 295                 300

Leu Arg Ala Glu Leu Arg Val Thr Glu Arg Arg Ala Glu Val Pro Thr
305                 310                 315                 320

Ala His Pro Ser Pro Ser Pro Arg Pro Ala Gly Gln Phe Gln Thr Leu
            325                 330                 335

Val Val Gly Val Val Gly Gly Leu Leu Gly Ser Leu Val Leu Leu Val
            340                 345                 350

Trp Val Leu Ala Val Ile Cys Ser Arg Ala Ala Arg Gly Thr Ile Gly
355                 360                 365

Ala Arg Arg Thr Gly Gln Pro Gly Trp Phe Leu Asp Ser Pro Asp Arg
            370                 375                 380

Pro Trp Asn Pro Pro Thr Phe Ser Pro Ala Leu Leu Val Val Thr Glu
385                 390                 395                 400

Gly Asp Asn Ala Thr Phe Thr Cys Ser Phe Ser Asn Thr Ser Glu Ser
            405                 410                 415

Phe Val Leu Asn Trp Tyr Arg Met Ser Pro Ser Asn Gln Thr Asp Lys
            420                 425                 430

Leu Ala Ala Phe Pro Glu Asp Arg Ser Gln Pro Gly Gln Asp Cys Arg
            435                 440                 445

Phe Arg Val Thr Gln Leu Pro Asn Gly Arg Asp Phe His Met Ser Val
450                 455                 460

Val Arg Ala Arg Arg Asn Asp Ser Gly Thr Tyr Leu Cys Gly Ala Ile
465                 470                 475                 480

Ser Leu Ala Pro Lys Ala Gln Ile Lys Glu Ser Leu Arg Ala Glu Leu
            485                 490                 495

Arg Val Thr Glu Arg Arg Ala Glu Val Pro Thr Ala His Pro Ser Pro
            500                 505                 510

Ser Pro Arg Pro Ala Gly Gln Phe Gln Thr Leu Val Val Gly Val Val
            515                 520                 525

Gly Gly Leu Leu Gly Ser Leu Val Leu Leu Val Trp Val Leu Ala Val
            530                 535                 540

Ile Cys Ser Arg Ala Ala Arg Gly Thr Ile Gly Ala Arg Arg Thr Gly
545                 550                 555                 560

Gln
```

<210> SEQ ID NO 5
<211> LENGTH: 187
<212> TYPE: PRT
<213> ORGANISM: Unknown
<220> FEATURE:
<223> OTHER INFORMATION: Description of Unknown:
      High-affinity (HA) PD1 ectodomain sequence

```
<400> SEQUENCE: 5

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln
            180                 185

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 7
<211> LENGTH: 187
<212> TYPE: PRT
<213> ORGANISM: Unknown
<220> FEATURE:
<223> OTHER INFORMATION: Description of Unknown:
      Dominant negative PD1 (21-207) sequence
```

<400> SEQUENCE: 7

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln
            180                 185
```

<210> SEQ ID NO 8
<211> LENGTH: 187
<212> TYPE: PRT
<213> ORGANISM: Unknown
<220> FEATURE:
<223> OTHER INFORMATION: Description of Unknown:
      Dominant negative high affinity PD1 sequence

<400> SEQUENCE: 8

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160
```

```
Leu Val Leu Leu Val Trp Val Leu Ala Val Ile Cys Ser Arg Ala Ala
                165                 170                 175

Arg Gly Thr Ile Gly Ala Arg Arg Thr Gly Gln
            180                 185

<210> SEQ ID NO 9
<211> LENGTH: 508
<212> TYPE: PRT
<213> ORGANISM: Homo sapiens

<400> SEQUENCE: 9

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
        50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
```

```
                340             345             350
Gly Pro Leu Leu Glu Pro Val Gly Ser Glu His Ala Gln Asp Thr Tyr
            355                 360                 365

Leu Val Leu Asp Lys Trp Leu Pro Arg Asn Pro Ser Glu Asp
        370                 375             380

Leu Pro Gly Pro Gly Ser Val Asp Ile Val Ala Met Asp Glu Gly
385                 390                 395                 400

Ser Glu Ala Ser Ser Cys Ser Ala Leu Ala Ser Lys Pro Ser Pro
                405                 410                 415

Glu Gly Ala Ser Ala Ser Phe Glu Tyr Thr Ile Leu Asp Pro Ser
                420                 425                 430

Ser Gln Leu Leu Arg Pro Trp Thr Leu Cys Pro Glu Leu Pro Pro Thr
            435                 440                 445

Pro Pro His Leu Lys Tyr Leu Tyr Leu Val Val Ser Asp Ser Gly Ile
            450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
                500                 505

<210> SEQ ID NO 10
<211> LENGTH: 918
<212> TYPE: PRT
<213> ORGANISM: Homo sapiens

<400> SEQUENCE: 10

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
        130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
            195                 200                 205
```

-continued

```
Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
            245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Val Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
```

```
                625                 630                 635                 640
        Phe Asn Lys Arg Asp Leu Ile Lys Lys His Ile Trp Pro Asn Val Pro
                        645                 650                 655
        Asp Pro Ser Lys Ser His Ile Ala Gln Trp Ser Pro His Thr Pro Pro
                        660                 665                 670
        Arg His Asn Phe Asn Ser Lys Asp Gln Met Tyr Ser Asp Gly Asn Phe
                        675                 680                 685
        Thr Asp Val Ser Val Val Glu Ile Glu Ala Asn Asp Lys Lys Pro Phe
                        690                 695                 700
        Pro Glu Asp Leu Lys Ser Leu Asp Leu Phe Lys Lys Glu Lys Ile Asn
        705                 710                 715                 720
        Thr Glu Gly His Ser Ser Gly Ile Gly Gly Ser Ser Cys Met Ser Ser
                        725                 730                 735
        Ser Arg Pro Ser Ile Ser Ser Asp Glu Asn Glu Ser Ser Gln Asn
                        740                 745                 750
        Thr Ser Ser Thr Val Gln Tyr Ser Thr Val Val His Ser Gly Tyr Arg
                        755                 760                 765
        His Gln Val Pro Ser Val Gln Val Phe Ser Arg Ser Glu Ser Thr Gln
                        770                 775                 780
        Pro Leu Leu Asp Ser Glu Arg Pro Glu Asp Leu Gln Leu Val Asp
        785                 790                 795                 800
        His Val Asp Gly Gly Asp Gly Ile Leu Pro Arg Gln Gln Tyr Phe Lys
                        805                 810                 815
        Gln Asn Cys Ser Gln His Glu Ser Ser Pro Asp Ile Ser His Phe Glu
                        820                 825                 830
        Arg Ser Lys Gln Val Ser Ser Val Asn Glu Glu Asp Phe Val Arg Leu
                        835                 840                 845
        Lys Gln Gln Ile Ser Asp His Ile Ser Gln Ser Cys Gly Ser Gly Gln
                        850                 855                 860
        Met Lys Met Phe Gln Glu Val Ser Ala Ala Asp Ala Phe Gly Pro Gly
        865                 870                 875                 880
        Thr Glu Gly Gln Val Glu Arg Phe Glu Thr Val Gly Met Glu Ala Ala
                        885                 890                 895
        Thr Asp Glu Gly Met Pro Lys Ser Tyr Leu Pro Gln Thr Val Arg Gln
                        900                 905                 910
        Gly Gly Tyr Met Pro Gln
                915

<210> SEQ ID NO 11
<211> LENGTH: 622
<212> TYPE: PRT
<213> ORGANISM: Homo sapiens

<400> SEQUENCE: 11

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
        50                  55                  60

His Arg Glu Gly Glu Thr Leu Met His Glu Cys Pro Asp Tyr Ile Thr
65                  70                  75                  80
```

```
Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
    450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
```

```
                  500              505              510
His Lys Val Asn Lys Asp Gly Ala Leu Ser Leu Leu Pro Lys Gln Arg
            515              520              525

Glu Asn Ser Gly Lys Pro Lys Pro Gly Thr Pro Glu Asn Asn Lys
        530              535              540

Glu Tyr Ala Lys Val Ser Gly Val Met Asp Asn Asn Ile Leu Val Leu
545             550              555              560

Val Pro Asp Pro His Ala Lys Asn Val Ala Cys Phe Glu Glu Ser Ala
                565              570              575

Lys Glu Ala Pro Pro Ser Leu Glu Gln Asn Gln Ala Glu Lys Ala Leu
            580              585              590

Ala Asn Phe Thr Ala Thr Ser Ser Lys Cys Arg Leu Gln Leu Gly Gly
        595              600              605

Leu Asp Tyr Leu Asp Pro Ala Cys Phe Thr His Ser Phe His
        610              615              620

<210> SEQ ID NO 12
<211> LENGTH: 638
<212> TYPE: PRT
<213> ORGANISM: Homo sapiens

<400> SEQUENCE: 12

Met Asp Leu Trp Gln Leu Leu Leu Thr Leu Ala Leu Ala Gly Ser Ser
1               5                10               15

Asp Ala Phe Ser Gly Ser Glu Ala Thr Ala Ala Ile Leu Ser Arg Ala
                20               25               30

Pro Trp Ser Leu Gln Ser Val Asn Pro Gly Leu Lys Thr Asn Ser Ser
            35               40               45

Lys Glu Pro Lys Phe Thr Lys Cys Arg Ser Pro Glu Arg Glu Thr Phe
        50               55               60

Ser Cys His Trp Thr Asp Glu Val His His Gly Thr Lys Asn Leu Gly
65               70               75               80

Pro Ile Gln Leu Phe Tyr Thr Arg Arg Asn Thr Gln Glu Trp Thr Gln
                85               90               95

Glu Trp Lys Glu Cys Pro Asp Tyr Val Ser Ala Gly Glu Asn Ser Cys
            100              105              110

Tyr Phe Asn Ser Ser Phe Thr Ser Ile Trp Ile Pro Tyr Cys Ile Lys
        115              120              125

Leu Thr Ser Asn Gly Gly Thr Val Asp Glu Lys Cys Phe Ser Val Asp
130              135              140

Glu Ile Val Gln Pro Asp Pro Pro Ile Ala Leu Asn Trp Thr Leu Leu
145              150              155              160

Asn Val Ser Leu Thr Gly Ile His Ala Asp Ile Gln Val Arg Trp Glu
                165              170              175

Ala Pro Arg Asn Ala Asp Ile Gln Lys Gly Trp Met Val Leu Glu Tyr
            180              185              190

Glu Leu Gln Tyr Lys Glu Val Asn Glu Thr Lys Trp Lys Met Met Asp
        195              200              205

Pro Ile Leu Thr Thr Ser Val Pro Val Tyr Ser Leu Lys Val Asp Lys
    210              215              220

Glu Tyr Glu Val Arg Val Arg Ser Lys Gln Arg Asn Ser Gly Asn Tyr
225              230              235              240

Gly Glu Phe Ser Glu Val Leu Tyr Val Thr Leu Pro Gln Met Ser Gln
                245              250              255
```

```
Phe Thr Cys Glu Glu Asp Phe Tyr Phe Pro Trp Leu Leu Ile Ile
            260                 265                 270

Phe Gly Ile Phe Gly Leu Thr Val Met Leu Phe Val Phe Leu Phe Ser
        275                 280                 285

Lys Gln Gln Arg Ile Lys Met Leu Ile Leu Pro Pro Val Pro Val Pro
    290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635

<210> SEQ ID NO 13
<211> LENGTH: 863
<212> TYPE: PRT
<213> ORGANISM: Homo sapiens

<400> SEQUENCE: 13
```

```
Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
        50                  55                  60

Leu Gly Ala Glu Leu Gln Pro Gly Gly Arg Gln Gln Arg Leu Ser Asp
65              70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
                100                 105                 110

Asp Gln Val Glu Leu Arg Ala Gly Tyr Pro Pro Ala Ile Pro His Asn
            115                 120                 125

Leu Ser Cys Leu Met Asn Leu Thr Thr Ser Ser Leu Ile Cys Gln Trp
            130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
            195                 200                 205

Leu Gly Thr Ser Met Ser Pro Gln Leu Cys Leu Asp Pro Met Asp Val
            210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
                260                 265                 270

Gln Arg Gly Glu Ala Ser Trp Ala Leu Val Gly Pro Leu Pro Leu Glu
            275                 280                 285

Ala Leu Gln Tyr Glu Leu Cys Gly Leu Leu Pro Ala Thr Ala Tyr Thr
            290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
            355                 360                 365

Gln Gly Tyr Val Val Ser Trp Arg Pro Ser Gly Gln Ala Gly Ala Ile
            370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415
```

```
Ser Arg Pro Thr Pro Val Val Phe Ser Glu Ser Gly Pro Ala Leu
                420                 425                 430

Thr Arg Leu His Ala Met Ala Arg Asp Pro His Ser Leu Trp Val Gly
        435                 440                 445

Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
        515                 520                 525

His Ala Pro Glu Leu His Leu Lys His Ile Gly Lys Thr Trp Ala Gln
    530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
        595                 600                 605

Thr Asn Ser Thr Val Leu Thr Leu Met Thr Leu Thr Pro Glu Gly Ser
    610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
            660                 665                 670

Trp Val Pro Thr Ile Met Glu Glu Leu Pro Gly Pro Arg Gln Gly Gln
        675                 680                 685

Trp Leu Gly Gln Thr Ser Glu Met Ser Arg Ala Leu Thr Pro His Pro
    690                 695                 700

Cys Val Gln Asp Ala Phe Gln Leu Pro Gly Leu Gly Thr Pro Pro Ile
705                 710                 715                 720

Thr Lys Leu Thr Val Leu Glu Glu Asp Glu Lys Lys Pro Val Pro Trp
                725                 730                 735

Glu Ser His Asn Ser Ser Glu Thr Cys Gly Leu Pro Thr Leu Val Gln
            740                 745                 750

Thr Tyr Val Leu Gln Gly Asp Pro Arg Ala Val Ser Thr Gln Pro Gln
        755                 760                 765

Ser Gln Ser Gly Thr Ser Asp Gln Val Leu Tyr Gly Gln Leu Leu Gly
    770                 775                 780

Ser Pro Thr Ser Pro Gly Pro Gly His Tyr Leu Arg Cys Asp Ser Thr
785                 790                 795                 800

Gln Pro Leu Leu Ala Gly Leu Thr Pro Ser Pro Lys Ser Tyr Glu Asn
                805                 810                 815

Leu Trp Phe Gln Ala Ser Pro Leu Gly Thr Leu Val Thr Pro Ala Pro
            820                 825                 830

Ser Gln Glu Asp Asp Cys Val Phe Gly Pro Leu Leu Asn Phe Pro Leu
```

```
                    835                 840                 845

Leu Gln Gly Ile Arg Val His Gly Met Glu Ala Leu Gly Ser Phe
        850                 855                 860

<210> SEQ ID NO 14
<211> LENGTH: 97
<212> TYPE: PRT
<213> ORGANISM: Unknown
<220> FEATURE:
<223> OTHER INFORMATION: Description of Unknown:
      GCSFR(614-710) sequence

<400> SEQUENCE: 14

Leu Thr Leu Met Thr Leu Thr Pro Glu Gly Ser Glu Leu His Ile Ile
1               5                   10                  15

Leu Gly Leu Phe Gly Leu Leu Leu Leu Thr Cys Leu Cys Gly Thr
            20                  25                  30

Ala Trp Leu Cys Cys Ser Pro Asn Arg Lys Asn Pro Leu Trp Pro Ser
            35                  40                  45

Val Pro Asp Pro Ala His Ser Ser Leu Gly Ser Trp Val Pro Thr Ile
    50                  55                  60

Met Glu Glu Asp Ala Phe Gln Leu Pro Gly Leu Gly Thr Pro Pro Ile
65                  70                  75                  80

Thr Lys Leu Thr Val Leu Glu Glu Asp Glu Lys Lys Pro Val Pro Trp
                85                  90                  95

Glu

<210> SEQ ID NO 15
<211> LENGTH: 92
<212> TYPE: PRT
<213> ORGANISM: Homo sapiens

<400> SEQUENCE: 15

Thr Thr Pro Lys Phe Ala Gln Gly Glu Ile Glu Ala Ile Val Val Pro
1               5                   10                  15

Val Cys Leu Ala Phe Leu Leu Thr Thr Leu Leu Gly Val Leu Phe Cys
            20                  25                  30

Phe Asn Lys Arg Asp Leu Ile Lys Lys His Ile Trp Pro Asn Val Pro
            35                  40                  45

Asp Pro Ser Lys Ser His Ile Ala Gln Trp Ser Pro His Thr Pro Pro
    50                  55                  60

Arg His Asn Phe Asn Ser Lys Asp Gln Met Tyr Ser Asp Gly Asn Phe
65                  70                  75                  80

Thr Asp Val Ser Val Val Glu Ile Glu Ala Asn Asp
                85                  90

<210> SEQ ID NO 16
<211> LENGTH: 105
<212> TYPE: PRT
<213> ORGANISM: Homo sapiens

<400> SEQUENCE: 16

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
            35                  40                  45
```

```
His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                    85                  90                  95

Ser Ser Glu Arg Thr Pro Leu Pro Leu
            100                 105

<210> SEQ ID NO 17
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Asp Pro Thr Arg Val Glu Thr Ala Thr Glu Thr Trp Ile Ser Leu
 1               5                  10                  15

Val Thr Ala Leu His Leu Val Leu Gly Leu Ser Ala Val Leu Gly Leu
                20                  25                  30

Leu Leu Leu Arg Trp Gln Phe Pro Ala His Tyr Arg Arg Leu Arg His
            35                  40                  45

Ala Leu Trp Pro Ser Leu Pro Asp Leu His Arg Val Leu Gly Gln Tyr
        50                  55                  60

Leu Arg Asp Thr Ala Ala Leu Ser Pro Pro Lys Ala Thr Val Ser Asp
 65                  70                  75                  80

Thr Cys Glu Glu Val Glu Pro Ser Leu Leu Glu Ile Leu Pro Lys Ser
                    85                  90                  95

Ser Glu Arg Thr Pro Leu Pro Leu
            100

<210> SEQ ID NO 18
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Asp Pro Thr Arg Val Glu Thr Ala Thr Glu Thr Ile Ser Leu Val
 1               5                  10                  15

Thr Ala Leu His Leu Val Leu Gly Leu Ser Ala Val Leu Gly Leu Leu
                20                  25                  30

Leu Leu Arg Trp Gln Phe Pro Ala His Tyr Arg Arg Leu Arg His Ala
            35                  40                  45

Leu Trp Pro Ser Leu Pro Asp Leu His Arg Val Leu Gly Gln Tyr Leu
        50                  55                  60

Arg Asp Thr Ala Ala Leu Ser Pro Pro Lys Ala Thr Val Ser Asp Thr
 65                  70                  75                  80

Cys Glu Glu Val Glu Pro Ser Leu Leu Glu Ile Leu Pro Lys Ser Ser
                    85                  90                  95

Glu Arg Thr Pro Leu Pro Leu
            100

<210> SEQ ID NO 19
<211> LENGTH: 104
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Asp Pro Thr Arg Val Glu Thr Ala Thr Glu Thr Leu Ile Ser Leu
1               5                   10                  15

Val Thr Ala Leu His Leu Val Leu Gly Leu Ser Ala Val Leu Gly Leu
            20                  25                  30

Leu Leu Leu Arg Trp Gln Phe Pro Ala His Tyr Arg Arg Leu Arg His
            35                  40                  45

Ala Leu Trp Pro Ser Leu Pro Asp Leu His Arg Val Leu Gly Gln Tyr
        50                  55                  60

Leu Arg Asp Thr Ala Ala Leu Ser Pro Pro Lys Ala Thr Val Ser Asp
65                  70                  75                  80

Thr Cys Glu Glu Val Glu Pro Ser Leu Leu Glu Ile Leu Pro Lys Ser
                85                  90                  95

Ser Glu Arg Thr Pro Leu Pro Leu
            100

<210> SEQ ID NO 20
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Asp Pro Thr Arg Val Glu Thr Ala Thr Glu Thr Ser Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
            35                  40                  45

Trp Pro Ser Leu Pro Asp Leu His Arg Val Leu Gly Gln Tyr Leu Arg
        50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
            100

<210> SEQ ID NO 21
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Asp Pro Thr Arg Val Glu Thr Ala Thr Glu Thr Leu Val Thr Ala
1               5                   10                  15

Leu His Leu Val Leu Gly Leu Ser Ala Val Leu Gly Leu Leu Leu Leu
            20                  25                  30

Arg Trp Gln Phe Pro Ala His Tyr Arg Arg Leu Arg His Ala Leu Trp
```

```
                35                  40                  45
Pro Ser Leu Pro Asp Leu His Arg Val Leu Gly Gln Tyr Leu Arg Asp
        50                  55                  60
Thr Ala Ala Leu Ser Pro Pro Lys Ala Thr Val Ser Asp Thr Cys Glu
65                  70                  75                  80
Glu Val Glu Pro Ser Leu Leu Glu Ile Leu Pro Lys Ser Ser Glu Arg
                85                  90                  95
Thr Pro Leu Pro Leu
            100

<210> SEQ ID NO 22
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Asp Pro Thr Arg Val Glu Thr Ala Thr Glu Thr Ile Leu Val Thr
1               5                  10                  15
Ala Leu His Leu Val Leu Gly Leu Ser Ala Val Leu Gly Leu Leu Leu
                20                  25                  30
Leu Arg Trp Gln Phe Pro Ala His Tyr Arg Arg Leu Arg His Ala Leu
            35                  40                  45
Trp Pro Ser Leu Pro Asp Leu His Arg Val Leu Gly Gln Tyr Leu Arg
        50                  55                  60
Asp Thr Ala Ala Leu Ser Pro Pro Lys Ala Thr Val Ser Asp Thr Cys
65                  70                  75                  80
Glu Glu Val Glu Pro Ser Leu Leu Glu Ile Leu Pro Lys Ser Ser Glu
                85                  90                  95
Arg Thr Pro Leu Pro Leu
            100

<210> SEQ ID NO 23
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Asp Pro Thr Arg Val Glu Thr Ala Thr Glu Thr Val Thr Ala Leu
1               5                  10                  15
His Leu Val Leu Gly Leu Ser Ala Val Leu Gly Leu Leu Leu Leu Arg
                20                  25                  30
Trp Gln Phe Pro Ala His Tyr Arg Arg Leu Arg His Ala Leu Trp Pro
            35                  40                  45
Ser Leu Pro Asp Leu His Arg Val Leu Gly Gln Tyr Leu Arg Asp Thr
        50                  55                  60
Ala Ala Leu Ser Pro Pro Lys Ala Thr Val Ser Asp Thr Cys Glu Glu
65                  70                  75                  80
Val Glu Pro Ser Leu Leu Glu Ile Leu Pro Lys Ser Ser Glu Arg Thr
                85                  90                  95
Pro Leu Pro Leu
            100
```

```
<210> SEQ ID NO 24
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Asp Pro Thr Arg Val Glu Thr Ala Thr Glu Thr Thr Ala Leu His
1               5                   10                  15

Leu Val Leu Gly Leu Ser Ala Val Leu Gly Leu Leu Leu Leu Arg Trp
            20                  25                  30

Gln Phe Pro Ala His Tyr Arg Arg Leu Arg His Ala Leu Trp Pro Ser
        35                  40                  45

Leu Pro Asp Leu His Arg Val Leu Gly Gln Tyr Leu Arg Asp Thr Ala
    50                  55                  60

Ala Leu Ser Pro Pro Lys Ala Thr Val Ser Asp Thr Cys Glu Glu Val
65                  70                  75                  80

Glu Pro Ser Leu Leu Glu Ile Leu Pro Lys Ser Ser Glu Arg Thr Pro
                85                  90                  95

Leu Pro Leu

<210> SEQ ID NO 25
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Asp Pro Thr Arg Val Glu Thr Ala Thr Glu Thr Ala Leu His Leu
1               5                   10                  15

Val Leu Gly Leu Ser Ala Val Leu Gly Leu Leu Leu Leu Arg Trp Gln
            20                  25                  30

Phe Pro Ala His Tyr Arg Arg Leu Arg His Ala Leu Trp Pro Ser Leu
        35                  40                  45

Pro Asp Leu His Arg Val Leu Gly Gln Tyr Leu Arg Asp Thr Ala Ala
    50                  55                  60

Leu Ser Pro Pro Lys Ala Thr Val Ser Asp Thr Cys Glu Glu Val Glu
65                  70                  75                  80

Pro Ser Leu Leu Glu Ile Leu Pro Lys Ser Ser Glu Arg Thr Pro Leu
                85                  90                  95

Pro Leu

<210> SEQ ID NO 26
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Asp Pro Thr Arg Val Glu Thr Ala Thr Glu Thr Leu His Leu Val
1               5                   10                  15

Leu Gly Leu Ser Ala Val Leu Gly Leu Leu Leu Leu Arg Trp Gln Phe
            20                  25                  30

Pro Ala His Tyr Arg Arg Leu Arg His Ala Leu Trp Pro Ser Leu Pro
```

```
                35                  40                  45
Asp Leu His Arg Val Leu Gly Gln Tyr Leu Arg Asp Thr Ala Ala Leu
         50                  55                  60

Ser Pro Pro Lys Ala Thr Val Ser Asp Thr Cys Glu Glu Val Glu Pro
 65                  70                  75                  80

Ser Leu Leu Glu Ile Leu Pro Lys Ser Ser Glu Arg Thr Pro Leu Pro
                 85                  90                  95

Leu

<210> SEQ ID NO 27
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Asp Pro Thr Arg Val Glu Thr Ala Thr Glu Thr His Leu Val Leu
 1               5                  10                  15

Gly Leu Ser Ala Val Leu Gly Leu Leu Leu Arg Trp Gln Phe Pro
                20                  25                  30

Ala His Tyr Arg Arg Leu Arg His Ala Leu Trp Pro Ser Leu Pro Asp
                35                  40                  45

Leu His Arg Val Leu Gly Gln Tyr Leu Arg Asp Thr Ala Ala Leu Ser
         50                  55                  60

Pro Pro Lys Ala Thr Val Ser Asp Thr Cys Glu Glu Val Glu Pro Ser
 65                  70                  75                  80

Leu Leu Glu Ile Leu Pro Lys Ser Ser Glu Arg Thr Pro Leu Pro Leu
                 85                  90                  95

<210> SEQ ID NO 28
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Asp Pro Thr Arg Val Glu Thr Ala Thr Glu Thr Leu Val Leu Gly
 1               5                  10                  15

Leu Ser Ala Val Leu Gly Leu Leu Leu Arg Trp Gln Phe Pro Ala
                20                  25                  30

His Tyr Arg Arg Leu Arg His Ala Leu Trp Pro Ser Leu Pro Asp Leu
                35                  40                  45

His Arg Val Leu Gly Gln Tyr Leu Arg Asp Thr Ala Ala Leu Ser Pro
         50                  55                  60

Pro Lys Ala Thr Val Ser Asp Thr Cys Glu Glu Val Glu Pro Ser Leu
 65                  70                  75                  80

Leu Glu Ile Leu Pro Lys Ser Ser Glu Arg Thr Pro Leu Pro Leu
                 85                  90                  95

<210> SEQ ID NO 29
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 29

Ser Asp Pro Thr Arg Val Glu Thr Ala Thr Glu Thr Val Leu Gly Leu
1               5                   10                  15

Ser Ala Val Leu Gly Leu Leu Leu Arg Trp Gln Phe Pro Ala His
            20                  25                  30

Tyr Arg Arg Leu Arg His Ala Leu Trp Pro Ser Leu Pro Asp Leu His
        35                  40                  45

Arg Val Leu Gly Gln Tyr Leu Arg Asp Thr Ala Ala Leu Ser Pro Pro
    50                  55                  60

Lys Ala Thr Val Ser Asp Thr Cys Glu Glu Val Glu Pro Ser Leu Leu
65                  70                  75                  80

Glu Ile Leu Pro Lys Ser Ser Glu Arg Thr Pro Leu Pro Leu
                85                  90

<210> SEQ ID NO 30
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ser Asp Pro Thr Arg Val Glu Thr Ala Thr Glu Thr Leu Gly Leu Ser
1               5                   10                  15

Ala Val Leu Gly Leu Leu Leu Arg Trp Gln Phe Pro Ala His Tyr
            20                  25                  30

Arg Arg Leu Arg His Ala Leu Trp Pro Ser Leu Pro Asp Leu His Arg
        35                  40                  45

Val Leu Gly Gln Tyr Leu Arg Asp Thr Ala Ala Leu Ser Pro Pro Lys
    50                  55                  60

Ala Thr Val Ser Asp Thr Cys Glu Glu Val Glu Pro Ser Leu Leu Glu
65                  70                  75                  80

Ile Leu Pro Lys Ser Ser Glu Arg Thr Pro Leu Pro Leu
                85                  90

<210> SEQ ID NO 31
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Ser Asp Pro Thr Arg Val Glu Thr Ala Thr Glu Thr Gly Leu Ser Ala
1               5                   10                  15

Val Leu Gly Leu Leu Leu Arg Trp Gln Phe Pro Ala His Tyr Arg
            20                  25                  30

Arg Leu Arg His Ala Leu Trp Pro Ser Leu Pro Asp Leu His Arg Val
        35                  40                  45

Leu Gly Gln Tyr Leu Arg Asp Thr Ala Ala Leu Ser Pro Pro Lys Ala
    50                  55                  60

Thr Val Ser Asp Thr Cys Glu Glu Val Glu Pro Ser Leu Leu Glu Ile
65                  70                  75                  80

Leu Pro Lys Ser Ser Glu Arg Thr Pro Leu Pro Leu
                85                  90

<210> SEQ ID NO 32
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Asp Pro Thr Arg Val Glu Thr Ala Thr Glu Thr Leu Ser Ala Val
1               5                   10                  15

Leu Gly Leu Leu Leu Arg Trp Gln Phe Pro Ala His Tyr Arg Arg
            20                  25                  30

Leu Arg His Ala Leu Trp Pro Ser Leu Pro Asp Leu His Arg Val Leu
        35                  40                  45

Gly Gln Tyr Leu Arg Asp Thr Ala Ala Leu Ser Pro Pro Lys Ala Thr
    50                  55                  60

Val Ser Asp Thr Cys Glu Glu Val Glu Pro Ser Leu Leu Glu Ile Leu
65                  70                  75                  80

Pro Lys Ser Ser Glu Arg Thr Pro Leu Pro Leu
                85                  90

<210> SEQ ID NO 33
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Asp Pro Thr Arg Val Glu Thr Ala Thr Glu Thr Ser Ala Val Leu
1               5                   10                  15

Gly Leu Leu Leu Leu Arg Trp Gln Phe Pro Ala His Tyr Arg Arg Leu
            20                  25                  30

Arg His Ala Leu Trp Pro Ser Leu Pro Asp Leu His Arg Val Leu Gly
        35                  40                  45

Gln Tyr Leu Arg Asp Thr Ala Ala Leu Ser Pro Pro Lys Ala Thr Val
    50                  55                  60

Ser Asp Thr Cys Glu Glu Val Glu Pro Ser Leu Leu Glu Ile Leu Pro
65                  70                  75                  80

Lys Ser Ser Glu Arg Thr Pro Leu Pro Leu
                85                  90

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Asp Pro Thr Arg Val Glu Thr Ala Thr Glu Thr Ala Val Leu Gly
1               5                   10                  15

Leu Leu Leu Leu Arg Trp Gln Phe Pro Ala His Tyr Arg Arg Leu Arg
            20                  25                  30

His Ala Leu Trp Pro Ser Leu Pro Asp Leu His Arg Val Leu Gly Gln
        35                  40                  45

Tyr Leu Arg Asp Thr Ala Ala Leu Ser Pro Pro Lys Ala Thr Val Ser

```
                50                  55                  60
Asp Thr Cys Glu Glu Val Glu Pro Ser Leu Leu Glu Ile Leu Pro Lys
 65                  70                  75                  80

Ser Ser Glu Arg Thr Pro Leu Pro Leu
                 85

<210> SEQ ID NO 35
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Asp Pro Thr Arg Val Glu Thr Ala Thr Glu Thr Val Leu Gly Leu
 1               5                  10                  15

Leu Leu Arg Trp Gln Phe Pro Ala His Tyr Arg Arg Leu Arg His
                20                  25                  30

Ala Leu Trp Pro Ser Leu Pro Asp Leu His Arg Val Leu Gly Gln Tyr
                 35                  40                  45

Leu Arg Asp Thr Ala Ala Leu Ser Pro Pro Lys Ala Thr Val Ser Asp
     50                  55                  60

Thr Cys Glu Glu Val Glu Pro Ser Leu Leu Glu Ile Leu Pro Lys Ser
 65                  70                  75                  80

Ser Glu Arg Thr Pro Leu Pro Leu
                 85

<210> SEQ ID NO 36
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Asp Pro Thr Arg Val Glu Thr Ala Thr Glu Thr Leu Gly Leu Leu
 1               5                  10                  15

Leu Leu Arg Trp Gln Phe Pro Ala His Tyr Arg Arg Leu Arg His Ala
                20                  25                  30

Leu Trp Pro Ser Leu Pro Asp Leu His Arg Val Leu Gly Gln Tyr Leu
                 35                  40                  45

Arg Asp Thr Ala Ala Leu Ser Pro Pro Lys Ala Thr Val Ser Asp Thr
     50                  55                  60

Cys Glu Glu Val Glu Pro Ser Leu Leu Glu Ile Leu Pro Lys Ser Ser
 65                  70                  75                  80

Glu Arg Thr Pro Leu Pro Leu
                 85

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Pro Thr Arg Val Glu Thr Ala Thr Glu Thr Ala Trp Leu Ile
 1               5                  10                  15
```

Ser Leu Val Thr Ala Leu His Leu Val Leu Gly Leu Ser Ala Val Leu
            20                  25                  30

Gly Leu Leu Leu Arg Trp Gln Phe Pro Ala His Tyr Arg Arg Leu
        35                  40                  45

Arg His Ala Leu Trp Pro Ser Leu Pro Asp Leu His Arg Val Leu Gly
 50                  55                  60

Gln Tyr Leu Arg Asp Thr Ala Ala Leu Ser Pro Pro Lys Ala Thr Val
 65                  70                  75                  80

Ser Asp Thr Cys Glu Glu Val Glu Pro Ser Leu Leu Glu Ile Leu Pro
                85                  90                  95

Lys Ser Ser Glu Arg Thr Pro Leu Pro Leu
            100                 105

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Asp Pro Thr Arg Val Glu Thr Ala Thr Glu Thr Ala Trp Val Leu
 1               5                  10                  15

Ile Ser Leu Val Thr Ala Leu His Leu Val Leu Gly Leu Ser Ala Val
            20                  25                  30

Leu Gly Leu Leu Leu Arg Trp Gln Phe Pro Ala His Tyr Arg Arg
        35                  40                  45

Leu Arg His Ala Leu Trp Pro Ser Leu Pro Asp Leu His Arg Val Leu
 50                  55                  60

Gly Gln Tyr Leu Arg Asp Thr Ala Ala Leu Ser Pro Pro Lys Ala Thr
 65                  70                  75                  80

Val Ser Asp Thr Cys Glu Glu Val Glu Pro Ser Leu Leu Glu Ile Leu
                85                  90                  95

Pro Lys Ser Ser Glu Arg Thr Pro Leu Pro Leu
            100                 105

<210> SEQ ID NO 39
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Asp Pro Thr Arg Val Glu Thr Ala Thr Glu Thr Ala Trp Leu Val
 1               5                  10                  15

Leu Ile Ser Leu Val Thr Ala Leu His Leu Val Leu Gly Leu Ser Ala
            20                  25                  30

Val Leu Gly Leu Leu Leu Arg Trp Gln Phe Pro Ala His Tyr Arg
        35                  40                  45

Arg Leu Arg His Ala Leu Trp Pro Ser Leu Pro Asp Leu His Arg Val
 50                  55                  60

Leu Gly Gln Tyr Leu Arg Asp Thr Ala Ala Leu Ser Pro Pro Lys Ala
 65                  70                  75                  80

Thr Val Ser Asp Thr Cys Glu Glu Val Glu Pro Ser Leu Leu Glu Ile
                85                  90                  95

```
Leu Pro Lys Ser Ser Glu Arg Thr Pro Leu Pro Leu
            100                 105

<210> SEQ ID NO 40
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Ser
            20                  25                  30

Ala Val Leu Gly Leu Leu Leu Arg Trp Gln Phe Pro Ala His Tyr
        35                  40                  45

Arg Arg Leu Arg His Ala Leu Trp Pro Ser Leu Pro Asp Leu His Arg
50                  55                  60

Val Leu Gly Gln Tyr Leu Arg Asp Thr Ala Ala Leu Ser Pro Pro Lys
65                  70                  75                  80

Ala Thr Val Ser Asp Thr Cys Glu Glu Val Glu Pro Ser Leu Leu Glu
                85                  90                  95

Ile Leu Pro Lys Ser Ser Glu Arg Thr Pro Leu Pro Leu
            100                 105

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Asp Pro Thr Arg Val Glu Thr Ala Thr Glu Thr Ala Trp Leu Ile
1               5                   10                  15

Leu Val Leu Ile Ser Leu Val Thr Ala Leu His Leu Val Leu Gly Leu
            20                  25                  30

Ser Ala Val Leu Gly Leu Leu Leu Arg Trp Gln Phe Pro Ala His
        35                  40                  45

Tyr Arg Arg Leu Arg His Ala Leu Trp Pro Ser Leu Pro Asp Leu His
    50                  55                  60

Arg Val Leu Gly Gln Tyr Leu Arg Asp Thr Ala Ala Leu Ser Pro Pro
65                  70                  75                  80

Lys Ala Thr Val Ser Asp Thr Cys Glu Glu Val Glu Pro Ser Leu Leu
                85                  90                  95

Glu Ile Leu Pro Lys Ser Ser Glu Arg Thr Pro Leu Pro Leu
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

Ser Asp Pro Thr Arg Val Glu Thr Ala Thr Glu Thr Ala Trp Leu Leu
1               5                   10                  15

Ile Leu Val Leu Ile Ser Leu Val Thr Ala Leu His Leu Val Leu Gly
            20                  25                  30

Leu Ser Ala Val Leu Gly Leu Leu Leu Leu Arg Trp Gln Phe Pro Ala
        35                  40                  45

His Tyr Arg Arg Leu Arg His Ala Leu Trp Pro Ser Leu Pro Asp Leu
    50                  55                  60

His Arg Val Leu Gly Gln Tyr Leu Arg Asp Thr Ala Ala Leu Ser Pro
65                  70                  75                  80

Pro Lys Ala Thr Val Ser Asp Thr Cys Glu Glu Val Glu Pro Ser Leu
                85                  90                  95

Leu Glu Ile Leu Pro Lys Ser Ser Glu Arg Thr Pro Leu Pro Leu
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Asp Pro Thr Arg Val Glu Thr Ala Thr Glu Thr Ala Trp Val Leu
1               5                   10                  15

Leu Ile Leu Val Leu Ile Ser Leu Val Thr Ala Leu His Leu Val Leu
            20                  25                  30

Gly Leu Ser Ala Val Leu Gly Leu Leu Leu Leu Arg Trp Gln Phe Pro
        35                  40                  45

Ala His Tyr Arg Arg Leu Arg His Ala Leu Trp Pro Ser Leu Pro Asp
    50                  55                  60

Leu His Arg Val Leu Gly Gln Tyr Leu Arg Asp Thr Ala Ala Leu Ser
65                  70                  75                  80

Pro Pro Lys Ala Thr Val Ser Asp Thr Cys Glu Glu Val Glu Pro Ser
                85                  90                  95

Leu Leu Glu Ile Leu Pro Lys Ser Ser Glu Arg Thr Pro Leu Pro Leu
            100                 105                 110

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Asp Pro Thr Arg Val Glu Thr Ala Thr Glu Thr Ala Trp Leu Val
1               5                   10                  15

Leu Leu Ile Leu Val Leu Ile Ser Leu Val Thr Ala Leu His Leu Val
            20                  25                  30

Leu Gly Leu Ser Ala Val Leu Gly Leu Leu Leu Leu Arg Trp Gln Phe
        35                  40                  45

Pro Ala His Tyr Arg Arg Leu Arg His Ala Leu Trp Pro Ser Leu Pro
    50                  55                  60

Asp Leu His Arg Val Leu Gly Gln Tyr Leu Arg Asp Thr Ala Ala Leu
65                  70                  75                  80

```
Ser Pro Pro Lys Ala Thr Val Ser Asp Thr Cys Glu Glu Val Glu Pro
                85                  90                  95

Ser Leu Leu Glu Ile Leu Pro Lys Ser Ser Glu Arg Thr Pro Leu Pro
            100                 105                 110

Leu

<210> SEQ ID NO 45
<211> LENGTH: 144
<212> TYPE: PRT
<213> ORGANISM: Unknown
<220> FEATURE:
<223> OTHER INFORMATION: Description of Unknown:
      IL7R(316-459) sequence

<400> SEQUENCE: 45

Ala Arg Asp Glu Val Glu Gly Phe Leu Gln Asp Thr Phe Pro Gln Gln
1               5                   10                  15

Leu Glu Glu Ser Glu Lys Gln Arg Leu Gly Gly Asp Val Gln Ser Pro
            20                  25                  30

Asn Cys Pro Ser Glu Asp Val Val Ile Thr Pro Glu Ser Phe Gly Arg
        35                  40                  45

Asp Ser Ser Leu Thr Cys Leu Ala Gly Asn Val Ser Ala Cys Asp Ala
    50                  55                  60

Pro Ile Leu Ser Ser Ser Arg Ser Leu Asp Cys Arg Glu Ser Gly Lys
65                  70                  75                  80

Asn Gly Pro His Val Tyr Gln Asp Leu Leu Leu Ser Leu Gly Thr Thr
                85                  90                  95

Asn Ser Thr Leu Pro Pro Pro Phe Ser Leu Gln Ser Gly Ile Leu Thr
            100                 105                 110

Leu Asn Pro Val Ala Gln Gly Gln Pro Ile Leu Thr Ser Leu Gly Ser
        115                 120                 125

Asn Gln Glu Glu Ala Tyr Val Thr Met Ser Ser Phe Tyr Gln Asn Gln
    130                 135                 140

<210> SEQ ID NO 46
<211> LENGTH: 219
<212> TYPE: PRT
<213> ORGANISM: Unknown
<220> FEATURE:
<223> OTHER INFORMATION: Description of Unknown:
      IL2Rb(333-551) sequence

<400> SEQUENCE: 46

Val Thr Gln Leu Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Tyr
            20                  25                  30

Phe Phe Phe His Leu Pro Asp Ala Leu Glu Ile Glu Ala Cys Gln Val
        35                  40                  45

Tyr Phe Thr Tyr Asp Pro Tyr Ser Glu Glu Asp Pro Asp Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Pro Ser Thr Ala
            100                 105                 110

Pro Gly Gly Ser Gly Ala Gly Glu Glu Arg Met Pro Pro Ser Leu Gln
```

```
                115                 120                 125
Glu Arg Val Pro Arg Asp Trp Asp Pro Gln Pro Leu Gly Pro Pro Thr
130                 135                 140

Pro Gly Val Pro Asp Leu Val Asp Phe Gln Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
                180                 185                 190

Leu Asn Ala Arg Leu Pro Leu Asn Thr Asp Ala Tyr Leu Ser Leu Gln
                195                 200                 205

Glu Leu Gln Gly Gln Asp Pro Thr His Leu Val
210                 215
```

<210> SEQ ID NO 47
<211> LENGTH: 50
<212> TYPE: PRT
<213> ORGANISM: Unknown
<220> FEATURE:
<223> OTHER INFORMATION: Description of Unknown:
      IFNAR1(508-557) sequence

<400> SEQUENCE: 47

```
Ile Ser Thr Ile Ala Thr Val Glu Glu Thr Asn Gln Thr Asp Glu Asp
1               5                   10                  15

His Lys Lys Tyr Ser Ser Gln Thr Ser Gln Asp Ser Gly Asn Tyr Ser
                20                  25                  30

Asn Glu Asp Glu Ser Glu Ser Lys Thr Ser Glu Glu Leu Gln Gln Asp
            35                  40                  45

Phe Val
    50
```

<210> SEQ ID NO 48
<211> LENGTH: 206
<212> TYPE: PRT
<213> ORGANISM: Unknown
<220> FEATURE:
<223> OTHER INFORMATION: Description of Unknown:
      IFNAR2(310-515) sequence

<400> SEQUENCE: 48

```
Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
                20                  25                  30

Leu Thr Val Arg Pro Leu Gly Gln Ala Ser Ala Thr Ser Thr Glu Ser
            35                  40                  45

Gln Leu Ile Asp Pro Glu Ser Glu Glu Glu Pro Asp Leu Pro Glu Val
    50                  55                  60

Asp Val Glu Leu Pro Thr Met Pro Lys Asp Ser Pro Gln Gln Leu Glu
65                  70                  75                  80

Leu Leu Ser Gly Pro Cys Glu Arg Arg Lys Ser Pro Leu Gln Asp Pro
                85                  90                  95

Phe Pro Glu Glu Asp Tyr Ser Ser Thr Glu Gly Ser Gly Gly Arg Ile
                100                 105                 110

Thr Phe Asn Val Asp Leu Asn Ser Val Phe Leu Arg Val Leu Asp Asp
                115                 120                 125

Glu Asp Ser Asp Asp Leu Glu Ala Pro Leu Met Leu Ser Ser His Leu
```

```
                130                 135                 140
Glu Met Val Asp Pro Glu Asp Pro Asp Asn Val Gln Ser Asn His
145                 150                 155                 160

Leu Leu Ala Ser Gly Glu Gly Thr Gln Pro Thr Phe Pro Ser Pro Ser
                165                 170                 175

Ser Glu Gly Leu Trp Ser Glu Asp Ala Pro Ser Asp Gln Ser Asp Thr
                180                 185                 190

Ser Glu Ser Asp Val Asp Leu Gly Asp Gly Tyr Ile Met Arg
                195                 200                 205

<210> SEQ ID NO 49
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ile Ser Thr Ile Ala Thr Val Glu Glu Thr Asn Gln Thr Asp Glu Asp
1               5                   10                  15

His Lys Lys Tyr Ser Ser Gln Thr Ser Gln Asp Ser Gly Asn Tyr Ser
                20                  25                  30

Asn Glu Asp Glu Ser Glu Ser Lys Thr Ser Glu Glu Leu Gln Gln Asp
                35                  40                  45

Phe Val Lys Lys Lys Val Trp Asp Tyr Asn Tyr Asp Asp Glu Ser Asp
    50                  55                  60

Ser Asp Thr Glu Ala Ala Pro Arg Thr Ser Gly Gly Gly Tyr Thr Met
65                  70                  75                  80

His Gly Leu Thr Val Arg Pro Leu Gly Gln Ala Ser Ala Thr Ser Thr
                85                  90                  95

Glu Ser Gln Leu Ile Asp Pro Glu Ser Glu Glu Pro Asp Leu Pro
                100                 105                 110

Glu Val Asp Val Glu Leu Pro Thr Met Pro Lys Asp Ser Pro Gln Gln
                115                 120                 125

Leu Glu Leu Leu Ser Gly Pro Cys Glu Arg Arg Lys Ser Pro Leu Gln
                130                 135                 140

Asp Pro Phe Pro Glu Glu Asp Tyr Ser Ser Thr Glu Gly Ser Gly Gly
145                 150                 155                 160

Arg Ile Thr Phe Asn Val Asp Leu Asn Ser Val Phe Leu Arg Val Leu
                165                 170                 175

Asp Asp Glu Asp Ser Asp Asp Leu Glu Ala Pro Leu Met Leu Ser Ser
                180                 185                 190

His Leu Glu Glu Met Val Asp Pro Glu Asp Pro Asp Asn Val Gln Ser
                195                 200                 205

Asn His Leu Leu Ala Ser Gly Glu Gly Thr Gln Pro Thr Phe Pro Ser
                210                 215                 220

Pro Ser Ser Glu Gly Leu Trp Ser Glu Asp Ala Pro Ser Asp Gln Ser
225                 230                 235                 240

Asp Thr Ser Glu Ser Asp Val Asp Leu Gly Asp Gly Tyr Ile Met Arg
                245                 250                 255

<210> SEQ ID NO 50
<211> LENGTH: 221
<212> TYPE: PRT
<213> ORGANISM: Unknown
<220> FEATURE:
```

-continued

<223> OTHER INFORMATION: Description of Unknown:
     IFNLR1(300-520) sequence

<400> SEQUENCE: 50

Arg Gly Val Arg Pro Thr Pro Arg Val Arg Ala Pro Ala Thr Gln Gln
1               5                   10                  15

Thr Arg Trp Lys Lys Asp Leu Ala Glu Asp Glu Glu Glu Asp Glu
            20                  25                  30

Glu Asp Thr Glu Asp Gly Val Ser Phe Gln Pro Tyr Ile Glu Pro Pro
            35                  40                  45

Ser Phe Leu Gly Gln Glu His Gln Ala Pro Gly His Ser Glu Ala Gly
        50                  55                  60

Gly Val Asp Ser Gly Arg Pro Arg Ala Pro Leu Val Pro Ser Glu Gly
65              70                  75                  80

Ser Ser Ala Trp Asp Ser Ser Asp Arg Ser Trp Ala Ser Thr Val Asp
                85                  90                  95

Ser Ser Trp Asp Arg Ala Gly Ser Ser Gly Tyr Leu Ala Glu Lys Gly
            100                 105                 110

Pro Gly Gln Gly Pro Gly Gly Asp Gly His Gln Glu Ser Leu Pro Pro
        115                 120                 125

Pro Glu Phe Ser Lys Asp Ser Gly Phe Leu Glu Glu Leu Pro Glu Asp
    130                 135                 140

Asn Leu Ser Ser Trp Ala Thr Trp Gly Thr Leu Pro Pro Glu Pro Asn
145                 150                 155                 160

Leu Val Pro Gly Gly Pro Pro Val Ser Leu Gln Thr Leu Thr Phe Cys
                165                 170                 175

Trp Glu Ser Ser Pro Glu Glu Glu Glu Ala Arg Glu Ser Glu Ile
            180                 185                 190

Glu Asp Ser Asp Ala Gly Ser Trp Gly Ala Glu Ser Thr Gln Arg Thr
            195                 200                 205

Glu Asp Arg Gly Arg Thr Leu Gly His Tyr Met Ala Arg
    210                 215                 220

<210> SEQ ID NO 51
<211> LENGTH: 35
<212> TYPE: PRT
<213> ORGANISM: Unknown
<220> FEATURE:
<223> OTHER INFORMATION: Description of Unknown:
     Common Gamma Chain(335-369) sequence

<400> SEQUENCE: 51

Ile Pro Pro Lys Gly Gly Ala Leu Gly Glu Gly Pro Gly Ala Ser Pro
1               5                   10                  15

Cys Asn Gln His Ser Pro Tyr Trp Ala Pro Pro Cys Tyr Thr Leu Lys
            20                  25                  30

Pro Glu Thr
        35

<210> SEQ ID NO 52
<211> LENGTH: 166
<212> TYPE: PRT
<213> ORGANISM: Unknown
<220> FEATURE:
<223> OTHER INFORMATION: Description of Unknown:
     IL9R(356-521) sequence

<400> SEQUENCE: 52

Thr Ala Leu Leu Thr Cys Gly Pro Ala Arg Pro Trp Lys Ser Val Ala

```
1               5                   10                  15
Leu Glu Glu Glu Gln Glu Gly Pro Gly Thr Arg Leu Pro Gly Asn Leu
                20                  25                  30

Ser Ser Glu Asp Val Leu Pro Ala Gly Cys Thr Glu Trp Arg Val Gln
            35                  40                  45

Thr Leu Ala Tyr Leu Pro Gln Glu Asp Trp Ala Pro Thr Ser Leu Thr
        50                  55                  60

Arg Pro Ala Pro Pro Asp Ser Glu Gly Ser Arg Ser Ser Ser Ser Ser
65                  70                  75                  80

Ser Ser Ser Asn Asn Asn Asn Tyr Cys Ala Leu Gly Cys Tyr Gly Gly
                85                  90                  95

Trp His Leu Ser Ala Leu Pro Gly Asn Thr Gln Ser Ser Gly Pro Ile
                100                 105                 110

Pro Ala Leu Ala Cys Gly Leu Ser Cys Asp His Gln Gly Leu Glu Thr
            115                 120                 125

Gln Gln Gly Val Ala Trp Val Leu Ala Gly His Cys Gln Arg Pro Gly
        130                 135                 140

Leu His Glu Asp Leu Gln Gly Met Leu Leu Pro Ser Val Leu Ser Lys
145                 150                 155                 160

Ala Arg Ser Trp Thr Phe
                165

<210> SEQ ID NO 53
<211> LENGTH: 217
<212> TYPE: PRT
<213> ORGANISM: Unknown
<220> FEATURE:
<223> OTHER INFORMATION: Description of Unknown:
      IL21R(322-538) sequence

<400> SEQUENCE: 53

Pro Arg Ser Pro Ala Lys Arg Leu Gln Leu Thr Glu Leu Gln Glu Pro
1               5                   10                  15

Ala Glu Leu Val Glu Ser Asp Gly Val Pro Lys Pro Ser Phe Trp Pro
                20                  25                  30

Thr Ala Gln Asn Ser Gly Gly Ser Ala Tyr Ser Glu Glu Arg Asp Arg
            35                  40                  45

Pro Tyr Gly Leu Val Ser Ile Asp Thr Val Thr Val Leu Asp Ala Glu
        50                  55                  60

Gly Pro Cys Thr Trp Pro Cys Ser Cys Glu Asp Asp Gly Tyr Pro Ala
65                  70                  75                  80

Leu Asp Leu Asp Ala Gly Leu Glu Pro Ser Pro Gly Leu Glu Asp Pro
                85                  90                  95

Leu Leu Asp Ala Gly Thr Thr Val Leu Ser Cys Gly Cys Val Ser Ala
                100                 105                 110

Gly Ser Pro Gly Leu Gly Gly Pro Leu Gly Ser Leu Leu Asp Arg Leu
            115                 120                 125

Lys Pro Pro Leu Ala Asp Gly Glu Asp Trp Ala Gly Gly Leu Pro Trp
        130                 135                 140

Gly Gly Arg Ser Pro Gly Gly Val Ser Glu Ser Glu Ala Gly Ser Pro
145                 150                 155                 160

Leu Ala Gly Leu Asp Met Asp Thr Phe Asp Ser Gly Phe Val Gly Ser
                165                 170                 175

Asp Cys Ser Ser Pro Val Glu Cys Asp Phe Thr Ser Pro Gly Asp Glu
                180                 185                 190
```

Gly Pro Pro Arg Ser Tyr Leu Arg Gln Trp Val Val Ile Pro Pro Pro
            195                 200                 205

Leu Ser Ser Pro Gly Pro Gln Ala Ser
            210                 215

<210> SEQ ID NO 54
<211> LENGTH: 286
<212> TYPE: PRT
<213> ORGANISM: Homo sapiens

<400> SEQUENCE: 54

Pro Asp Glu Lys Thr Glu Glu Ser Asp Thr Asp Arg Leu Leu Ser Ser
1               5                   10                  15

Asp His Glu Lys Ser His Ser Asn Leu Gly Val Lys Asp Gly Asp Ser
            20                  25                  30

Gly Arg Thr Ser Cys Cys Glu Pro Asp Ile Leu Glu Thr Asp Phe Asn
        35                  40                  45

Ala Asn Asp Ile His Glu Gly Thr Ser Glu Val Ala Gln Pro Gln Arg
    50                  55                  60

Leu Lys Gly Glu Ala Asp Leu Leu Cys Leu Asp Gln Lys Asn Gln Asn
65                  70                  75                  80

Asn Ser Pro Tyr His Asp Ala Cys Pro Ala Thr Gln Gln Pro Ser Val
                85                  90                  95

Ile Gln Ala Glu Lys Asn Lys Pro Gln Pro Leu Pro Thr Glu Gly Ala
            100                 105                 110

Glu Ser Thr His Gln Ala Ala His Ile Gln Leu Ser Asn Pro Ser Ser
        115                 120                 125

Leu Ser Asn Ile Asp Phe Tyr Ala Gln Val Ser Asp Ile Thr Pro Ala
    130                 135                 140

Gly Ser Val Val Leu Ser Pro Gly Gln Lys Asn Lys Ala Gly Met Ser
145                 150                 155                 160

Gln Cys Asp Met His Pro Glu Met Val Ser Leu Cys Gln Glu Asn Phe
                165                 170                 175

Leu Met Asp Asn Ala Tyr Phe Cys Glu Ala Asp Ala Lys Lys Cys Ile
            180                 185                 190

Pro Val Ala Pro His Ile Lys Val Glu Ser His Ile Gln Pro Ser Leu
        195                 200                 205

Asn Gln Glu Asp Ile Tyr Ile Thr Thr Glu Ser Leu Thr Thr Ala Ala
    210                 215                 220

Gly Arg Pro Gly Thr Gly Glu His Val Pro Gly Ser Glu Met Pro Val
225                 230                 235                 240

Pro Asp Tyr Thr Ser Ile His Ile Val Gln Ser Pro Gln Gly Leu Ile
                245                 250                 255

Leu Asn Ala Thr Ala Leu Pro Leu Pro Asp Lys Glu Phe Leu Ser Ser
            260                 265                 270

Cys Gly Tyr Val Ser Thr Asp Gln Leu Asn Lys Ile Met Pro
        275                 280                 285

<210> SEQ ID NO 55
<211> LENGTH: 170
<212> TYPE: PRT
<213> ORGANISM: Homo sapiens

<400> SEQUENCE: 55

Trp Gly Thr Met Gln Ala Val Glu Pro Gly Thr Asp Asp Glu Gly Pro
1               5                   10                  15

```
Leu Leu Glu Pro Val Gly Ser Glu His Ala Gln Asp Thr Tyr Leu Val
             20                  25                  30

Leu Asp Lys Trp Leu Leu Pro Arg Asn Pro Ser Glu Asp Leu Pro
         35                  40                  45

Gly Pro Gly Gly Ser Val Asp Ile Val Ala Met Asp Glu Gly Ser Glu
 50                  55                  60

Ala Ser Cys Ser Ser Ala Leu Ala Ser Lys Pro Ser Pro Glu Gly
 65                  70                  75                  80

Ala Ser Ala Ala Ser Phe Glu Tyr Thr Ile Leu Asp Pro Ser Ser Gln
                 85                  90                  95

Leu Leu Arg Pro Trp Thr Leu Cys Pro Glu Leu Pro Thr Pro Pro
            100                 105                 110

His Leu Lys Tyr Leu Tyr Leu Val Val Ser Asp Ser Gly Ile Ser Thr
            115                 120                 125

Asp Tyr Ser Ser Gly Asp Ser Gln Gly Ala Gln Gly Gly Leu Ser Asp
            130                 135                 140

Gly Pro Tyr Ser Asn Pro Tyr Glu Asn Ser Leu Ile Pro Ala Ala Glu
145                 150                 155                 160

Pro Leu Pro Pro Ser Tyr Val Ala Cys Ser
                165                 170

<210> SEQ ID NO 56
<211> LENGTH: 203
<212> TYPE: PRT
<213> ORGANISM: Mus musculus

<400> SEQUENCE: 56

Ala Val Gln Leu Leu Leu Gln Lys Asp Ser Ala Pro Leu Pro Ser
1               5                   10                  15

Pro Ser Gly His Ser Gln Ala Ser Cys Phe Thr Asn Gln Gly Tyr Phe
                 20                  25                  30

Phe Phe His Leu Pro Asn Ala Leu Glu Ile Glu Ser Cys Gln Val Tyr
             35                  40                  45

Phe Thr Tyr Asp Pro Cys Val Glu Glu Val Glu Glu Asp Gly Ser
 50                  55                  60

Arg Leu Pro Glu Gly Ser Pro His Pro Pro Leu Leu Pro Leu Ala Gly
 65                  70                  75                  80

Glu Gln Asp Asp Tyr Cys Ala Phe Pro Pro Arg Asp Asp Leu Leu Leu
                 85                  90                  95

Phe Ser Pro Ser Leu Ser Thr Pro Asn Thr Ala Tyr Gly Gly Ser Arg
            100                 105                 110

Ala Pro Glu Glu Arg Ser Pro Leu Ser Leu His Glu Gly Leu Pro Ser
            115                 120                 125

Leu Ala Ser Arg Asp Leu Met Gly Leu Gln Arg Pro Leu Glu Arg Met
            130                 135                 140

Pro Glu Gly Asp Gly Glu Gly Leu Ser Ala Asn Ser Ser Gly Glu Gln
145                 150                 155                 160

Ala Ser Val Pro Glu Gly Asn Leu His Gly Gln Asp Gln Asp Arg Gly
                165                 170                 175

Gln Gly Pro Ile Leu Thr Leu Asn Thr Asp Ala Tyr Leu Ser Leu Gln
            180                 185                 190

Glu Leu Gln Ala Gln Asp Ser Val His Leu Ile
        195                 200

<210> SEQ ID NO 57
```

```
<211> LENGTH: 144
<212> TYPE: PRT
<213> ORGANISM: Mus musculus

<400> SEQUENCE: 57

Ala Arg Asp Glu Val Glu Ser Phe Leu Pro Asn Asp Leu Pro Ala Gln
1               5                   10                  15

Pro Glu Glu Leu Glu Thr Gln Gly His Arg Ala Ala Val His Ser Ala
            20                  25                  30

Asn Arg Ser Pro Glu Thr Ser Val Ser Pro Pro Glu Thr Val Arg Arg
        35                  40                  45

Glu Ser Pro Leu Arg Cys Leu Ala Arg Asn Leu Ser Thr Cys Asn Ala
50                  55                  60

Pro Pro Leu Leu Ser Ser Arg Ser Pro Asp Tyr Arg Asp Gly Asp Arg
65                  70                  75                  80

Asn Arg Pro Pro Val Tyr Gln Asp Leu Leu Pro Asn Ser Gly Asn Thr
                85                  90                  95

Asn Val Pro Val Pro Val Pro Gln Pro Leu Pro Phe Gln Ser Gly Ile
            100                 105                 110

Leu Ile Pro Val Ser Gln Arg Gln Pro Ile Ser Thr Ser Ser Val Leu
        115                 120                 125

Asn Gln Glu Glu Ala Tyr Val Thr Met Ser Ser Phe Tyr Gln Asn Lys
130                 135                 140

<210> SEQ ID NO 58
<211> LENGTH: 231
<212> TYPE: PRT
<213> ORGANISM: Unknown
<220> FEATURE:
<223> OTHER INFORMATION: Description of Unknown:
      EGFR(955-1186) sequence

<400> SEQUENCE: 58

Val Ile Gln Gly Asp Glu Arg Met His Leu Pro Ser Pro Thr Asp Ser
1               5                   10                  15

Asn Phe Tyr Arg Ala Leu Met Asp Glu Glu Asp Met Asp Asp Val Val
            20                  25                  30

Asp Ala Asp Glu Tyr Leu Ile Pro Gln Gln Gly Phe Phe Ser Ser Pro
        35                  40                  45

Ser Thr Ser Arg Thr Pro Leu Leu Ser Ser Leu Ser Ala Thr Ser Asn
50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Tyr Ser Ser Asp Pro Thr Gly
                85                  90                  95

Ala Leu Thr Glu Asp Ser Ile Asp Thr Phe Leu Pro Val Pro Glu
            100                 105                 110

Tyr Ile Asn Gln Ser Val Pro Lys Arg Pro Ala Gly Ser Val Gln Asn
        115                 120                 125

Pro Val Tyr His Asn Gln Pro Leu Asn Pro Ala Pro Ser Arg Asp Pro
130                 135                 140

His Tyr Gln Asp Pro His Ser Thr Ala Val Gly Asn Pro Glu Tyr Leu
145                 150                 155                 160

Asn Thr Val Gln Pro Thr Cys Val Asn Ser Thr Phe Asp Ser Pro Ala
                165                 170                 175

His Trp Ala Gln Lys Gly Ser His Gln Ile Ser Leu Asp Asn Pro Asp
            180                 185                 190
```

```
Tyr Gln Gln Asp Phe Phe Pro Lys Glu Ala Lys Pro Asn Gly Ile Phe
        195                 200                 205

Lys Gly Ser Thr Ala Glu Asn Ala Glu Tyr Leu Arg Val Ala Pro Gln
210                 215                 220

Ser Ser Glu Phe Ile Gly Ala
225                 230

<210> SEQ ID NO 59
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Ile Gln Gly Asp Glu Arg Met His Leu Pro Ser Pro Thr Asp Ser
1               5                   10                  15

Asn Phe Phe Arg Ala Leu Met Asp Glu Asp Met Asp Asp Val Val
            20                  25                  30

Asp Ala Asp Glu Tyr Leu Ile Pro Gln Gln Gly Phe Phe Ser Ser Pro
            35                  40                  45

Ser Thr Ser Arg Thr Pro Leu Leu Ser Ser Leu Ser Ala Thr Ser Asn
50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Ile Asp Asp Thr Phe Leu Pro
                85                  90                  95

Val Pro Glu Tyr Ile Asn Gln Ser Val Pro Lys Arg Pro Ala Gly Ser
            100                 105                 110

Val Gln Asn Pro Val Tyr His Asn Gln Pro Leu Asn Pro Ala Pro Ser
        115                 120                 125

Arg Asp Pro His Tyr Gln Asp Pro His Ser Thr Ala Val Gly Asn Pro
    130                 135                 140

Glu Tyr Leu Asn Thr Val Gln Pro Thr Cys Val Asn Ser Thr Phe Asp
145                 150                 155                 160

Ser Pro Ala His Trp Ala Gln Lys Gly Ser His Gln Ile Ser Leu Asp
                165                 170                 175

Asn Pro Asp Tyr Gln Gln Asp Phe Phe Pro Lys Glu Ala Lys Pro Asn
            180                 185                 190

Gly Ile Phe Lys Gly Ser Thr Ala Glu Asn Ala Glu Tyr Leu Arg Val
        195                 200                 205

Ala Pro Gln Ser Ser Glu Phe Ile Gly Ala
    210                 215

<210> SEQ ID NO 60
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Val Ile Gln Gly Asp Glu Arg Met His Leu Pro Ser Pro Thr Asp Ser
1               5                   10                  15

Asn Phe Phe Arg Ala Leu Met Asp Glu Asp Met Asp Asp Val Val
            20                  25                  30
```

-continued

```
Asp Ala Asp Glu Tyr Leu Ile Pro Gln Gln Gly Phe Phe Ser Ser Pro
        35                  40                  45

Ser Thr Ser Arg Thr Pro
    50

<210> SEQ ID NO 61
<211> LENGTH: 54
<212> TYPE: PRT
<213> ORGANISM: Unknown
<220> FEATURE:
<223> OTHER INFORMATION: Description of Unknown:
      EGFR(1019-1085) sequence

<400> SEQUENCE: 61

Asn Asn Ser Thr Val Ala Cys Ile Asp Arg Asn Gly Leu Gln Ser Cys
1               5                   10                  15

Pro Ile Lys Glu Asp Ser Phe Leu Gln Arg Ile Asp Asp Thr Phe Leu
            20                  25                  30

Pro Val Pro Glu Tyr Ile Asn Gln Ser Val Pro Lys Arg Pro Ala Gly
        35                  40                  45

Ser Val Gln Asn Pro Val
    50

<210> SEQ ID NO 62
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Lys Glu Asp Ser Phe Leu Gln Arg Ile Asp Asp Thr Phe Leu Pro Val
1               5                   10                  15

Pro Glu Phe Ile Asn Gln Ser Val Pro Lys Arg Pro Ala Gly Ser Val
            20                  25                  30

Gln Asn Pro Val Tyr His Asn Gln Pro Leu Asn Pro Ala Pro Ser Arg
        35                  40                  45

Asp Pro His Phe Gln Asp
    50

<210> SEQ ID NO 63
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Val Pro Glu Phe Ile Asn Gln Ser Val Pro Lys Arg Pro Ala Gly Ser
1               5                   10                  15

Val Gln Asn Pro Val Phe His Asn Gln Pro Leu Asn Pro Ala Pro Ser
            20                  25                  30

Arg Asp Pro His Tyr Gln Asp Pro His Ser Thr Ala Val Gly Asn Pro
        35                  40                  45

Glu Tyr Leu Asn Thr Val
    50

<210> SEQ ID NO 64
<211> LENGTH: 54
```

```
<212> TYPE: PRT
<213> ORGANISM: Unknown
<220> FEATURE:
<223> OTHER INFORMATION: Description of Unknown:
      EGFR(1122-1165) sequence

<400> SEQUENCE: 64

Pro Glu Tyr Leu Asn Thr Val Gln Pro Thr Cys Val Asn Ser Thr Phe
1               5                   10                  15

Asp Ser Pro Ala His Trp Ala Gln Lys Gly Ser His Gln Ile Ser Leu
            20                  25                  30

Asp Asn Pro Asp Tyr Gln Gln Asp Phe Phe Pro Lys Glu Ala Lys Pro
        35                  40                  45

Asn Gly Ile Phe Lys Gly
    50

<210> SEQ ID NO 65
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Trp Ala Gln Lys Gly Ser His Gln Ile Ser Leu Asp Asn Pro Asp Phe
1               5                   10                  15

Gln Gln Asp Phe Phe Pro Lys Glu Ala Lys Pro Asn Gly Ile Phe Lys
            20                  25                  30

Gly Ser Thr Ala Glu Asn Ala Glu Tyr Leu Arg Val Ala Pro Gln Ser
        35                  40                  45

Ser Glu Phe Ile Gly Ala
    50

<210> SEQ ID NO 66
<211> LENGTH: 51
<212> TYPE: PRT
<213> ORGANISM: Unknown
<220> FEATURE:
<223> OTHER INFORMATION: Description of Unknown:
      IL12Rb2(775-825) sequence

<400> SEQUENCE: 66

Ser Asp Pro Lys Pro Glu Asn Pro Ala Cys Pro Trp Thr Val Leu Pro
1               5                   10                  15

Ala Gly Asp Leu Pro Thr His Asp Gly Tyr Leu Pro Ser Asn Ile Asp
            20                  25                  30

Asp Leu Pro Ser His Glu Ala Pro Leu Ala Asp Ser Leu Glu Glu Leu
        35                  40                  45

Glu Pro Gln
    50

<210> SEQ ID NO 67
<211> LENGTH: 41
<212> TYPE: PRT
<213> ORGANISM: Unknown
<220> FEATURE:
<223> OTHER INFORMATION: Description of Unknown:
      IL7R(376-416) sequence

<400> SEQUENCE: 67

Ala Cys Asp Ala Pro Ile Leu Ser Ser Ser Arg Ser Leu Asp Cys Arg
1               5                   10                  15
```

Glu Ser Gly Lys Asn Gly Pro His Val Tyr Gln Asp Leu Leu Leu Ser
            20                  25                  30

Leu Gly Thr Thr Asn Ser Thr Leu Pro
        35                  40

<210> SEQ ID NO 68
<211> LENGTH: 36
<212> TYPE: PRT
<213> ORGANISM: Unknown
<220> FEATURE:
<223> OTHER INFORMATION: Description of Unknown:
      IL7R(424-459) sequence

<400> SEQUENCE: 68

Gly Ile Leu Thr Leu Asn Pro Val Ala Gln Gly Gln Pro Ile Leu Thr
1               5                   10                  15

Ser Leu Gly Ser Asn Gln Glu Glu Ala Tyr Val Thr Met Ser Ser Phe
            20                  25                  30

Tyr Gln Asn Gln
        35

<210> SEQ ID NO 69
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Tyr Gln Asn Gln
65

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Ile Leu Thr Leu Asn Pro Val Ala Gln Gly Gln Pro Ile Leu Thr
1               5                   10                  15

Ser Leu Gly Ser Asn Gln Glu Glu Ala Tyr Val Thr Met Ser Ser Phe
            20                  25                  30

Phe Gln Asn Gln
        35

<210> SEQ ID NO 71
<211> LENGTH: 68
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 71

Ala Cys Asp Ala Pro Ile Leu Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Phe Gln Asn Gln
65

<210> SEQ ID NO 72
<211> LENGTH: 75
<212> TYPE: PRT
<213> ORGANISM: Unknown
<220> FEATURE:
<223> OTHER INFORMATION: Description of Unknown:
      IL2small(393-433) sequence

<400> SEQUENCE: 72

Asp Glu Gly Val Ala Gly Ala Pro Thr Gly Ser Ser Pro Gln Pro Leu
1               5                   10                  15

Gln Pro Leu Ser Gly Glu Asp Asp Ala Tyr Cys Thr Phe Pro Ser Arg
            20                  25                  30

Asp Asp Leu Leu Leu Phe Ser Pro Ser Gly Gln Gly Glu Phe Arg Ala
        35                  40                  45

Leu Asn Ala Arg Leu Pro Leu Asn Thr Asp Ala Tyr Leu Ser Leu Gln
    50                  55                  60

Glu Leu Gln Gly Gln Asp Pro Thr His Leu Val
65                  70                  75

<210> SEQ ID NO 73
<211> LENGTH: 34
<212> TYPE: PRT
<213> ORGANISM: Unknown
<220> FEATURE:
<223> OTHER INFORMATION: Description of Unknown:
      IL2small(518-551) sequence

<400> SEQUENCE: 73

Gly Gln Gly Glu Phe Arg Ala Leu Asn Ala Arg Leu Pro Leu Asn Thr
1               5                   10                  15

Asp Ala Tyr Leu Ser Leu Gln Glu Leu Gln Gly Gln Asp Pro Thr His
            20                  25                  30

Leu Val

<210> SEQ ID NO 74
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Gln Asp Lys Val Pro Glu Pro Ala Ser Leu Ser Ser Asn His Ser
1               5                   10                  15
```

Leu Thr Ser Cys Phe Thr Asn Gln Gly Tyr Phe Phe His Leu Pro
            20                  25                  30

Asp Ala Leu Glu Ile Glu Ala Cys Gln Asp Glu Gly Val Ala Gly Ala
            35                  40                  45

Pro Thr Gly Ser Ser Pro Gln Pro Leu Gln Pro Leu Ser Gly Glu Asp
 50                  55                  60

Asp Ala Tyr Cys Thr Phe Pro Ser Arg Asp Asp Leu Leu Leu Phe Ser
65                  70                  75                  80

Pro Ser

<210> SEQ ID NO 75
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Gln Asp Lys Val Pro Glu Pro Ala Ser Leu Ser Ser Asn His Ser
1               5                   10                  15

Leu Thr Ser Cys Phe Thr Asn Gln Gly Tyr Phe Phe His Leu Pro
            20                  25                  30

Asp Ala Leu Glu Ile Glu Ala Cys Gln Gly Gln Gly Glu Phe Arg Ala
            35                  40                  45

Leu Asn Ala Arg Leu Pro Leu Asn Thr Asp Ala Tyr Leu Ser Leu Gln
        50                  55                  60

Glu Leu Gln Gly Gln Asp Pro Thr His Leu Val
65                  70                  75

<210> SEQ ID NO 76
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Glu Gly Val Ala Gly Ala Pro Thr Gly Ser Ser Pro Gln Pro Leu
1               5                   10                  15

Gln Pro Leu Ser Gly Glu Asp Ala Tyr Cys Thr Phe Pro Ser Arg
            20                  25                  30

Asp Asp Leu Leu Leu Phe Ser Pro Ser Gly Gln Gly Glu Phe Arg Ala
            35                  40                  45

Leu Asn Ala Arg Leu Pro Leu Asn Thr Asp Ala Tyr Leu Ser Leu Gln
        50                  55                  60

Glu Leu Gln Gly Gln Asp Pro Thr His Leu Val
65                  70                  75

<210> SEQ ID NO 77
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Gln Asp Lys Val Pro Glu Pro Ala Ser Leu Ser Ser Asn His Ser
1               5                   10                  15

```
Leu Thr Ser Cys Phe Thr Asn Gln Gly Tyr Phe Phe His Leu Pro
        20                  25                  30

Asp Ala Leu Glu Ile Glu Ala Cys Gln Asp Gly Val Ala Gly Ala
        35                  40                  45

Pro Thr Gly Ser Ser Pro Gln Pro Leu Gln Pro Leu Ser Gly Glu Asp
50                  55                  60

Asp Ala Tyr Cys Thr Phe Pro Ser Arg Asp Leu Leu Leu Phe Ser
65                  70                  75                  80

Pro Ser Gly Gln Gly Glu Phe Arg Ala Leu Asn Ala Arg Leu Pro Leu
                85                  90                  95

Asn Thr Asp Ala Tyr Leu Ser Leu Gln Glu Leu Gln Gly Gln Asp Pro
        100                 105                 110

Thr His Leu Val
        115

<210> SEQ ID NO 78
<211> LENGTH: 43
<212> TYPE: PRT
<213> ORGANISM: Unknown
<220> FEATURE:
<223> OTHER INFORMATION: Description of Unknown:
      IFNAR2small(310-352) sequence

<400> SEQUENCE: 78

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala
        35                  40

<210> SEQ ID NO 79
<211> LENGTH: 29
<212> TYPE: PRT
<213> ORGANISM: Unknown
<220> FEATURE:
<223> OTHER INFORMATION: Description of Unknown:
      IFNAR2small(486-515) sequence

<400> SEQUENCE: 79

Glu Gly Leu Trp Ser Glu Asp Ala Pro Ser Asp Gln Ser Asp Thr Ser
1               5                   10                  15

Glu Ser Asp Val Asp Leu Gly Asp Gly Tyr Ile Met Arg
            20                  25

<210> SEQ ID NO 80
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala Glu Gly Leu Trp Ser
        35                  40                  45
```

```
Glu Asp Ala Pro Ser Asp Gln Ser Asp Thr Ser Glu Ser Asp Val Asp
            50                  55                  60

Leu Gly Asp Gly Tyr Ile Met Arg
 65                  70

<210> SEQ ID NO 81
<211> LENGTH: 156
<212> TYPE: PRT
<213> ORGANISM: Unknown
<220> FEATURE:
<223> OTHER INFORMATION: Description of Unknown:
      BLNK(53-208) sequence

<400> SEQUENCE: 81

Ala Ser Glu Ser Pro Ala Asp Glu Glu Gln Trp Ser Asp Asp Phe
 1               5                  10                  15

Asp Ser Asp Tyr Glu Asn Pro Asp Glu His Ser Asp Ser Glu Met Tyr
                20                  25                  30

Val Met Pro Ala Glu Glu Asn Ala Asp Asp Ser Tyr Glu Pro Pro Pro
            35                  40                  45

Val Glu Gln Glu Thr Arg Pro Val His Pro Ala Leu Pro Phe Ala Arg
 50                  55                  60

Gly Glu Tyr Ile Asp Asn Arg Ser Ser Gln Arg His Ser Pro Pro Phe
 65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155

<210> SEQ ID NO 82
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ser Glu Ser Pro Ala Asp Glu Glu Gln Trp Ser Asp Asp Phe
 1               5                  10                  15

Asp Ser Asp Phe Glu Asn Pro Asp Glu His Ser Asp Ser Glu Met Tyr
                20                  25                  30

Val Met Pro Ala Glu Glu Asn Ala Asp Asp Ser Tyr Glu Pro Pro Pro
            35                  40                  45

Val Glu Gln Glu Thr Arg Pro Val His Pro Ala Leu Pro Phe Ala Arg
 50                  55                  60

Gly Glu Tyr Ile Asp Asn Arg Ser Ser Gln Arg His Ser Pro Pro Phe
 65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110
```

```
Pro Pro Lys Pro Lys Gly Leu Leu Glu Asp Glu Ala Asp Tyr Val Val
            115                 120                 125

Pro Val Glu Asp Asn Asp Glu Asn Tyr Ile His Pro Thr Glu Ser Ser
        130                 135                 140

Ser Pro Pro Pro Glu Lys Ala Pro Met Val Asn Arg
145                 150                 155

<210> SEQ ID NO 83
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Ser Glu Ser Pro Ala Asp Glu Glu Gln Trp Ser Asp Asp Phe
1               5                   10                  15

Asp Ser Asp Phe Glu Asn Pro Asp Glu His Ser Asp Ser Glu Met Tyr
            20                  25                  30

Val Met Pro Ala Glu Glu Asn Ala Asp Asp Ser Phe Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155

<210> SEQ ID NO 84
<211> LENGTH: 170
<212> TYPE: PRT
<213> ORGANISM: Homo sapiens

<400> SEQUENCE: 84

Trp Gly Thr Met Gln Ala Val Glu Pro Gly Thr Asp Asp Glu Gly Pro
1               5                   10                  15

Leu Leu Glu Pro Val Gly Ser Glu His Ala Gln Asp Thr Tyr Leu Val
            20                  25                  30

Leu Asp Lys Trp Leu Leu Pro Arg Asn Pro Pro Ser Glu Asp Leu Pro
        35                  40                  45

Gly Pro Gly Gly Ser Val Asp Ile Val Ala Met Asp Glu Gly Ser Glu
    50                  55                  60

Ala Ser Ser Cys Ser Ser Ala Leu Ala Ser Lys Pro Ser Pro Glu Gly
65                  70                  75                  80

Ala Ser Ala Ala Ser Phe Glu Tyr Thr Ile Leu Asp Pro Ser Ser Gln
                85                  90                  95

Leu Leu Arg Pro Trp Thr Leu Cys Pro Glu Leu Pro Pro Thr Pro Pro
            100                 105                 110
```

```
His Leu Lys Tyr Leu Tyr Leu Val Ser Asp Ser Gly Ile Ser Thr
            115                 120                 125

Asp Tyr Ser Ser Gly Ser Gln Gly Ala Gln Gly Gly Leu Ser Asp
        130                 135                 140

Gly Pro Tyr Ser Asn Pro Tyr Glu Asn Ser Leu Ile Pro Ala Ala Glu
145                 150                 155                 160

Pro Leu Pro Pro Ser Tyr Val Ala Cys Ser
                165                 170

<210> SEQ ID NO 85
<211> LENGTH: 149
<212> TYPE: PRT
<213> ORGANISM: Unknown
<220> FEATURE:
<223> OTHER INFORMATION: Description of Unknown:
      IL12Rb2(714-862) sequence

<400> SEQUENCE: 85

Val Thr Pro Val Phe Arg His Pro Pro Cys Ser Asn Trp Pro Gln Arg
1               5                   10                  15

Glu Lys Gly Ile Gln Gly His Gln Ala Ser Glu Lys Asp Met Met His
            20                  25                  30

Ser Ala Ser Ser Pro Pro Pro Arg Ala Leu Gln Ala Glu Ser Arg
        35                  40                  45

Gln Leu Val Asp Leu Tyr Lys Val Leu Glu Ser Arg Gly Ser Asp Pro
    50                  55                  60

Lys Pro Glu Asn Pro Ala Cys Pro Trp Thr Val Leu Pro Ala Gly Asp
65                  70                  75                  80

Leu Pro Thr His Asp Gly Tyr Leu Pro Ser Asn Ile Asp Asp Leu Pro
                85                  90                  95

Ser His Glu Ala Pro Leu Ala Asp Ser Leu Glu Glu Leu Glu Pro Gln
            100                 105                 110

His Ile Ser Leu Ser Val Phe Pro Ser Ser Ser Leu His Pro Leu Thr
        115                 120                 125

Phe Ser Cys Gly Asp Lys Leu Thr Leu Asp Gln Leu Lys Met Arg Cys
    130                 135                 140

Asp Ser Leu Met Leu
145

<210> SEQ ID NO 86
<211> LENGTH: 40
<212> TYPE: PRT
<213> ORGANISM: Unknown
<220> FEATURE:
<223> OTHER INFORMATION: Description of Unknown:
      IL12Rb1(622-662) sequence

<400> SEQUENCE: 86

Trp Asp Lys Gly Glu Arg Thr Glu Pro Leu Glu Lys Thr Glu Leu Pro
1               5                   10                  15

Glu Gly Ala Pro Glu Leu Ala Leu Asp Thr Glu Leu Ser Leu Glu Asp
            20                  25                  30

Gly Asp Arg Cys Lys Ala Lys Met
        35                  40

<210> SEQ ID NO 87
<211> LENGTH: 275
<212> TYPE: PRT
<213> ORGANISM: Unknown
<220> FEATURE:
```

<223> OTHER INFORMATION: Description of Unknown:
      IL10R1(304-578) sequence

<400> SEQUENCE: 87

Val Ser Pro Glu Leu Lys Asn Leu Asp Leu His Gly Ser Thr Asp Ser
1               5                   10                  15

Gly Phe Gly Ser Thr Lys Pro Ser Leu Gln Thr Glu Glu Pro Gln Phe
            20                  25                  30

Leu Leu Pro Asp Pro His Pro Gln Ala Asp Arg Thr Leu Gly Asn Arg
        35                  40                  45

Glu Pro Pro Val Leu Gly Asp Ser Cys Ser Ser Gly Ser Ser Asn Ser
50                  55                  60

Thr Asp Ser Gly Ile Cys Leu Gln Glu Pro Ser Leu Ser Pro Ser Thr
65                  70                  75                  80

Gly Pro Thr Trp Glu Gln Gln Val Gly Ser Asn Ser Arg Gly Gln Asp
                85                  90                  95

Asp Ser Gly Ile Asp Leu Val Gln Asn Ser Glu Gly Arg Ala Gly Asp
            100                 105                 110

Thr Gln Gly Gly Ser Ala Leu Gly His His Ser Pro Glu Pro Glu
        115                 120                 125

Val Pro Gly Glu Glu Asp Pro Ala Ala Val Ala Phe Gln Gly Tyr Leu
130                 135                 140

Arg Gln Thr Arg Cys Ala Glu Glu Lys Ala Thr Lys Thr Gly Cys Leu
145                 150                 155                 160

Glu Glu Glu Ser Pro Leu Thr Asp Gly Leu Gly Pro Lys Phe Gly Arg
                165                 170                 175

Cys Leu Val Asp Glu Ala Gly Leu His Pro Ala Leu Ala Lys Gly
            180                 185                 190

Tyr Leu Lys Gln Asp Pro Leu Glu Met Thr Leu Ala Ser Ser Gly Ala
        195                 200                 205

Pro Thr Gly Gln Trp Asn Gln Pro Thr Glu Glu Trp Ser Leu Leu Ala
210                 215                 220

Leu Ser Ser Cys Ser Asp Leu Gly Ile Ser Asp Trp Ser Phe Ala His
225                 230                 235                 240

Asp Leu Ala Pro Leu Gly Cys Val Ala Ala Pro Gly Gly Leu Leu Gly
                245                 250                 255

Ser Phe Asn Ser Asp Leu Val Thr Leu Pro Leu Ile Ser Ser Leu Gln
            260                 265                 270

Ser Ser Glu
        275

<210> SEQ ID NO 88
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

```
Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
                180                 185                 190

Val Glu Thr Ala Thr Glu Thr Ala Trp Ile Ser Leu Val Thr Ala Leu
                195                 200                 205

His Leu Val Leu Gly Leu Ser Ala Val Leu Gly Leu Leu Leu Leu Arg
210                 215                 220

Trp Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
                260                 265                 270

Val Glu Pro Ser Leu Leu Glu Ile Leu Pro Lys Ser Ser Glu Arg Thr
                275                 280                 285

Pro Leu Pro Leu Ala Arg Asp Glu Val Glu Gly Phe Leu Gln Asp Thr
                290                 295                 300

Phe Pro Gln Gln Leu Glu Glu Ser Glu Lys Gln Arg Leu Gly Gly Asp
305                 310                 315                 320

Val Gln Ser Pro Asn Cys Pro Ser Glu Asp Val Val Ile Thr Pro Glu
                325                 330                 335

Ser Phe Gly Arg Asp Ser Ser Leu Thr Cys Leu Ala Gly Asn Val Ser
                340                 345                 350

Ala Cys Asp Ala Pro Ile Leu Ser Ser Arg Ser Leu Asp Cys Arg
                355                 360                 365

Glu Ser Gly Lys Asn Gly Pro His Val Tyr Gln Asp Leu Leu Leu Ser
                370                 375                 380

Leu Gly Thr Thr Asn Ser Thr Leu Pro Pro Pro Phe Ser Leu Gln Ser
385                 390                 395                 400

Gly Ile Leu Thr Leu Asn Pro Val Ala Gln Gly Gln Pro Ile Leu Thr
                405                 410                 415

Ser Leu Gly Ser Asn Gln Glu Glu Ala Tyr Val Thr Met Ser Ser Phe
                420                 425                 430

Tyr Gln Asn Gln Ser Asp Pro Lys Pro Glu Asn Pro Ala Cys Pro Trp
                435                 440                 445

Thr Val Leu Pro Ala Gly Asp Leu Pro Thr His Asp Gly Tyr Leu Pro
450                 455                 460

Ser Asn Ile Asp Asp Leu Pro Ser His Glu Ala Pro Leu Ala Asp Ser
```

Leu Glu Glu Leu Glu Pro Gln
                485

<210> SEQ ID NO 89
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Leu Thr Leu Met Thr
            180                 185                 190

Leu Thr Pro Glu Gly Ser Glu Leu His Ile Ile Leu Gly Leu Phe Gly
        195                 200                 205

Leu Leu Leu Leu Leu Thr Cys Leu Cys Gly Thr Ala Trp Leu Cys Cys
    210                 215                 220

Ser Pro Asn Arg Lys Asn Pro Leu Trp Pro Ser Val Pro Asp Pro Ala
225                 230                 235                 240

His Ser Ser Leu Gly Ser Trp Val Pro Thr Ile Met Glu Glu Asp Ala
                245                 250                 255

Phe Gln Leu Pro Gly Leu Gly Thr Pro Pro Ile Thr Lys Leu Thr Val
            260                 265                 270

Leu Glu Glu Asp Glu Lys Lys Pro Val Pro Trp Glu Ala Arg Asp Glu
        275                 280                 285

Val Glu Gly Phe Leu Gln Asp Thr Phe Pro Gln Gln Leu Glu Glu Ser
    290                 295                 300

Glu Lys Gln Arg Leu Gly Gly Asp Val Gln Ser Pro Asn Cys Pro Ser
305                 310                 315                 320

Glu Asp Val Val Ile Thr Pro Glu Ser Phe Gly Arg Asp Ser Ser Leu
                325                 330                 335

```
Thr Cys Leu Ala Gly Asn Val Ser Ala Cys Asp Ala Pro Ile Leu Ser
            340                 345                 350

Ser Ser Arg Ser Leu Asp Cys Arg Glu Ser Gly Lys Asn Gly Pro His
        355                 360                 365

Val Tyr Gln Asp Leu Leu Leu Ser Leu Gly Thr Thr Asn Ser Thr Leu
    370                 375                 380

Pro Pro Pro Phe Ser Leu Gln Ser Gly Ile Leu Thr Leu Asn Pro Val
385                 390                 395                 400

Ala Gln Gly Gln Pro Ile Leu Thr Ser Leu Gly Ser Asn Gln Glu Glu
                405                 410                 415

Ala Tyr Val Thr Met Ser Ser Phe Tyr Gln Asn Gln Ser Asp Pro Lys
    420                 425                 430

Pro Glu Asn Pro Ala Cys Pro Trp Thr Val Leu Pro Ala Gly Asp Leu
        435                 440                 445

Pro Thr His Asp Gly Tyr Leu Pro Ser Asn Ile Asp Asp Leu Pro Ser
    450                 455                 460

His Glu Ala Pro Leu Ala Asp Ser Leu Glu Glu Leu Glu Pro Gln
465                 470                 475

<210> SEQ ID NO 90
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Thr Pro Lys Phe
            180                 185                 190

Ala Gln Gly Glu Ile Glu Ala Ile Val Val Pro Val Cys Leu Ala Phe
        195                 200                 205

Leu Leu Thr Thr Leu Leu Gly Val Leu Phe Cys Phe Asn Lys Arg Asp
    210                 215                 220
```

```
Leu Ile Lys Lys His Ile Trp Pro Asn Val Pro Asp Pro Ser Lys Ser
225                 230                 235                 240

His Ile Ala Gln Trp Ser Pro His Thr Pro Arg His Asn Phe Asn
            245                 250                 255

Ser Lys Asp Gln Met Tyr Ser Asp Gly Asn Phe Thr Val Ser Val
            260                 265                 270

Val Glu Ile Glu Ala Asn Asp Ala Arg Asp Glu Val Glu Gly Phe Leu
            275                 280                 285

Gln Asp Thr Phe Pro Gln Gln Leu Glu Glu Ser Glu Lys Gln Arg Leu
            290                 295                 300

Gly Gly Asp Val Gln Ser Pro Asn Cys Pro Ser Glu Val Val Ile
305                 310                 315                 320

Thr Pro Glu Ser Phe Gly Arg Asp Ser Ser Leu Thr Cys Leu Ala Gly
                325                 330                 335

Asn Val Ser Ala Cys Asp Ala Pro Ile Leu Ser Ser Arg Ser Leu
            340                 345                 350

Asp Cys Arg Glu Ser Gly Lys Asn Gly Pro His Val Tyr Gln Asp Leu
            355                 360                 365

Leu Leu Ser Leu Gly Thr Thr Asn Ser Thr Leu Pro Pro Phe Ser
370                 375                 380

Leu Gln Ser Gly Ile Leu Thr Leu Asn Pro Val Ala Gln Gly Pro
385                 390                 395                 400

Ile Leu Thr Ser Leu Gly Ser Asn Gln Glu Glu Ala Tyr Val Thr Met
                405                 410                 415

Ser Ser Phe Tyr Gln Asn Gln
            420

<210> SEQ ID NO 91
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
```

-continued

```
            145                 150                 155                 160
        Leu Val Leu Leu Val Trp Val Leu Ala Val Ile Cys Ser Arg Ala Ala
                        165                 170                 175
        Arg Gly Thr Ile Gly Ala Arg Arg Thr Gly Gln Pro Gly Trp Phe Leu
                        180                 185                 190
        Asp Ser Pro Asp Arg Pro Trp Asn Pro Pro Thr Phe Ser Pro Ala Leu
                        195                 200                 205
        Leu Val Val Thr Glu Gly Asp Asn Ala Thr Phe Thr Cys Ser Phe Ser
                        210                 215                 220
        Asn Thr Ser Glu Ser Phe Val Leu Asn Trp Tyr Arg Met Ser Pro Ser
        225                 230                 235                 240
        Asn Gln Thr Asp Lys Leu Ala Ala Phe Pro Glu Asp Arg Ser Gln Pro
                        245                 250                 255
        Gly Gln Asp Cys Arg Phe Arg Val Thr Gln Leu Pro Asn Gly Arg Asp
                        260                 265                 270
        Phe His Met Ser Val Val Arg Ala Arg Arg Asn Asp Ser Gly Thr Tyr
                        275                 280                 285
        Leu Cys Gly Ala Ile Ser Leu Ala Pro Lys Ala Gln Ile Lys Glu Ser
                        290                 295                 300
        Leu Arg Ala Glu Leu Arg Val Thr Glu Arg Arg Ala Glu Val Pro Thr
        305                 310                 315                 320
        Ala His Pro Ser Pro Ser Pro Arg Pro Ala Gly Gln Phe Gln Thr Leu
                        325                 330                 335
        Val Val Gly Val Val Gly Gly Leu Leu Gly Ser Leu Val Leu Leu Val
                        340                 345                 350
        Trp Val Leu Ala Val Ile Cys Ser Arg Ala Ala Arg Gly Thr Ile Gly
                        355                 360                 365
        Ala Arg Arg Thr Gly Gln Ser Asp Pro Thr Arg Val Glu Thr Ala Thr
                        370                 375                 380
        Glu Thr Ala Trp Ile Ser Leu Val Thr Ala Leu His Leu Val Leu Gly
        385                 390                 395                 400
        Leu Ser Ala Val Leu Gly Leu Leu Leu Arg Trp Gln Phe Pro Ala
                        405                 410                 415
        His Tyr Arg Arg Leu Arg His Ala Leu Trp Pro Ser Leu Pro Asp Leu
                        420                 425                 430
        His Arg Val Leu Gly Gln Tyr Leu Arg Asp Thr Ala Ala Leu Ser Pro
                        435                 440                 445
        Pro Lys Ala Thr Val Ser Asp Thr Cys Glu Glu Val Glu Pro Ser Leu
                        450                 455                 460
        Leu Glu Ile Leu Pro Lys Ser Ser Glu Arg Thr Pro Leu Pro Leu Ala
        465                 470                 475                 480
        Arg Asp Glu Val Glu Gly Phe Leu Gln Asp Thr Phe Pro Gln Gln Leu
                        485                 490                 495
        Glu Glu Ser Glu Lys Gln Arg Leu Gly Gly Asp Val Gln Ser Pro Asn
                        500                 505                 510
        Cys Pro Ser Glu Asp Val Val Ile Thr Pro Glu Ser Phe Gly Arg Asp
                        515                 520                 525
        Ser Ser Leu Thr Cys Leu Ala Gly Asn Val Ser Ala Cys Asp Ala Pro
                        530                 535                 540
        Ile Leu Ser Ser Ser Arg Ser Leu Asp Cys Arg Glu Ser Gly Lys Asn
        545                 550                 555                 560
        Gly Pro His Val Tyr Gln Asp Leu Leu Leu Ser Leu Gly Thr Thr Asn
                        565                 570                 575
```

-continued

```
Ser Thr Leu Pro Pro Phe Ser Leu Gln Ser Gly Ile Leu Thr Leu
            580                 585                 590

Asn Pro Val Ala Gln Gly Gln Pro Ile Leu Thr Ser Leu Gly Ser Asn
        595                 600                 605

Gln Glu Glu Ala Tyr Val Thr Met Ser Ser Phe Tyr Gln Asn Gln Ser
610                 615                 620

Asp Pro Lys Pro Glu Asn Pro Ala Cys Pro Trp Thr Val Leu Pro Ala
625                 630                 635                 640

Gly Asp Leu Pro Thr His Asp Gly Tyr Leu Pro Ser Asn Ile Asp Asp
                645                 650                 655

Leu Pro Ser His Glu Ala Pro Leu Ala Asp Ser Leu Glu Glu Leu Glu
            660                 665                 670

Pro Gln
```

<210> SEQ ID NO 92
<211> LENGTH: 861
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 92

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Gly Trp Phe Leu
            180                 185                 190

Asp Ser Pro Asp Arg Pro Trp Asn Pro Pro Thr Phe Ser Pro Ala Leu
        195                 200                 205

Leu Val Val Thr Glu Gly Asp Asn Ala Thr Phe Thr Cys Ser Phe Ser
    210                 215                 220

Asn Thr Ser Glu Ser Phe Val Leu Asn Trp Tyr Arg Met Ser Pro Ser
225                 230                 235                 240

Asn Gln Thr Asp Lys Leu Ala Ala Phe Pro Glu Asp Arg Ser Gln Pro
            245                 250                 255
```

```
Gly Gln Asp Cys Arg Phe Arg Val Thr Gln Leu Pro Asn Gly Arg Asp
                260                 265                 270

Phe His Met Ser Val Val Arg Ala Arg Arg Asn Asp Ser Gly Thr Tyr
            275                 280                 285

Leu Cys Gly Ala Ile Ser Leu Ala Pro Lys Ala Gln Ile Lys Glu Ser
        290                 295                 300

Leu Arg Ala Glu Leu Arg Val Thr Glu Arg Arg Ala Glu Val Pro Thr
305                 310                 315                 320

Ala His Pro Ser Pro Ser Pro Arg Pro Ala Gly Gln Phe Gln Thr Leu
                325                 330                 335

Val Val Gly Val Val Gly Gly Leu Leu Gly Ser Leu Val Leu Leu Val
            340                 345                 350

Trp Val Leu Ala Val Ile Cys Ser Arg Ala Ala Arg Gly Thr Ile Gly
        355                 360                 365

Ala Arg Arg Thr Gly Gln Pro Gly Trp Phe Leu Asp Ser Pro Asp Arg
        370                 375                 380

Pro Trp Asn Pro Pro Thr Phe Ser Pro Ala Leu Leu Val Val Thr Glu
385                 390                 395                 400

Gly Asp Asn Ala Thr Phe Thr Cys Ser Phe Ser Asn Thr Ser Glu Ser
                405                 410                 415

Phe Val Leu Asn Trp Tyr Arg Met Ser Pro Ser Asn Gln Thr Asp Lys
            420                 425                 430

Leu Ala Ala Phe Pro Glu Asp Arg Ser Gln Pro Gly Gln Asp Cys Arg
        435                 440                 445

Phe Arg Val Thr Gln Leu Pro Asn Gly Arg Asp Phe His Met Ser Val
        450                 455                 460

Val Arg Ala Arg Arg Asn Asp Ser Gly Thr Tyr Leu Cys Gly Ala Ile
465                 470                 475                 480

Ser Leu Ala Pro Lys Ala Gln Ile Lys Glu Ser Leu Arg Ala Glu Leu
                485                 490                 495

Arg Val Thr Glu Arg Arg Ala Glu Val Pro Thr Ala His Pro Ser Pro
            500                 505                 510

Ser Pro Arg Pro Ala Gly Gln Phe Gln Thr Leu Val Val Gly Val Val
        515                 520                 525

Gly Gly Leu Leu Gly Ser Leu Val Leu Leu Val Trp Val Leu Ala Val
        530                 535                 540

Ile Cys Ser Arg Ala Ala Arg Gly Thr Ile Gly Ala Arg Arg Thr Gly
545                 550                 555                 560

Gln Ser Asp Pro Thr Arg Val Glu Thr Ala Thr Glu Thr Ala Trp Ile
                565                 570                 575

Ser Leu Val Thr Ala Leu His Leu Val Leu Gly Leu Ser Ala Val Leu
            580                 585                 590

Gly Leu Leu Leu Arg Trp Gln Phe Pro Ala His Tyr Arg Arg Leu
        595                 600                 605

Arg His Ala Leu Trp Pro Ser Leu Pro Asp Leu His Arg Val Leu Gly
        610                 615                 620

Gln Tyr Leu Arg Asp Thr Ala Ala Leu Ser Pro Pro Lys Ala Thr Val
625                 630                 635                 640

Ser Asp Thr Cys Glu Glu Val Glu Pro Ser Leu Leu Glu Ile Leu Pro
                645                 650                 655

Lys Ser Ser Glu Arg Thr Pro Leu Pro Leu Ala Arg Asp Glu Val Glu
            660                 665                 670
```

-continued

```
Gly Phe Leu Gln Asp Thr Phe Pro Gln Gln Leu Glu Glu Ser Glu Lys
            675                 680                 685

Gln Arg Leu Gly Gly Asp Val Gln Ser Pro Asn Cys Pro Ser Glu Asp
690                 695                 700

Val Val Ile Thr Pro Glu Ser Phe Gly Arg Asp Ser Ser Leu Thr Cys
705                 710                 715                 720

Leu Ala Gly Asn Val Ser Ala Cys Asp Ala Pro Ile Leu Ser Ser Ser
                725                 730                 735

Arg Ser Leu Asp Cys Arg Glu Ser Gly Lys Asn Gly Pro His Val Tyr
            740                 745                 750

Gln Asp Leu Leu Leu Ser Leu Gly Thr Thr Asn Ser Thr Leu Pro Pro
        755                 760                 765

Pro Phe Ser Leu Gln Ser Gly Ile Leu Thr Leu Asn Pro Val Ala Gln
    770                 775                 780

Gly Gln Pro Ile Leu Thr Ser Leu Gly Ser Asn Gln Glu Glu Ala Tyr
785                 790                 795                 800

Val Thr Met Ser Ser Phe Tyr Gln Asn Gln Ser Asp Pro Lys Pro Glu
                805                 810                 815

Asn Pro Ala Cys Pro Trp Thr Val Leu Pro Ala Gly Asp Leu Pro Thr
            820                 825                 830

His Asp Gly Tyr Leu Pro Ser Asn Ile Asp Asp Leu Pro Ser His Glu
        835                 840                 845

Ala Pro Leu Ala Asp Ser Leu Glu Glu Leu Glu Pro Gln
    850                 855                 860

<210> SEQ ID NO 93
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175
```

Arg Gly Thr Ile Gly Ala Arg Arg Thr Gly Gln Ser Asp Pro Thr Arg
            180                 185                 190

Val Glu Thr Ala Thr Glu Thr Ala Trp Ile Ser Leu Val Thr Ala Leu
        195                 200                 205

His Leu Val Leu Gly Leu Ser Ala Val Leu Gly Leu Leu Leu Leu Arg
    210                 215                 220

Trp Gln Phe Pro Ala His Tyr Arg Arg Leu Arg His Ala Leu Trp Pro
225                 230                 235                 240

Ser Leu Pro Asp Leu His Arg Val Leu Gly Gln Tyr Leu Arg Asp Thr
                245                 250                 255

Ala Ala Leu Ser Pro Pro Lys Ala Thr Val Ser Asp Thr Cys Glu Glu
                260                 265                 270

Val Glu Pro Ser Leu Leu Glu Ile Leu Pro Lys Ser Ser Glu Arg Thr
            275                 280                 285

Pro Leu Pro Leu Ala Arg Asp Glu Val Glu Gly Phe Leu Gln Asp Thr
290                 295                 300

Phe Pro Gln Gln Leu Glu Glu Ser Glu Lys Gln Arg Leu Gly Gly Asp
305                 310                 315                 320

Val Gln Ser Pro Asn Cys Pro Ser Glu Asp Val Val Ile Thr Pro Glu
                325                 330                 335

Ser Phe Gly Arg Asp Ser Ser Leu Thr Cys Leu Ala Gly Asn Val Ser
                340                 345                 350

Ala Cys Asp Ala Pro Ile Leu Ser Ser Ser Arg Ser Leu Asp Cys Arg
            355                 360                 365

Glu Ser Gly Lys Asn Gly Pro His Val Tyr Gln Asp Leu Leu Leu Ser
        370                 375                 380

Leu Gly Thr Thr Asn Ser Thr Leu Pro Pro Pro Phe Ser Leu Gln Ser
385                 390                 395                 400

Gly Ile Leu Thr Leu Asn Pro Val Ala Gln Gly Gln Pro Ile Leu Thr
                405                 410                 415

Ser Leu Gly Ser Asn Gln Glu Glu Ala Tyr Val Thr Met Ser Ser Phe
                420                 425                 430

Tyr Gln Asn Gln Ser Asp Pro Lys Pro Glu Asn Pro Ala Cys Pro Trp
            435                 440                 445

Thr Val Leu Pro Ala Gly Asp Leu Pro Thr His Asp Gly Tyr Leu Pro
        450                 455                 460

Ser Asn Ile Asp Asp Leu Pro Ser His Glu Ala Pro Leu Ala Asp Ser
465                 470                 475                 480

Leu Glu Glu Leu Glu Pro Gln
                485

<210> SEQ ID NO 94
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His

```
              35                  40                  45
Arg Glu Ser Pro Ser Gly Gln Thr Asp Thr Leu Ala Ala Phe Pro Glu
     50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Arg Ala Arg Arg Asn
                 85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
                180                 185                 190

Val Glu Thr Ala Thr Glu Thr Trp Ile Ser Leu Val Thr Ala Leu His
            195                 200                 205

Leu Val Leu Gly Leu Ser Ala Val Leu Gly Leu Leu Leu Arg Trp
        210                 215                 220

Gln Phe Pro Ala His Tyr Arg Arg Leu Arg His Ala Leu Trp Pro Ser
225                 230                 235                 240

Leu Pro Asp Leu His Arg Val Leu Gly Gln Tyr Leu Arg Asp Thr Ala
                245                 250                 255

Ala Leu Ser Pro Pro Lys Ala Thr Val Ser Asp Thr Cys Glu Val
                260                 265                 270

Glu Pro Ser Leu Leu Glu Ile Leu Pro Lys Ser Ser Glu Arg Thr Pro
            275                 280                 285

Leu Pro Leu Ala Arg Asp Glu Val Glu Gly Phe Leu Gln Asp Thr Phe
        290                 295                 300

Pro Gln Gln Leu Glu Glu Ser Glu Lys Gln Arg Leu Gly Gly Asp Val
305                 310                 315                 320

Gln Ser Pro Asn Cys Pro Ser Glu Asp Val Val Ile Thr Pro Glu Ser
                325                 330                 335

Phe Gly Arg Asp Ser Ser Leu Thr Cys Leu Ala Gly Asn Val Ser Ala
                340                 345                 350

Cys Asp Ala Pro Ile Leu Ser Ser Ser Arg Ser Leu Asp Cys Arg Glu
            355                 360                 365

Ser Gly Lys Asn Gly Pro His Val Tyr Gln Asp Leu Leu Leu Ser Leu
        370                 375                 380

Gly Thr Thr Asn Ser Thr Leu Pro Pro Pro Phe Ser Leu Gln Ser Gly
385                 390                 395                 400

Ile Leu Thr Leu Asn Pro Val Ala Gln Gly Gln Pro Ile Leu Thr Ser
                405                 410                 415

Leu Gly Ser Asn Gln Glu Glu Ala Tyr Val Thr Met Ser Ser Phe Tyr
                420                 425                 430

Gln Asn Gln Ser Asp Pro Lys Pro Glu Asn Pro Ala Cys Pro Trp Thr
            435                 440                 445

Val Leu Pro Ala Gly Asp Leu Pro Thr His Asp Gly Tyr Leu Pro Ser
        450                 455                 460
```

```
Asn Ile Asp Asp Leu Pro Ser His Glu Ala Pro Leu Ala Asp Ser Leu
465                 470                 475                 480

Glu Glu Leu Glu Pro Gln
                485

<210> SEQ ID NO 95
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ile Ser Leu Val Thr Ala Leu His Leu
        195                 200                 205

Val Leu Gly Leu Ser Ala Val Leu Gly Leu Leu Leu Arg Trp Gln
210                 215                 220

Phe Pro Ala His Tyr Arg Arg Leu Arg His Ala Leu Trp Pro Ser Leu
225                 230                 235                 240

Pro Asp Leu His Arg Val Leu Gly Gln Tyr Leu Arg Asp Thr Ala Ala
                245                 250                 255

Leu Ser Pro Pro Lys Ala Thr Val Ser Asp Thr Cys Glu Glu Val Glu
            260                 265                 270

Pro Ser Leu Leu Glu Ile Leu Pro Lys Ser Ser Glu Arg Thr Pro Leu
        275                 280                 285

Pro Leu Ala Arg Asp Glu Val Glu Gly Phe Leu Gln Asp Thr Phe Pro
290                 295                 300

Gln Gln Leu Glu Glu Ser Glu Lys Gln Arg Leu Gly Gly Asp Val Gln
305                 310                 315                 320

Ser Pro Asn Cys Pro Ser Glu Asp Val Val Ile Thr Pro Glu Ser Phe
```

```
                    325                 330                 335
Gly Arg Asp Ser Ser Leu Thr Cys Leu Ala Gly Asn Val Ser Ala Cys
            340                 345                 350
Asp Ala Pro Ile Leu Ser Ser Ser Arg Ser Leu Asp Cys Arg Glu Ser
            355                 360                 365
Gly Lys Asn Gly Pro His Val Tyr Gln Asp Leu Leu Leu Ser Leu Gly
            370                 375                 380
Thr Thr Asn Ser Thr Leu Pro Pro Phe Ser Leu Gln Ser Gly Ile
385                 390                 395                 400
Leu Thr Leu Asn Pro Val Ala Gln Gly Gln Pro Ile Leu Thr Ser Leu
                405                 410                 415
Gly Ser Asn Gln Glu Glu Ala Tyr Val Thr Met Ser Ser Phe Tyr Gln
            420                 425                 430
Asn Gln Ser Asp Pro Lys Pro Glu Asn Pro Ala Cys Pro Trp Thr Val
            435                 440                 445
Leu Pro Ala Gly Asp Leu Pro Thr His Asp Gly Tyr Leu Pro Ser Asn
450                 455                 460
Ile Asp Asp Leu Pro Ser His Glu Ala Pro Leu Ala Asp Ser Leu Glu
465                 470                 475                 480
Glu Leu Glu Pro Gln
            485

<210> SEQ ID NO 96
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Ser Phe His Val Ile Trp His
            35                  40                  45
Arg Glu Ser Pro Ser Gly Gln Thr Asp Thr Leu Ala Ala Phe Pro Glu
        50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Val Cys Gly Val Ile Ser Leu Ala Pro Lys Ile
            100                 105                 110
Gln Ile Lys Glu Ser Leu Arg Ala Glu Leu Arg Val Thr Glu Arg Arg
        115                 120                 125
Ala Glu Val Pro Thr Ala His Pro Ser Pro Ser Pro Arg Pro Ala Gly
    130                 135                 140
Gln Phe Gln Thr Leu Val Val Gly Val Val Gly Gly Leu Leu Gly Ser
145                 150                 155                 160
Leu Val Leu Leu Val Trp Val Leu Ala Val Ile Cys Ser Arg Ala Ala
                165                 170                 175
Arg Gly Thr Ile Gly Ala Arg Arg Thr Gly Gln Ser Asp Pro Thr Arg
            180                 185                 190
```

```
Val Glu Thr Ala Thr Glu Thr Leu Ile Ser Leu Val Thr Ala Leu His
    195                 200                 205

Leu Val Leu Gly Leu Ser Ala Val Leu Gly Leu Leu Leu Arg Trp
210                 215                 220

Gln Phe Pro Ala His Tyr Arg Arg Leu Arg His Ala Leu Trp Pro Ser
225                 230                 235                 240

Leu Pro Asp Leu His Arg Val Leu Gly Gln Tyr Leu Arg Asp Thr Ala
                245                 250                 255

Ala Leu Ser Pro Pro Lys Ala Thr Val Ser Asp Thr Cys Glu Val
            260                 265                 270

Glu Pro Ser Leu Leu Glu Ile Leu Pro Lys Ser Ser Glu Arg Thr Pro
                275                 280                 285

Leu Pro Leu Ala Arg Asp Glu Val Glu Gly Phe Leu Gln Asp Thr Phe
            290                 295                 300

Pro Gln Gln Leu Glu Glu Ser Glu Lys Gln Arg Leu Gly Gly Asp Val
305                 310                 315                 320

Gln Ser Pro Asn Cys Pro Ser Glu Asp Val Val Ile Thr Pro Glu Ser
                325                 330                 335

Phe Gly Arg Asp Ser Ser Leu Thr Cys Leu Ala Gly Asn Val Ser Ala
                340                 345                 350

Cys Asp Ala Pro Ile Leu Ser Ser Arg Ser Leu Asp Cys Arg Glu
            355                 360                 365

Ser Gly Lys Asn Gly Pro His Val Tyr Gln Asp Leu Leu Ser Leu
370                 375                 380

Gly Thr Thr Asn Ser Thr Leu Pro Pro Phe Ser Leu Gln Ser Gly
385                 390                 395                 400

Ile Leu Thr Leu Asn Pro Val Ala Gln Gly Gln Pro Ile Leu Thr Ser
                405                 410                 415

Leu Gly Ser Asn Gln Glu Glu Ala Tyr Val Thr Met Ser Ser Phe Tyr
                420                 425                 430

Gln Asn Gln Ser Asp Pro Lys Pro Glu Asn Pro Ala Cys Pro Trp Thr
                435                 440                 445

Val Leu Pro Ala Gly Asp Leu Pro Thr His Asp Gly Tyr Leu Pro Ser
450                 455                 460

Asn Ile Asp Asp Leu Pro Ser His Glu Ala Pro Leu Ala Asp Ser Leu
465                 470                 475                 480

Glu Glu Leu Glu Pro Gln
            485

<210> SEQ ID NO 97
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
50                  55                  60
```

```
Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
             85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ser Leu Val Thr Ala Leu His Leu Val
        195                 200                 205

Leu Gly Leu Ser Ala Val Leu Gly Leu Leu Leu Arg Trp Gln Phe
210                 215                 220

Pro Ala His Tyr Arg Arg Leu Arg His Ala Leu Trp Pro Ser Leu Pro
225                 230                 235                 240

Asp Leu His Arg Val Leu Gly Gln Tyr Leu Arg Asp Thr Ala Ala Leu
                245                 250                 255

Ser Pro Pro Lys Ala Thr Val Ser Asp Thr Cys Glu Glu Val Glu Pro
            260                 265                 270

Ser Leu Leu Glu Ile Leu Pro Lys Ser Ser Glu Arg Thr Pro Leu Pro
        275                 280                 285

Leu Ala Arg Asp Glu Val Glu Gly Phe Leu Gln Asp Thr Phe Pro Gln
290                 295                 300

Gln Leu Glu Glu Ser Glu Lys Gln Arg Leu Gly Gly Asp Val Gln Ser
305                 310                 315                 320

Pro Asn Cys Pro Ser Glu Asp Val Val Ile Thr Pro Glu Ser Phe Gly
                325                 330                 335

Arg Asp Ser Ser Leu Thr Cys Leu Ala Gly Asn Val Ser Ala Cys Asp
            340                 345                 350

Ala Pro Ile Leu Ser Ser Ser Arg Ser Leu Asp Cys Arg Glu Ser Gly
        355                 360                 365

Lys Asn Gly Pro His Val Tyr Gln Asp Leu Leu Ser Leu Gly Thr
370                 375                 380

Thr Asn Ser Thr Leu Pro Pro Phe Ser Leu Gln Ser Gly Ile Leu
385                 390                 395                 400

Thr Leu Asn Pro Val Ala Gln Gly Gln Pro Ile Leu Thr Ser Leu Gly
                405                 410                 415

Ser Asn Gln Glu Glu Ala Tyr Val Thr Met Ser Ser Phe Tyr Gln Asn
            420                 425                 430

Gln Ser Asp Pro Lys Pro Glu Asn Pro Ala Cys Pro Trp Thr Val Leu
        435                 440                 445

Pro Ala Gly Asp Leu Pro Thr His Asp Gly Tyr Leu Pro Ser Asn Ile
    450                 455                 460

Asp Asp Leu Pro Ser His Glu Ala Pro Leu Ala Asp Ser Leu Glu Glu
465                 470                 475                 480
```

Leu Glu Pro Gln

<210> SEQ ID NO 98
<211> LENGTH: 483
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 98

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Leu Val Thr Ala Leu His Leu Val Leu
        195                 200                 205

Gly Leu Ser Ala Val Leu Gly Leu Leu Leu Arg Trp Gln Phe Pro
210                 215                 220

Ala His Tyr Arg Arg Leu Arg His Ala Leu Trp Pro Ser Leu Pro Asp
225                 230                 235                 240

Leu His Arg Val Leu Gly Gln Tyr Leu Arg Asp Thr Ala Ala Leu Ser
                245                 250                 255

Pro Pro Lys Ala Thr Val Ser Asp Thr Cys Glu Glu Val Glu Pro Ser
            260                 265                 270

Leu Leu Glu Ile Leu Pro Lys Ser Ser Glu Arg Thr Pro Leu Pro Leu
        275                 280                 285

Ala Arg Asp Glu Val Glu Gly Phe Leu Gln Asp Thr Phe Pro Gln Gln
290                 295                 300

Leu Glu Glu Ser Glu Lys Gln Arg Leu Gly Gly Asp Val Gln Ser Pro
305                 310                 315                 320

Asn Cys Pro Ser Glu Asp Val Val Ile Thr Pro Glu Ser Phe Gly Arg
                325                 330                 335

Asp Ser Ser Leu Thr Cys Leu Ala Gly Asn Val Ser Ala Cys Asp Ala
            340                 345                 350

-continued

Pro Ile Leu Ser Ser Arg Ser Leu Asp Cys Arg Glu Ser Gly Lys
        355                 360                 365

Asn Gly Pro His Val Tyr Gln Asp Leu Leu Ser Leu Gly Thr Thr
370                 375                 380

Asn Ser Thr Leu Pro Pro Phe Ser Leu Gln Ser Gly Ile Leu Thr
385                 390                 395                 400

Leu Asn Pro Val Ala Gln Gly Gln Pro Ile Leu Thr Ser Leu Gly Ser
                405                 410                 415

Asn Gln Glu Ala Tyr Val Thr Met Ser Ser Phe Tyr Gln Asn Gln
            420                 425                 430

Ser Asp Pro Lys Pro Glu Asn Pro Ala Cys Pro Trp Thr Val Leu Pro
        435                 440                 445

Ala Gly Asp Leu Pro Thr His Asp Gly Tyr Leu Pro Ser Asn Ile Asp
450                 455                 460

Asp Leu Pro Ser His Glu Ala Pro Leu Ala Asp Ser Leu Glu Glu Leu
465                 470                 475                 480

Glu Pro Gln

<210> SEQ ID NO 99
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ile Leu Val Thr Ala Leu His Leu Val
        195                 200                 205

Leu Gly Leu Ser Ala Val Leu Gly Leu Leu Leu Arg Trp Gln Phe
    210                 215                 220

Pro Ala His Tyr Arg Arg Leu Arg His Ala Leu Trp Pro Ser Leu Pro
225                 230                 235                 240

Asp Leu His Arg Val Leu Gly Gln Tyr Leu Arg Asp Thr Ala Ala Leu
                245                 250                 255

Ser Pro Pro Lys Ala Thr Val Ser Asp Thr Cys Glu Glu Val Glu Pro
            260                 265                 270

Ser Leu Leu Glu Ile Leu Pro Lys Ser Ser Glu Arg Thr Pro Leu Pro
        275                 280                 285

Leu Ala Arg Asp Glu Val Glu Gly Phe Leu Gln Asp Thr Phe Pro Gln
    290                 295                 300

Gln Leu Glu Glu Ser Glu Lys Gln Arg Leu Gly Gly Asp Val Gln Ser
305                 310                 315                 320

Pro Asn Cys Pro Ser Glu Asp Val Val Ile Thr Pro Glu Ser Phe Gly
                325                 330                 335

Arg Asp Ser Ser Leu Thr Cys Leu Ala Gly Asn Val Ser Ala Cys Asp
                340                 345                 350

Ala Pro Ile Leu Ser Ser Arg Ser Leu Asp Cys Arg Glu Ser Gly
                355                 360                 365

Lys Asn Gly Pro His Val Tyr Gln Asp Leu Leu Ser Leu Gly Thr
370                 375                 380

Thr Asn Ser Thr Leu Pro Pro Phe Ser Leu Gln Ser Gly Ile Leu
385                 390                 395                 400

Thr Leu Asn Pro Val Ala Gln Gly Gln Pro Ile Leu Thr Ser Leu Gly
                405                 410                 415

Ser Asn Gln Glu Glu Ala Tyr Val Thr Met Ser Ser Phe Tyr Gln Asn
                420                 425                 430

Gln Ser Asp Pro Lys Pro Glu Asn Pro Ala Cys Pro Trp Thr Val Leu
            435                 440                 445

Pro Ala Gly Asp Leu Pro Thr His Asp Gly Tyr Leu Pro Ser Asn Ile
    450                 455                 460

Asp Asp Leu Pro Ser His Glu Ala Pro Leu Ala Asp Ser Leu Glu Glu
465                 470                 475                 480

Leu Glu Pro Gln

<210> SEQ ID NO 100
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Val Thr Ala Leu His Leu Val Leu Gly
        195                 200                 205

Leu Ser Ala Val Leu Gly Leu Leu Leu Arg Trp Gln Phe Pro Ala
210                 215                 220

His Tyr Arg Arg Leu Arg His Ala Leu Trp Pro Ser Leu Pro Asp Leu
225                 230                 235                 240

His Arg Val Leu Gly Gln Tyr Leu Arg Asp Thr Ala Ala Leu Ser Pro
                245                 250                 255

Pro Lys Ala Thr Val Ser Asp Thr Cys Glu Glu Val Glu Pro Ser Leu
            260                 265                 270

Leu Glu Ile Leu Pro Lys Ser Ser Glu Arg Thr Pro Leu Pro Leu Ala
        275                 280                 285

Arg Asp Glu Val Glu Gly Phe Leu Gln Asp Thr Phe Pro Gln Gln Leu
290                 295                 300

Glu Glu Ser Glu Lys Gln Arg Leu Gly Gly Asp Val Gln Ser Pro Asn
305                 310                 315                 320

Cys Pro Ser Glu Asp Val Val Ile Thr Pro Glu Ser Phe Gly Arg Asp
                325                 330                 335

Ser Ser Leu Thr Cys Leu Ala Gly Asn Val Ser Ala Cys Asp Ala Pro
            340                 345                 350

Ile Leu Ser Ser Ser Arg Ser Leu Asp Cys Arg Glu Ser Gly Lys Asn
        355                 360                 365

Gly Pro His Val Tyr Gln Asp Leu Leu Leu Ser Leu Gly Thr Thr Asn
370                 375                 380

Ser Thr Leu Pro Pro Pro Phe Ser Leu Gln Ser Gly Ile Leu Thr Leu
385                 390                 395                 400

Asn Pro Val Ala Gln Gly Gln Pro Ile Leu Thr Ser Leu Gly Ser Asn
                405                 410                 415

Gln Glu Glu Ala Tyr Val Thr Met Ser Ser Phe Tyr Gln Asn Gln Ser
            420                 425                 430

Asp Pro Lys Pro Glu Asn Pro Ala Cys Pro Trp Thr Val Leu Pro Ala
        435                 440                 445

Gly Asp Leu Pro Thr His Asp Gly Tyr Leu Pro Ser Asn Ile Asp Asp
450                 455                 460

Leu Pro Ser His Glu Ala Pro Leu Ala Asp Ser Leu Glu Glu Leu Glu
465                 470                 475                 480

Pro Gln

<210> SEQ ID NO 101
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

| | | | | | | | | | | | | | | |
|---|---|---|---|---|---|---|---|---|---|---|---|---|---|---|
| Pro | Gly | Trp | Phe | Leu | Asp | Ser | Pro | Asp | Arg | Pro | Trp | Asn | Pro | Thr |
| 1 | | | | 5 | | | | | 10 | | | | | 15 |
| Phe | Ser | Pro | Ala | Leu | Leu | Val | Val | Thr | Glu | Gly | Asp | Asn | Ala | Thr | Phe |
| | | | 20 | | | | | 25 | | | | | 30 | | |
| Thr | Cys | Ser | Phe | Ser | Asn | Thr | Ser | Glu | Ser | Phe | His | Val | Ile | Trp | His |
| | | 35 | | | | | 40 | | | | | 45 | | | |
| Arg | Glu | Ser | Pro | Ser | Gly | Gln | Thr | Asp | Thr | Leu | Ala | Ala | Phe | Pro | Glu |
| | 50 | | | | | 55 | | | | | 60 | | | | |
| Asp | Arg | Ser | Gln | Pro | Gly | Gln | Asp | Cys | Arg | Phe | Arg | Val | Thr | Gln | Leu |
| 65 | | | | | 70 | | | | | 75 | | | | | 80 |
| Pro | Asn | Gly | Arg | Asp | Phe | His | Met | Ser | Val | Val | Arg | Ala | Arg | Arg | Asn |
| | | | | 85 | | | | | 90 | | | | | 95 | |
| Asp | Ser | Gly | Thr | Tyr | Val | Cys | Gly | Val | Ile | Ser | Leu | Ala | Pro | Lys | Ile |
| | | | 100 | | | | | 105 | | | | | 110 | | |
| Gln | Ile | Lys | Glu | Ser | Leu | Arg | Ala | Glu | Leu | Arg | Val | Thr | Glu | Arg | Arg |
| | | 115 | | | | | 120 | | | | | 125 | | | |
| Ala | Glu | Val | Pro | Thr | Ala | His | Pro | Ser | Pro | Ser | Pro | Arg | Pro | Ala | Gly |
| | 130 | | | | | 135 | | | | | 140 | | | | |
| Gln | Phe | Gln | Thr | Leu | Val | Val | Gly | Val | Val | Gly | Gly | Leu | Leu | Gly | Ser |
| 145 | | | | | 150 | | | | | 155 | | | | | 160 |
| Leu | Val | Leu | Leu | Val | Trp | Val | Leu | Ala | Val | Ile | Cys | Ser | Arg | Ala | Ala |
| | | | | 165 | | | | | 170 | | | | | 175 | |
| Arg | Gly | Thr | Ile | Gly | Ala | Arg | Arg | Thr | Gly | Gln | Ser | Asp | Pro | Thr | Arg |
| | | | 180 | | | | | 185 | | | | | 190 | | |
| Val | Glu | Thr | Ala | Thr | Glu | Thr | Thr | Ala | Leu | His | Leu | Val | Leu | Gly | Leu |
| | | 195 | | | | | 200 | | | | | 205 | | | |
| Ser | Ala | Val | Leu | Gly | Leu | Leu | Leu | Leu | Arg | Trp | Gln | Phe | Pro | Ala | His |
| | 210 | | | | | 215 | | | | | 220 | | | | |
| Tyr | Arg | Arg | Leu | Arg | His | Ala | Leu | Trp | Pro | Ser | Leu | Pro | Asp | Leu | His |
| 225 | | | | | 230 | | | | | 235 | | | | | 240 |
| Arg | Val | Leu | Gly | Gln | Tyr | Leu | Arg | Asp | Thr | Ala | Ala | Leu | Ser | Pro | Pro |
| | | | | 245 | | | | | 250 | | | | | 255 | |
| Lys | Ala | Thr | Val | Ser | Asp | Thr | Cys | Glu | Val | Glu | Pro | Ser | Leu | Leu |
| | | | 260 | | | | | 265 | | | | | 270 | | |
| Glu | Ile | Leu | Pro | Lys | Ser | Ser | Glu | Arg | Thr | Pro | Leu | Pro | Leu | Ala | Arg |
| | | 275 | | | | | 280 | | | | | 285 | | | |
| Asp | Glu | Val | Glu | Gly | Phe | Leu | Gln | Asp | Thr | Phe | Pro | Gln | Gln | Leu | Glu |
| | 290 | | | | | 295 | | | | | 300 | | | | |
| Glu | Ser | Glu | Lys | Gln | Arg | Leu | Gly | Gly | Asp | Val | Gln | Ser | Pro | Asn | Cys |
| 305 | | | | | 310 | | | | | 315 | | | | | 320 |
| Pro | Ser | Glu | Asp | Val | Val | Ile | Thr | Pro | Glu | Ser | Phe | Gly | Arg | Asp | Ser |
| | | | | 325 | | | | | 330 | | | | | 335 | |
| Ser | Leu | Thr | Cys | Leu | Ala | Gly | Asn | Val | Ser | Ala | Cys | Asp | Ala | Pro | Ile |
| | | | 340 | | | | | 345 | | | | | 350 | | |
| Leu | Ser | Ser | Ser | Arg | Ser | Leu | Asp | Cys | Arg | Glu | Ser | Gly | Lys | Asn | Gly |
| | | | 355 | | | | | 360 | | | | | 365 | | |
| Pro | His | Val | Tyr | Gln | Asp | Leu | Leu | Ser | Leu | Gly | Thr | Thr | Asn | Ser |
| | | 370 | | | | | 375 | | | | | 380 | | | |
| Thr | Leu | Pro | Pro | Pro | Phe | Ser | Leu | Gln | Ser | Gly | Ile | Leu | Thr | Leu | Asn |

```
                385                 390                 395                 400
Pro Val Ala Gln Gly Gln Pro Ile Leu Thr Ser Leu Gly Ser Asn Gln
            405                 410                 415

Glu Glu Ala Tyr Val Thr Met Ser Ser Phe Tyr Gln Asn Gln Ser Asp
        420                 425                 430

Pro Lys Pro Glu Asn Pro Ala Cys Pro Trp Thr Val Leu Pro Ala Gly
    435                 440                 445

Asp Leu Pro Thr His Asp Gly Tyr Leu Pro Ser Asn Ile Asp Asp Leu
450                 455                 460

Pro Ser His Glu Ala Pro Leu Ala Asp Ser Leu Glu Glu Leu Glu Pro
465                 470                 475                 480

Gln

<210> SEQ ID NO 102
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Leu His Leu Val Leu Gly Leu Ser
        195                 200                 205

Ala Val Leu Gly Leu Leu Leu Arg Trp Gln Phe Pro Ala His Tyr
    210                 215                 220

Arg Arg Leu Arg His Ala Leu Trp Pro Ser Leu Pro Asp Leu His Arg
225                 230                 235                 240

Val Leu Gly Gln Tyr Leu Arg Asp Thr Ala Ala Leu Ser Pro Pro Lys
                245                 250                 255

Ala Thr Val Ser Asp Thr Cys Glu Glu Val Glu Pro Ser Leu Leu Glu
```

```
                260                 265                 270
Ile Leu Pro Lys Ser Ser Glu Arg Thr Pro Leu Pro Leu Ala Arg Asp
            275                 280                 285

Glu Val Glu Gly Phe Leu Gln Asp Thr Phe Pro Gln Gln Leu Glu Glu
            290                 295                 300

Ser Glu Lys Gln Arg Leu Gly Gly Asp Val Gln Ser Pro Asn Cys Pro
305                 310                 315                 320

Ser Glu Asp Val Val Ile Thr Pro Glu Ser Phe Gly Arg Asp Ser Ser
                325                 330                 335

Leu Thr Cys Leu Ala Gly Asn Val Ser Ala Cys Asp Ala Pro Ile Leu
            340                 345                 350

Ser Ser Ser Arg Ser Leu Asp Cys Arg Glu Ser Gly Lys Asn Gly Pro
            355                 360                 365

His Val Tyr Gln Asp Leu Leu Leu Ser Leu Gly Thr Thr Asn Ser Thr
            370                 375                 380

Leu Pro Pro Pro Phe Ser Leu Gln Ser Gly Ile Leu Thr Leu Asn Pro
385                 390                 395                 400

Val Ala Gln Gly Gln Pro Ile Leu Thr Ser Leu Gly Ser Asn Gln Glu
                405                 410                 415

Glu Ala Tyr Val Thr Met Ser Ser Phe Tyr Gln Asn Gln Ser Asp Pro
            420                 425                 430

Lys Pro Glu Asn Pro Ala Cys Pro Trp Thr Val Leu Pro Ala Gly Asp
            435                 440                 445

Leu Pro Thr His Asp Gly Tyr Leu Pro Ser Asn Ile Asp Asp Leu Pro
            450                 455                 460

Ser His Glu Ala Pro Leu Ala Asp Ser Leu Glu Glu Leu Glu Pro Gln
465                 470                 475                 480

<210> SEQ ID NO 103
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140
```

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
                180                 185                 190

Val Glu Thr Ala Thr Glu Thr Leu His Leu Val Leu Gly Leu Ser Ala
            195                 200                 205

Val Leu Gly Leu Leu Leu Arg Trp Gln Phe Pro Ala His Tyr Arg
        210                 215                 220

Arg Leu Arg His Ala Leu Trp Pro Ser Leu Pro Asp Leu His Arg Val
225                 230                 235                 240

Leu Gly Gln Tyr Leu Arg Asp Thr Ala Ala Leu Ser Pro Pro Lys Ala
                245                 250                 255

Thr Val Ser Asp Thr Cys Glu Glu Val Glu Pro Ser Leu Leu Glu Ile
                260                 265                 270

Leu Pro Lys Ser Ser Glu Arg Thr Pro Leu Pro Leu Ala Arg Asp Glu
            275                 280                 285

Val Glu Gly Phe Leu Gln Asp Thr Phe Pro Gln Gln Leu Glu Glu Ser
        290                 295                 300

Glu Lys Gln Arg Leu Gly Gly Asp Val Gln Ser Pro Asn Cys Pro Ser
305                 310                 315                 320

Glu Asp Val Val Ile Thr Pro Glu Ser Phe Gly Arg Asp Ser Ser Leu
                325                 330                 335

Thr Cys Leu Ala Gly Asn Val Ser Ala Cys Asp Ala Pro Ile Leu Ser
                340                 345                 350

Ser Ser Arg Ser Leu Asp Cys Arg Glu Ser Gly Lys Asn Gly Pro His
            355                 360                 365

Val Tyr Gln Asp Leu Leu Leu Ser Leu Gly Thr Thr Asn Ser Thr Leu
        370                 375                 380

Pro Pro Pro Phe Ser Leu Gln Ser Gly Ile Leu Thr Leu Asn Pro Val
385                 390                 395                 400

Ala Gln Gly Gln Pro Ile Leu Thr Ser Leu Gly Ser Asn Gln Glu Glu
                405                 410                 415

Ala Tyr Val Thr Met Ser Ser Phe Tyr Gln Asn Gln Ser Asp Pro Lys
                420                 425                 430

Pro Glu Asn Pro Ala Cys Pro Trp Thr Val Leu Pro Ala Gly Asp Leu
            435                 440                 445

Pro Thr His Asp Gly Tyr Leu Pro Ser Asn Ile Asp Asp Leu Pro Ser
        450                 455                 460

His Glu Ala Pro Leu Ala Asp Ser Leu Glu Glu Leu Glu Pro Gln
465                 470                 475

<210> SEQ ID NO 104
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

```
Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr His Leu Val Leu Gly Leu Ser Ala Val
            195                 200                 205

Leu Gly Leu Leu Leu Leu Arg Trp Gln Phe Pro Ala His Tyr Arg Arg
210                 215                 220

Leu Arg His Ala Leu Trp Pro Ser Leu Pro Asp Leu His Arg Val Leu
225                 230                 235                 240

Gly Gln Tyr Leu Arg Asp Thr Ala Ala Leu Ser Pro Pro Lys Ala Thr
                245                 250                 255

Val Ser Asp Thr Cys Glu Glu Val Glu Pro Ser Leu Leu Glu Ile Leu
                260                 265                 270

Pro Lys Ser Ser Glu Arg Thr Pro Leu Pro Leu Ala Arg Asp Glu Val
            275                 280                 285

Glu Gly Phe Leu Gln Asp Thr Phe Pro Gln Gln Leu Glu Glu Ser Glu
            290                 295                 300

Lys Gln Arg Leu Gly Gly Asp Val Gln Ser Pro Asn Cys Pro Ser Glu
305                 310                 315                 320

Asp Val Val Ile Thr Pro Glu Ser Phe Gly Arg Asp Ser Ser Leu Thr
                325                 330                 335

Cys Leu Ala Gly Asn Val Ser Ala Cys Asp Ala Pro Ile Leu Ser Ser
                340                 345                 350

Ser Arg Ser Leu Asp Cys Arg Glu Ser Gly Lys Asn Gly Pro His Val
            355                 360                 365

Tyr Gln Asp Leu Leu Leu Ser Leu Gly Thr Thr Asn Ser Thr Leu Pro
            370                 375                 380

Pro Pro Phe Ser Leu Gln Ser Gly Ile Leu Thr Leu Asn Pro Val Ala
385                 390                 395                 400

Gln Gly Gln Pro Ile Leu Thr Ser Leu Gly Ser Asn Gln Glu Glu Ala
                405                 410                 415

Tyr Val Thr Met Ser Ser Phe Tyr Gln Asn Gln Ser Asp Pro Lys Pro
                420                 425                 430

Glu Asn Pro Ala Cys Pro Trp Thr Val Leu Pro Ala Gly Asp Leu Pro
            435                 440                 445
```

```
Thr His Asp Gly Tyr Leu Pro Ser Asn Ile Asp Asp Leu Pro Ser His
    450                 455                 460
Glu Ala Pro Leu Ala Asp Ser Leu Glu Glu Leu Glu Pro Gln
465                 470                 475

<210> SEQ ID NO 105
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Leu Val Leu Gly Leu Ser Ala Val Leu
        195                 200                 205

Gly Leu Leu Leu Leu Arg Trp Gln Phe Pro Ala His Tyr Arg Arg Leu
    210                 215                 220

Arg His Ala Leu Trp Pro Ser Leu Pro Asp Leu His Arg Val Leu Gly
225                 230                 235                 240

Gln Tyr Leu Arg Asp Thr Ala Ala Leu Ser Pro Pro Lys Ala Thr Val
                245                 250                 255

Ser Asp Thr Cys Glu Glu Val Glu Pro Ser Leu Leu Glu Ile Leu Pro
            260                 265                 270

Lys Ser Ser Glu Arg Thr Pro Leu Pro Leu Ala Arg Asp Glu Val Glu
        275                 280                 285

Gly Phe Leu Gln Asp Thr Phe Pro Gln Gln Leu Glu Glu Ser Glu Lys
    290                 295                 300

Gln Arg Leu Gly Gly Asp Val Gln Ser Pro Asn Cys Pro Ser Glu Asp
305                 310                 315                 320

Val Val Ile Thr Pro Glu Ser Phe Gly Arg Asp Ser Ser Leu Thr Cys
                325                 330                 335
```

Leu Ala Gly Asn Val Ser Ala Cys Asp Ala Pro Ile Leu Ser Ser Ser
                340                 345                 350

Arg Ser Leu Asp Cys Arg Glu Ser Gly Lys Asn Gly Pro His Val Tyr
            355                 360                 365

Gln Asp Leu Leu Leu Ser Leu Gly Thr Thr Asn Ser Thr Leu Pro Pro
        370                 375                 380

Pro Phe Ser Leu Gln Ser Gly Ile Leu Thr Leu Asn Pro Val Ala Gln
385                 390                 395                 400

Gly Gln Pro Ile Leu Thr Ser Leu Gly Ser Asn Gln Glu Glu Ala Tyr
                405                 410                 415

Val Thr Met Ser Ser Phe Tyr Gln Asn Gln Ser Asp Pro Lys Pro Glu
            420                 425                 430

Asn Pro Ala Cys Pro Trp Thr Val Leu Pro Ala Gly Asp Leu Pro Thr
        435                 440                 445

His Asp Gly Tyr Leu Pro Ser Asn Ile Asp Asp Leu Pro Ser His Glu
    450                 455                 460

Ala Pro Leu Ala Asp Ser Leu Glu Glu Leu Glu Pro Gln
465                 470                 475

<210> SEQ ID NO 106
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Val Leu Gly Leu Ser Ala Val Leu Gly
        195                 200                 205

Leu Leu Leu Leu Arg Trp Gln Phe Pro Ala His Tyr Arg Arg Leu Arg

```
                210                 215                 220
His Ala Leu Trp Pro Ser Leu Pro Asp Leu His Arg Val Leu Gly Gln
225                 230                 235                 240

Tyr Leu Arg Asp Thr Ala Ala Leu Ser Pro Pro Lys Ala Thr Val Ser
                245                 250                 255

Asp Thr Cys Glu Glu Val Glu Pro Ser Leu Leu Glu Ile Leu Pro Lys
                260                 265                 270

Ser Ser Glu Arg Thr Pro Leu Pro Leu Ala Arg Asp Glu Val Glu Gly
            275                 280                 285

Phe Leu Gln Asp Thr Phe Pro Gln Gln Leu Glu Glu Ser Glu Lys Gln
290                 295                 300

Arg Leu Gly Gly Asp Val Gln Ser Pro Asn Cys Pro Ser Glu Asp Val
305                 310                 315                 320

Val Ile Thr Pro Glu Ser Phe Gly Arg Asp Ser Ser Leu Thr Cys Leu
                325                 330                 335

Ala Gly Asn Val Ser Ala Cys Asp Ala Pro Ile Leu Ser Ser Ser Arg
                340                 345                 350

Ser Leu Asp Cys Arg Glu Ser Gly Lys Asn Gly Pro His Val Tyr Gln
                355                 360                 365

Asp Leu Leu Leu Ser Leu Gly Thr Thr Asn Ser Thr Leu Pro Pro Pro
            370                 375                 380

Phe Ser Leu Gln Ser Gly Ile Leu Thr Leu Asn Pro Val Ala Gln Gly
385                 390                 395                 400

Gln Pro Ile Leu Thr Ser Leu Gly Ser Asn Gln Glu Glu Ala Tyr Val
                405                 410                 415

Thr Met Ser Ser Phe Tyr Gln Asn Gln Ser Asp Pro Lys Pro Glu Asn
                420                 425                 430

Pro Ala Cys Pro Trp Thr Val Leu Pro Ala Gly Asp Leu Pro Thr His
            435                 440                 445

Asp Gly Tyr Leu Pro Ser Asn Ile Asp Asp Leu Pro Ser His Glu Ala
        450                 455                 460

Pro Leu Ala Asp Ser Leu Glu Glu Leu Glu Pro Gln
465                 470                 475

<210> SEQ ID NO 107
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

```
Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Val Gly Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Leu Gly Leu Ser Ala Val Leu Gly Leu
        195                 200                 205

Leu Leu Leu Arg Trp Gln Phe Pro Ala His Tyr Arg Arg Leu Arg His
210                 215                 220

Ala Leu Trp Pro Ser Leu Pro Asp Leu His Arg Val Leu Gly Gln Tyr
225                 230                 235                 240

Leu Arg Asp Thr Ala Ala Leu Ser Pro Pro Lys Ala Thr Val Ser Asp
            245                 250                 255

Thr Cys Glu Glu Val Glu Pro Ser Leu Leu Glu Ile Leu Pro Lys Ser
        260                 265                 270

Ser Glu Arg Thr Pro Leu Pro Leu Ala Arg Asp Glu Val Glu Gly Phe
    275                 280                 285

Leu Gln Asp Thr Phe Pro Gln Gln Leu Glu Glu Ser Glu Lys Gln Arg
290                 295                 300

Leu Gly Gly Asp Val Gln Ser Pro Asn Cys Pro Ser Glu Asp Val Val
305                 310                 315                 320

Ile Thr Pro Glu Ser Phe Gly Arg Asp Ser Ser Leu Thr Cys Leu Ala
            325                 330                 335

Gly Asn Val Ser Ala Cys Asp Ala Pro Ile Leu Ser Ser Arg Ser
        340                 345                 350

Leu Asp Cys Arg Glu Ser Gly Lys Asn Gly Pro His Val Tyr Gln Asp
    355                 360                 365

Leu Leu Leu Ser Leu Gly Thr Thr Asn Ser Thr Leu Pro Pro Phe
370                 375                 380

Ser Leu Gln Ser Gly Ile Leu Thr Leu Asn Pro Val Ala Gln Gly Gln
385                 390                 395                 400

Pro Ile Leu Thr Ser Leu Gly Ser Asn Gln Glu Glu Ala Tyr Val Thr
            405                 410                 415

Met Ser Ser Phe Tyr Gln Asn Gln Ser Asp Pro Lys Pro Glu Asn Pro
        420                 425                 430

Ala Cys Pro Trp Thr Val Leu Pro Ala Gly Asp Leu Pro Thr His Asp
    435                 440                 445

Gly Tyr Leu Pro Ser Asn Ile Asp Asp Leu Pro Ser His Glu Ala Pro
450                 455                 460

Leu Ala Asp Ser Leu Glu Glu Leu Glu Pro Gln
465                 470                 475

<210> SEQ ID NO 108
<211> LENGTH: 474
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 108

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Gly Leu Ser Ala Val Leu Gly Leu Leu
        195                 200                 205

Leu Leu Arg Trp Gln Phe Pro Ala His Tyr Arg Arg Leu Arg His Ala
    210                 215                 220

Leu Trp Pro Ser Leu Pro Asp Leu His Arg Val Leu Gly Gln Tyr Leu
225                 230                 235                 240

Arg Asp Thr Ala Ala Leu Ser Pro Pro Lys Ala Thr Val Ser Asp Thr
                245                 250                 255

Cys Glu Glu Val Glu Pro Ser Leu Leu Glu Ile Leu Pro Lys Ser Ser
            260                 265                 270

Glu Arg Thr Pro Leu Pro Leu Ala Arg Asp Glu Val Glu Gly Phe Leu
        275                 280                 285

Gln Asp Thr Phe Pro Gln Gln Leu Glu Glu Ser Glu Lys Gln Arg Leu
290                 295                 300

Gly Gly Asp Val Gln Ser Pro Asn Cys Pro Ser Glu Asp Val Val Ile
305                 310                 315                 320

Thr Pro Glu Ser Phe Gly Arg Asp Ser Ser Leu Thr Cys Leu Ala Gly
                325                 330                 335

Asn Val Ser Ala Cys Asp Ala Pro Ile Leu Ser Ser Ser Arg Ser Leu
            340                 345                 350

Asp Cys Arg Glu Ser Gly Lys Asn Gly Pro His Val Tyr Gln Asp Leu
        355                 360                 365

Leu Leu Ser Leu Gly Thr Thr Asn Ser Thr Leu Pro Pro Pro Phe Ser
    370                 375                 380

Leu Gln Ser Gly Ile Leu Thr Leu Asn Pro Val Ala Gln Gly Gln Pro
385                 390                 395                 400
```

```
Ile Leu Thr Ser Leu Gly Ser Asn Gln Glu Ala Tyr Val Thr Met
                405                 410                 415

Ser Ser Phe Tyr Gln Asn Gln Ser Asp Pro Lys Pro Glu Asn Pro Ala
            420                 425                 430

Cys Pro Trp Thr Val Leu Pro Ala Gly Asp Leu Pro Thr His Asp Gly
            435                 440                 445

Tyr Leu Pro Ser Asn Ile Asp Asp Leu Pro Ser His Glu Ala Pro Leu
            450                 455                 460

Ala Asp Ser Leu Glu Glu Leu Glu Pro Gln
465                 470

<210> SEQ ID NO 109
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Leu Ser Ala Val Leu Gly Leu Leu Leu
        195                 200                 205

Leu Arg Trp Gln Phe Pro Ala His Tyr Arg Arg Leu Arg His Ala Leu
    210                 215                 220

Trp Pro Ser Leu Pro Asp Leu His Arg Val Leu Gly Gln Tyr Leu Arg
225                 230                 235                 240

Asp Thr Ala Ala Leu Ser Pro Pro Lys Ala Thr Val Ser Asp Thr Cys
                245                 250                 255

Glu Glu Val Glu Pro Ser Leu Leu Glu Ile Leu Pro Lys Ser Ser Glu
            260                 265                 270

Arg Thr Pro Leu Pro Leu Ala Arg Asp Glu Val Glu Gly Phe Leu Gln
        275                 280                 285
```

```
Asp Thr Phe Pro Gln Gln Leu Glu Glu Ser Glu Lys Gln Arg Leu Gly
    290                 295                 300

Gly Asp Val Gln Ser Pro Asn Cys Pro Ser Glu Asp Val Val Ile Thr
305                 310                 315                 320

Pro Glu Ser Phe Gly Arg Asp Ser Ser Leu Thr Cys Leu Ala Gly Asn
                325                 330                 335

Val Ser Ala Cys Asp Ala Pro Ile Leu Ser Ser Ser Arg Ser Leu Asp
            340                 345                 350

Cys Arg Glu Ser Gly Lys Asn Gly Pro His Val Tyr Gln Asp Leu Leu
        355                 360                 365

Leu Ser Leu Gly Thr Thr Asn Ser Thr Leu Pro Pro Pro Phe Ser Leu
    370                 375                 380

Gln Ser Gly Ile Leu Thr Leu Asn Pro Val Ala Gln Gly Gln Pro Ile
385                 390                 395                 400

Leu Thr Ser Leu Gly Ser Asn Gln Glu Glu Ala Tyr Val Thr Met Ser
                405                 410                 415

Ser Phe Tyr Gln Asn Gln Ser Asp Pro Lys Pro Glu Asn Pro Ala Cys
            420                 425                 430

Pro Trp Thr Val Leu Pro Ala Gly Asp Leu Pro Thr His Asp Gly Tyr
        435                 440                 445

Leu Pro Ser Asn Ile Asp Asp Leu Pro Ser His Glu Ala Pro Leu Ala
    450                 455                 460

Asp Ser Leu Glu Glu Leu Glu Pro Gln
465                 470

<210> SEQ ID NO 110
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
```

```
                165                 170                 175
Arg Gly Thr Ile Gly Ala Arg Arg Thr Gly Gln Ser Asp Pro Thr Arg
            180                 185                 190

Val Glu Thr Ala Thr Glu Thr Ser Ala Val Leu Gly Leu Leu Leu Leu
            195                 200                 205

Arg Trp Gln Phe Pro Ala His Tyr Arg Arg Leu Arg His Ala Leu Trp
            210                 215                 220

Pro Ser Leu Pro Asp Leu His Arg Val Leu Gly Gln Tyr Leu Arg Asp
225                 230                 235                 240

Thr Ala Ala Leu Ser Pro Pro Lys Ala Thr Val Ser Asp Thr Cys Glu
            245                 250                 255

Glu Val Glu Pro Ser Leu Leu Glu Ile Leu Pro Lys Ser Ser Glu Arg
            260                 265                 270

Thr Pro Leu Pro Leu Ala Arg Asp Glu Val Gly Phe Leu Gln Asp
            275                 280                 285

Thr Phe Pro Gln Gln Leu Glu Glu Ser Glu Lys Gln Arg Leu Gly Gly
            290                 295                 300

Asp Val Gln Ser Pro Asn Cys Pro Ser Glu Asp Val Val Ile Thr Pro
305                 310                 315                 320

Glu Ser Phe Gly Arg Asp Ser Ser Leu Thr Cys Leu Ala Gly Asn Val
            325                 330                 335

Ser Ala Cys Asp Ala Pro Ile Leu Ser Ser Ser Arg Ser Leu Asp Cys
            340                 345                 350

Arg Glu Ser Gly Lys Asn Gly Pro His Val Tyr Gln Asp Leu Leu Leu
            355                 360                 365

Ser Leu Gly Thr Thr Asn Ser Thr Leu Pro Pro Pro Phe Ser Leu Gln
            370                 375                 380

Ser Gly Ile Leu Thr Leu Asn Pro Val Ala Gln Gly Gln Pro Ile Leu
385                 390                 395                 400

Thr Ser Leu Gly Ser Asn Gln Glu Glu Ala Tyr Val Thr Met Ser Ser
            405                 410                 415

Phe Tyr Gln Asn Gln Ser Asp Pro Lys Pro Glu Asn Pro Ala Cys Pro
            420                 425                 430

Trp Thr Val Leu Pro Ala Gly Asp Leu Pro Thr His Asp Gly Tyr Leu
            435                 440                 445

Pro Ser Asn Ile Asp Asp Leu Pro Ser His Glu Ala Pro Leu Ala Asp
            450                 455                 460

Ser Leu Glu Glu Leu Glu Pro Gln
465                 470

<210> SEQ ID NO 111
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
            35                  40                  45
```

```
Arg Glu Ser Pro Ser Gly Gln Thr Asp Thr Leu Ala Ala Phe Pro Glu
     50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
                180                 185                 190

Val Glu Thr Ala Thr Glu Thr Ala Val Leu Gly Leu Leu Leu Leu Arg
            195                 200                 205

Trp Gln Phe Pro Ala His Tyr Arg Arg Leu Arg His Ala Leu Trp Pro
            210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
                260                 265                 270

Pro Leu Pro Leu Ala Arg Asp Glu Val Glu Gly Phe Leu Gln Asp Thr
            275                 280                 285

Phe Pro Gln Gln Leu Glu Glu Ser Glu Lys Gln Arg Leu Gly Gly Asp
            290                 295                 300

Val Gln Ser Pro Asn Cys Pro Ser Glu Asp Val Val Ile Thr Pro Glu
305                 310                 315                 320

Ser Phe Gly Arg Asp Ser Ser Leu Thr Cys Leu Ala Gly Asn Val Ser
                325                 330                 335

Ala Cys Asp Ala Pro Ile Leu Ser Ser Ser Arg Ser Leu Asp Cys Arg
            340                 345                 350

Glu Ser Gly Lys Asn Gly Pro His Val Tyr Gln Asp Leu Leu Leu Ser
            355                 360                 365

Leu Gly Thr Thr Asn Ser Thr Leu Pro Pro Pro Phe Ser Leu Gln Ser
            370                 375                 380

Gly Ile Leu Thr Leu Asn Pro Val Ala Gln Gly Gln Pro Ile Leu Thr
385                 390                 395                 400

Ser Leu Gly Ser Asn Gln Glu Glu Ala Tyr Val Thr Met Ser Ser Phe
                405                 410                 415

Tyr Gln Asn Gln Ser Asp Pro Lys Pro Glu Asn Pro Ala Cys Pro Trp
            420                 425                 430

Thr Val Leu Pro Ala Gly Asp Leu Pro Thr His Asp Gly Tyr Leu Pro
            435                 440                 445

Ser Asn Ile Asp Asp Leu Pro Ser His Glu Ala Pro Leu Ala Asp Ser
450                 455                 460

Leu Glu Glu Leu Glu Pro Gln
```

465         470

<210> SEQ ID NO 112
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Val Leu Gly Leu Leu Leu Leu Arg Trp
        195                 200                 205

Gln Phe Pro Ala His Tyr Arg Arg Leu Arg His Ala Leu Trp Pro Ser
    210                 215                 220

Leu Pro Asp Leu His Arg Val Leu Gly Gln Tyr Leu Arg Asp Thr Ala
225                 230                 235                 240

Ala Leu Ser Pro Pro Lys Ala Thr Val Ser Asp Thr Cys Glu Glu Val
                245                 250                 255

Glu Pro Ser Leu Leu Glu Ile Leu Pro Lys Ser Ser Glu Arg Thr Pro
            260                 265                 270

Leu Pro Leu Ala Arg Asp Glu Val Glu Gly Phe Leu Gln Asp Thr Phe
        275                 280                 285

Pro Gln Gln Leu Glu Glu Ser Glu Lys Gln Arg Leu Gly Gly Asp Val
    290                 295                 300

Gln Ser Pro Asn Cys Pro Ser Glu Asp Val Val Ile Thr Pro Glu Ser
305                 310                 315                 320

Phe Gly Arg Asp Ser Ser Leu Thr Cys Leu Ala Gly Asn Val Ser Ala
                325                 330                 335

Cys Asp Ala Pro Ile Leu Ser Ser Arg Ser Leu Asp Cys Arg Glu
            340                 345                 350

```
Ser Gly Lys Asn Gly Pro His Val Tyr Gln Asp Leu Leu Leu Ser Leu
        355                 360                 365

Gly Thr Thr Asn Ser Thr Leu Pro Pro Pro Phe Ser Leu Gln Ser Gly
    370                 375                 380

Ile Leu Thr Leu Asn Pro Val Ala Gln Gly Gln Pro Ile Leu Thr Ser
385                 390                 395                 400

Leu Gly Ser Asn Gln Glu Ala Tyr Val Thr Met Ser Ser Phe Tyr
            405                 410                 415

Gln Asn Gln Ser Asp Pro Lys Pro Glu Asn Pro Ala Cys Pro Trp Thr
                420                 425                 430

Val Leu Pro Ala Gly Asp Leu Pro Thr His Asp Gly Tyr Leu Pro Ser
            435                 440                 445

Asn Ile Asp Asp Leu Pro Ser His Glu Ala Pro Leu Ala Asp Ser Leu
    450                 455                 460

Glu Glu Leu Glu Pro Gln
465                 470

<210> SEQ ID NO 113
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Leu Gly Leu Leu Leu Arg Trp Gln
        195                 200                 205

Phe Pro Ala His Tyr Arg Arg Leu Arg His Ala Leu Trp Pro Ser Leu
    210                 215                 220

Pro Asp Leu His Arg Val Leu Gly Gln Tyr Leu Arg Asp Thr Ala Ala
225                 230                 235                 240
```

```
Leu Ser Pro Pro Lys Ala Thr Val Ser Asp Thr Cys Glu Glu Val Glu
                245                 250                 255

Pro Ser Leu Leu Glu Ile Leu Pro Lys Ser Ser Glu Arg Thr Pro Leu
            260                 265                 270

Pro Leu Ala Arg Asp Glu Val Glu Gly Phe Leu Gln Asp Thr Phe Pro
            275                 280                 285

Gln Gln Leu Glu Glu Ser Glu Lys Gln Arg Leu Gly Gly Asp Val Gln
        290                 295                 300

Ser Pro Asn Cys Pro Ser Glu Asp Val Val Ile Thr Pro Glu Ser Phe
305                 310                 315                 320

Gly Arg Asp Ser Ser Leu Thr Cys Leu Ala Gly Asn Val Ser Ala Cys
                325                 330                 335

Asp Ala Pro Ile Leu Ser Ser Ser Arg Ser Leu Asp Cys Arg Glu Ser
                340                 345                 350

Gly Lys Asn Gly Pro His Val Tyr Gln Asp Leu Leu Leu Ser Leu Gly
            355                 360                 365

Thr Thr Asn Ser Thr Leu Pro Pro Pro Phe Ser Leu Gln Ser Gly Ile
    370                 375                 380

Leu Thr Leu Asn Pro Val Ala Gln Gly Gln Pro Ile Leu Thr Ser Leu
385                 390                 395                 400

Gly Ser Asn Gln Glu Glu Ala Tyr Val Thr Met Ser Ser Phe Tyr Gln
                405                 410                 415

Asn Gln Ser Asp Pro Lys Pro Glu Asn Pro Ala Cys Pro Trp Thr Val
                420                 425                 430

Leu Pro Ala Gly Asp Leu Pro Thr His Asp Gly Tyr Leu Pro Ser Asn
            435                 440                 445

Ile Asp Asp Leu Pro Ser His Glu Ala Pro Leu Ala Asp Ser Leu Glu
450                 455                 460

Glu Leu Glu Pro Gln
465

<210> SEQ ID NO 114
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
```

```
            115                 120                 125
Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Leu Ile Ser Leu Val Thr Ala
        195                 200                 205

Leu His Leu Val Leu Gly Leu Ser Ala Val Leu Gly Leu Leu Leu Leu
    210                 215                 220

Arg Trp Gln Phe Pro Ala His Tyr Arg Arg Leu Arg His Ala Leu Trp
225                 230                 235                 240

Pro Ser Leu Pro Asp Leu His Arg Val Leu Gly Gln Tyr Leu Arg Asp
                245                 250                 255

Thr Ala Leu Ser Pro Pro Lys Ala Thr Val Ser Asp Thr Cys Glu
            260                 265                 270

Glu Val Glu Pro Ser Leu Leu Glu Ile Leu Pro Lys Ser Ser Glu Arg
        275                 280                 285

Thr Pro Leu Pro Leu Ala Arg Asp Glu Val Glu Gly Phe Leu Gln Asp
    290                 295                 300

Thr Phe Pro Gln Gln Leu Glu Glu Ser Glu Lys Gln Arg Leu Gly Gly
305                 310                 315                 320

Asp Val Gln Ser Pro Asn Cys Pro Ser Glu Asp Val Val Ile Thr Pro
                325                 330                 335

Glu Ser Phe Gly Arg Asp Ser Ser Leu Thr Cys Leu Ala Gly Asn Val
            340                 345                 350

Ser Ala Cys Asp Ala Pro Ile Leu Ser Ser Ser Arg Ser Leu Asp Cys
        355                 360                 365

Arg Glu Ser Gly Lys Asn Gly Pro His Val Tyr Gln Asp Leu Leu Leu
    370                 375                 380

Ser Leu Gly Thr Thr Asn Ser Thr Leu Pro Pro Pro Phe Ser Leu Gln
385                 390                 395                 400

Ser Gly Ile Leu Thr Leu Asn Pro Val Ala Gln Gly Gln Pro Ile Leu
                405                 410                 415

Thr Ser Leu Gly Ser Asn Gln Glu Glu Ala Tyr Val Thr Met Ser Ser
            420                 425                 430

Phe Tyr Gln Asn Gln Ser Asp Pro Lys Pro Glu Asn Pro Ala Cys Pro
        435                 440                 445

Trp Thr Val Leu Pro Ala Gly Asp Leu Pro Thr His Asp Gly Tyr Leu
    450                 455                 460

Pro Ser Asn Ile Asp Asp Leu Pro Ser His Glu Ala Pro Leu Ala Asp
465                 470                 475                 480

Ser Leu Glu Glu Leu Glu Pro Gln
                485

<210> SEQ ID NO 115
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 115

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Val Leu Ile Ser Leu Val Thr
        195                 200                 205

Ala Leu His Leu Val Leu Gly Leu Ser Ala Val Leu Gly Leu Leu Leu
    210                 215                 220

Leu Arg Trp Gln Phe Pro Ala His Tyr Arg Arg Leu Arg His Ala Leu
225                 230                 235                 240

Trp Pro Ser Leu Pro Asp Leu His Arg Val Leu Gly Gln Tyr Leu Arg
                245                 250                 255

Asp Thr Ala Ala Leu Ser Pro Pro Lys Ala Thr Val Ser Asp Thr Cys
            260                 265                 270

Glu Glu Val Glu Pro Ser Leu Leu Glu Ile Leu Pro Lys Ser Ser Glu
        275                 280                 285

Arg Thr Pro Leu Pro Leu Ala Arg Asp Glu Val Glu Gly Phe Leu Gln
    290                 295                 300

Asp Thr Phe Pro Gln Gln Leu Glu Glu Ser Glu Lys Gln Arg Leu Gly
305                 310                 315                 320

Gly Asp Val Gln Ser Pro Asn Cys Pro Ser Glu Asp Val Val Ile Thr
                325                 330                 335

Pro Glu Ser Phe Gly Arg Asp Ser Ser Leu Thr Cys Leu Ala Gly Asn
            340                 345                 350

Val Ser Ala Cys Asp Ala Pro Ile Leu Ser Ser Ser Arg Ser Leu Asp
        355                 360                 365

Cys Arg Glu Ser Gly Lys Asn Gly Pro His Val Tyr Gln Asp Leu Leu
    370                 375                 380

Leu Ser Leu Gly Thr Thr Asn Ser Thr Leu Pro Pro Pro Phe Ser Leu
385                 390                 395                 400

Gln Ser Gly Ile Leu Thr Leu Asn Pro Val Ala Gln Gly Gln Pro Ile
```

```
                    405                 410                 415
Leu Thr Ser Leu Gly Ser Asn Gln Glu Glu Ala Tyr Val Thr Met Ser
            420                 425                 430

Ser Phe Tyr Gln Asn Gln Ser Asp Pro Lys Pro Glu Asn Pro Ala Cys
        435                 440                 445

Pro Trp Thr Val Leu Pro Ala Gly Asp Leu Pro Thr His Asp Gly Tyr
450                 455                 460

Leu Pro Ser Asn Ile Asp Asp Leu Pro Ser His Glu Ala Pro Leu Ala
465                 470                 475                 480

Asp Ser Leu Glu Glu Leu Glu Pro Gln
                485

<210> SEQ ID NO 116
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Leu Val Leu Ile Ser Leu Val
        195                 200                 205

Thr Ala Leu His Leu Val Leu Gly Leu Ser Ala Val Leu Gly Leu Leu
    210                 215                 220

Leu Leu Arg Trp Gln Phe Pro Ala His Tyr Arg Arg Leu Arg His Ala
225                 230                 235                 240

Leu Trp Pro Ser Leu Pro Asp Leu His Arg Val Leu Gly Gln Tyr Leu
                245                 250                 255

Arg Asp Thr Ala Ala Leu Ser Pro Pro Lys Ala Thr Val Ser Asp Thr
            260                 265                 270
```

```
Cys Glu Glu Val Glu Pro Ser Leu Glu Ile Leu Pro Lys Ser Ser
            275                 280                 285

Glu Arg Thr Pro Leu Pro Leu Ala Arg Asp Glu Val Glu Gly Phe Leu
290                 295                 300

Gln Asp Thr Phe Pro Gln Gln Leu Glu Glu Ser Glu Lys Gln Arg Leu
305                 310                 315                 320

Gly Gly Asp Val Gln Ser Pro Asn Cys Pro Ser Glu Asp Val Val Ile
                325                 330                 335

Thr Pro Glu Ser Phe Gly Arg Asp Ser Ser Leu Thr Cys Leu Ala Gly
            340                 345                 350

Asn Val Ser Ala Cys Asp Ala Pro Ile Leu Ser Ser Ser Arg Ser Leu
            355                 360                 365

Asp Cys Arg Glu Ser Gly Lys Asn Gly Pro His Val Tyr Gln Asp Leu
        370                 375                 380

Leu Leu Ser Leu Gly Thr Thr Asn Ser Thr Leu Pro Pro Pro Phe Ser
385                 390                 395                 400

Leu Gln Ser Gly Ile Leu Thr Leu Asn Pro Val Ala Gln Gly Gln Pro
                405                 410                 415

Ile Leu Thr Ser Leu Gly Ser Asn Gln Glu Glu Ala Tyr Val Thr Met
            420                 425                 430

Ser Ser Phe Tyr Gln Asn Gln Ser Asp Pro Lys Pro Glu Asn Pro Ala
        435                 440                 445

Cys Pro Trp Thr Val Leu Pro Ala Gly Asp Leu Pro Thr His Asp Gly
    450                 455                 460

Tyr Leu Pro Ser Asn Ile Asp Asp Leu Pro Ser His Glu Ala Pro Leu
465                 470                 475                 480

Ala Asp Ser Leu Glu Glu Leu Glu Pro Gln
                485                 490

<210> SEQ ID NO 117
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140
```

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Ile Leu Val Leu Ile Ser Leu
        195                 200                 205

Val Thr Ala Leu His Leu Val Leu Gly Leu Ser Ala Val Leu Gly Leu
    210                 215                 220

Leu Leu Leu Arg Trp Gln Phe Pro Ala His Tyr Arg Arg Leu Arg His
225                 230                 235                 240

Ala Leu Trp Pro Ser Leu Pro Asp Leu His Arg Val Leu Gly Gln Tyr
                245                 250                 255

Leu Arg Asp Thr Ala Ala Leu Ser Pro Pro Lys Ala Thr Val Ser Asp
            260                 265                 270

Thr Cys Glu Glu Val Glu Pro Ser Leu Leu Glu Ile Leu Pro Lys Ser
        275                 280                 285

Ser Glu Arg Thr Pro Leu Pro Leu Ala Arg Asp Glu Val Glu Gly Phe
    290                 295                 300

Leu Gln Asp Thr Phe Pro Gln Gln Leu Glu Glu Ser Glu Lys Gln Arg
305                 310                 315                 320

Leu Gly Gly Asp Val Gln Ser Pro Asn Cys Pro Ser Glu Asp Val Val
                325                 330                 335

Ile Thr Pro Glu Ser Phe Gly Arg Asp Ser Ser Leu Thr Cys Leu Ala
            340                 345                 350

Gly Asn Val Ser Ala Cys Asp Ala Pro Ile Leu Ser Ser Ser Arg Ser
        355                 360                 365

Leu Asp Cys Arg Glu Ser Gly Lys Asn Gly Pro His Val Tyr Gln Asp
    370                 375                 380

Leu Leu Leu Ser Leu Gly Thr Thr Asn Ser Thr Leu Pro Pro Pro Phe
385                 390                 395                 400

Ser Leu Gln Ser Gly Ile Leu Thr Leu Asn Pro Val Ala Gln Gly Gln
                405                 410                 415

Pro Ile Leu Thr Ser Leu Gly Ser Asn Gln Glu Glu Ala Tyr Val Thr
            420                 425                 430

Met Ser Ser Phe Tyr Gln Asn Gln Ser Asp Pro Lys Pro Glu Asn Pro
        435                 440                 445

Ala Cys Pro Trp Thr Val Leu Pro Ala Gly Asp Leu Pro Thr His Asp
    450                 455                 460

Gly Tyr Leu Pro Ser Asn Ile Asp Asp Leu Pro Ser His Glu Ala Pro
465                 470                 475                 480

Leu Ala Asp Ser Leu Glu Glu Leu Glu Pro Gln
                485                 490

<210> SEQ ID NO 118
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Pro Gly Trp Phe Leu Asp Ser Pro Asp Arg Pro Trp Asn Pro Pro Thr

```
              1               5                  10                 15
            Phe Ser Pro Ala Leu Leu Val Val Thr Glu Gly Asp Asn Ala Thr Phe
                             20                 25                 30
            Thr Cys Ser Phe Ser Asn Thr Ser Glu Ser Phe His Val Ile Trp His
                             35                 40                 45
            Arg Glu Ser Pro Ser Gly Gln Thr Asp Thr Leu Ala Ala Phe Pro Glu
                             50                 55                 60
            Asp Arg Ser Gln Pro Gly Gln Asp Cys Arg Phe Arg Val Thr Gln Leu
             65                 70                 75                 80
            Pro Asn Gly Arg Asp Phe His Met Ser Val Val Arg Ala Arg Arg Asn
                                 85                 90                 95
            Asp Ser Gly Thr Tyr Val Cys Gly Val Ile Ser Leu Ala Pro Lys Ile
                                100                105                110
            Gln Ile Lys Glu Ser Leu Arg Ala Glu Leu Arg Val Thr Glu Arg Arg
                            115                120                125
            Ala Glu Val Pro Thr Ala His Pro Ser Pro Ser Pro Arg Pro Ala Gly
                            130                135                140
            Gln Phe Gln Thr Leu Val Val Gly Val Val Gly Gly Leu Leu Gly Ser
            145                150                155                160
            Leu Val Leu Leu Val Trp Val Leu Ala Val Ile Cys Ser Arg Ala Ala
                            165                170                175
            Arg Gly Thr Ile Gly Ala Arg Arg Thr Gly Gln Ser Asp Pro Thr Arg
                            180                185                190
            Val Glu Thr Ala Thr Glu Thr Ala Trp Leu Ile Leu Val Leu Ile Ser
                            195                200                205
            Leu Val Thr Ala Leu His Leu Val Leu Gly Leu Ser Ala Val Leu Gly
                            210                215                220
            Leu Leu Leu Leu Arg Trp Gln Phe Pro Ala His Tyr Arg Arg Leu Arg
            225                230                235                240
            His Ala Leu Trp Pro Ser Leu Pro Asp Leu His Arg Val Leu Gly Gln
                            245                250                255
            Tyr Leu Arg Asp Thr Ala Ala Leu Ser Pro Pro Lys Ala Thr Val Ser
                            260                265                270
            Asp Thr Cys Glu Glu Val Glu Pro Ser Leu Leu Glu Ile Leu Pro Lys
                            275                280                285
            Ser Ser Glu Arg Thr Pro Leu Pro Leu Ala Arg Asp Glu Val Glu Gly
                            290                295                300
            Phe Leu Gln Asp Thr Phe Pro Gln Gln Leu Glu Glu Ser Glu Lys Gln
            305                310                315                320
            Arg Leu Gly Gly Asp Val Gln Ser Pro Asn Cys Pro Ser Glu Asp Val
                            325                330                335
            Val Ile Thr Pro Glu Ser Phe Gly Arg Asp Ser Ser Leu Thr Cys Leu
                            340                345                350
            Ala Gly Asn Val Ser Ala Cys Asp Ala Pro Ile Leu Ser Ser Ser Arg
                            355                360                365
            Ser Leu Asp Cys Arg Glu Ser Gly Lys Asn Gly Pro His Val Tyr Gln
                            370                375                380
            Asp Leu Leu Leu Ser Leu Gly Thr Thr Asn Ser Thr Leu Pro Pro Pro
            385                390                395                400
            Phe Ser Leu Gln Ser Gly Ile Leu Thr Leu Asn Pro Val Ala Gln Gly
                            405                410                415
            Gln Pro Ile Leu Thr Ser Leu Gly Ser Asn Gln Glu Glu Ala Tyr Val
                            420                425                430
```

```
Thr Met Ser Ser Phe Tyr Gln Asn Gln Ser Asp Pro Lys Pro Glu Asn
        435                 440                 445

Pro Ala Cys Pro Trp Thr Val Leu Pro Ala Gly Asp Leu Pro Thr His
    450                 455                 460

Asp Gly Tyr Leu Pro Ser Asn Ile Asp Asp Leu Pro Ser His Glu Ala
465                 470                 475                 480

Pro Leu Ala Asp Ser Leu Glu Glu Leu Glu Pro Gln
            485                 490

<210> SEQ ID NO 119
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Gly Gly Leu Leu Gly Ser
145                 150                 155             160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Leu Leu Ile Leu Val Leu Ile
        195                 200                 205

Ser Leu Val Thr Ala Leu His Leu Val Leu Gly Leu Ser Ala Val Leu
    210                 215                 220

Gly Leu Leu Leu Leu Arg Trp Gln Phe Pro Ala His Tyr Arg Arg Leu
225                 230                 235                 240

Arg His Ala Leu Trp Pro Ser Leu Pro Asp Leu His Arg Val Leu Gly
                245                 250                 255

Gln Tyr Leu Arg Asp Thr Ala Ala Leu Ser Pro Pro Lys Ala Thr Val
            260                 265                 270

Ser Asp Thr Cys Glu Glu Val Glu Pro Ser Leu Leu Glu Ile Leu Pro
        275                 280                 285

Lys Ser Ser Glu Arg Thr Pro Leu Pro Leu Ala Arg Asp Glu Val Glu
```

```
                290                 295                 300
Gly Phe Leu Gln Asp Thr Phe Pro Gln Gln Leu Glu Glu Ser Glu Lys
305                 310                 315                 320

Gln Arg Leu Gly Gly Asp Val Gln Ser Pro Asn Cys Pro Ser Glu Asp
                325                 330                 335

Val Val Ile Thr Pro Glu Ser Phe Gly Arg Asp Ser Ser Leu Thr Cys
                340                 345                 350

Leu Ala Gly Asn Val Ser Ala Cys Asp Ala Pro Ile Leu Ser Ser Ser
            355                 360                 365

Arg Ser Leu Asp Cys Arg Glu Ser Gly Lys Asn Gly Pro His Val Tyr
        370                 375                 380

Gln Asp Leu Leu Leu Ser Leu Gly Thr Thr Asn Ser Thr Leu Pro Pro
385                 390                 395                 400

Pro Phe Ser Leu Gln Ser Gly Ile Leu Thr Leu Asn Pro Val Ala Gln
                405                 410                 415

Gly Gln Pro Ile Leu Thr Ser Leu Gly Ser Asn Gln Glu Glu Ala Tyr
            420                 425                 430

Val Thr Met Ser Ser Phe Tyr Gln Asn Gln Ser Asp Pro Lys Pro Glu
        435                 440                 445

Asn Pro Ala Cys Pro Trp Thr Val Leu Pro Ala Gly Asp Leu Pro Thr
    450                 455                 460

His Asp Gly Tyr Leu Pro Ser Asn Ile Asp Asp Leu Pro Ser His Glu
465                 470                 475                 480

Ala Pro Leu Ala Asp Ser Leu Glu Glu Leu Glu Pro Gln
                485                 490

<210> SEQ ID NO 120
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160
```

```
Leu Val Leu Leu Val Trp Val Leu Ala Val Ile Cys Ser Arg Ala Ala
                165                 170                 175

Arg Gly Thr Ile Gly Ala Arg Thr Gly Gln Ser Asp Pro Thr Arg
            180                 185                 190

Val Glu Thr Ala Thr Glu Thr Ala Trp Val Leu Ile Leu Val Leu
            195                 200                 205

Ile Ser Leu Val Thr Ala Leu His Leu Val Leu Gly Leu Ser Ala Val
210                 215                 220

Leu Gly Leu Leu Leu Arg Trp Gln Phe Pro Ala His Tyr Arg Arg
225                 230                 235                 240

Leu Arg His Ala Leu Trp Pro Ser Leu Pro Asp Leu His Arg Val Leu
                245                 250                 255

Gly Gln Tyr Leu Arg Asp Thr Ala Ala Leu Ser Pro Pro Lys Ala Thr
            260                 265                 270

Val Ser Asp Thr Cys Glu Glu Val Glu Pro Ser Leu Leu Glu Ile Leu
            275                 280                 285

Pro Lys Ser Ser Glu Arg Thr Pro Leu Pro Leu Ala Arg Asp Glu Val
            290                 295                 300

Glu Gly Phe Leu Gln Asp Thr Phe Pro Gln Gln Leu Glu Glu Ser Glu
305                 310                 315                 320

Lys Gln Arg Leu Gly Gly Asp Val Gln Ser Pro Asn Cys Pro Ser Glu
                325                 330                 335

Asp Val Val Ile Thr Pro Glu Ser Phe Gly Arg Asp Ser Ser Leu Thr
            340                 345                 350

Cys Leu Ala Gly Asn Val Ser Ala Cys Asp Ala Pro Ile Leu Ser Ser
            355                 360                 365

Ser Arg Ser Leu Asp Cys Arg Glu Ser Gly Lys Asn Gly Pro His Val
            370                 375                 380

Tyr Gln Asp Leu Leu Leu Ser Leu Gly Thr Thr Asn Ser Thr Leu Pro
385                 390                 395                 400

Pro Pro Phe Ser Leu Gln Ser Gly Ile Leu Thr Leu Asn Pro Val Ala
                405                 410                 415

Gln Gly Gln Pro Ile Leu Thr Ser Leu Gly Ser Asn Gln Glu Glu Ala
            420                 425                 430

Tyr Val Thr Met Ser Ser Phe Tyr Gln Asn Gln Ser Asp Pro Lys Pro
            435                 440                 445

Glu Asn Pro Ala Cys Pro Trp Thr Val Leu Pro Ala Gly Asp Leu Pro
            450                 455                 460

Thr His Asp Gly Tyr Leu Pro Ser Asn Ile Asp Asp Leu Pro Ser His
465                 470                 475                 480

Glu Ala Pro Leu Ala Asp Ser Leu Glu Glu Leu Glu Pro Gln
                485                 490

<210> SEQ ID NO 121
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30
```

```
Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Ser Asp Pro Thr Arg
            180                 185                 190

Val Glu Thr Ala Thr Glu Thr Ala Trp Leu Val Leu Leu Ile Leu Val
        195                 200                 205

Leu Ile Ser Leu Val Thr Ala Leu His Leu Val Leu Gly Leu Ser Ala
        210                 215                 220

Val Leu Gly Leu Leu Leu Arg Trp Gln Phe Pro Ala His Tyr Arg
225                 230                 235                 240

Arg Leu Arg His Ala Leu Trp Pro Ser Leu Pro Asp Leu His Arg Val
                245                 250                 255

Leu Gly Gln Tyr Leu Arg Asp Thr Ala Ala Leu Ser Pro Pro Lys Ala
            260                 265                 270

Thr Val Ser Asp Thr Cys Glu Glu Val Glu Pro Ser Leu Leu Glu Ile
        275                 280                 285

Leu Pro Lys Ser Ser Glu Arg Thr Pro Leu Pro Leu Ala Arg Asp Glu
        290                 295                 300

Val Glu Gly Phe Leu Gln Asp Thr Phe Pro Gln Gln Leu Glu Glu Ser
305                 310                 315                 320

Glu Lys Gln Arg Leu Gly Gly Asp Val Gln Ser Pro Asn Cys Pro Ser
                325                 330                 335

Glu Asp Val Val Ile Thr Pro Glu Ser Phe Gly Arg Asp Ser Ser Leu
                340                 345                 350

Thr Cys Leu Ala Gly Asn Val Ser Ala Cys Asp Ala Pro Ile Leu Ser
        355                 360                 365

Ser Ser Arg Ser Leu Asp Cys Arg Glu Ser Gly Lys Asn Gly Pro His
        370                 375                 380

Val Tyr Gln Asp Leu Leu Leu Ser Leu Gly Thr Thr Asn Ser Thr Leu
385                 390                 395                 400

Pro Pro Pro Phe Ser Leu Gln Ser Gly Ile Leu Thr Leu Asn Pro Val
                405                 410                 415

Ala Gln Gly Gln Pro Ile Leu Thr Ser Leu Gly Ser Asn Gln Glu Glu
            420                 425                 430

Ala Tyr Val Thr Met Ser Ser Phe Tyr Gln Asn Gln Ser Asp Pro Lys
            435                 440                 445
```

Pro Glu Asn Pro Ala Cys Pro Trp Thr Val Leu Pro Ala Gly Asp Leu
            450                 455                 460

Pro Thr His Asp Gly Tyr Leu Pro Ser Asn Ile Asp Asp Leu Pro Ser
465                 470                 475                 480

His Glu Ala Pro Leu Ala Asp Ser Leu Glu Glu Leu Glu Pro Gln
                485                 490                 495

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Pro Asn Pro Leu Leu Gly Leu Asp Ser Thr
1               5                   10

<210> SEQ ID NO 123
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Ser Gly Gly Gly Gly
        115                 120                 125

Ser Gly Gly Gly Gly Ser Asp Val Val Met Thr Gln Ser Pro Asp Ser
130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

```
Thr Lys Val Glu Ile Lys
            245
```

<210> SEQ ID NO 124
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 125
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 126
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
```

<210> SEQ ID NO 127
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230

<210> SEQ ID NO 128
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 129
<211> LENGTH: 208
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 129

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Val Gly Val Val Gly
                165                 170                 175

Gly Leu Leu Gly Ser Leu Val Leu Leu Val Trp Val Leu Ala Val Ile
            180                 185                 190

Cys Ser Arg Ala Ala Arg Gly Thr Ile Gly Ala Arg Arg Thr Gly Gln
        195                 200                 205
```

<210> SEQ ID NO 130
<211> LENGTH: 208
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
```

```
            115                 120                 125
Leu Ala Pro Lys Ile Gln Ile Lys Glu Ser Leu Arg Ala Glu Leu Arg
        130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Val Gly Val Val Gly
                165                 170                 175

Gly Leu Leu Gly Ser Leu Val Leu Leu Val Trp Val Leu Ala Val Ile
            180                 185                 190

Cys Ser Arg Ala Ala Arg Gly Thr Ile Gly Ala Arg Arg Thr Gly Gln
        195                 200                 205

<210> SEQ ID NO 131
<211> LENGTH: 635
<212> TYPE: PRT
<213> ORGANISM: Homo sapiens

<400> SEQUENCE: 131

Met Pro Ser Trp Ala Leu Phe Met Val Thr Ser Cys Leu Leu Leu Ala
1                5                  10                  15

Pro Gln Asn Leu Ala Gln Val Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285
```

Leu Gln Cys Phe Thr Leu Asp Leu Lys Asn Val Thr Cys Gln Trp Gln
290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
                340                 345                 350

His Phe Lys Ser Arg Asn Asp Ser Ile Ile His Ile Leu Val Glu Val
                355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
                435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
                500                 505                 510

Leu Arg Trp Gln Phe Pro Ala His Tyr Arg Arg Leu Arg His Ala Leu
                515                 520                 525

Trp Pro Ser Leu Pro Asp Leu His Arg Val Leu Gly Gln Tyr Leu Arg
530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
                580                 585                 590

Arg Leu Gln Pro Ser Cys Leu Gly Thr Met Pro Leu Ser Val Cys Pro
                595                 600                 605

Pro Met Ala Glu Ser Gly Ser Cys Cys Thr Thr His Ile Ala Asn His
610                 615                 620

Ser Tyr Leu Pro Leu Ser Tyr Trp Gln Gln Pro
625                 630                 635

<210> SEQ ID NO 132
<211> LENGTH: 150
<212> TYPE: PRT
<213> ORGANISM: Unknown
<220> FEATURE:
<223> OTHER INFORMATION: Description of Unknown:
    PD1 ectodomain sequence

<400> SEQUENCE: 132

Pro Gly Trp Phe Leu Asp Ser Pro Asp Arg Pro Trp Asn Pro Pro Thr
1               5                   10                  15

```
Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 133
<211> LENGTH: 150
<212> TYPE: PRT
<213> ORGANISM: Unknown
<220> FEATURE:
<223> OTHER INFORMATION: Description of Unknown:
      High-affinity (HA) PD1 ectodomain sequence

<400> SEQUENCE: 133

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105
```

<210> SEQ ID NO 135
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105
```

<210> SEQ ID NO 136
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80
```

```
Pro Asn Gly Arg Asp Phe His Met Ser Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu Leu Val Leu Gly
                165                 170                 175

Leu Asn Ala Val Leu Gly Leu Leu Leu Arg Lys Gln Phe Pro Ala
                180                 185                 190

His Tyr Arg Arg Leu Arg His Ala Leu Trp Pro Ser Leu Pro Asp Leu
                195                 200                 205

His Arg Val Leu Gly Gln Tyr Leu Arg Asp Thr Ala Ala Leu Ser Pro
                210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Ala
                245                 250                 255

Arg Asp Glu Val Glu Gly Phe Leu Gln Asp Thr Phe Pro Gln Gln Leu
                260                 265                 270

Glu Glu Ser Glu Lys Gln Arg Leu Gly Gly Asp Val Gln Ser Pro Asn
                275                 280                 285

Cys Pro Ser Glu Asp Val Val Ile Thr Pro Glu Ser Phe Gly Arg Asp
                290                 295                 300

Ser Ser Leu Thr Cys Leu Ala Gly Asn Val Ser Ala Cys Asp Ala Pro
305                 310                 315                 320

Ile Leu Ser Ser Ser Arg Ser Leu Asp Cys Arg Glu Ser Gly Lys Asn
                325                 330                 335

Gly Pro His Val Tyr Gln Asp Leu Leu Leu Ser Leu Gly Thr Thr Asn
                340                 345                 350

Ser Thr Leu Pro Pro Pro Phe Ser Leu Gln Ser Gly Ile Leu Thr Leu
                355                 360                 365

Asn Pro Val Ala Gln Gly Gln Pro Ile Leu Thr Ser Leu Gly Ser Asn
                370                 375                 380

Gln Glu Glu Ala Tyr Val Thr Met Ser Ser Phe Tyr Gln Asn Gln
385                 390                 395

<210> SEQ ID NO 137
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
```

```
                35                  40                  45
Arg Glu Ser Pro Ser Gly Gln Thr Asp Thr Leu Ala Ala Phe Pro Glu
 50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Arg Ala Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Asn Ala Val Leu Gly Leu Leu Leu Leu Arg Lys Gln Phe Pro Ala
                180                 185                 190

His Tyr Arg Arg Leu Arg His Ala Leu Trp Pro Ser Leu Pro Asp Leu
            195                 200                 205

His Arg Val Leu Gly Gln Tyr Leu Arg Asp Thr Ala Ala Leu Ser Pro
            210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Asp
                245                 250                 255

Glu Gly Val Ala Gly Ala Pro Thr Gly Ser Ser Pro Gln Pro Leu Gln
                260                 265                 270

Pro Leu Ser Gly Glu Asp Asp Ala Tyr Cys Thr Phe Pro Ser Arg Asp
            275                 280                 285

Asp Leu Leu Leu Phe Ser Pro Ser Gly Gln Gly Glu Phe Arg Ala Leu
            290                 295                 300

Asn Ala Arg Leu Pro Leu Asn Thr Asp Ala Tyr Leu Ser Leu Gln Glu
305                 310                 315                 320

Leu Gln Gly Gln Asp Pro Thr His Leu Val
                325                 330

<210> SEQ ID NO 138
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
 50                  55                  60
```

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln
            180                 185

<210> SEQ ID NO 139
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Ser Ala Val Leu Gly Leu Leu Leu Arg Trp Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

```
Leu Glu Ile Leu Pro Lys Ser Ser Glu Arg Thr Pro Leu Pro Leu Ala
                245                 250                 255

Arg Asp Glu Val Glu Gly Phe Leu Gln Asp Thr Phe Pro Gln Gln Leu
                260                 265                 270

Glu Glu Ser Glu Lys Gln Arg Leu Gly Gly Asp Val Gln Ser Pro Asn
            275                 280                 285

Cys Pro Ser Glu Asp Val Val Ile Thr Pro Glu Ser Phe Gly Arg Asp
        290                 295                 300

Ser Ser Leu Thr Cys Leu Ala Gly Asn Val Ser Ala Cys Asp Ala Pro
305                 310                 315                 320

Ile Leu Ser Ser Ser Arg Ser Leu Asp Cys Arg Glu Ser Gly Lys Asn
                325                 330                 335

Gly Pro His Val Tyr Gln Asp Leu Leu Leu Ser Leu Gly Thr Thr Asn
                340                 345                 350

Ser Thr Leu Pro Pro Pro Phe Ser Leu Gln Ser Gly Ile Leu Thr Leu
            355                 360                 365

Asn Pro Val Ala Gln Gly Gln Pro Ile Leu Thr Ser Leu Gly Ser Asn
        370                 375                 380

Gln Glu Glu Ala Tyr Val Thr Met Ser Ser Phe Tyr Gln Asn Gln
385                 390                 395

<210> SEQ ID NO 140
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Ser Ala Val Leu Gly Leu Leu Leu Leu Arg Trp Gln Phe Pro Ala
            180                 185                 190

His Tyr Arg Arg Leu Arg His Ala Leu Trp Pro Ser Leu Pro Asp Leu
```

```
            195                 200                 205
His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Asp
                245                 250                 255

Glu Gly Val Ala Gly Ala Pro Thr Gly Ser Ser Pro Gln Pro Leu Gln
            260                 265                 270

Pro Leu Ser Gly Glu Asp Asp Ala Tyr Cys Thr Phe Pro Ser Arg Asp
                275                 280                 285

Asp Leu Leu Leu Phe Ser Pro Ser Gly Gln Gly Glu Phe Arg Ala Leu
        290                 295                 300

Asn Ala Arg Leu Pro Leu Asn Thr Asp Ala Tyr Leu Ser Leu Gln Glu
305                 310                 315                 320

Leu Gln Gly Gln Asp Pro Thr His Leu Val
                325                 330

<210> SEQ ID NO 141
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

Leu Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
    210                 215                 220
```

```
Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Ala Arg Asp Glu Val Glu Gly Phe Leu Gln Asp Thr
        275                 280                 285

Phe Pro Gln Gln Leu Glu Glu Ser Glu Lys Gln Arg Leu Gly Gly Asp
    290                 295                 300

Val Gln Ser Pro Asn Cys Pro Ser Glu Asp Val Val Ile Thr Pro Glu
305                 310                 315                 320

Ser Phe Gly Arg Asp Ser Ser Leu Thr Cys Leu Ala Gly Asn Val Ser
                325                 330                 335

Ala Cys Asp Ala Pro Ile Leu Ser Ser Ser Arg Ser Leu Asp Cys Arg
                340                 345                 350

Glu Ser Gly Lys Asn Gly Pro His Val Tyr Gln Asp Leu Leu Leu Ser
            355                 360                 365

Leu Gly Thr Thr Asn Ser Thr Leu Pro Pro Pro Phe Ser Leu Gln Ser
370                 375                 380

Gly Ile Leu Thr Leu Asn Pro Val Ala Gln Gly Gln Pro Ile Leu Thr
385                 390                 395                 400

Ser Leu Gly Ser Asn Gln Glu Glu Ala Tyr Val Thr Met Ser Ser Phe
                405                 410                 415

Tyr Gln Asn Gln
            420

<210> SEQ ID NO 142
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
        50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160
```

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Asp Glu Gly Val Ala Gly Ala Pro Thr Gly Ser Ser
        275                 280                 285

Pro Gln Pro Leu Gln Pro Leu Ser Gly Glu Asp Asp Ala Tyr Cys Thr
    290                 295                 300

Phe Pro Ser Arg Asp Asp Leu Leu Leu Phe Ser Pro Ser Gly Gln Gly
305                 310                 315                 320

Glu Phe Arg Ala Leu Asn Ala Arg Leu Pro Leu Asn Thr Asp Ala Tyr
                325                 330                 335

Leu Ser Leu Gln Glu Leu Gln Gly Gln Asp Pro Thr His Leu Val
            340                 345                 350

<210> SEQ ID NO 143
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
        50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Val Gly Val Val Gly

```
            165                 170                 175
Gly Leu Leu Gly Ser Leu Val Leu Val Trp Val Leu Ala Val Ile
            180                 185                 190

Cys Ser Arg Ala Ala Arg Gly Thr Ile Gly Ala Arg Thr Gly Gln
            195                 200                 205

<210> SEQ ID NO 144
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ala Leu Pro Val Thr Ala Leu Leu Leu Pro Leu Ala Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
            115                 120                 125

Leu Ala Pro Lys Ile Gln Ile Lys Glu Ser Leu Arg Ala Glu Leu Arg
130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Ser Ala Val Leu Gly Leu Leu Leu Leu Arg
            195                 200                 205

Trp Gln Phe Pro Ala His Tyr Arg Arg Leu Arg His Ala Leu Trp Pro
            210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Ala Arg Asp Glu Val Glu Gly Phe Leu Gln Asp Thr
            275                 280                 285

Phe Pro Gln Gln Leu Glu Glu Ser Glu Lys Gln Arg Leu Gly Gly Asp
            290                 295                 300

Val Gln Ser Pro Asn Cys Pro Ser Glu Asp Val Val Ile Thr Pro Glu
305                 310                 315                 320
```

```
Ser Phe Gly Arg Asp Ser Ser Leu Thr Cys Leu Ala Gly Asn Val Ser
                325                 330                 335

Ala Cys Asp Ala Pro Ile Leu Ser Ser Arg Ser Leu Asp Cys Arg
            340                 345                 350

Glu Ser Gly Lys Asn Gly Pro His Val Tyr Gln Asp Leu Leu Leu Ser
            355                 360                 365

Leu Gly Thr Thr Asn Ser Thr Leu Pro Pro Phe Ser Leu Gln Ser
        370                 375                 380

Gly Ile Leu Thr Leu Asn Pro Val Ala Gln Gly Gln Pro Ile Leu Thr
385                 390                 395                 400

Ser Leu Gly Ser Asn Gln Glu Glu Ala Tyr Val Thr Met Ser Ser Phe
            405                 410                 415

Tyr Gln Asn Gln
            420

<210> SEQ ID NO 145
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Ser Ala Val Leu Gly Leu Leu Leu Leu Arg
        195                 200                 205

Trp Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255
```

```
Val Glu Pro Ser Leu Leu Glu Ile Leu Pro Lys Ser Ser Glu Arg Thr
            260                 265                 270

Pro Leu Pro Leu Asp Glu Gly Val Ala Gly Ala Pro Thr Gly Ser Ser
            275                 280                 285

Pro Gln Pro Leu Gln Pro Leu Ser Gly Glu Asp Ala Tyr Cys Thr
        290                 295                 300

Phe Pro Ser Arg Asp Asp Leu Leu Phe Ser Pro Ser Gly Gln Gly
305                 310                 315                 320

Glu Phe Arg Ala Leu Asn Ala Arg Leu Pro Leu Asn Thr Asp Ala Tyr
                325                 330                 335

Leu Ser Leu Gln Glu Leu Gln Gly Gln Asp Pro Thr His Leu Val
            340                 345                 350

<210> SEQ ID NO 146
<211> LENGTH: 55
<212> TYPE: PRT
<213> ORGANISM: Homo sapiens

<400> SEQUENCE: 146

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu
    50                  55

<210> SEQ ID NO 147
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ser Asp Pro Thr Arg Val Glu Thr Ala Thr Glu Thr Trp Ile Ser Leu
1               5                   10                  15

Val Thr Ala Leu His Leu Val Leu Gly Leu Ser Ala Val Leu Gly Leu
            20                  25                  30

Leu Leu Leu Arg Trp Gln Phe Pro Ala His Tyr Arg Arg Leu Arg His
        35                  40                  45

Ala Leu Trp Pro Ser Leu
    50

<210> SEQ ID NO 148
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Asp Pro Thr Arg Val Glu Thr Ala Thr Glu Thr Ile Ser Leu Val
1               5                   10                  15

Thr Ala Leu His Leu Val Leu Gly Leu Ser Ala Val Leu Gly Leu Leu
            20                  25                  30
```

```
Leu Leu Arg Trp Gln Phe Pro Ala His Tyr Arg Arg Leu Arg His Ala
        35                  40                  45

Leu Trp Pro Ser Leu
    50

<210> SEQ ID NO 149
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ser Asp Pro Thr Arg Val Glu Thr Ala Thr Glu Thr Leu Ile Ser Leu
1               5                   10                  15

Val Thr Ala Leu His Leu Val Leu Gly Leu Ser Ala Val Leu Gly Leu
            20                  25                  30

Leu Leu Leu Arg Trp Gln Phe Pro Ala His Tyr Arg Arg Leu Arg His
        35                  40                  45

Ala Leu Trp Pro Ser Leu
    50

<210> SEQ ID NO 150
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Asp Pro Thr Arg Val Glu Thr Ala Thr Glu Thr Ser Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu
    50

<210> SEQ ID NO 151
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ser Asp Pro Thr Arg Val Glu Thr Ala Thr Glu Thr Leu Val Thr Ala
1               5                   10                  15

Leu His Leu Val Leu Gly Leu Ser Ala Val Leu Gly Leu Leu Leu Leu
            20                  25                  30

Arg Trp Gln Phe Pro Ala His Tyr Arg Arg Leu Arg His Ala Leu Trp
        35                  40                  45

Pro Ser Leu
    50

<210> SEQ ID NO 152
<211> LENGTH: 52
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 152

Ser Asp Pro Thr Arg Val Glu Thr Ala Thr Glu Thr Ile Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu
    50

<210> SEQ ID NO 153
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Asp Pro Thr Arg Val Glu Thr Ala Thr Glu Thr Val Thr Ala Leu
1               5                   10                  15

His Leu Val Leu Gly Leu Ser Ala Val Leu Gly Leu Leu Leu Arg
            20                  25                  30

Trp Gln Phe Pro Ala His Tyr Arg Arg Leu Arg His Ala Leu Trp Pro
        35                  40                  45

Ser Leu
    50

<210> SEQ ID NO 154
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ser Asp Pro Thr Arg Val Glu Thr Ala Thr Glu Thr Thr Ala Leu His
1               5                   10                  15

Leu Val Leu Gly Leu Ser Ala Val Leu Gly Leu Leu Leu Arg Trp
            20                  25                  30

Gln Phe Pro Ala His Tyr Arg Arg Leu Arg His Ala Leu Trp Pro Ser
        35                  40                  45

Leu

<210> SEQ ID NO 155
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Ser Asp Pro Thr Arg Val Glu Thr Ala Thr Glu Thr Ala Leu His Leu
1               5                   10                  15

Val Leu Gly Leu Ser Ala Val Leu Gly Leu Leu Leu Arg Trp Gln
```

```
                    20                  25                  30

Phe Pro Ala His Tyr Arg Arg Leu Arg His Ala Leu Trp Pro Ser Leu
            35                  40                  45

<210> SEQ ID NO 156
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ser Asp Pro Thr Arg Val Glu Thr Ala Thr Glu Thr Leu His Leu Val
1               5                   10                  15

Leu Gly Leu Ser Ala Val Leu Gly Leu Leu Leu Arg Trp Gln Phe
            20                  25                  30

Pro Ala His Tyr Arg Arg Leu Arg His Ala Leu Trp Pro Ser Leu
            35                  40                  45

<210> SEQ ID NO 157
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ser Asp Pro Thr Arg Val Glu Thr Ala Thr Glu Thr His Leu Val Leu
1               5                   10                  15

Gly Leu Ser Ala Val Leu Gly Leu Leu Leu Arg Trp Gln Phe Pro
            20                  25                  30

Ala His Tyr Arg Arg Leu Arg His Ala Leu Trp Pro Ser Leu
            35                  40                  45

<210> SEQ ID NO 158
<211> LENGTH: 55
<212> TYPE: PRT
<213> ORGANISM: Homo sapiens

<400> SEQUENCE: 158

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Arg Trp Gln Phe Pro Ala His Tyr Arg Arg Leu Arg
            35                  40                  45

His Ala Leu Trp Pro Ser Leu
        50                  55

<210> SEQ ID NO 159
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ser Asp Pro Thr Arg Val Glu Thr Ala Thr Glu Thr Ala Trp Leu Ile
1               5                   10                  15
```

Ser Leu Val Thr Ala Leu His Leu Val Leu Gly Leu Ser Ala Val Leu
                20                  25                  30

Gly Leu Leu Leu Leu Arg Trp Gln Phe Pro Ala His Tyr Arg Arg Leu
            35                  40                  45

Arg His Ala Leu Trp Pro Ser Leu
    50                  55

<210> SEQ ID NO 160
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Asp Pro Thr Arg Val Glu Thr Ala Thr Glu Thr Ala Trp Val Leu
1               5                   10                  15

Ile Ser Leu Val Thr Ala Leu His Leu Val Leu Gly Leu Ser Ala Val
                20                  25                  30

Leu Gly Leu Leu Leu Leu Arg Trp Gln Phe Pro Ala His Tyr Arg Arg
            35                  40                  45

Leu Arg His Ala Leu Trp Pro Ser Leu
    50                  55

<210> SEQ ID NO 161
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ser Asp Pro Thr Arg Val Glu Thr Ala Thr Glu Thr Ala Trp Leu Val
1               5                   10                  15

Leu Ile Ser Leu Val Thr Ala Leu His Leu Val Leu Gly Leu Ser Ala
                20                  25                  30

Val Leu Gly Leu Leu Leu Arg Trp Gln Phe Pro Ala His Tyr Arg
            35                  40                  45

Arg Leu Arg His Ala Leu Trp Pro Ser Leu
    50                  55

<210> SEQ ID NO 162
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Ser
                20                  25                  30

Ala Val Leu Gly Leu Leu Leu Arg Trp Gln Phe Pro Ala His Tyr
            35                  40                  45

Arg Arg Leu Arg His Ala Leu Trp Pro Ser Leu
    50                  55

<210> SEQ ID NO 163
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ser Asp Pro Thr Arg Val Glu Thr Ala Thr Glu Thr Ala Trp Leu Ile
1               5                   10                  15

Leu Val Leu Ile Ser Leu Val Thr Ala Leu His Leu Val Leu Gly Leu
            20                  25                  30

Ser Ala Val Leu Gly Leu Leu Leu Arg Trp Gln Phe Pro Ala His
        35                  40                  45

Tyr Arg Arg Leu Arg His Ala Leu Trp Pro Ser Leu
    50                  55                  60

<210> SEQ ID NO 164
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ser Asp Pro Thr Arg Val Glu Thr Ala Thr Glu Thr Ala Trp Leu Leu
1               5                   10                  15

Ile Leu Val Leu Ile Ser Leu Val Thr Ala Leu His Leu Val Leu Gly
            20                  25                  30

Leu Ser Ala Val Leu Gly Leu Leu Leu Arg Trp Gln Phe Pro Ala
        35                  40                  45

His Tyr Arg Arg Leu Arg His Ala Leu Trp Pro Ser Leu
    50                  55                  60

<210> SEQ ID NO 165
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ser Asp Pro Thr Arg Val Glu Thr Ala Thr Glu Thr Ala Trp Val Leu
1               5                   10                  15

Leu Ile Leu Val Leu Ile Ser Leu Val Thr Ala Leu His Leu Val Leu
            20                  25                  30

Gly Leu Ser Ala Val Leu Gly Leu Leu Leu Arg Trp Gln Phe Pro
        35                  40                  45

Ala His Tyr Arg Arg Leu Arg His Ala Leu Trp Pro Ser Leu
    50                  55                  60

<210> SEQ ID NO 166
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ser Asp Pro Thr Arg Val Glu Thr Ala Thr Glu Ala Trp Leu Val
1               5                   10                  15

Leu Leu Ile Leu Val Leu Ile Ser Leu Val Thr Ala Leu His Leu Val
            20                  25                  30

Leu Gly Leu Ser Ala Val Leu Gly Leu Leu Leu Leu Arg Trp Gln Phe
                35                  40                  45

Pro Ala His Tyr Arg Arg Leu Arg His Ala Leu Trp Pro Ser Leu
    50                  55                  60

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Pro Ile Pro Asn Pro Leu Leu Gly Leu Asp Ser Thr
1               5                   10

<210> SEQ ID NO 168
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Pro Gly Trp Phe Leu Asp Ser Pro Asp
145                 150                 155                 160

Arg Pro Trp Asn Pro Pro Thr Phe Ser Pro Ala Leu Leu Val Val Thr
                165                 170                 175

Glu Gly Asp Asn Ala Thr Phe Thr Cys Ser Phe Ser Asn Thr Ser Glu
            180                 185                 190

Ser Phe Val Leu Asn Trp Tyr Arg Met Ser Pro Ser Asn Gln Thr Asp
        195                 200                 205

Lys Leu Ala Ala Phe Pro Glu Asp Arg Ser Gln Pro Gly Gln Asp Cys
    210                 215                 220

```
Arg Phe Arg Val Thr Gln Leu Pro Asn Gly Arg Asp Phe His Met Ser
225                 230                 235                 240

Val Val Arg Ala Arg Arg Asn Asp Ser Gly Thr Tyr Leu Cys Gly Ala
                245                 250                 255

Ile Ser Leu Ala Pro Lys Ala Gln Ile Lys Glu Ser Leu Arg Ala Glu
            260                 265                 270

Leu Arg Val Thr Glu Arg Arg Ala Glu Val Pro Thr Ala His Pro Ser
        275                 280                 285

Pro Ser Pro Arg Pro Ala Gly Gln Phe Gln Thr Leu Val
    290                 295                 300
```

<210> SEQ ID NO 169
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Pro Gly Trp Phe Leu Asp Ser Pro Asp
145                 150                 155                 160

Arg Pro Trp Asn Pro Pro Thr Phe Ser Pro Ala Leu Leu Val Val Thr
                165                 170                 175

Glu Gly Asp Asn Ala Thr Phe Thr Cys Ser Phe Ser Asn Thr Ser Glu
            180                 185                 190

Ser Phe Val Leu Asn Trp Tyr Arg Met Ser Pro Ser Asn Gln Thr Asp
        195                 200                 205

Lys Leu Ala Ala Phe Pro Glu Asp Arg Ser Gln Pro Gly Gln Asp Cys
    210                 215                 220

Arg Phe Arg Val Thr Gln Leu Pro Asn Gly Arg Asp Phe His Met Ser
225                 230                 235                 240

Val Val Arg Ala Arg Arg Asn Asp Ser Gly Thr Tyr Leu Cys Gly Ala
                245                 250                 255

Ile Ser Leu Ala Pro Lys Ala Gln Ile Lys Glu Ser Leu Arg Ala Glu
            260                 265                 270

Leu Arg Val Thr Glu Arg Arg Ala Glu Val Pro Thr Ala His Pro Ser
        275                 280                 285
```

```
Pro Ser Pro Arg Pro Ala Gly Gln Phe Gln Thr Leu Val Gly Pro Gly
    290                 295                 300

Trp Phe Leu Asp Ser Pro Asp Arg Pro Trp Asn Pro Thr Phe Ser
305                 310                 315                 320

Pro Ala Leu Leu Val Val Thr Glu Gly Asp Asn Ala Thr Phe Thr Cys
                325                 330                 335

Ser Phe Ser Asn Thr Ser Glu Ser Phe Val Leu Asn Trp Tyr Arg Met
                340                 345                 350

Ser Pro Ser Asn Gln Thr Asp Lys Leu Ala Ala Phe Pro Glu Asp Arg
            355                 360                 365

Ser Gln Pro Gly Gln Asp Cys Arg Phe Arg Val Thr Gln Leu Pro Asn
        370                 375                 380

Gly Arg Asp Phe His Met Ser Val Val Arg Ala Arg Arg Asn Asp Ser
385                 390                 395                 400

Gly Thr Tyr Leu Cys Gly Ala Ile Ser Leu Ala Pro Lys Ala Gln Ile
                405                 410                 415

Lys Glu Ser Leu Arg Ala Glu Leu Arg Val Thr Glu Arg Arg Ala Glu
                420                 425                 430

Val Pro Thr Ala His Pro Ser Pro Ser Pro Arg Pro Ala Gly Gln Phe
            435                 440                 445

Gln Thr Leu Val
    450

<210> SEQ ID NO 170
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Val Thr Gln Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Tyr
                20                  25                  30

Phe Phe Phe His Leu Pro Asp Ala Leu Glu Ile Glu Ala Cys Gln Val
            35                  40                  45

Ser Phe Thr Ser Asp Pro Ser Ser Glu Glu Asp Pro Asp Glu Gly Val
        50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Pro Ser Thr Ala
            100                 105                 110

Pro Gly Gly Ser Gly Ala Gly Glu Glu Arg Met Pro Pro Ser Leu Gln
        115                 120                 125

Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
```

```
                    180                 185                 190
Leu Asn Ala Arg Leu Pro Leu Asn Thr Asp Ala Tyr Leu Ser Leu Gln
            195                 200                 205
Glu Leu Gln Gly Gln Asp Pro Thr His Leu Val
        210                 215

<210> SEQ ID NO 171
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Val Thr Gln Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Ser
            20                  25                  30

Phe Phe Phe His Leu Pro Asp Ala Leu Glu Ile Glu Ala Cys Gln Val
        35                  40                  45

Ser Phe Thr Ser Asp Pro Ser Ser Glu Glu Asp Pro Asp Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Ser Thr Ala
            100                 105                 110

Pro Gly Gly Ser Gly Ala Gly Glu Glu Arg Met Pro Pro Ser Leu Gln
        115                 120                 125

Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
            180                 185                 190

Leu Asn Ala Arg Leu Pro Leu Asn Thr Asp Ala Tyr Leu Ser Leu Gln
        195                 200                 205

Glu Leu Gln Gly Gln Asp Pro Thr His Leu Val
    210                 215

<210> SEQ ID NO 172
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
```

-continued

```
            35                  40                  45
Arg Met Ser Pro Ser Asn Gln Thr Asp Lys Leu Ala Ala Phe Pro Glu
 50                  55                  60
Asp Arg Ser Gln Pro Gly Gln Asp Cys Arg Phe Arg Val Thr Gln Leu
 65                  70                  75                  80
Pro Asn Gly Arg Asp Phe His Met Ser Val Arg Ala Arg Arg Asn
                 85                  90                  95
Asp Ser Gly Thr Tyr Leu Cys Gly Ala Ile Ser Leu Ala Pro Lys Ala
                100                 105                 110
Gln Ile Lys Glu Ser Leu Arg Ala Glu Leu Arg Val Thr Glu Arg Arg
            115                 120                 125
Ala Glu Val Pro Thr Ala His Pro Ser Pro Ser Pro Arg Pro Ala Gly
            130                 135                 140
Gln Phe Gln Thr Leu Val Ser Asp Pro Thr Arg Val Glu Thr Ala Thr
145                 150                 155                 160
Glu Thr Ala Trp Ile Ser Leu Val Thr Ala Leu His Leu Val Leu Gly
                165                 170                 175
Leu Ser Ala Val Leu Gly Leu Leu Leu Arg Trp Gln Phe Pro Ala
            180                 185                 190
His Tyr Arg Arg Leu Arg His Ala Leu Trp Pro Ser Leu Pro Asp Leu
            195                 200                 205
His Arg Val Leu Gly Gln Tyr Leu Arg Asp Thr Ala Ala Leu Ser Pro
            210                 215                 220
Pro Lys Ala Thr Val Ser Asp Thr Cys Glu Glu Val Glu Pro Ser Leu
225                 230                 235                 240
Leu Glu Ile Leu Pro Lys Ser Ser Glu Arg Thr Pro Leu Pro Leu Leu
                245                 250                 255
Glu Ala Arg Asp Glu Val Glu Gly Phe Leu Gln Asp Thr Phe Pro Gln
            260                 265                 270
Gln Leu Glu Glu Ser Glu Lys Gln Arg Leu Gly Gly Asp Val Gln Ser
            275                 280                 285
Pro Asn Cys Pro Ser Glu Asp Val Val Ile Thr Pro Glu Ser Phe Gly
            290                 295                 300
Arg Asp Ser Ser Leu Thr Cys Leu Ala Gly Asn Val Ser Ala Cys Asp
305                 310                 315                 320
Ala Pro Ile Leu Ser Ser Arg Ser Leu Asp Cys Arg Glu Ser Gly
                325                 330                 335
Lys Asn Gly Pro His Val Tyr Gln Asp Leu Leu Leu Ser Leu Gly Thr
                340                 345                 350
Thr Asn Ser Thr Leu Pro Pro Phe Ser Leu Gln Ser Gly Ile Leu
            355                 360                 365
Thr Leu Asn Pro Val Ala Gln Gly Gln Pro Ile Leu Thr Ser Leu Gly
            370                 375                 380
Ser Asn Gln Glu Glu Ala Tyr Val Thr Met Ser Ser Phe Tyr Gln Asn
385                 390                 395                 400
Gln Gly Ser Gly Ser Arg Ser Asp Pro Lys Pro Glu Asn Pro Ala Cys
                405                 410                 415
Pro Trp Thr Val Leu Pro Ala Gly Asp Leu Pro Thr His Asp Gly Tyr
                420                 425                 430
Leu Pro Ser Asn Ile Asp Asp Leu Pro Ser His Glu Ala Pro Leu Ala
            435                 440                 445
Asp Ser Leu Glu Glu Leu Glu Pro Gln
            450                 455
```

```
<210> SEQ ID NO 173
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Leu Thr Leu Met Thr Leu Thr Pro Glu Gly
145                 150                 155                 160

Ser Glu Leu His Ile Ile Leu Gly Leu Phe Gly Leu Leu Leu Leu Leu
                165                 170                 175

Thr Cys Leu Cys Gly Thr Ala Trp Leu Cys Cys Ser Pro Asn Arg Lys
            180                 185                 190

Asn Pro Leu Trp Pro Ser Val Pro Asp Pro Ala His Ser Ser Leu Gly
        195                 200                 205

Ser Trp Val Pro Thr Ile Met Glu Glu Asp Ala Phe Gln Leu Pro Gly
    210                 215                 220

Leu Gly Thr Pro Pro Ile Thr Lys Leu Thr Val Leu Glu Glu Asp Glu
225                 230                 235                 240

Lys Lys Pro Val Pro Trp Glu Leu Glu Ala Arg Asp Glu Val Glu Gly
                245                 250                 255

Phe Leu Gln Asp Thr Phe Pro Gln Gln Leu Glu Glu Ser Glu Lys Gln
            260                 265                 270

Arg Leu Gly Gly Asp Val Gln Ser Pro Asn Cys Pro Ser Glu Asp Val
        275                 280                 285

Val Ile Thr Pro Glu Ser Phe Gly Arg Asp Ser Ser Leu Thr Cys Leu
    290                 295                 300

Ala Gly Asn Val Ser Ala Cys Asp Ala Pro Ile Leu Ser Ser Ser Arg
305                 310                 315                 320

Ser Leu Asp Cys Arg Glu Ser Gly Lys Asn Gly Pro His Val Tyr Gln
                325                 330                 335

Asp Leu Leu Leu Ser Leu Gly Thr Thr Asn Ser Thr Leu Pro Pro Pro
            340                 345                 350

Phe Ser Leu Gln Ser Gly Ile Leu Thr Leu Asn Pro Val Ala Gln Gly
```

```
                     355                 360                 365

Gln Pro Ile Leu Thr Ser Leu Gly Ser Asn Gln Glu Glu Ala Tyr Val
            370                 375                 380

Thr Met Ser Ser Phe Tyr Gln Asn Gln Gly Ser Gly Ser Arg Ser Asp
385                 390                 395                 400

Pro Lys Pro Glu Asn Pro Ala Cys Pro Trp Thr Val Leu Pro Ala Gly
                405                 410                 415

Asp Leu Pro Thr His Asp Gly Tyr Leu Pro Ser Asn Ile Asp Asp Leu
            420                 425                 430

Pro Ser His Glu Ala Pro Leu Ala Asp Ser Leu Glu Glu Leu Glu Pro
        435                 440                 445

Gln

<210> SEQ ID NO 174
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Pro Lys Phe Ala Gln Gly Glu Ile
145                 150                 155                 160

Glu Ala Ile Val Val Pro Val Cys Leu Ala Phe Leu Leu Thr Thr Leu
                165                 170                 175

Leu Gly Val Leu Phe Cys Phe Asn Lys Arg Asp Leu Ile Lys Lys His
            180                 185                 190

Ile Trp Pro Asn Val Pro Asp Pro Ser Lys Ser His Ile Ala Gln Trp
        195                 200                 205

Ser Pro His Thr Pro Pro Arg His Asn Phe Asn Ser Lys Asp Gln Met
    210                 215                 220

Tyr Ser Asp Gly Asn Phe Thr Asp Val Ser Val Val Glu Ile Glu Ala
225                 230                 235                 240

Asn Asp Leu Glu Ala Arg Asp Glu Val Glu Gly Phe Leu Gln Asp Thr
                245                 250                 255

Phe Pro Gln Gln Leu Glu Glu Ser Glu Lys Gln Arg Leu Gly Gly Asp
```

```
                260                 265                 270
Val Gln Ser Pro Asn Cys Pro Ser Glu Asp Val Ile Thr Pro Glu
        275                 280                 285

Ser Phe Gly Arg Asp Ser Ser Leu Thr Cys Leu Ala Gly Asn Val Ser
        290                 295                 300

Ala Cys Asp Ala Pro Ile Leu Ser Ser Arg Ser Leu Asp Cys Arg
305                 310                 315                 320

Glu Ser Gly Lys Asn Gly Pro His Val Tyr Gln Asp Leu Leu Ser
                325                 330                 335

Leu Gly Thr Thr Asn Ser Thr Leu Pro Pro Phe Ser Leu Gln Ser
                340                 345                 350

Gly Ile Leu Thr Leu Asn Pro Val Ala Gln Gly Gln Pro Ile Leu Thr
                355                 360                 365

Ser Leu Gly Ser Asn Gln Glu Glu Ala Tyr Val Thr Met Ser Ser Phe
        370                 375                 380

Tyr Gln Asn Gln Gly Ser Gly Ser Arg Ser Asp Pro Lys Pro Glu Asn
385                 390                 395                 400

Pro Ala Cys Pro Trp Thr Val Leu Pro Ala Gly Asp Leu Pro Thr His
                405                 410                 415

Asp Gly Tyr Leu Pro Ser Asn Ile Asp Asp Leu Pro Ser His Glu Ala
                420                 425                 430

Pro Leu Ala Asp Ser Leu Glu Glu Leu Glu Pro Gln
        435                 440
```

<210> SEQ ID NO 175
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Arg Pro Ala Gly
130                 135                 140

Gln Phe Gln Thr Leu Val Gly Pro Gly Trp Phe Leu Asp Ser Pro Asp
145                 150                 155                 160

Arg Pro Trp Asn Pro Pro Thr Phe Ser Pro Ala Leu Leu Val Val Thr
                165                 170                 175
```

```
Glu Gly Asp Asn Ala Thr Phe Thr Cys Ser Phe Ser Asn Thr Ser Glu
            180                 185                 190

Ser Phe Val Leu Asn Trp Tyr Arg Met Ser Pro Ser Asn Gln Thr Asp
        195                 200                 205

Lys Leu Ala Ala Phe Pro Glu Asp Arg Ser Gln Pro Gly Gln Asp Cys
        210                 215                 220

Arg Phe Arg Val Thr Gln Leu Pro Asn Gly Arg Asp Phe His Met Ser
225                 230                 235                 240

Val Val Arg Ala Arg Arg Asn Asp Ser Gly Thr Tyr Leu Cys Gly Ala
                245                 250                 255

Ile Ser Leu Ala Pro Lys Ala Gln Ile Lys Glu Ser Leu Arg Ala Glu
            260                 265                 270

Leu Arg Val Thr Glu Arg Arg Ala Glu Val Pro Thr Ala His Pro Ser
        275                 280                 285

Pro Ser Pro Arg Pro Ala Gly Gln Phe Gln Thr Leu Val Ser Asp Pro
        290                 295                 300

Thr Arg Val Glu Thr Ala Thr Glu Thr Ala Trp Ile Ser Leu Val Thr
305                 310                 315                 320

Ala Leu His Leu Val Leu Gly Leu Ser Ala Val Leu Gly Leu Leu Leu
                325                 330                 335

Leu Arg Trp Gln Phe Pro Ala His Tyr Arg Arg Leu Arg His Ala Leu
            340                 345                 350

Trp Pro Ser Leu Pro Asp Leu His Arg Val Leu Gly Gln Tyr Leu Arg
        355                 360                 365

Asp Thr Ala Ala Leu Ser Pro Pro Lys Ala Thr Val Ser Asp Thr Cys
        370                 375                 380

Glu Glu Val Glu Pro Ser Leu Leu Glu Ile Leu Pro Lys Ser Ser Glu
385                 390                 395                 400

Arg Thr Pro Leu Pro Leu Leu Glu Ala Arg Asp Val Glu Gly Phe
                405                 410                 415

Leu Gln Asp Thr Phe Pro Gln Gln Leu Glu Glu Ser Glu Lys Gln Arg
            420                 425                 430

Leu Gly Gly Asp Val Gln Ser Pro Asn Cys Pro Ser Glu Asp Val Val
        435                 440                 445

Ile Thr Pro Glu Ser Phe Gly Arg Asp Ser Ser Leu Thr Cys Leu Ala
        450                 455                 460

Gly Asn Val Ser Ala Cys Asp Ala Pro Ile Leu Ser Ser Ser Arg Ser
465                 470                 475                 480

Leu Asp Cys Arg Glu Ser Gly Lys Asn Gly Pro His Val Tyr Gln Asp
                485                 490                 495

Leu Leu Leu Ser Leu Gly Thr Thr Asn Ser Thr Leu Pro Pro Pro Phe
            500                 505                 510

Ser Leu Gln Ser Gly Ile Leu Thr Leu Asn Pro Val Ala Gln Gly Gln
        515                 520                 525

Pro Ile Leu Thr Ser Leu Gly Ser Asn Gln Glu Glu Ala Tyr Val Thr
        530                 535                 540

Met Ser Ser Phe Tyr Gln Asn Gln Gly Ser Gly Ser Arg Ser Asp Pro
545                 550                 555                 560

Lys Pro Glu Asn Pro Ala Cys Pro Trp Thr Val Leu Pro Ala Gly Asp
                565                 570                 575

Leu Pro Thr His Asp Gly Tyr Leu Pro Ser Asn Ile Asp Asp Leu Pro
            580                 585                 590

Ser His Glu Ala Pro Leu Ala Asp Ser Leu Glu Glu Leu Glu Pro Gln
```

-continued

```
            595                 600                 605
```

<210> SEQ ID NO 176
<211> LENGTH: 759
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Arg Pro Ala Gly
    130                 135                 140

Gln Phe Gln Thr Leu Val Gly Pro Gly Trp Phe Leu Asp Ser Pro Asp
145                 150                 155                 160

Arg Pro Trp Asn Pro Pro Thr Phe Ser Pro Ala Leu Leu Val Val Thr
                165                 170                 175

Glu Gly Asp Asn Ala Thr Phe Thr Cys Ser Phe Ser Asn Thr Ser Glu
            180                 185                 190

Ser Phe Val Leu Asn Trp Tyr Arg Met Ser Pro Ser Asn Gln Thr Asp
        195                 200                 205

Lys Leu Ala Ala Phe Pro Glu Asp Arg Ser Gln Pro Gly Gln Asp Cys
    210                 215                 220

Arg Phe Arg Val Thr Gln Leu Pro Asn Gly Arg Asp Phe His Met Ser
225                 230                 235                 240

Val Val Arg Ala Arg Arg Asn Asp Ser Gly Thr Tyr Leu Cys Gly Ala
                245                 250                 255

Ile Ser Leu Ala Pro Lys Ala Gln Ile Lys Glu Ser Leu Arg Ala Glu
            260                 265                 270

Leu Arg Val Thr Glu Arg Arg Ala Glu Val Pro Thr Ala His Pro Ser
        275                 280                 285

Pro Ser Pro Arg Pro Ala Gly Gln Phe Gln Thr Leu Val Gly Pro Gly
    290                 295                 300

Trp Phe Leu Asp Ser Pro Asp Arg Pro Trp Asn Pro Pro Thr Phe Ser
305                 310                 315                 320

Pro Ala Leu Leu Val Val Thr Glu Gly Asp Asn Ala Thr Phe Thr Cys
                325                 330                 335

Ser Phe Ser Asn Thr Ser Glu Ser Phe Val Leu Asn Trp Tyr Arg Met
            340                 345                 350
```

-continued

```
Ser Pro Ser Asn Gln Thr Asp Lys Leu Ala Ala Phe Pro Glu Asp Arg
            355                 360                 365

Ser Gln Pro Gly Gln Asp Cys Arg Phe Arg Val Thr Gln Leu Pro Asn
    370                 375                 380

Gly Arg Asp Phe His Met Ser Val Val Arg Ala Arg Arg Asn Asp Ser
385                 390                 395                 400

Gly Thr Tyr Leu Cys Gly Ala Ile Ser Leu Ala Pro Lys Ala Gln Ile
                405                 410                 415

Lys Glu Ser Leu Arg Ala Glu Leu Arg Val Thr Glu Arg Arg Ala Glu
                420                 425                 430

Val Pro Thr Ala His Pro Ser Pro Ser Pro Arg Pro Ala Gly Gln Phe
            435                 440                 445

Gln Thr Leu Val Ser Asp Pro Thr Arg Val Glu Thr Ala Thr Glu Thr
        450                 455                 460

Ala Trp Ile Ser Leu Val Thr Ala Leu His Leu Val Leu Gly Leu Ser
465                 470                 475                 480

Ala Val Leu Gly Leu Leu Leu Arg Trp Gln Phe Pro Ala His Tyr
                485                 490                 495

Arg Arg Leu Arg His Ala Leu Trp Pro Ser Leu Pro Asp Leu His Arg
            500                 505                 510

Val Leu Gly Gln Tyr Leu Arg Asp Thr Ala Ala Leu Ser Pro Pro Lys
        515                 520                 525

Ala Thr Val Ser Asp Thr Cys Glu Glu Val Glu Pro Ser Leu Leu Glu
            530                 535                 540

Ile Leu Pro Lys Ser Ser Glu Arg Thr Pro Leu Pro Leu Leu Glu Ala
545                 550                 555                 560

Arg Asp Glu Val Glu Gly Phe Leu Gln Asp Thr Phe Pro Gln Gln Leu
                565                 570                 575

Glu Glu Ser Glu Lys Gln Arg Leu Gly Gly Asp Val Gln Ser Pro Asn
            580                 585                 590

Cys Pro Ser Glu Asp Val Val Ile Thr Pro Glu Ser Phe Gly Arg Asp
        595                 600                 605

Ser Ser Leu Thr Cys Leu Ala Gly Asn Val Ser Ala Cys Asp Ala Pro
    610                 615                 620

Ile Leu Ser Ser Ser Arg Ser Leu Asp Cys Arg Glu Ser Gly Lys Asn
625                 630                 635                 640

Gly Pro His Val Tyr Gln Asp Leu Leu Leu Ser Leu Gly Thr Thr Asn
                645                 650                 655

Ser Thr Leu Pro Pro Pro Phe Ser Leu Gln Ser Gly Ile Leu Thr Leu
            660                 665                 670

Asn Pro Val Ala Gln Gly Gln Pro Ile Leu Thr Ser Leu Gly Ser Asn
        675                 680                 685

Gln Glu Glu Ala Tyr Val Thr Met Ser Ser Phe Tyr Gln Asn Gln Gly
    690                 695                 700

Ser Gly Ser Arg Ser Asp Pro Lys Pro Glu Asn Pro Ala Cys Pro Trp
705                 710                 715                 720

Thr Val Leu Pro Ala Gly Asp Leu Pro Thr His Asp Gly Tyr Leu Pro
                725                 730                 735

Ser Asn Ile Asp Asp Leu Pro Ser His Glu Ala Pro Leu Ala Asp Ser
            740                 745                 750

Leu Glu Glu Leu Glu Pro Gln
        755
```

```
<210> SEQ ID NO 177
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177
```

| | | | | | | | | | | | | | | |
|---|---|---|---|---|---|---|---|---|---|---|---|---|---|---|
| Pro | Gly | Trp | Phe | Leu | Asp | Ser | Pro | Asp | Arg | Pro | Trp | Asn | Pro | Pro | Thr |
| 1 | | | | 5 | | | | | 10 | | | | | 15 | |
| Phe | Ser | Pro | Ala | Leu | Leu | Val | Val | Thr | Glu | Gly | Asp | Asn | Ala | Thr | Phe |
| | | | 20 | | | | | 25 | | | | | 30 | | |
| Thr | Cys | Ser | Phe | Ser | Asn | Thr | Ser | Glu | Ser | Phe | His | Val | Ile | Trp | His |
| | | 35 | | | | | 40 | | | | | 45 | | | |
| Arg | Glu | Ser | Pro | Ser | Gly | Gln | Thr | Asp | Thr | Leu | Ala | Ala | Phe | Pro | Glu |
| | 50 | | | | | 55 | | | | | 60 | | | | |
| Asp | Arg | Ser | Gln | Pro | Gly | Gln | Asp | Cys | Arg | Phe | Arg | Val | Thr | Gln | Leu |
| 65 | | | | | 70 | | | | | 75 | | | | | 80 |
| Pro | Asn | Gly | Arg | Asp | Phe | His | Met | Ser | Val | Val | Arg | Ala | Arg | Arg | Asn |
| | | | | 85 | | | | | 90 | | | | | 95 | |
| Asp | Ser | Gly | Thr | Tyr | Val | Cys | Gly | Val | Ile | Ser | Leu | Ala | Pro | Lys | Ile |
| | | | 100 | | | | | 105 | | | | | 110 | | |
| Gln | Ile | Lys | Glu | Ser | Leu | Arg | Ala | Glu | Leu | Arg | Val | Thr | Glu | Arg | Arg |
| | | 115 | | | | | 120 | | | | | 125 | | | |
| Ala | Glu | Val | Pro | Thr | Ala | His | Pro | Ser | Pro | Ser | Pro | Arg | Pro | Ala | Gly |
| | 130 | | | | | 135 | | | | | 140 | | | | |
| Gln | Phe | Gln | Thr | Leu | Val | Ser | Asp | Pro | Thr | Arg | Val | Glu | Thr | Ala | Thr |
| 145 | | | | | 150 | | | | | 155 | | | | | 160 |
| Glu | Thr | Ala | Trp | Ile | Ser | Leu | Val | Thr | Ala | Leu | His | Leu | Val | Leu | Gly |
| | | | | 165 | | | | | 170 | | | | | 175 | |
| Leu | Ser | Ala | Val | Leu | Gly | Leu | Leu | Leu | Arg | Trp | Gln | Phe | Pro | Ala | |
| | | | 180 | | | | | 185 | | | | | 190 | | |
| His | Tyr | Arg | Arg | Leu | Arg | His | Ala | Leu | Trp | Pro | Ser | Leu | Pro | Asp | Leu |
| | | 195 | | | | | 200 | | | | | 205 | | | |
| His | Arg | Val | Leu | Gly | Gln | Tyr | Leu | Arg | Asp | Thr | Ala | Ala | Leu | Ser | Pro |
| | 210 | | | | | 215 | | | | | 220 | | | | |
| Pro | Lys | Ala | Thr | Val | Ser | Asp | Thr | Cys | Glu | Glu | Val | Glu | Pro | Ser | Leu |
| 225 | | | | | 230 | | | | | 235 | | | | | 240 |
| Leu | Glu | Ile | Leu | Pro | Lys | Ser | Ser | Glu | Arg | Thr | Pro | Leu | Pro | Leu | Leu |
| | | | | 245 | | | | | 250 | | | | | 255 | |
| Glu | Ala | Arg | Asp | Glu | Val | Glu | Gly | Phe | Leu | Gln | Asp | Thr | Phe | Pro | Gln |
| | | | 260 | | | | | 265 | | | | | 270 | | |
| Gln | Leu | Glu | Glu | Ser | Glu | Lys | Gln | Arg | Leu | Gly | Gly | Asp | Val | Gln | Ser |
| | | 275 | | | | | 280 | | | | | 285 | | | |
| Pro | Asn | Cys | Pro | Ser | Glu | Asp | Val | Val | Ile | Thr | Pro | Glu | Ser | Phe | Gly |
| | 290 | | | | | 295 | | | | | 300 | | | | |
| Arg | Asp | Ser | Ser | Leu | Thr | Cys | Leu | Ala | Gly | Asn | Val | Ser | Ala | Cys | Asp |
| 305 | | | | | 310 | | | | | 315 | | | | | 320 |
| Ala | Pro | Ile | Leu | Ser | Ser | Ser | Arg | Ser | Leu | Asp | Cys | Arg | Glu | Ser | Gly |
| | | | | 325 | | | | | 330 | | | | | 335 | |
| Lys | Asn | Gly | Pro | His | Val | Tyr | Gln | Asp | Leu | Leu | Leu | Ser | Leu | Gly | Thr |
| | | | 340 | | | | | 345 | | | | | 350 | | |
| Thr | Asn | Ser | Thr | Leu | Pro | Pro | Pro | Phe | Ser | Leu | Gln | Ser | Gly | Ile | Leu |
| | | 355 | | | | | 360 | | | | | 365 | | | |

```
Thr Leu Asn Pro Val Ala Gln Gly Gln Pro Ile Leu Thr Ser Leu Gly
    370                 375                 380

Ser Asn Gln Glu Glu Ala Tyr Val Thr Met Ser Ser Phe Tyr Gln Asn
385                 390                 395                 400

Gln Gly Ser Gly Ser Arg Ser Asp Pro Lys Pro Glu Asn Pro Ala Cys
                405                 410                 415

Pro Trp Thr Val Leu Pro Ala Gly Asp Leu Pro Thr His Asp Gly Tyr
                420                 425                 430

Leu Pro Ser Asn Ile Asp Asp Leu Pro Ser His Glu Ala Pro Leu Ala
                435                 440                 445

Asp Ser Leu Glu Glu Leu Glu Pro Gln
    450                 455

<210> SEQ ID NO 178
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
                35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr Trp Ile Ser Leu Val Thr Ala Leu His Leu Val Leu Gly Leu
                165                 170                 175

Ser Ala Val Leu Gly Leu Leu Leu Arg Trp Gln Phe Pro Ala His
                180                 185                 190

Tyr Arg Arg Leu Arg His Ala Leu Trp Pro Ser Leu Pro Asp Leu His
            195                 200                 205

Arg Val Leu Gly Gln Tyr Leu Arg Asp Thr Ala Ala Leu Ser Pro Pro
        210                 215                 220

Lys Ala Thr Val Ser Asp Thr Cys Glu Glu Val Glu Pro Ser Leu Leu
225                 230                 235                 240

Glu Ile Leu Pro Lys Ser Ser Glu Arg Thr Pro Leu Pro Leu Leu Glu
                245                 250                 255

Ala Arg Asp Glu Val Glu Gly Phe Leu Gln Asp Thr Phe Pro Gln Gln
                260                 265                 270
```

```
Leu Glu Glu Ser Glu Lys Gln Arg Leu Gly Gly Asp Val Gln Ser Pro
            275                 280                 285

Asn Cys Pro Ser Glu Asp Val Val Ile Thr Pro Glu Ser Phe Gly Arg
        290                 295                 300

Asp Ser Ser Leu Thr Cys Leu Ala Gly Asn Val Ser Ala Cys Asp Ala
305                 310                 315                 320

Pro Ile Leu Ser Ser Arg Ser Leu Asp Cys Arg Glu Ser Gly Lys
                325                 330                 335

Asn Gly Pro His Val Tyr Gln Asp Leu Leu Ser Leu Gly Thr Thr
            340                 345                 350

Asn Ser Thr Leu Pro Pro Phe Ser Leu Gln Ser Gly Ile Leu Thr
            355                 360                 365

Leu Asn Pro Val Ala Gln Gly Gln Pro Ile Leu Thr Ser Leu Gly Ser
    370                 375                 380

Asn Gln Glu Glu Ala Tyr Val Thr Met Ser Ser Phe Tyr Gln Asn Gln
385                 390                 395                 400

Gly Ser Gly Ser Arg Ser Asp Pro Lys Pro Glu Asn Pro Ala Cys Pro
                405                 410                 415

Trp Thr Val Leu Pro Ala Gly Asp Leu Pro Thr His Asp Gly Tyr Leu
            420                 425                 430

Pro Ser Asn Ile Asp Asp Leu Pro Ser His Glu Ala Pro Leu Ala Asp
            435                 440                 445

Ser Leu Glu Glu Leu Glu Pro Gln
            450                 455

<210> SEQ ID NO 179
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ile Ser Leu Val Thr Ala Leu His Leu Val Leu Gly Leu Ser
```

165                 170                 175
Ala Val Leu Gly Leu Leu Leu Arg Trp Gln Phe Pro Ala His Tyr
            180                 185                 190

Arg Arg Leu Arg His Ala Leu Trp Pro Ser Leu Pro Asp Leu His Arg
            195                 200                 205

Val Leu Gly Gln Tyr Leu Arg Asp Thr Ala Ala Leu Ser Pro Pro Lys
            210                 215                 220

Ala Thr Val Ser Asp Thr Cys Glu Val Glu Pro Ser Leu Leu Glu
225                 230                 235                 240

Ile Leu Pro Lys Ser Ser Glu Arg Thr Pro Leu Pro Leu Leu Glu Ala
            245                 250                 255

Arg Asp Glu Val Glu Gly Phe Leu Gln Asp Thr Phe Pro Gln Gln Leu
            260                 265                 270

Glu Glu Ser Glu Lys Gln Arg Leu Gly Gly Asp Val Gln Ser Pro Asn
            275                 280                 285

Cys Pro Ser Glu Asp Val Val Ile Thr Pro Glu Ser Phe Gly Arg Asp
            290                 295                 300

Ser Ser Leu Thr Cys Leu Ala Gly Asn Val Ser Ala Cys Asp Ala Pro
305                 310                 315                 320

Ile Leu Ser Ser Ser Arg Ser Leu Asp Cys Arg Glu Ser Gly Lys Asn
            325                 330                 335

Gly Pro His Val Tyr Gln Asp Leu Leu Leu Ser Leu Gly Thr Thr Asn
            340                 345                 350

Ser Thr Leu Pro Pro Pro Phe Ser Leu Gln Ser Gly Ile Leu Thr Leu
            355                 360                 365

Asn Pro Val Ala Gln Gly Gln Pro Ile Leu Thr Ser Leu Gly Ser Asn
            370                 375                 380

Gln Glu Glu Ala Tyr Val Thr Met Ser Ser Phe Tyr Gln Asn Gln Gly
385                 390                 395                 400

Ser Gly Ser Arg Ser Asp Pro Lys Pro Glu Asn Pro Ala Cys Pro Trp
            405                 410                 415

Thr Val Leu Pro Ala Gly Asp Leu Pro Thr His Asp Gly Tyr Leu Pro
            420                 425                 430

Ser Asn Ile Asp Asp Leu Pro Ser His Glu Ala Pro Leu Ala Asp Ser
            435                 440                 445

Leu Glu Glu Leu Glu Pro Gln
    450                 455

<210> SEQ ID NO 180
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Leu Ile Ser Leu Val Thr Ala Leu His Leu Val Leu Gly Leu
                165                 170                 175

Ser Ala Val Leu Gly Leu Leu Leu Arg Trp Gln Phe Pro Ala His
            180                 185                 190

Tyr Arg Arg Leu Arg His Ala Leu Trp Pro Ser Leu Pro Asp Leu His
        195                 200                 205

Arg Val Leu Gly Gln Tyr Leu Arg Asp Thr Ala Ala Leu Ser Pro Pro
210                 215                 220

Lys Ala Thr Val Ser Asp Thr Cys Glu Glu Val Glu Pro Ser Leu Leu
225                 230                 235                 240

Glu Ile Leu Pro Lys Ser Ser Glu Arg Thr Pro Leu Pro Leu Leu Glu
                245                 250                 255

Ala Arg Asp Glu Val Glu Gly Phe Leu Gln Asp Thr Phe Pro Gln Gln
            260                 265                 270

Leu Glu Glu Ser Glu Lys Gln Arg Leu Gly Gly Asp Val Gln Ser Pro
        275                 280                 285

Asn Cys Pro Ser Glu Asp Val Val Ile Thr Pro Glu Ser Phe Gly Arg
290                 295                 300

Asp Ser Ser Leu Thr Cys Leu Ala Gly Asn Val Ser Ala Cys Asp Ala
305                 310                 315                 320

Pro Ile Leu Ser Ser Ser Arg Ser Leu Asp Cys Arg Glu Ser Gly Lys
                325                 330                 335

Asn Gly Pro His Val Tyr Gln Asp Leu Leu Leu Ser Leu Gly Thr Thr
            340                 345                 350

Asn Ser Thr Leu Pro Pro Pro Phe Ser Leu Gln Ser Gly Ile Leu Thr
        355                 360                 365

Leu Asn Pro Val Ala Gln Gly Gln Pro Ile Leu Thr Ser Leu Gly Ser
370                 375                 380

Asn Gln Glu Glu Ala Tyr Val Thr Met Ser Ser Phe Tyr Gln Asn Gln
385                 390                 395                 400

Gly Ser Gly Ser Arg Ser Asp Pro Lys Pro Glu Asn Pro Ala Cys Pro
                405                 410                 415

Trp Thr Val Leu Pro Ala Gly Asp Leu Pro Thr His Asp Gly Tyr Leu
            420                 425                 430

Pro Ser Asn Ile Asp Asp Leu Pro Ser His Glu Ala Pro Leu Ala Asp
        435                 440                 445

Ser Leu Glu Glu Leu Glu Pro Gln
        450                 455

<210> SEQ ID NO 181
<211> LENGTH: 454
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 181

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ser Leu Val Thr Ala Leu His Leu Val Leu Gly Leu Ser Ala
                165                 170                 175

Val Leu Gly Leu Leu Leu Arg Trp Gln Phe Pro Ala His Tyr Arg
            180                 185                 190

Arg Leu Arg His Ala Leu Trp Pro Ser Leu Pro Asp Leu His Arg Val
        195                 200                 205

Leu Gly Gln Tyr Leu Arg Asp Thr Ala Ala Leu Ser Pro Pro Lys Ala
    210                 215                 220

Thr Val Ser Asp Thr Cys Glu Glu Val Glu Pro Ser Leu Leu Glu Ile
225                 230                 235                 240

Leu Pro Lys Ser Ser Glu Arg Thr Pro Leu Pro Leu Leu Glu Ala Arg
                245                 250                 255

Asp Glu Val Glu Gly Phe Leu Gln Asp Thr Phe Pro Gln Gln Leu Glu
            260                 265                 270

Glu Ser Glu Lys Gln Arg Leu Gly Gly Asp Val Gln Ser Pro Asn Cys
        275                 280                 285

Pro Ser Glu Asp Val Val Ile Thr Pro Glu Ser Phe Gly Arg Asp Ser
    290                 295                 300

Ser Leu Thr Cys Leu Ala Gly Asn Val Ser Ala Cys Asp Ala Pro Ile
305                 310                 315                 320

Leu Ser Ser Ser Arg Ser Leu Asp Cys Arg Glu Ser Gly Lys Asn Gly
                325                 330                 335

Pro His Val Tyr Gln Asp Leu Leu Leu Ser Leu Gly Thr Thr Asn Ser
            340                 345                 350

Thr Leu Pro Pro Pro Phe Ser Leu Gln Ser Gly Ile Leu Thr Leu Asn
        355                 360                 365

Pro Val Ala Gln Gly Gln Pro Ile Leu Thr Ser Leu Gly Ser Asn Gln
    370                 375                 380

```
Glu Glu Ala Tyr Val Thr Met Ser Ser Phe Tyr Gln Asn Gln Gly Ser
385                 390                 395                 400

Gly Ser Arg Ser Asp Pro Lys Pro Glu Asn Pro Ala Cys Pro Trp Thr
            405                 410                 415

Val Leu Pro Ala Gly Asp Leu Pro Thr His Asp Gly Tyr Leu Pro Ser
            420                 425                 430

Asn Ile Asp Asp Leu Pro Ser His Glu Ala Pro Leu Ala Asp Ser Leu
            435                 440                 445

Glu Glu Leu Glu Pro Gln
        450

<210> SEQ ID NO 182
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Leu Val Thr Ala Leu His Leu Val Leu Gly Leu Ser Ala Val
                165                 170                 175

Leu Gly Leu Leu Leu Leu Arg Trp Gln Phe Pro Ala His Tyr Arg Arg
            180                 185                 190

Leu Arg His Ala Leu Trp Pro Ser Leu Pro Asp Leu His Arg Val Leu
        195                 200                 205

Gly Gln Tyr Leu Arg Asp Thr Ala Ala Leu Ser Pro Pro Lys Ala Thr
    210                 215                 220

Val Ser Asp Thr Cys Glu Glu Val Glu Pro Ser Leu Leu Glu Ile Leu
225                 230                 235                 240

Pro Lys Ser Ser Glu Arg Thr Pro Leu Pro Leu Leu Glu Ala Arg Asp
                245                 250                 255

Glu Val Glu Gly Phe Leu Gln Asp Thr Phe Pro Gln Gln Leu Glu Glu
            260                 265                 270

Ser Glu Lys Gln Arg Leu Gly Gly Asp Val Gln Ser Pro Asn Cys Pro
        275                 280                 285
```

Ser Glu Asp Val Val Ile Thr Pro Glu Ser Phe Gly Arg Asp Ser Ser
          290                 295                 300

Leu Thr Cys Leu Ala Gly Asn Val Ser Ala Cys Asp Ala Pro Ile Leu
305                 310                 315                 320

Ser Ser Ser Arg Ser Leu Asp Cys Arg Glu Ser Gly Lys Asn Gly Pro
                325                 330                 335

His Val Tyr Gln Asp Leu Leu Leu Ser Leu Gly Thr Thr Asn Ser Thr
            340                 345                 350

Leu Pro Pro Pro Phe Ser Leu Gln Ser Gly Ile Leu Thr Leu Asn Pro
        355                 360                 365

Val Ala Gln Gly Gln Pro Ile Leu Thr Ser Leu Gly Ser Asn Gln Glu
    370                 375                 380

Glu Ala Tyr Val Thr Met Ser Ser Phe Tyr Gln Asn Gln Gly Ser Gly
385                 390                 395                 400

Ser Arg Ser Asp Pro Lys Pro Glu Asn Pro Ala Cys Pro Trp Thr Val
                405                 410                 415

Leu Pro Ala Gly Asp Leu Pro Thr His Asp Gly Tyr Leu Pro Ser Asn
            420                 425                 430

Ile Asp Asp Leu Pro Ser His Glu Ala Pro Leu Ala Asp Ser Leu Glu
        435                 440                 445

Glu Leu Glu Pro Gln
450

<210> SEQ ID NO 183
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ile Leu Val Thr Ala Leu His Leu Val Leu Gly Leu Ser Ala
                165                 170                 175

Val Leu Gly Leu Leu Leu Leu Arg Trp Gln Phe Pro Ala His Tyr Arg

```
                    180                 185                 190
Arg Leu Arg His Ala Leu Trp Pro Ser Leu Pro Asp Leu His Arg Val
            195                 200                 205
Leu Gly Gln Tyr Leu Arg Asp Thr Ala Ala Leu Ser Pro Pro Lys Ala
            210                 215                 220
Thr Val Ser Asp Thr Cys Glu Glu Val Glu Pro Ser Leu Leu Glu Ile
225                 230                 235                 240
Leu Pro Lys Ser Ser Glu Arg Thr Pro Leu Pro Leu Leu Glu Ala Arg
            245                 250                 255
Asp Glu Val Glu Gly Phe Leu Gln Asp Thr Phe Pro Gln Gln Leu Glu
            260                 265                 270
Glu Ser Glu Lys Gln Arg Leu Gly Gly Asp Val Gln Ser Pro Asn Cys
            275                 280                 285
Pro Ser Glu Asp Val Val Ile Thr Pro Glu Ser Phe Gly Arg Asp Ser
            290                 295                 300
Ser Leu Thr Cys Leu Ala Gly Asn Val Ser Ala Cys Asp Ala Pro Ile
305                 310                 315                 320
Leu Ser Ser Arg Ser Leu Asp Cys Arg Glu Ser Gly Lys Asn Gly
            325                 330                 335
Pro His Val Tyr Gln Asp Leu Leu Ser Leu Gly Thr Thr Asn Ser
            340                 345                 350
Thr Leu Pro Pro Pro Phe Ser Leu Gln Ser Gly Ile Leu Thr Leu Asn
            355                 360                 365
Pro Val Ala Gln Gly Gln Pro Ile Leu Thr Ser Leu Gly Ser Asn Gln
            370                 375                 380
Glu Glu Ala Tyr Val Thr Met Ser Ser Phe Tyr Gln Asn Gln Gly Ser
385                 390                 395                 400
Gly Ser Arg Ser Asp Pro Lys Pro Glu Asn Pro Ala Cys Pro Trp Thr
            405                 410                 415
Val Leu Pro Ala Gly Asp Leu Pro Thr His Asp Gly Tyr Leu Pro Ser
            420                 425                 430
Asn Ile Asp Asp Leu Pro Ser His Glu Ala Pro Leu Ala Asp Ser Leu
            435                 440                 445
Glu Glu Leu Glu Pro Gln
            450

<210> SEQ ID NO 184
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Ser Phe His Val Ile Trp His
                35                  40                  45
Arg Glu Ser Pro Ser Gly Gln Thr Asp Thr Leu Ala Ala Phe Pro Glu
            50                  55                  60
Asp Arg Ser Gln Pro Gly Gln Asp Cys Arg Phe Arg Val Thr Gln Leu
65                  70                  75                  80
```

-continued

Pro Asn Gly Arg Asp Phe His Met Ser Val Arg Ala Arg Arg Asn
             85                  90                  95

Asp Ser Gly Thr Tyr Val Cys Gly Val Ile Ser Leu Ala Pro Lys Ile
        100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Val Thr Ala Leu His Leu Val Leu Gly Leu Ser Ala Val Leu
                165                 170                 175

Gly Leu Leu Leu Leu Arg Trp Gln Phe Pro Ala His Tyr Arg Arg Leu
            180                 185                 190

Arg His Ala Leu Trp Pro Ser Leu Pro Asp Leu His Arg Val Leu Gly
            195                 200                 205

Gln Tyr Leu Arg Asp Thr Ala Ala Leu Ser Pro Pro Lys Ala Thr Val
        210                 215                 220

Ser Asp Thr Cys Glu Glu Val Glu Pro Ser Leu Leu Glu Ile Leu Pro
225                 230                 235                 240

Lys Ser Ser Glu Arg Thr Pro Leu Pro Leu Leu Glu Ala Arg Asp Glu
                245                 250                 255

Val Glu Gly Phe Leu Gln Asp Thr Phe Pro Gln Gln Leu Glu Glu Ser
            260                 265                 270

Glu Lys Gln Arg Leu Gly Gly Asp Val Gln Ser Pro Asn Cys Pro Ser
        275                 280                 285

Glu Asp Val Val Ile Thr Pro Glu Ser Phe Gly Arg Asp Ser Ser Leu
290                 295                 300

Thr Cys Leu Ala Gly Asn Val Ser Ala Cys Asp Ala Pro Ile Leu Ser
305                 310                 315                 320

Ser Ser Arg Ser Leu Asp Cys Arg Glu Ser Gly Lys Asn Gly Pro His
                325                 330                 335

Val Tyr Gln Asp Leu Leu Leu Ser Leu Gly Thr Thr Asn Ser Thr Leu
            340                 345                 350

Pro Pro Pro Phe Ser Leu Gln Ser Gly Ile Leu Thr Leu Asn Pro Val
        355                 360                 365

Ala Gln Gly Gln Pro Ile Leu Thr Ser Leu Gly Ser Asn Gln Glu Glu
370                 375                 380

Ala Tyr Val Thr Met Ser Ser Phe Tyr Gln Asn Gln Gly Ser Gly Ser
385                 390                 395                 400

Arg Ser Asp Pro Lys Pro Glu Asn Pro Ala Cys Pro Trp Thr Val Leu
                405                 410                 415

Pro Ala Gly Asp Leu Pro Thr His Asp Gly Tyr Leu Pro Ser Asn Ile
            420                 425                 430

Asp Asp Leu Pro Ser His Glu Ala Pro Leu Ala Asp Ser Leu Glu Glu
        435                 440                 445

Leu Glu Pro Gln
    450

<210> SEQ ID NO 185
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Thr Ala Leu His Leu Val Leu Gly Leu Ser Ala Val Leu Gly
                165                 170                 175

Leu Leu Leu Leu Arg Trp Gln Phe Pro Ala His Tyr Arg Arg Leu Arg
            180                 185                 190

His Ala Leu Trp Pro Ser Leu Pro Asp Leu His Arg Val Leu Gly Gln
        195                 200                 205

Tyr Leu Arg Asp Thr Ala Ala Leu Ser Pro Pro Lys Ala Thr Val Ser
    210                 215                 220

Asp Thr Cys Glu Glu Val Glu Pro Ser Leu Leu Glu Ile Leu Pro Lys
225                 230                 235                 240

Ser Ser Glu Arg Thr Pro Leu Pro Leu Leu Glu Ala Arg Asp Glu Val
                245                 250                 255

Glu Gly Phe Leu Gln Asp Thr Phe Pro Gln Gln Leu Glu Glu Ser Glu
            260                 265                 270

Lys Gln Arg Leu Gly Gly Asp Val Gln Ser Pro Asn Cys Pro Ser Glu
        275                 280                 285

Asp Val Val Ile Thr Pro Glu Ser Phe Gly Arg Asp Ser Ser Leu Thr
    290                 295                 300

Cys Leu Ala Gly Asn Val Ser Ala Cys Asp Ala Pro Ile Leu Ser Ser
305                 310                 315                 320

Ser Arg Ser Leu Asp Cys Arg Glu Ser Gly Lys Asn Gly Pro His Val
                325                 330                 335

Tyr Gln Asp Leu Leu Leu Ser Leu Gly Thr Thr Asn Ser Thr Leu Pro
            340                 345                 350

Pro Pro Phe Ser Leu Gln Ser Gly Ile Leu Thr Leu Asn Pro Val Ala
        355                 360                 365

Gln Gly Gln Pro Ile Leu Thr Ser Leu Gly Ser Asn Gln Glu Glu Ala
    370                 375                 380

Tyr Val Thr Met Ser Ser Phe Tyr Gln Asn Gln Gly Ser Gly Ser Arg
385                 390                 395                 400
```

Ser Asp Pro Lys Pro Glu Asn Pro Ala Cys Pro Trp Thr Val Leu Pro
            405                 410                 415

Ala Gly Asp Leu Pro Thr His Asp Gly Tyr Leu Pro Ser Asn Ile Asp
            420                 425                 430

Asp Leu Pro Ser His Glu Ala Pro Leu Ala Asp Ser Leu Glu Glu Leu
            435                 440                 445

Glu Pro Gln
    450

<210> SEQ ID NO 186
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Leu His Leu Val Leu Gly Leu Ser Ala Val Leu Gly Leu
                165                 170                 175

Leu Leu Leu Arg Trp Gln Phe Pro Ala His Tyr Arg Arg Leu Arg His
            180                 185                 190

Ala Leu Trp Pro Ser Leu Pro Asp Leu His Arg Val Leu Gly Gln Tyr
        195                 200                 205

Leu Arg Asp Thr Ala Ala Leu Ser Pro Pro Lys Ala Thr Val Ser Asp
    210                 215                 220

Thr Cys Glu Glu Val Glu Pro Ser Leu Leu Glu Ile Leu Pro Lys Ser
225                 230                 235                 240

Ser Glu Arg Thr Pro Leu Pro Leu Leu Glu Ala Arg Asp Glu Val Glu
                245                 250                 255

Gly Phe Leu Gln Asp Thr Phe Pro Gln Gln Leu Glu Glu Ser Glu Lys
            260                 265                 270

Gln Arg Leu Gly Gly Asp Val Gln Ser Pro Asn Cys Pro Ser Glu Asp
        275                 280                 285

Val Val Ile Thr Pro Glu Ser Phe Gly Arg Asp Ser Ser Leu Thr Cys
    290                 295                 300

```
Leu Ala Gly Asn Val Ser Ala Cys Asp Ala Pro Ile Leu Ser Ser Ser
305                 310                 315                 320

Arg Ser Leu Asp Cys Arg Glu Ser Gly Lys Asn Gly Pro His Val Tyr
            325                 330                 335

Gln Asp Leu Leu Leu Ser Leu Gly Thr Thr Asn Ser Thr Leu Pro Pro
            340                 345                 350

Pro Phe Ser Leu Gln Ser Gly Ile Leu Thr Leu Asn Pro Val Ala Gln
            355                 360                 365

Gly Gln Pro Ile Leu Thr Ser Leu Gly Ser Asn Gln Glu Glu Ala Tyr
        370                 375                 380

Val Thr Met Ser Ser Phe Tyr Gln Asn Gln Gly Ser Gly Ser Arg Ser
385                 390                 395                 400

Asp Pro Lys Pro Glu Asn Pro Ala Cys Pro Trp Thr Val Leu Pro Ala
            405                 410                 415

Gly Asp Leu Pro Thr His Asp Gly Tyr Leu Pro Ser Asn Ile Asp Asp
            420                 425                 430

Leu Pro Ser His Glu Ala Pro Leu Ala Asp Ser Leu Glu Glu Leu Glu
            435                 440                 445

Pro Gln
    450

<210> SEQ ID NO 187
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Leu His Leu Val Leu Gly Leu Ser Ala Val Leu Gly Leu Leu
                165                 170                 175

Leu Leu Arg Trp Gln Phe Pro Ala His Tyr Arg Arg Leu Arg His Ala
            180                 185                 190

Leu Trp Pro Ser Leu Pro Asp Leu His Arg Val Leu Gly Gln Tyr Leu
```

```
            195                 200                 205
Arg Asp Thr Ala Ala Leu Ser Pro Pro Lys Ala Thr Val Ser Asp Thr
210                 215                 220

Cys Glu Glu Val Glu Pro Ser Leu Leu Glu Ile Leu Pro Lys Ser Ser
225                 230                 235                 240

Glu Arg Thr Pro Leu Pro Leu Glu Ala Arg Asp Glu Val Glu Gly
                    245                 250                 255

Phe Leu Gln Asp Thr Phe Pro Gln Gln Leu Glu Glu Ser Lys Gln
                260                 265                 270

Arg Leu Gly Gly Asp Val Gln Ser Pro Asn Cys Pro Ser Glu Asp Val
                275                 280                 285

Val Ile Thr Pro Glu Ser Phe Gly Arg Asp Ser Ser Leu Thr Cys Leu
                290                 295                 300

Ala Gly Asn Val Ser Ala Cys Asp Ala Pro Ile Leu Ser Ser Ser Arg
305                 310                 315                 320

Ser Leu Asp Cys Arg Glu Ser Gly Lys Asn Gly Pro His Val Tyr Gln
                    325                 330                 335

Asp Leu Leu Ser Leu Gly Thr Thr Asn Ser Thr Leu Pro Pro Pro
                340                 345                 350

Phe Ser Leu Gln Ser Gly Ile Leu Thr Leu Asn Pro Val Ala Gln Gly
                355                 360                 365

Gln Pro Ile Leu Thr Ser Leu Gly Ser Asn Gln Glu Glu Ala Tyr Val
                370                 375                 380

Thr Met Ser Ser Phe Tyr Gln Asn Gln Gly Ser Gly Ser Arg Ser Asp
385                 390                 395                 400

Pro Lys Pro Glu Asn Pro Ala Cys Pro Trp Thr Val Leu Pro Ala Gly
                    405                 410                 415

Asp Leu Pro Thr His Asp Gly Tyr Leu Pro Ser Asn Ile Asp Asp Leu
                420                 425                 430

Pro Ser His Glu Ala Pro Leu Ala Asp Ser Leu Glu Glu Leu Glu Pro
                435                 440                 445

Gln

<210> SEQ ID NO 188
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
                35                  40                  45

Arg Glu Ser Pro Ser Gly Gln Thr Asp Thr Leu Ala Ala Phe Pro Glu
            50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
```

```
            100                 105                 110
Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr His Leu Val Leu Gly Leu Ser Ala Val Leu Gly Leu Leu Leu
                165                 170                 175

Leu Arg Trp Gln Phe Pro Ala His Tyr Arg Arg Leu Arg His Ala Leu
                180                 185                 190

Trp Pro Ser Leu Pro Asp Leu His Arg Val Leu Gly Gln Tyr Leu Arg
            195                 200                 205

Asp Thr Ala Ala Leu Ser Pro Pro Lys Ala Thr Val Ser Asp Thr Cys
        210                 215                 220

Glu Glu Val Glu Pro Ser Leu Leu Glu Ile Leu Pro Lys Ser Ser Glu
225                 230                 235                 240

Arg Thr Pro Leu Pro Leu Leu Glu Ala Arg Asp Glu Val Glu Gly Phe
                245                 250                 255

Leu Gln Asp Thr Phe Pro Gln Gln Leu Glu Glu Ser Glu Lys Gln Arg
                260                 265                 270

Leu Gly Gly Asp Val Gln Ser Pro Asn Cys Pro Ser Glu Asp Val Val
            275                 280                 285

Ile Thr Pro Glu Ser Phe Gly Arg Asp Ser Ser Leu Thr Cys Leu Ala
        290                 295                 300

Gly Asn Val Ser Ala Cys Asp Ala Pro Ile Leu Ser Ser Ser Arg Ser
305                 310                 315                 320

Leu Asp Cys Arg Glu Ser Gly Lys Asn Gly Pro His Val Tyr Gln Asp
                325                 330                 335

Leu Leu Leu Ser Leu Gly Thr Thr Asn Ser Thr Leu Pro Pro Pro Phe
                340                 345                 350

Ser Leu Gln Ser Gly Ile Leu Thr Leu Asn Pro Val Ala Gln Gly Gln
            355                 360                 365

Pro Ile Leu Thr Ser Leu Gly Ser Asn Gln Glu Glu Ala Tyr Val Thr
        370                 375                 380

Met Ser Ser Phe Tyr Gln Asn Gln Gly Ser Gly Ser Arg Ser Asp Pro
385                 390                 395                 400

Lys Pro Glu Asn Pro Ala Cys Pro Trp Thr Val Leu Pro Ala Gly Asp
                405                 410                 415

Leu Pro Thr His Asp Gly Tyr Leu Pro Ser Asn Ile Asp Asp Leu Pro
                420                 425                 430

Ser His Glu Ala Pro Leu Ala Asp Ser Leu Glu Glu Leu Glu Pro Gln
            435                 440                 445
```

<210> SEQ ID NO 189
<211> LENGTH: 447
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 189

```
Pro Gly Trp Phe Leu Asp Ser Pro Asp Arg Pro Trp Asn Pro Pro Thr
1               5                   10                  15
```

```
Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr Leu Val Leu Gly Leu Ser Ala Val Leu Gly Leu Leu Leu
                165                 170                 175

Arg Trp Gln Phe Pro Ala His Tyr Arg Arg Leu Arg His Ala Leu Trp
                180                 185                 190

Pro Ser Leu Pro Asp Leu His Arg Val Leu Gly Gln Tyr Leu Arg Asp
            195                 200                 205

Thr Ala Ala Leu Ser Pro Pro Lys Ala Thr Val Ser Asp Thr Cys Glu
210                 215                 220

Glu Val Glu Pro Ser Leu Leu Glu Ile Leu Pro Lys Ser Ser Glu Arg
225                 230                 235                 240

Thr Pro Leu Pro Leu Leu Glu Ala Arg Asp Glu Val Glu Gly Phe Leu
            245                 250                 255

Gln Asp Thr Phe Pro Gln Gln Leu Glu Glu Ser Glu Lys Gln Arg Leu
        260                 265                 270

Gly Gly Asp Val Gln Ser Pro Asn Cys Pro Ser Glu Asp Val Val Ile
    275                 280                 285

Thr Pro Glu Ser Phe Gly Arg Asp Ser Ser Leu Thr Cys Leu Ala Gly
290                 295                 300

Asn Val Ser Ala Cys Asp Ala Pro Ile Leu Ser Ser Ser Arg Ser Leu
305                 310                 315                 320

Asp Cys Arg Glu Ser Gly Lys Asn Gly Pro His Val Tyr Gln Asp Leu
            325                 330                 335

Leu Leu Ser Leu Gly Thr Thr Asn Ser Thr Leu Pro Pro Pro Phe Ser
        340                 345                 350

Leu Gln Ser Gly Ile Leu Thr Leu Asn Pro Val Ala Gln Gly Gln Pro
    355                 360                 365

Ile Leu Thr Ser Leu Gly Ser Asn Gln Glu Glu Ala Tyr Val Thr Met
370                 375                 380

Ser Ser Phe Tyr Gln Asn Gln Gly Ser Gly Ser Arg Ser Asp Pro Lys
385                 390                 395                 400

Pro Glu Asn Pro Ala Cys Pro Trp Thr Val Leu Pro Ala Gly Asp Leu
            405                 410                 415

Pro Thr His Asp Gly Tyr Leu Pro Ser Asn Ile Asp Asp Leu Pro Ser
        420                 425                 430

His Glu Ala Pro Leu Ala Asp Ser Leu Glu Glu Leu Glu Pro Gln
```

<210> SEQ ID NO 190
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Val Leu Gly Leu Ser Ala Val Leu Gly Leu Leu Leu Leu Arg
                165                 170                 175

Trp Gln Phe Pro Ala His Tyr Arg Arg Leu Arg His Ala Leu Trp Pro
            180                 185                 190

Ser Leu Pro Asp Leu His Arg Val Leu Gly Gln Tyr Leu Arg Asp Thr
        195                 200                 205

Ala Ala Leu Ser Pro Pro Lys Ala Thr Val Ser Asp Thr Cys Glu Glu
    210                 215                 220

Val Glu Pro Ser Leu Leu Glu Ile Leu Pro Lys Ser Ser Glu Arg Thr
225                 230                 235                 240

Pro Leu Pro Leu Leu Glu Ala Arg Asp Glu Val Glu Gly Phe Leu Gln
                245                 250                 255

Asp Thr Phe Pro Gln Gln Leu Glu Glu Ser Glu Lys Gln Arg Leu Gly
            260                 265                 270

Gly Asp Val Gln Ser Pro Asn Cys Pro Ser Glu Asp Val Val Ile Thr
        275                 280                 285

Pro Glu Ser Phe Gly Arg Asp Ser Ser Leu Thr Cys Leu Ala Gly Asn
    290                 295                 300

Val Ser Ala Cys Asp Ala Pro Ile Leu Ser Ser Ser Arg Ser Leu Asp
305                 310                 315                 320

Cys Arg Glu Ser Gly Lys Asn Gly Pro His Val Tyr Gln Asp Leu Leu
                325                 330                 335

Leu Ser Leu Gly Thr Thr Asn Ser Thr Leu Pro Pro Pro Phe Ser Leu
            340                 345                 350
```

```
Gln Ser Gly Ile Leu Thr Leu Asn Pro Val Ala Gln Gly Gln Pro Ile
            355                 360                 365

Leu Thr Ser Leu Gly Ser Asn Gln Glu Glu Ala Tyr Val Thr Met Ser
    370                 375                 380

Ser Phe Tyr Gln Asn Gln Gly Ser Gly Ser Arg Ser Asp Pro Lys Pro
385                 390                 395                 400

Glu Asn Pro Ala Cys Pro Trp Thr Val Leu Pro Ala Gly Asp Leu Pro
                405                 410                 415

Thr His Asp Gly Tyr Leu Pro Ser Asn Ile Asp Asp Leu Pro Ser His
            420                 425                 430

Glu Ala Pro Leu Ala Asp Ser Leu Glu Glu Leu Glu Pro Gln
            435                 440                 445

<210> SEQ ID NO 191
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Leu Gly Leu Ser Ala Val Leu Gly Leu Leu Leu Arg Trp
                165                 170                 175

Gln Phe Pro Ala His Tyr Arg Arg Leu Arg His Ala Leu Trp Pro Ser
                180                 185                 190

Leu Pro Asp Leu His Arg Val Leu Gly Gln Tyr Leu Arg Asp Thr Ala
            195                 200                 205

Ala Leu Ser Pro Pro Lys Ala Thr Val Ser Asp Thr Cys Glu Glu Val
    210                 215                 220

Glu Pro Ser Leu Leu Glu Ile Leu Pro Lys Ser Ser Glu Arg Thr Pro
225                 230                 235                 240

Leu Pro Leu Leu Glu Ala Arg Asp Glu Val Glu Gly Phe Leu Gln Asp
                245                 250                 255

Thr Phe Pro Gln Gln Leu Glu Glu Ser Glu Lys Gln Arg Leu Gly Gly
                260                 265                 270
```

```
Asp Val Gln Ser Pro Asn Cys Pro Ser Glu Asp Val Val Ile Thr Pro
            275                 280                 285

Glu Ser Phe Gly Arg Asp Ser Ser Leu Thr Cys Leu Ala Gly Asn Val
        290                 295                 300

Ser Ala Cys Asp Ala Pro Ile Leu Ser Ser Arg Ser Leu Asp Cys
305                 310                 315                 320

Arg Glu Ser Gly Lys Asn Gly Pro His Val Tyr Gln Asp Leu Leu
                325                 330                 335

Ser Leu Gly Thr Thr Asn Ser Thr Leu Pro Pro Phe Ser Leu Gln
            340                 345                 350

Ser Gly Ile Leu Thr Leu Asn Pro Val Ala Gln Gly Gln Pro Ile Leu
            355                 360                 365

Thr Ser Leu Gly Ser Asn Gln Glu Ala Tyr Val Thr Met Ser Ser
        370                 375                 380

Phe Tyr Gln Asn Gln Gly Ser Gly Ser Arg Ser Asp Pro Lys Pro Glu
385                 390                 395                 400

Asn Pro Ala Cys Pro Trp Thr Val Leu Pro Ala Gly Asp Leu Pro Thr
                405                 410                 415

His Asp Gly Tyr Leu Pro Ser Asn Ile Asp Asp Leu Pro Ser His Glu
            420                 425                 430

Ala Pro Leu Ala Asp Ser Leu Glu Glu Leu Glu Pro Gln
            435                 440                 445

<210> SEQ ID NO 192
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Gly Leu Ser Ala Val Leu Gly Leu Leu Leu Leu Arg Trp Gln
                165                 170                 175

Phe Pro Ala His Tyr Arg Arg Leu Arg His Ala Leu Trp Pro Ser Leu
```

```
                180                 185                 190
Pro Asp Leu His Arg Val Leu Gly Gln Tyr Leu Arg Asp Thr Ala Ala
            195                 200                 205

Leu Ser Pro Pro Lys Ala Thr Val Ser Asp Thr Cys Glu Glu Val Glu
        210                 215                 220

Pro Ser Leu Leu Glu Ile Leu Pro Lys Ser Ser Glu Arg Thr Pro Leu
225                 230                 235                 240

Pro Leu Leu Glu Ala Arg Asp Glu Val Glu Gly Phe Leu Gln Asp Thr
            245                 250                 255

Phe Pro Gln Gln Leu Glu Glu Ser Gly Lys Gln Arg Leu Gly Gly Asp
        260                 265                 270

Val Gln Ser Pro Asn Cys Pro Ser Glu Asp Val Val Ile Thr Pro Glu
    275                 280                 285

Ser Phe Gly Arg Asp Ser Ser Leu Thr Cys Leu Ala Gly Asn Val Ser
    290                 295                 300

Ala Cys Asp Ala Pro Ile Leu Ser Ser Arg Ser Leu Asp Cys Arg
305                 310                 315                 320

Glu Ser Gly Lys Asn Gly Pro His Val Tyr Gln Asp Leu Leu Leu Ser
            325                 330                 335

Leu Gly Thr Thr Asn Ser Thr Leu Pro Pro Phe Ser Leu Gln Ser
        340                 345                 350

Gly Ile Leu Thr Leu Asn Pro Val Ala Gln Gly Gln Pro Ile Leu Thr
    355                 360                 365

Ser Leu Gly Ser Asn Gln Glu Glu Ala Tyr Val Thr Met Ser Ser Phe
    370                 375                 380

Tyr Gln Asn Gln Gly Ser Gly Ser Arg Ser Asp Pro Lys Pro Glu Asn
385                 390                 395                 400

Pro Ala Cys Pro Trp Thr Val Leu Pro Ala Gly Asp Leu Pro Thr His
            405                 410                 415

Asp Gly Tyr Leu Pro Ser Asn Ile Asp Asp Leu Pro Ser His Glu Ala
        420                 425                 430

Pro Leu Ala Asp Ser Leu Glu Glu Leu Glu Pro Gln
        435                 440

<210> SEQ ID NO 193
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95
```

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr Leu Ser Ala Val Leu Gly Leu Leu Leu Arg Trp Gln Phe
                165                 170                 175

Pro Ala His Tyr Arg Arg Leu Arg His Ala Leu Trp Pro Ser Leu Pro
                180                 185                 190

Asp Leu His Arg Val Leu Gly Gln Tyr Leu Arg Asp Thr Ala Ala Leu
            195                 200                 205

Ser Pro Pro Lys Ala Thr Val Ser Asp Thr Cys Glu Glu Val Glu Pro
        210                 215                 220

Ser Leu Leu Glu Ile Leu Pro Lys Ser Ser Glu Arg Thr Pro Leu Pro
225                 230                 235                 240

Leu Leu Glu Ala Arg Asp Glu Val Gly Phe Leu Gln Asp Thr Phe
                245                 250                 255

Pro Gln Gln Leu Glu Glu Ser Glu Lys Gln Arg Leu Gly Gly Asp Val
                260                 265                 270

Gln Ser Pro Asn Cys Pro Ser Glu Asp Val Val Ile Thr Pro Glu Ser
            275                 280                 285

Phe Gly Arg Asp Ser Ser Leu Thr Cys Leu Ala Gly Asn Val Ser Ala
        290                 295                 300

Cys Asp Ala Pro Ile Leu Ser Ser Ser Arg Ser Leu Asp Cys Arg Glu
305                 310                 315                 320

Ser Gly Lys Asn Gly Pro His Val Tyr Gln Asp Leu Leu Ser Leu
                325                 330                 335

Gly Thr Thr Asn Ser Thr Leu Pro Pro Phe Ser Leu Gln Ser Gly
                340                 345                 350

Ile Leu Thr Leu Asn Pro Val Ala Gln Gly Gln Pro Ile Leu Thr Ser
            355                 360                 365

Leu Gly Ser Asn Gln Glu Glu Ala Tyr Val Thr Met Ser Ser Phe Tyr
370                 375                 380

Gln Asn Gln Gly Ser Gly Ser Arg Ser Asp Pro Lys Pro Glu Asn Pro
385                 390                 395                 400

Ala Cys Pro Trp Thr Val Leu Pro Ala Gly Asp Leu Pro Thr His Asp
                405                 410                 415

Gly Tyr Leu Pro Ser Asn Ile Asp Asp Leu Pro Ser His Glu Ala Pro
                420                 425                 430

Leu Ala Asp Ser Leu Glu Glu Leu Glu Pro Gln
            435                 440

<210> SEQ ID NO 194
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Pro Gly Trp Phe Leu Asp Ser Pro Asp Arg Pro Trp Asn Pro Pro Thr
1               5                   10                  15

-continued

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ser Ala Val Leu Gly Leu Leu Leu Arg Trp Gln Phe Pro
                165                 170                 175

Ala His Tyr Arg Arg Leu Arg His Ala Leu Trp Pro Ser Leu Pro Asp
            180                 185                 190

Leu His Arg Val Leu Gly Gln Tyr Leu Arg Asp Thr Ala Ala Leu Ser
        195                 200                 205

Pro Pro Lys Ala Thr Val Ser Asp Thr Cys Glu Glu Val Glu Pro Ser
210                 215                 220

Leu Leu Glu Ile Leu Pro Lys Ser Ser Glu Arg Thr Pro Leu Pro Leu
225                 230                 235                 240

Leu Glu Ala Arg Asp Glu Val Glu Gly Phe Leu Gln Asp Thr Phe Pro
                245                 250                 255

Gln Gln Leu Glu Glu Ser Glu Lys Gln Arg Leu Gly Gly Asp Val Gln
            260                 265                 270

Ser Pro Asn Cys Pro Ser Glu Asp Val Val Ile Thr Pro Glu Ser Phe
        275                 280                 285

Gly Arg Asp Ser Ser Leu Thr Cys Leu Ala Gly Asn Val Ser Ala Cys
290                 295                 300

Asp Ala Pro Ile Leu Ser Ser Ser Arg Ser Leu Asp Cys Arg Glu Ser
305                 310                 315                 320

Gly Lys Asn Gly Pro His Val Tyr Gln Asp Leu Leu Leu Ser Leu Gly
                325                 330                 335

Thr Thr Asn Ser Thr Leu Pro Pro Pro Phe Ser Leu Gln Ser Gly Ile
            340                 345                 350

Leu Thr Leu Asn Pro Val Ala Gln Gly Gln Pro Ile Leu Thr Ser Leu
        355                 360                 365

Gly Ser Asn Gln Glu Glu Ala Tyr Val Thr Met Ser Ser Phe Tyr Gln
370                 375                 380

Asn Gln Gly Ser Gly Ser Arg Ser Asp Pro Lys Pro Glu Asn Pro Ala
385                 390                 395                 400

Cys Pro Trp Thr Val Leu Pro Ala Gly Asp Leu Pro Thr His Asp Gly
                405                 410                 415

Tyr Leu Pro Ser Asn Ile Asp Asp Leu Pro Ser His Glu Ala Pro Leu
            420                 425                 430

```
Ala Asp Ser Leu Glu Glu Leu Glu Pro Gln
        435                 440
```

```
<210> SEQ ID NO 195
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195
```

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Val Leu Gly Leu Leu Leu Arg Trp Gln Phe Pro Ala
                165                 170                 175

His Tyr Arg Arg Leu Arg His Ala Leu Trp Pro Ser Leu Pro Asp Leu
            180                 185                 190

His Arg Val Leu Gly Gln Tyr Leu Arg Asp Thr Ala Ala Leu Ser Pro
        195                 200                 205

Pro Lys Ala Thr Val Ser Asp Thr Cys Glu Glu Val Glu Pro Ser Leu
    210                 215                 220

Leu Glu Ile Leu Pro Lys Ser Ser Glu Arg Thr Pro Leu Pro Leu Leu
225                 230                 235                 240

Glu Ala Arg Asp Glu Val Gly Phe Leu Gln Asp Thr Phe Pro Gln
                245                 250                 255

Gln Leu Glu Glu Ser Glu Lys Gln Arg Leu Gly Gly Asp Val Gln Ser
            260                 265                 270

Pro Asn Cys Pro Ser Glu Asp Val Val Ile Thr Pro Glu Ser Phe Gly
        275                 280                 285

Arg Asp Ser Ser Leu Thr Cys Leu Ala Gly Asn Val Ser Ala Cys Asp
    290                 295                 300

Ala Pro Ile Leu Ser Ser Ser Arg Ser Leu Asp Cys Arg Glu Ser Gly
305                 310                 315                 320

Lys Asn Gly Pro His Val Tyr Gln Asp Leu Leu Leu Ser Leu Gly Thr
                325                 330                 335

Thr Asn Ser Thr Leu Pro Pro Pro Phe Ser Leu Gln Ser Gly Ile Leu
            340                 345                 350
```

Thr Leu Asn Pro Val Ala Gln Gly Gln Pro Ile Leu Thr Ser Leu Gly
            355                 360                 365

Ser Asn Gln Glu Glu Ala Tyr Val Thr Met Ser Ser Phe Tyr Gln Asn
        370                 375                 380

Gln Gly Ser Gly Ser Arg Ser Asp Pro Lys Pro Glu Asn Pro Ala Cys
385                 390                 395                 400

Pro Trp Thr Val Leu Pro Ala Gly Asp Leu Pro Thr His Asp Gly Tyr
                405                 410                 415

Leu Pro Ser Asn Ile Asp Asp Leu Pro Ser His Glu Ala Pro Leu Ala
            420                 425                 430

Asp Ser Leu Glu Glu Leu Glu Pro Gln
            435                 440

<210> SEQ ID NO 196
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Val Leu Gly Leu Leu Leu Arg Trp Gln Phe Pro Ala His
                165                 170                 175

Tyr Arg Arg Leu Arg His Ala Leu Trp Pro Ser Leu Pro Asp Leu His
            180                 185                 190

Arg Val Leu Gly Gln Tyr Leu Arg Asp Thr Ala Ala Leu Ser Pro Pro
        195                 200                 205

Lys Ala Thr Val Ser Asp Thr Cys Glu Glu Val Glu Pro Ser Leu Leu
    210                 215                 220

Glu Ile Leu Pro Lys Ser Ser Glu Arg Thr Pro Leu Pro Leu Leu Glu
225                 230                 235                 240

Ala Arg Asp Glu Val Glu Gly Phe Leu Gln Asp Thr Phe Pro Gln Gln
                245                 250                 255

Leu Glu Glu Ser Glu Lys Gln Arg Leu Gly Gly Asp Val Gln Ser Pro

```
                    260                 265                 270
Asn Cys Pro Ser Glu Asp Val Val Ile Thr Pro Glu Ser Phe Gly Arg
                275                 280                 285

Asp Ser Ser Leu Thr Cys Leu Ala Gly Asn Val Ser Ala Cys Asp Ala
            290                 295                 300

Pro Ile Leu Ser Ser Ser Arg Ser Leu Asp Cys Arg Glu Ser Gly Lys
305                 310                 315                 320

Asn Gly Pro His Val Tyr Gln Asp Leu Leu Ser Leu Gly Thr Thr
                325                 330                 335

Asn Ser Thr Leu Pro Pro Phe Ser Leu Gln Ser Gly Ile Leu Thr
            340                 345                 350

Leu Asn Pro Val Ala Gln Gly Gln Pro Ile Leu Thr Ser Leu Gly Ser
                355                 360                 365

Asn Gln Glu Glu Ala Tyr Val Thr Met Ser Ser Phe Tyr Gln Asn Gln
            370                 375                 380

Gly Ser Gly Ser Arg Ser Asp Pro Lys Pro Glu Asn Pro Ala Cys Pro
385                 390                 395                 400

Trp Thr Val Leu Pro Ala Gly Asp Leu Pro Thr His Asp Gly Tyr Leu
                405                 410                 415

Pro Ser Asn Ile Asp Asp Leu Pro Ser His Glu Ala Pro Leu Ala Asp
                420                 425                 430

Ser Leu Glu Glu Leu Glu Pro Gln
            435                 440

<210> SEQ ID NO 197
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Leu Gly Leu Leu Leu Arg Trp Gln Phe Pro Ala His Tyr
                165                 170                 175
```

```
Arg Arg Leu Arg His Ala Leu Trp Pro Ser Leu Pro Asp Leu His Arg
            180                 185                 190

Val Leu Gly Gln Tyr Leu Arg Asp Thr Ala Ala Leu Ser Pro Pro Lys
        195                 200                 205

Ala Thr Val Ser Asp Thr Cys Glu Glu Val Glu Pro Ser Leu Leu Glu
    210                 215                 220

Ile Leu Pro Lys Ser Ser Glu Arg Thr Pro Leu Pro Leu Leu Glu Ala
225                 230                 235                 240

Arg Asp Glu Val Glu Gly Phe Leu Gln Asp Thr Phe Pro Gln Gln Leu
                245                 250                 255

Glu Glu Ser Glu Lys Gln Arg Leu Gly Gly Asp Val Gln Ser Pro Asn
            260                 265                 270

Cys Pro Ser Glu Asp Val Val Ile Thr Pro Glu Ser Phe Gly Arg Asp
        275                 280                 285

Ser Ser Leu Thr Cys Leu Ala Gly Asn Val Ser Ala Cys Asp Ala Pro
    290                 295                 300

Ile Leu Ser Ser Ser Arg Ser Leu Asp Cys Arg Glu Ser Gly Lys Asn
305                 310                 315                 320

Gly Pro His Val Tyr Gln Asp Leu Leu Leu Ser Leu Gly Thr Thr Asn
                325                 330                 335

Ser Thr Leu Pro Pro Pro Phe Ser Leu Gln Ser Gly Ile Leu Thr Leu
            340                 345                 350

Asn Pro Val Ala Gln Gly Gln Pro Ile Leu Thr Ser Leu Gly Ser Asn
        355                 360                 365

Gln Glu Glu Ala Tyr Val Thr Met Ser Ser Phe Tyr Gln Asn Gln Gly
    370                 375                 380

Ser Gly Ser Arg Ser Asp Pro Lys Pro Glu Asn Pro Ala Cys Pro Trp
385                 390                 395                 400

Thr Val Leu Pro Ala Gly Asp Leu Pro Thr His Asp Gly Tyr Leu Pro
                405                 410                 415

Ser Asn Ile Asp Asp Leu Pro Ser His Glu Ala Pro Leu Ala Asp Ser
            420                 425                 430

Leu Glu Glu Leu Glu Pro Gln
        435

<210> SEQ ID NO 198
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Leu Ile Ser Leu Val Thr Ala Leu His Leu Val Leu
                165                 170                 175

Gly Leu Ser Ala Val Leu Gly Leu Leu Leu Arg Trp Gln Phe Pro
            180                 185                 190

Ala His Tyr Arg Arg Leu Arg His Ala Leu Trp Pro Ser Leu Pro Asp
            195                 200                 205

Leu His Arg Val Leu Gly Gln Tyr Leu Arg Asp Thr Ala Ala Leu Ser
        210                 215                 220

Pro Pro Lys Ala Thr Val Ser Asp Thr Cys Glu Glu Val Glu Pro Ser
225                 230                 235                 240

Leu Leu Glu Ile Leu Pro Lys Ser Ser Glu Arg Thr Pro Leu Pro Leu
                245                 250                 255

Leu Glu Ala Arg Asp Glu Val Glu Gly Phe Leu Gln Asp Thr Phe Pro
            260                 265                 270

Gln Gln Leu Glu Glu Ser Glu Lys Gln Arg Leu Gly Gly Asp Val Gln
        275                 280                 285

Ser Pro Asn Cys Pro Ser Glu Asp Val Val Ile Thr Pro Glu Ser Phe
    290                 295                 300

Gly Arg Asp Ser Ser Leu Thr Cys Leu Ala Gly Asn Val Ser Ala Cys
305                 310                 315                 320

Asp Ala Pro Ile Leu Ser Ser Arg Ser Leu Asp Cys Arg Glu Ser
                325                 330                 335

Gly Lys Asn Gly Pro His Val Tyr Gln Asp Leu Leu Leu Ser Leu Gly
            340                 345                 350

Thr Thr Asn Ser Thr Leu Pro Pro Phe Ser Leu Gln Ser Gly Ile
            355                 360                 365

Leu Thr Leu Asn Pro Val Ala Gln Gly Gln Pro Ile Leu Thr Ser Leu
        370                 375                 380

Gly Ser Asn Gln Glu Glu Ala Tyr Val Thr Met Ser Ser Phe Tyr Gln
385                 390                 395                 400

Asn Gln Gly Ser Gly Ser Arg Ser Asp Pro Lys Pro Glu Asn Pro Ala
                405                 410                 415

Cys Pro Trp Thr Val Leu Pro Ala Gly Asp Leu Pro Thr His Asp Gly
            420                 425                 430

Tyr Leu Pro Ser Asn Ile Asp Asp Leu Pro Ser His Glu Ala Pro Leu
        435                 440                 445

Ala Asp Ser Leu Glu Glu Leu Glu Pro Gln
    450                 455

<210> SEQ ID NO 199
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Val Leu Ile Ser Leu Val Thr Ala Leu His Leu Val
                165                 170                 175

Leu Gly Leu Ser Ala Val Leu Gly Leu Leu Leu Arg Trp Gln Phe
            180                 185                 190

Pro Ala His Tyr Arg Arg Leu Arg His Ala Leu Trp Pro Ser Leu Pro
                195                 200                 205

Asp Leu His Arg Val Leu Gly Gln Tyr Leu Arg Asp Thr Ala Ala Leu
            210                 215                 220

Ser Pro Pro Lys Ala Thr Val Ser Asp Thr Cys Glu Glu Val Glu Pro
225                 230                 235                 240

Ser Leu Leu Glu Ile Leu Pro Lys Ser Glu Arg Thr Pro Leu Pro
                245                 250                 255

Leu Leu Glu Ala Arg Asp Glu Val Glu Gly Phe Leu Gln Asp Thr Phe
            260                 265                 270

Pro Gln Gln Leu Glu Glu Ser Glu Lys Gln Arg Leu Gly Gly Asp Val
        275                 280                 285

Gln Ser Pro Asn Cys Pro Ser Glu Asp Val Val Ile Thr Pro Glu Ser
    290                 295                 300

Phe Gly Arg Asp Ser Ser Leu Thr Cys Leu Ala Gly Asn Val Ser Ala
305                 310                 315                 320

Cys Asp Ala Pro Ile Leu Ser Ser Ser Arg Ser Leu Asp Cys Arg Glu
                325                 330                 335

Ser Gly Lys Asn Gly Pro His Val Tyr Gln Asp Leu Leu Leu Ser Leu
            340                 345                 350

Gly Thr Thr Asn Ser Thr Leu Pro Pro Pro Phe Ser Leu Gln Ser Gly
        355                 360                 365

Ile Leu Thr Leu Asn Pro Val Ala Gln Gly Gln Pro Ile Leu Thr Ser
    370                 375                 380

Leu Gly Ser Asn Gln Glu Glu Ala Tyr Val Thr Met Ser Ser Phe Tyr
385                 390                 395                 400

Gln Asn Gln Gly Ser Gly Ser Arg Ser Asp Pro Lys Pro Glu Asn Pro
                405                 410                 415
```

```
Ala Cys Pro Trp Thr Val Leu Pro Ala Gly Asp Leu Pro Thr His Asp
            420                 425                 430

Gly Tyr Leu Pro Ser Asn Ile Asp Asp Leu Pro Ser His Glu Ala Pro
            435                 440                 445

Leu Ala Asp Ser Leu Glu Glu Leu Glu Pro Gln
            450                 455

<210> SEQ ID NO 200
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr Ala Trp Leu Val Leu Ile Ser Leu Val Thr Ala Leu His Leu
                165                 170                 175

Val Leu Gly Leu Ser Ala Val Leu Gly Leu Leu Leu Leu Arg Trp Gln
            180                 185                 190

Phe Pro Ala His Tyr Arg Arg Leu Arg His Ala Leu Trp Pro Ser Leu
        195                 200                 205

Pro Asp Leu His Arg Val Leu Gly Gln Tyr Leu Arg Asp Thr Ala Ala
    210                 215                 220

Leu Ser Pro Pro Lys Ala Thr Val Ser Asp Thr Cys Glu Glu Val Glu
225                 230                 235                 240

Pro Ser Leu Leu Glu Ile Leu Pro Lys Ser Ser Glu Arg Thr Pro Leu
                245                 250                 255

Pro Leu Leu Glu Ala Arg Asp Glu Val Glu Gly Phe Leu Gln Asp Thr
            260                 265                 270

Phe Pro Gln Gln Leu Glu Glu Ser Glu Lys Gln Arg Leu Gly Gly Asp
        275                 280                 285

Val Gln Ser Pro Asn Cys Pro Ser Glu Asp Val Val Ile Thr Pro Glu
    290                 295                 300

Ser Phe Gly Arg Asp Ser Ser Leu Thr Cys Leu Ala Gly Asn Val Ser
```

```
                305                 310                 315                 320
Ala Cys Asp Ala Pro Ile Leu Ser Ser Arg Ser Leu Asp Cys Arg
                325                 330                 335

Glu Ser Gly Lys Asn Gly Pro His Val Tyr Gln Asp Leu Leu Leu Ser
                340                 345                 350

Leu Gly Thr Thr Asn Ser Thr Leu Pro Pro Phe Ser Leu Gln Ser
                355                 360                 365

Gly Ile Leu Thr Leu Asn Pro Val Ala Gln Gly Gln Pro Ile Leu Thr
                370                 375                 380

Ser Leu Gly Ser Asn Gln Glu Glu Ala Tyr Val Thr Met Ser Ser Phe
385                 390                 395                 400

Tyr Gln Asn Gln Gly Ser Gly Ser Arg Ser Asp Pro Lys Pro Glu Asn
                405                 410                 415

Pro Ala Cys Pro Trp Thr Val Leu Pro Ala Gly Asp Leu Pro Thr His
                420                 425                 430

Asp Gly Tyr Leu Pro Ser Asn Ile Asp Asp Leu Pro Ser His Glu Ala
                435                 440                 445

Pro Leu Ala Asp Ser Leu Glu Glu Leu Glu Pro Gln
                450                 455                 460

<210> SEQ ID NO 201
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
                35                  40                  45

Arg Glu Ser Pro Ser Gly Gln Thr Asp Thr Leu Ala Ala Phe Pro Glu
            50                  55                  60

Asp Arg Ser Gln Pro Gly Gln Asp Cys Arg Phe Arg Val Thr Gln Leu
65              70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val Ser Asp Pro Thr Arg Val Glu Thr Ala Thr
145                 150                 155                 160

Glu Thr Ala Trp Ile Leu Val Leu Ile Ser Leu Val Thr Ala Leu His
                165                 170                 175

Leu Val Leu Gly Leu Ser Ala Val Leu Gly Leu Leu Leu Leu Arg Trp
                180                 185                 190

Gln Phe Pro Ala His Tyr Arg Arg Leu Arg His Ala Leu Trp Pro Ser
            195                 200                 205
```

```
Leu Pro Asp Leu His Arg Val Leu Gly Gln Tyr Leu Arg Asp Thr Ala
            210                 215                 220
Ala Leu Ser Pro Pro Lys Ala Thr Val Ser Asp Thr Cys Glu Val
225                 230                 235                 240
Glu Pro Ser Leu Leu Glu Ile Leu Pro Lys Ser Ser Glu Arg Thr Pro
                245                 250                 255
Leu Pro Leu Leu Glu Ala Arg Asp Glu Val Glu Gly Phe Leu Gln Asp
            260                 265                 270
Thr Phe Pro Gln Gln Leu Glu Ser Glu Lys Gln Arg Leu Gly Gly
                275                 280                 285
Asp Val Gln Ser Pro Asn Cys Pro Ser Glu Asp Val Val Ile Thr Pro
290                 295                 300
Glu Ser Phe Gly Arg Asp Ser Ser Leu Thr Cys Leu Ala Gly Asn Val
305                 310                 315                 320
Ser Ala Cys Asp Ala Pro Ile Leu Ser Ser Arg Ser Leu Asp Cys
                325                 330                 335
Arg Glu Ser Gly Lys Asn Gly Pro His Val Tyr Gln Asp Leu Leu
                340                 345                 350
Ser Leu Gly Thr Thr Asn Ser Thr Leu Pro Pro Phe Ser Leu Gln
            355                 360                 365
Ser Gly Ile Leu Thr Leu Asn Pro Val Ala Gln Gly Gln Pro Ile Leu
370                 375                 380
Thr Ser Leu Gly Ser Asn Gln Glu Glu Ala Tyr Val Thr Met Ser Ser
385                 390                 395                 400
Phe Tyr Gln Asn Gln Gly Ser Gly Ser Arg Ser Asp Pro Lys Pro Glu
                405                 410                 415
Asn Pro Ala Cys Pro Trp Thr Val Leu Pro Ala Gly Asp Leu Pro Thr
                420                 425                 430
His Asp Gly Tyr Leu Pro Ser Asn Ile Asp Asp Leu Pro Ser His Glu
            435                 440                 445
Ala Pro Leu Ala Asp Ser Leu Glu Glu Leu Glu Pro Gln
            450                 455                 460

<210> SEQ ID NO 202
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Ser Phe His Val Ile Trp His
            35                  40                  45
Arg Glu Ser Pro Ser Gly Gln Thr Asp Thr Leu Ala Ala Phe Pro Glu
50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Val Cys Gly Val Ile Ser Leu Ala Pro Lys Ile
                100                 105                 110
```

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Leu Ile Leu Val Leu Ile Ser Leu Val Thr Ala Leu
                165                 170                 175

His Leu Val Leu Gly Leu Ser Ala Val Leu Gly Leu Leu Leu Leu Arg
            180                 185                 190

Trp Gln Phe Pro Ala His Tyr Arg Arg Leu Arg His Ala Leu Trp Pro
        195                 200                 205

Ser Leu Pro Asp Leu His Arg Val Leu Gly Gln Tyr Leu Arg Asp Thr
    210                 215                 220

Ala Ala Leu Ser Pro Pro Lys Ala Thr Val Ser Asp Thr Cys Glu Glu
225                 230                 235                 240

Val Glu Pro Ser Leu Leu Glu Ile Leu Pro Lys Ser Ser Glu Arg Thr
                245                 250                 255

Pro Leu Pro Leu Leu Glu Ala Arg Asp Glu Val Glu Gly Phe Leu Gln
            260                 265                 270

Asp Thr Phe Pro Gln Gln Leu Glu Glu Ser Glu Lys Gln Arg Leu Gly
        275                 280                 285

Gly Asp Val Gln Ser Pro Asn Cys Pro Ser Glu Asp Val Val Ile Thr
    290                 295                 300

Pro Glu Ser Phe Gly Arg Asp Ser Ser Leu Thr Cys Leu Ala Gly Asn
305                 310                 315                 320

Val Ser Ala Cys Asp Ala Pro Ile Leu Ser Ser Ser Arg Ser Leu Asp
                325                 330                 335

Cys Arg Glu Ser Gly Lys Asn Gly Pro His Val Tyr Gln Asp Leu Leu
            340                 345                 350

Leu Ser Leu Gly Thr Thr Asn Ser Thr Leu Pro Pro Pro Phe Ser Leu
        355                 360                 365

Gln Ser Gly Ile Leu Thr Leu Asn Pro Val Ala Gln Gly Gln Pro Ile
    370                 375                 380

Leu Thr Ser Leu Gly Ser Asn Gln Glu Glu Ala Tyr Val Thr Met Ser
385                 390                 395                 400

Ser Phe Tyr Gln Asn Gln Gly Ser Gly Ser Arg Ser Asp Pro Lys Pro
                405                 410                 415

Glu Asn Pro Ala Cys Pro Trp Thr Val Leu Pro Ala Gly Asp Leu Pro
            420                 425                 430

Thr His Asp Gly Tyr Leu Pro Ser Asn Ile Asp Asp Leu Pro Ser His
        435                 440                 445

Glu Ala Pro Leu Ala Asp Ser Leu Glu Glu Leu Glu Pro Gln
    450                 455                 460

<210> SEQ ID NO 203
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Pro Gly Trp Phe Leu Asp Ser Pro Asp Arg Pro Trp Asn Pro Pro Thr

```
             1               5                  10                 15
         Phe Ser Pro Ala Leu Leu Val Val Thr Glu Gly Asp Asn Ala Thr Phe
                          20                 25                 30

Thr Cys Ser Phe Ser Asn Thr Ser Glu Ser Phe His Val Ile Trp His
                          35                 40                 45

Arg Glu Ser Pro Ser Gly Gln Thr Asp Thr Leu Ala Ala Phe Pro Glu
                          50                 55                 60

Asp Arg Ser Gln Pro Gly Gln Asp Cys Arg Phe Arg Val Thr Gln Leu
         65                      70                 75                 80

Pro Asn Gly Arg Asp Phe His Met Ser Val Arg Ala Arg Arg Asn
                              85                 90                 95

Asp Ser Gly Thr Tyr Val Cys Gly Val Ile Ser Leu Ala Pro Lys Ile
                             100                105                110

Gln Ile Lys Glu Ser Leu Arg Ala Glu Leu Arg Val Thr Glu Arg Arg
                             115                120                125

Ala Glu Val Pro Thr Ala His Pro Ser Pro Ser Pro Arg Pro Ala Gly
         130                     135                140

Gln Phe Gln Thr Leu Val Ser Asp Pro Thr Arg Val Glu Thr Ala Thr
         145                     150                155                160

Glu Thr Ala Trp Leu Leu Ile Leu Val Leu Ile Ser Leu Val Thr Ala
                             165                170                175

Leu His Leu Val Leu Gly Leu Ser Ala Val Leu Gly Leu Leu Leu Leu
                             180                185                190

Arg Trp Gln Phe Pro Ala His Tyr Arg Arg Leu Arg His Ala Leu Trp
                             195                200                205

Pro Ser Leu Pro Asp Leu His Arg Val Leu Gly Gln Tyr Leu Arg Asp
                 210                215                220

Thr Ala Ala Leu Ser Pro Pro Lys Ala Thr Val Ser Asp Thr Cys Glu
         225                     230                235                240

Glu Val Glu Pro Ser Leu Leu Glu Ile Leu Pro Lys Ser Ser Glu Arg
                             245                250                255

Thr Pro Leu Pro Leu Leu Glu Ala Arg Asp Glu Val Glu Gly Phe Leu
                             260                265                270

Gln Asp Thr Phe Pro Gln Gln Leu Glu Glu Ser Glu Lys Gln Arg Leu
                             275                280                285

Gly Gly Asp Val Gln Ser Pro Asn Cys Pro Ser Glu Asp Val Val Ile
                 290                295                300

Thr Pro Glu Ser Phe Gly Arg Asp Ser Ser Leu Thr Cys Leu Ala Gly
         305                     310                315                320

Asn Val Ser Ala Cys Asp Ala Pro Ile Leu Ser Ser Ser Arg Ser Leu
                             325                330                335

Asp Cys Arg Glu Ser Gly Lys Asn Gly Pro His Val Tyr Gln Asp Leu
                             340                345                350

Leu Leu Ser Leu Gly Thr Thr Asn Ser Thr Leu Pro Pro Pro Phe Ser
                             355                360                365

Leu Gln Ser Gly Ile Leu Thr Leu Asn Pro Val Ala Gln Gly Gln Pro
                 370                375                380

Ile Leu Thr Ser Leu Gly Ser Asn Gln Glu Glu Ala Tyr Val Thr Met
         385                     390                395                400

Ser Ser Phe Tyr Gln Asn Gln Gly Ser Gly Ser Arg Ser Asp Pro Lys
                             405                410                415

Pro Glu Asn Pro Ala Cys Pro Trp Thr Val Leu Pro Ala Gly Asp Leu
                             420                425                430
```

```
Pro Thr His Asp Gly Tyr Leu Pro Ser Asn Ile Asp Asp Leu Pro Ser
        435                 440                 445

His Glu Ala Pro Leu Ala Asp Ser Leu Glu Glu Leu Glu Pro Gln
    450                 455                 460

<210> SEQ ID NO 204
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Val Leu Leu Ile Leu Val Leu Ile Ser Leu Val Thr
                165                 170                 175

Ala Leu His Leu Val Leu Gly Leu Ser Ala Val Leu Gly Leu Leu Leu
            180                 185                 190

Leu Arg Trp Gln Phe Pro Ala His Tyr Arg Arg Leu Arg His Ala Leu
        195                 200                 205

Trp Pro Ser Leu Pro Asp Leu His Arg Val Leu Gly Gln Tyr Leu Arg
    210                 215                 220

Asp Thr Ala Ala Leu Ser Pro Pro Lys Ala Thr Val Ser Asp Thr Cys
225                 230                 235                 240

Glu Glu Val Glu Pro Ser Leu Leu Glu Ile Leu Pro Lys Ser Ser Glu
                245                 250                 255

Arg Thr Pro Leu Pro Leu Leu Glu Ala Arg Asp Glu Val Glu Gly Phe
            260                 265                 270

Leu Gln Asp Thr Phe Pro Gln Gln Leu Glu Glu Ser Glu Lys Gln Arg
        275                 280                 285

Leu Gly Gly Asp Val Gln Ser Pro Asn Cys Pro Ser Glu Asp Val Val
    290                 295                 300

Ile Thr Pro Glu Ser Phe Gly Arg Asp Ser Ser Leu Thr Cys Leu Ala
305                 310                 315                 320

Gly Asn Val Ser Ala Cys Asp Ala Pro Ile Leu Ser Ser Ser Arg Ser
```

```
                    325                 330                 335
Leu Asp Cys Arg Glu Ser Gly Lys Asn Gly Pro His Val Tyr Gln Asp
                340                 345                 350

Leu Leu Leu Ser Leu Gly Thr Thr Asn Ser Thr Leu Pro Pro Pro Phe
                355                 360                 365

Ser Leu Gln Ser Gly Ile Leu Thr Leu Asn Pro Val Ala Gln Gly Gln
                370                 375                 380

Pro Ile Leu Thr Ser Leu Gly Ser Asn Gln Glu Glu Ala Tyr Val Thr
385                 390                 395                 400

Met Ser Ser Phe Tyr Gln Asn Gln Gly Ser Gly Ser Arg Ser Asp Pro
                405                 410                 415

Lys Pro Glu Asn Pro Ala Cys Pro Trp Thr Val Leu Pro Ala Gly Asp
                420                 425                 430

Leu Pro Thr His Asp Gly Tyr Leu Pro Ser Asn Ile Asp Asp Leu Pro
                435                 440                 445

Ser His Glu Ala Pro Leu Ala Asp Ser Leu Glu Glu Leu Glu Pro Gln
                450                 455                 460

<210> SEQ ID NO 205
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
                35                  40                  45

Arg Glu Ser Pro Ser Gly Gln Thr Asp Thr Leu Ala Ala Phe Pro Glu
            50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Leu Val Leu Leu Ile Leu Val Leu Ile Ser Leu Val
                165                 170                 175

Thr Ala Leu His Leu Val Leu Gly Leu Ser Ala Val Leu Gly Leu Leu
                180                 185                 190

Leu Leu Arg Trp Gln Phe Pro Ala His Tyr Arg Arg Leu Arg His Ala
                195                 200                 205

Leu Trp Pro Ser Leu Pro Asp Leu His Arg Val Leu Gly Gln Tyr Leu
                210                 215                 220
```

```
Arg Asp Thr Ala Ala Leu Ser Pro Pro Lys Ala Thr Val Ser Asp Thr
225                 230                 235                 240

Cys Glu Glu Val Glu Pro Ser Leu Leu Glu Ile Leu Pro Lys Ser Ser
            245                 250                 255

Glu Arg Thr Pro Leu Pro Leu Leu Glu Ala Arg Asp Glu Val Glu Gly
        260                 265                 270

Phe Leu Gln Asp Thr Phe Pro Gln Gln Leu Glu Glu Ser Glu Lys Gln
    275                 280                 285

Arg Leu Gly Gly Asp Val Gln Ser Pro Asn Cys Pro Ser Glu Asp Val
290                 295                 300

Val Ile Thr Pro Glu Ser Phe Gly Arg Asp Ser Ser Leu Thr Cys Leu
305                 310                 315                 320

Ala Gly Asn Val Ser Ala Cys Asp Ala Pro Ile Leu Ser Ser Ser Arg
            325                 330                 335

Ser Leu Asp Cys Arg Glu Ser Gly Lys Asn Gly Pro His Val Tyr Gln
        340                 345                 350

Asp Leu Leu Leu Ser Leu Gly Thr Thr Asn Ser Thr Leu Pro Pro Pro
    355                 360                 365

Phe Ser Leu Gln Ser Gly Ile Leu Thr Leu Asn Pro Val Ala Gln Gly
370                 375                 380

Gln Pro Ile Leu Thr Ser Leu Gly Ser Asn Gln Glu Glu Ala Tyr Val
385                 390                 395                 400

Thr Met Ser Ser Phe Tyr Gln Asn Gln Gly Ser Gly Ser Arg Ser Asp
            405                 410                 415

Pro Lys Pro Glu Asn Pro Ala Cys Pro Trp Thr Val Leu Pro Ala Gly
        420                 425                 430

Asp Leu Pro Thr His Asp Gly Tyr Leu Pro Ser Asn Ile Asp Asp Leu
    435                 440                 445

Pro Ser His Glu Ala Pro Leu Ala Asp Ser Leu Glu Glu Leu Glu Pro
450                 455                 460

Gln
465

<210> SEQ ID NO 206
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Val Cys Gly Val Ile Ser Leu Ala Pro Lys Ile
        100                 105                 110
```

```
Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu Leu Leu Val Leu Gly
                165                 170                 175

Leu Asn Ala Val Leu Gly Leu Leu Leu Arg Lys Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Ala Arg Asp Glu Val Glu Gly Phe Leu Gln Asp Thr Phe Pro Gln
            260                 265                 270

Gln Leu Glu Glu Ser Glu Lys Gln Arg Leu Gly Gly Asp Val Gln Ser
        275                 280                 285

Pro Asn Cys Pro Ser Glu Asp Val Val Ile Thr Pro Glu Ser Phe Gly
    290                 295                 300

Arg Asp Ser Ser Leu Thr Cys Leu Ala Gly Asn Val Ser Ala Cys Asp
305                 310                 315                 320

Ala Pro Ile Leu Ser Ser Arg Ser Leu Asp Cys Arg Glu Ser Gly
                325                 330                 335

Lys Asn Gly Pro His Val Tyr Gln Asp Leu Leu Leu Ser Leu Gly Thr
            340                 345                 350

Thr Asn Ser Thr Leu Pro Pro Pro Phe Ser Leu Gln Ser Gly Ile Leu
        355                 360                 365

Thr Leu Asn Pro Val Ala Gln Gly Gln Pro Ile Leu Thr Ser Leu Gly
    370                 375                 380

Ser Asn Gln Glu Glu Ala Tyr Val Thr Met Ser Ser Phe Tyr Gln Asn
385                 390                 395                 400

Gln

<210> SEQ ID NO 207
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60
```

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Asn Ala Val Leu Gly Leu Leu Leu Arg Lys Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Asp Glu Gly Val Ala Gly Ala Pro Thr Gly Ser Ser Pro Gln Pro
            260                 265                 270

Leu Gln Pro Leu Ser Gly Glu Asp Asp Ala Tyr Cys Thr Phe Pro Ser
        275                 280                 285

Arg Asp Asp Leu Leu Leu Phe Ser Pro Ser Gly Gln Gly Glu Phe Arg
290                 295                 300

Ala Leu Asn Ala Arg Leu Pro Leu Asn Thr Asp Ala Tyr Leu Ser Leu
305                 310                 315                 320

Gln Glu Leu Gln Gly Gln Asp Pro Thr His Leu Val
                325                 330

<210> SEQ ID NO 208
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn

```
                    85                  90                  95
Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Ser Ala Val Leu Gly Leu Leu Leu Arg Trp Gln Phe Pro Ala
                180                 185                 190

His Tyr Arg Arg Leu Arg His Ala Leu Trp Pro Ser Leu Pro Asp Leu
            195                 200                 205

His Arg Val Leu Gly Gln Tyr Leu Arg Asp Thr Ala Ala Leu Ser Pro
        210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Ala Arg Asp Glu Val Glu Gly Phe Leu Gln Asp Thr Phe Pro Gln
            260                 265                 270

Gln Leu Glu Glu Ser Glu Lys Gln Arg Leu Gly Gly Asp Val Gln Ser
        275                 280                 285

Pro Asn Cys Pro Ser Glu Asp Val Val Ile Thr Pro Glu Ser Phe Gly
290                 295                 300

Arg Asp Ser Ser Leu Thr Cys Leu Ala Gly Asn Val Ser Ala Cys Asp
305                 310                 315                 320

Ala Pro Ile Leu Ser Ser Arg Ser Leu Asp Cys Arg Glu Ser Gly
                325                 330                 335

Lys Asn Gly Pro His Val Tyr Gln Asp Leu Leu Leu Ser Leu Gly Thr
            340                 345                 350

Thr Asn Ser Thr Leu Pro Pro Pro Phe Ser Leu Gln Ser Gly Ile Leu
        355                 360                 365

Thr Leu Asn Pro Val Ala Gln Gly Gln Pro Ile Leu Thr Ser Leu Gly
        370                 375                 380

Ser Asn Gln Glu Glu Ala Tyr Val Thr Met Ser Ser Phe Tyr Gln Asn
385                 390                 395                 400

Gln

<210> SEQ ID NO 209
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
```

```
                35                  40                  45
Arg Glu Ser Pro Ser Gly Gln Thr Asp Thr Leu Ala Ala Phe Pro Glu
 50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Ser Ala Val Leu Gly Leu Leu Leu Arg Trp Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Glu Arg Thr Pro Leu Pro Leu Leu
                245                 250                 255

Glu Asp Glu Gly Val Ala Gly Ala Pro Thr Gly Ser Ser Pro Gln Pro
            260                 265                 270

Leu Gln Pro Leu Ser Gly Glu Asp Asp Ala Tyr Cys Thr Phe Pro Ser
        275                 280                 285

Arg Asp Asp Leu Leu Leu Phe Ser Pro Ser Gly Gln Gly Glu Phe Arg
    290                 295                 300

Ala Leu Asn Ala Arg Leu Pro Leu Asn Thr Asp Ala Tyr Leu Ser Leu
305                 310                 315                 320

Gln Glu Leu Gln Gly Gln Asp Pro Thr His Leu Val
                325                 330

<210> SEQ ID NO 210
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Ala Leu Pro Val Thr Ala Leu Leu Leu Pro Leu Ala Leu Leu Leu
1               5                  10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60
```

```
His Val Ile Trp His Arg Glu Ser Pro Ser Gly Gln Thr Asp Thr Leu
 65                  70                  75                  80

Ala Ala Phe Pro Glu Asp Arg Ser Gln Pro Gly Gln Asp Cys Arg Phe
             85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

Leu Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Leu Glu Ala Arg Asp Glu Val Glu Gly Phe Leu Gln
        275                 280                 285

Asp Thr Phe Pro Gln Gln Leu Glu Glu Ser Glu Lys Gln Arg Leu Gly
    290                 295                 300

Gly Asp Val Gln Ser Pro Asn Cys Pro Ser Glu Asp Val Val Ile Thr
305                 310                 315                 320

Pro Glu Ser Phe Gly Arg Asp Ser Ser Leu Thr Cys Leu Ala Gly Asn
                325                 330                 335

Val Ser Ala Cys Asp Ala Pro Ile Leu Ser Ser Ser Arg Ser Leu Asp
            340                 345                 350

Cys Arg Glu Ser Gly Lys Asn Gly Pro His Val Tyr Gln Asp Leu Leu
        355                 360                 365

Leu Ser Leu Gly Thr Thr Asn Ser Thr Leu Pro Pro Pro Phe Ser Leu
    370                 375                 380

Gln Ser Gly Ile Leu Thr Leu Asn Pro Val Ala Gln Gly Gln Pro Ile
385                 390                 395                 400

Leu Thr Ser Leu Gly Ser Asn Gln Glu Glu Ala Tyr Val Thr Met Ser
                405                 410                 415

Ser Phe Tyr Gln Asn Gln
            420
```

<210> SEQ ID NO 211
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Asn Ala Val Leu Gly Leu Leu Leu Leu Arg
        195                 200                 205

Lys Gln Phe Pro Ala His Tyr Arg Arg Leu Arg His Ala Leu Trp Pro
210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Leu Glu Asp Glu Gly Val Ala Gly Ala Pro Thr Gly
        275                 280                 285

Ser Ser Pro Gln Pro Leu Gln Pro Leu Ser Gly Glu Asp Asp Ala Tyr
    290                 295                 300

Cys Thr Phe Pro Ser Arg Asp Asp Leu Leu Leu Phe Ser Pro Ser Gly
305                 310                 315                 320

Gln Gly Glu Phe Arg Ala Leu Asn Ala Arg Leu Pro Leu Asn Thr Asp
                325                 330                 335

Ala Tyr Leu Ser Leu Gln Glu Leu Gln Gly Gln Asp Pro Thr His Leu
            340                 345                 350

Val
```

<210> SEQ ID NO 212
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

-continued

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
        50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Ser Ala Val Leu Gly Leu Leu Leu Leu Arg
        195                 200                 205

Trp Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Leu Glu Ala Arg Asp Glu Val Glu Gly Phe Leu Gln
        275                 280                 285

Asp Thr Phe Pro Gln Gln Leu Glu Glu Ser Glu Lys Gln Arg Leu Gly
    290                 295                 300

Gly Asp Val Gln Ser Pro Asn Cys Pro Ser Glu Asp Val Val Ile Thr
305                 310                 315                 320

Pro Glu Ser Phe Gly Arg Asp Ser Ser Leu Thr Cys Leu Ala Gly Asn
                325                 330                 335

Val Ser Ala Cys Asp Ala Pro Ile Leu Ser Ser Ser Arg Ser Leu Asp
            340                 345                 350

Cys Arg Glu Ser Gly Lys Asn Gly Pro His Val Tyr Gln Asp Leu Leu
        355                 360                 365

Leu Ser Leu Gly Thr Thr Asn Ser Thr Leu Pro Pro Pro Phe Ser Leu
    370                 375                 380

Gln Ser Gly Ile Leu Thr Leu Asn Pro Val Ala Gln Gly Gln Pro Ile
385                 390                 395                 400

Leu Thr Ser Leu Gly Ser Asn Gln Glu Glu Ala Tyr Val Thr Met Ser
                405                 410                 415
```

```
Ser Phe Tyr Gln Asn Gln
            420
```

<210> SEQ ID NO 213
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

His Val Ile Trp His Arg Glu Ser Pro Ser Gly Gln Thr Asp Thr Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Val Cys Gly Val Ile Ser
        115                 120                 125

Leu Ala Pro Lys Ile Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Ser Asp Pro Thr Arg
                165                 170                 175

Val Glu Thr Ala Thr Glu Thr Ala Trp Ile Ser Leu Val Thr Ala Leu
            180                 185                 190

His Leu Val Leu Gly Leu Ser Ala Val Leu Gly Leu Leu Leu Leu Arg
        195                 200                 205

Trp Gln Phe Pro Ala His Tyr Arg Arg Leu Arg His Ala Leu Trp Pro
    210                 215                 220

Ser Leu Pro Asp Leu His Arg Val Leu Gly Gln Tyr Leu Arg Asp Thr
225                 230                 235                 240

Ala Ala Leu Ser Pro Pro Lys Ala Thr Val Ser Asp Thr Cys Glu Glu
                245                 250                 255

Val Glu Pro Ser Leu Leu Glu Ile Leu Pro Lys Ser Ser Glu Arg Thr
            260                 265                 270

Pro Leu Pro Leu Leu Glu Asp Glu Gly Val Ala Gly Ala Pro Thr Gly
        275                 280                 285

Ser Ser Pro Gln Pro Leu Gln Pro Leu Ser Gly Glu Asp Asp Ala Tyr
    290                 295                 300

Cys Thr Phe Pro Ser Arg Asp Asp Leu Leu Leu Phe Ser Pro Ser Gly
305                 310                 315                 320

Gln Gly Glu Phe Arg Ala Leu Asn Ala Arg Leu Pro Leu Asn Thr Asp
                325                 330                 335

Ala Tyr Leu Ser Leu Gln Glu Leu Gln Gly Gln Asp Pro Thr His Leu
            340                 345                 350
```

Val

<210> SEQ ID NO 214
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Asn Ala Val Leu Gly Leu Leu Leu Arg Lys Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Gln Gln Asp Lys Val Pro Glu Pro Ala Ser Leu Ser Ser Asn His
            260                 265                 270

Ser Leu Thr Ser Cys Phe Thr Asn Gln Gly Tyr Phe Phe Phe His Leu
        275                 280                 285

Pro Asp Ala Leu Glu Ile Glu Ala Cys Gln Asp Glu Gly Val Ala Gly
    290                 295                 300

Ala Pro Thr Gly Ser Ser Pro Gln Pro Leu Gln Pro Leu Ser Gly Glu
305                 310                 315                 320

Asp Asp Ala Tyr Cys Thr Phe Pro Ser Arg Asp Asp Leu Leu Leu Phe
                325                 330                 335

Ser Pro Ser Gly Gln Gly Glu Phe Arg Ala Leu Asn Ala Arg Leu Pro
            340                 345                 350

-continued

```
Leu Asn Thr Asp Ala Tyr Leu Ser Leu Gln Glu Leu Gln Gly Gln Asp
        355                 360                 365

Pro Thr His Leu Val
    370

<210> SEQ ID NO 215
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu Leu Leu Val Leu Gly
                165                 170                 175

Leu Asn Ala Val Leu Gly Leu Leu Leu Arg Lys Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Gln Gln Asp Lys Val Pro Glu Pro Ala Ser Leu Ser Ser Asn His
            260                 265                 270

Ser Leu Thr Ser Cys Phe Thr Asn Gln Gly Tyr Phe Phe Phe His Leu
        275                 280                 285

Pro Asp Ala Leu Glu Ile Glu Ala Cys Gln Asp Glu Gly Val Ala Gly
    290                 295                 300

Ala Pro Thr Gly Ser Ser Pro Gln Pro Leu Gln Pro Leu Ser Gly Glu
305                 310                 315                 320

Asp Asp Ala Tyr Cys Thr Phe Pro Ser Arg Asp Asp Leu Leu Leu Phe
```

```
                    325                 330                 335
Ser Pro Ser Gly Gln Gly Glu Phe Arg Ala Leu Asn Ala Arg Leu Pro
            340                 345                 350

Leu Asn Thr Asp Ala Tyr Leu Ser Leu Gln Glu Leu Gln Gly Gln Asp
        355                 360                 365

Pro Thr His Leu Val
    370

<210> SEQ ID NO 216
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Pro Gly Trp Phe Leu Asp Ser Pro Asp Arg Pro Trp Asn Pro Pro Thr
1               5                  10                   15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Ser Ala Val Leu Gly Leu Leu Leu Arg Trp Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Gln Gln Asp Lys Val Pro Glu Pro Ala Ser Leu Ser Ser Asn His
            260                 265                 270

Ser Leu Thr Ser Cys Phe Thr Asn Gln Gly Tyr Phe Phe Phe His Leu
        275                 280                 285

Pro Asp Ala Leu Glu Ile Glu Ala Cys Gln Asp Glu Gly Val Ala Gly
    290                 295                 300
```

```
Ala Pro Thr Gly Ser Ser Pro Gln Pro Leu Gln Pro Leu Ser Gly Glu
305                 310                 315                 320

Asp Asp Ala Tyr Cys Thr Phe Pro Ser Arg Asp Asp Leu Leu Leu Phe
            325                 330                 335

Ser Pro Ser Gly Gln Gly Glu Phe Arg Ala Leu Asn Ala Arg Leu Pro
        340                 345                 350

Leu Asn Thr Asp Ala Tyr Leu Ser Leu Gln Glu Leu Gln Gly Gln Asp
        355                 360                 365

Pro Thr His Leu Val
    370

<210> SEQ ID NO 217
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Leu His Leu Val Leu Gly Leu Ser Ala Val Leu Gly Leu
                165                 170                 175

Leu Leu Leu Arg Trp Gln Phe Pro Ala His Tyr Arg Arg Leu Arg His
            180                 185                 190

Ala Leu Trp Pro Ser Leu Pro Asp Leu His Arg Val Leu Gly Gln Tyr
        195                 200                 205

Leu Arg Asp Thr Ala Ala Leu Ser Pro Lys Ala Thr Val Ser Asp
    210                 215                 220

Thr Cys Glu Glu Val Glu Pro Ser Leu Leu Glu Ile Leu Pro Lys Ser
225                 230                 235                 240

Ser Glu Arg Thr Pro Leu Pro Leu Leu Glu Asp Glu Gly Val Ala Gly
                245                 250                 255

Ala Pro Thr Gly Ser Ser Pro Gln Pro Leu Gln Pro Leu Ser Gly Glu
            260                 265                 270

Asp Asp Ala Tyr Cys Thr Phe Pro Ser Arg Asp Asp Leu Leu Leu Phe
        275                 280                 285
```

```
Ser Pro Ser Gly Gln Gly Glu Phe Arg Ala Leu Asn Ala Arg Leu Pro
    290                 295                 300

Leu Asn Thr Asp Ala Tyr Leu Ser Leu Gln Glu Leu Gln Gly Gln Asp
305                 310                 315                 320

Pro Thr His Leu Val
                325

<210> SEQ ID NO 218
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Leu His Leu Val Leu Gly Leu Ser Ala Val Leu Gly Leu Leu
                165                 170                 175

Leu Leu Arg Trp Gln Phe Pro Ala His Tyr Arg Arg Leu Arg His Ala
            180                 185                 190

Leu Trp Pro Ser Leu Pro Asp Leu His Arg Val Leu Gly Gln Tyr Leu
        195                 200                 205

Arg Asp Thr Ala Ala Leu Ser Pro Pro Lys Ala Thr Val Ser Asp Thr
    210                 215                 220

Cys Glu Glu Val Glu Pro Ser Leu Leu Glu Ile Leu Pro Lys Ser Ser
225                 230                 235                 240

Glu Arg Thr Pro Leu Pro Leu Leu Glu Asp Glu Gly Val Ala Gly Ala
                245                 250                 255

Pro Thr Gly Ser Ser Pro Gln Pro Leu Gln Pro Leu Ser Gly Glu Asp
            260                 265                 270

Asp Ala Tyr Cys Thr Phe Pro Ser Arg Asp Asp Leu Leu Leu Phe Ser
        275                 280                 285

Pro Ser Gly Gln Gly Glu Phe Arg Ala Leu Asn Ala Arg Leu Pro Leu
    290                 295                 300

Asn Thr Asp Ala Tyr Leu Ser Leu Gln Glu Leu Gln Gly Gln Asp Pro
```

Thr His Leu Val

<210> SEQ ID NO 219
<211> LENGTH: 323
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr His Leu Val Leu Gly Leu Ser Ala Val Leu Gly Leu Leu Leu
                165                 170                 175

Leu Arg Trp Gln Phe Pro Ala His Tyr Arg Arg Leu Arg His Ala Leu
            180                 185                 190

Trp Pro Ser Leu Pro Asp Leu His Arg Val Leu Gly Gln Tyr Leu Arg
        195                 200                 205

Asp Thr Ala Ala Leu Ser Pro Pro Lys Ala Thr Val Ser Asp Thr Cys
    210                 215                 220

Glu Glu Val Glu Pro Ser Leu Leu Glu Ile Leu Pro Lys Ser Ser Glu
225                 230                 235                 240

Arg Thr Pro Leu Pro Leu Leu Glu Asp Glu Gly Val Ala Gly Ala Pro
                245                 250                 255

Thr Gly Ser Ser Pro Gln Pro Leu Gln Pro Leu Ser Gly Glu Asp Asp
            260                 265                 270

Ala Tyr Cys Thr Phe Pro Ser Arg Asp Asp Leu Leu Leu Phe Ser Pro
        275                 280                 285

Ser Gly Gln Gly Glu Phe Arg Ala Leu Asn Ala Arg Leu Pro Leu Asn
    290                 295                 300

Thr Asp Ala Tyr Leu Ser Leu Gln Glu Leu Gln Gly Gln Asp Pro Thr
305                 310                 315                 320

His Leu Val

<210> SEQ ID NO 220

<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr Ala Leu His Leu Val Leu Gly Leu Ser Ala Val Leu Gly Leu
                165                 170                 175

Leu Leu Leu Arg Trp Gln Phe Pro Ala His Tyr Arg Arg Leu Arg His
            180                 185                 190

Ala Leu Trp Pro Ser Leu Pro Asp Leu His Arg Val Leu Gly Gln Tyr
        195                 200                 205

Leu Arg Asp Thr Ala Ala Leu Ser Pro Pro Lys Ala Thr Val Ser Asp
    210                 215                 220

Thr Cys Glu Glu Val Glu Pro Ser Leu Leu Glu Ile Leu Pro Lys Ser
225                 230                 235                 240

Ser Glu Arg Thr Pro Leu Pro Leu Leu Glu Gln Asp Lys Val Pro
                245                 250                 255

Glu Pro Ala Ser Leu Ser Ser Asn His Ser Leu Thr Ser Cys Phe Thr
        260                 265                 270

Asn Gln Gly Tyr Phe Phe Phe His Leu Pro Asp Ala Leu Glu Ile Glu
    275                 280                 285

Ala Cys Gln Asp Glu Gly Val Ala Gly Ala Pro Thr Gly Ser Ser Pro
290                 295                 300

Gln Pro Leu Gln Pro Leu Ser Gly Glu Asp Ala Tyr Cys Thr Phe
305                 310                 315                 320

Pro Ser Arg Asp Asp Leu Leu Leu Phe Ser Pro Ser Gly Gln Gly Glu
            325                 330                 335

Phe Arg Ala Leu Asn Ala Arg Leu Pro Leu Asn Thr Asp Ala Tyr Leu
        340                 345                 350

Ser Leu Gln Glu Leu Gln Gly Gln Asp Pro Thr His Leu Val
    355                 360                 365

```
<210> SEQ ID NO 221
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Leu His Leu Val Leu Gly Leu Ser Ala Val Leu Gly Leu Leu
                165                 170                 175

Leu Leu Arg Trp Gln Phe Pro Ala His Tyr Arg Arg Leu Arg His Ala
            180                 185                 190

Leu Trp Pro Ser Leu Pro Asp Leu His Arg Val Leu Gly Gln Tyr Leu
        195                 200                 205

Arg Asp Thr Ala Ala Leu Ser Pro Pro Lys Ala Thr Val Ser Asp Thr
210                 215                 220

Cys Glu Glu Val Glu Pro Ser Leu Leu Glu Ile Leu Pro Lys Ser Ser
225                 230                 235                 240

Glu Arg Thr Pro Leu Pro Leu Glu Gln Gln Asp Lys Val Pro Glu
                245                 250                 255

Pro Ala Ser Leu Ser Ser Asn His Ser Leu Thr Ser Cys Phe Thr Asn
            260                 265                 270

Gln Gly Tyr Phe Phe Phe His Leu Pro Asp Ala Leu Glu Ile Glu Ala
        275                 280                 285

Cys Gln Asp Glu Gly Val Ala Gly Ala Pro Thr Gly Ser Ser Pro Gln
290                 295                 300

Pro Leu Gln Pro Leu Ser Gly Glu Asp Ala Tyr Cys Thr Phe Pro
305                 310                 315                 320

Ser Arg Asp Asp Leu Leu Leu Phe Ser Pro Ser Gly Gln Gly Glu Phe
                325                 330                 335

Arg Ala Leu Asn Ala Arg Leu Pro Leu Asn Thr Asp Ala Tyr Leu Ser
            340                 345                 350

Leu Gln Glu Leu Gln Gly Gln Asp Pro Thr His Leu Val
        355                 360                 365
```

```
<210> SEQ ID NO 222
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Ser Asp Pro Thr Arg Val Glu Thr Ala Thr
145                 150                 155                 160

Glu Thr His Leu Val Leu Gly Leu Ser Ala Val Leu Gly Leu Leu Leu
                165                 170                 175

Leu Arg Trp Gln Phe Pro Ala His Tyr Arg Arg Leu Arg His Ala Leu
            180                 185                 190

Trp Pro Ser Leu Pro Asp Leu His Arg Val Leu Gly Gln Tyr Leu Arg
        195                 200                 205

Asp Thr Ala Ala Leu Ser Pro Pro Lys Ala Thr Val Ser Asp Thr Cys
    210                 215                 220

Glu Glu Val Glu Pro Ser Leu Leu Glu Ile Leu Pro Lys Ser Ser Glu
225                 230                 235                 240

Arg Thr Pro Leu Pro Leu Leu Glu Gln Gln Asp Lys Val Pro Glu Pro
                245                 250                 255

Ala Ser Leu Ser Ser Asn His Ser Leu Thr Ser Cys Phe Thr Asn Gln
            260                 265                 270

Gly Tyr Phe Phe Phe His Leu Pro Asp Ala Leu Glu Ile Glu Ala Cys
        275                 280                 285

Gln Asp Glu Gly Val Ala Gly Ala Pro Thr Gly Ser Ser Pro Gln Pro
    290                 295                 300

Leu Gln Pro Leu Ser Gly Glu Asp Asp Ala Tyr Cys Thr Phe Pro Ser
305                 310                 315                 320

Arg Asp Asp Leu Leu Leu Phe Ser Pro Ser Gln Gly Glu Phe Arg
                325                 330                 335

Ala Leu Asn Ala Arg Leu Pro Leu Asn Thr Asp Ala Tyr Leu Ser Leu
            340                 345                 350

Gln Glu Leu Gln Gly Gln Asp Pro Thr His Leu Val
        355                 360
```

<210> SEQ ID NO 223
<211> LENGTH: 332
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe His Val Ile Trp His
        35                  40                  45

Arg Glu Ser Pro Ser Gly Gln Thr Asp Thr Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu Leu Leu Val Leu Gly
                165                 170                 175

Leu Asn Ala Val Leu Gly Leu Leu Leu Arg Lys Gln Phe Pro Ala
            180                 185                 190

His Tyr Arg Arg Leu Arg His Ala Leu Trp Pro Ser Leu Pro Asp Leu
        195                 200                 205

His Arg Val Leu Gly Gln Tyr Leu Arg Asp Thr Ala Ala Leu Ser Pro
    210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Asp Glu Gly Val Ala Gly Ala Pro Thr Gly Ser Ser Pro Gln Pro
            260                 265                 270

Leu Gln Pro Leu Ser Gly Glu Asp Asp Ala Tyr Cys Thr Phe Pro Ser
        275                 280                 285

Arg Asp Asp Leu Leu Phe Ser Pro Ser Gly Gln Gly Glu Phe Arg
    290                 295                 300

Ala Leu Asn Ala Arg Leu Pro Leu Asn Thr Asp Ala Tyr Leu Ser Leu
305                 310                 315                 320

Gln Glu Leu Gln Gly Gln Asp Pro Thr His Leu Val
                325                 330

<210> SEQ ID NO 224
<211> LENGTH: 401
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 224

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe His Val Ile Trp His
            35                  40                  45

Arg Glu Ser Pro Ser Gly Gln Thr Asp Thr Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Val Cys Gly Val Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Ser Asp Pro Thr Arg Val Glu Thr Ala Thr
145                 150                 155                 160

Glu Thr Ala Trp Ile Ser Leu Val Thr Ala Leu His Leu Val Leu Gly
                165                 170                 175

Leu Asn Ala Val Leu Gly Leu Leu Leu Leu Arg Lys Gln Phe Pro Ala
                180                 185                 190

His Tyr Arg Arg Leu Arg His Ala Leu Trp Pro Ser Leu Pro Asp Leu
            195                 200                 205

His Arg Val Leu Gly Gln Tyr Leu Arg Asp Thr Ala Ala Leu Ser Pro
        210                 215                 220

Pro Lys Ala Thr Val Ser Asp Thr Cys Glu Glu Val Glu Pro Ser Leu
225                 230                 235                 240

Leu Glu Ile Leu Pro Lys Ser Ser Glu Arg Thr Pro Leu Pro Leu Leu
                245                 250                 255

Glu Ala Arg Asp Glu Val Glu Gly Phe Leu Gln Asp Thr Phe Pro Gln
                260                 265                 270

Gln Leu Glu Glu Ser Glu Lys Gln Arg Leu Gly Gly Asp Val Gln Ser
            275                 280                 285

Pro Asn Cys Pro Ser Glu Asp Val Val Ile Thr Pro Glu Ser Phe Gly
        290                 295                 300

Arg Asp Ser Ser Leu Thr Cys Leu Ala Gly Asn Val Ser Ala Cys Asp
305                 310                 315                 320

Ala Pro Ile Leu Ser Ser Ser Arg Ser Leu Asp Cys Arg Glu Ser Gly
                325                 330                 335

Lys Asn Gly Pro His Val Tyr Gln Asp Leu Leu Leu Ser Leu Gly Thr
                340                 345                 350

Thr Asn Ser Thr Leu Pro Pro Pro Phe Ser Leu Gln Ser Gly Ile Leu
            355                 360                 365

Thr Leu Asn Pro Val Ala Gln Gly Gln Pro Ile Leu Thr Ser Leu Gly
        370                 375                 380
```

-continued

```
Ser Asn Gln Glu Glu Ala Tyr Val Thr Met Ser Ser Phe Tyr Gln Asn
385                 390                 395                 400

Gln
```